US008455244B2

(12) United States Patent
Rentzeperis et al.

(10) Patent No.: US 8,455,244 B2
(45) Date of Patent: Jun. 4, 2013

(54) CO-CRYSTALLIZATION OF ERR-α WITH A LIGAND THAT FORMS A REVERSIBLE COVALENT BOND

(75) Inventors: Dionisios Rentzeperis, Downingtown, PA (US); Marta Cristina Abad, Downingtown, PA (US); Ludmila A. Barnakova, Downingtown, PA (US); Frank A. Lewandowski, Washington Crossing, PA (US); Cynthia M. Milligan, Rutledge, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 13/459,672

(22) Filed: Apr. 30, 2012

(65) Prior Publication Data

US 2012/0226021 A1 Sep. 6, 2012

Related U.S. Application Data

(62) Division of application No. 12/850,076, filed on Aug. 4, 2010, now Pat. No. 8,187,871.

(60) Provisional application No. 61/232,977, filed on Aug. 11, 2009.

(51) Int. Cl.
*C12N 15/00* (2006.01)
*C12N 5/00* (2006.01)
*C07K 14/00* (2006.01)
*G01N 31/00* (2006.01)

(52) U.S. Cl.
USPC ............ 435/320.1; 435/325; 530/350; 436/4

(58) Field of Classification Search
None
See application file for complete search history.

(56) References Cited

U.S. PATENT DOCUMENTS

| | | | |
|---|---|---|---|
| 4,906,122 A | 3/1990 | Barrett et al. | |
| 5,030,103 A | 7/1991 | Buist et al. | |
| 5,200,910 A | 4/1993 | Subbiah | |
| 5,365,456 A | 11/1994 | Subbiah | |
| 5,583,973 A | 12/1996 | DeLisi et al. | |
| 5,612,894 A | 3/1997 | Wertz | |
| 5,733,720 A | 3/1998 | Olivo | |
| 5,763,263 A | 6/1998 | Dehlinger | |
| 5,942,428 A | 8/1999 | Mohammadi et al. | |
| 5,994,503 A | 11/1999 | Xu et al. | |
| 5,998,593 A | 12/1999 | Huff et al. | |
| 6,037,117 A | 3/2000 | Qiu et al. | |
| 6,075,014 A | 6/2000 | Weston et al. | |
| 6,075,123 A | 6/2000 | Lahti et al. | |
| 6,080,576 A | 6/2000 | Zambrowicz et al. | |
| 6,093,573 A | 7/2000 | Beamer et al. | |
| 2005/0208490 A1 | 9/2005 | Moras et al. | |
| 2006/0014812 A1 | 1/2006 | Player et al. | |
| 2006/0079494 A1 | 4/2006 | Santi et al. | |
| 2006/0148876 A1 | 7/2006 | Deuschle et al. | |
| 2006/0149521 A1 | 7/2006 | Baxter et al. | |
| 2008/0221179 A1 | 9/2008 | Gaul et al. | |
| 2009/0111855 A1 | 4/2009 | Gaul | |

FOREIGN PATENT DOCUMENTS

WO WO 2009/040003 A1 4/2009

OTHER PUBLICATIONS

Kallen et al., "Crystal Structure of Human Estrogen-related Receptor alpha in Complex with a Synthetic Inverse Agonist Reveals Its Novel Molecular Mechanism", JBC, 2007, 285(32):23231-23239.*
Kallen et al., "Evidence of Ligand-independent Transcriptional Activation of the Human Estrogen-related Receptor alpha (ERRalpha)", JBC, 2004, 279(19):49330-49337.*
Cudney R. Protein Crystallization and Dumb Luck. The Rigaku Journal. 1999. vol. 16, No. 1, pp. 1-7.*
Adams, P. D., et al. (2002). "PHENIX: building new software for automated crystallographic structure determination." Acta Crystallogr D Biol Crystallogr 58(Pt 11): 1948-54.
Altschul, S. F. (1993). "A protein alignment scoring system sensitive at all evolutionary distances." J. Mol. Evol. 36: 290.
Altschul, S. F., et al. (1994). "Issues in searching molecular sequence databases." Nature Genetics 6: 119.
Aranda, A. and A. Pascual (2001). "Nuclear hormone receptors and gene expression." Physiol Rev 81(3): 1269.
Ariazi, E. A., et al. (2002). "Estrogen-related receptor alpha and estrogen-related receptor gamma associate with unfavorable and favorable biomarkers, respectively, in human breast cancer." Cancer Res 62(22): 6510-8.
Bacon, D. J. And J. Moult (1992). "Docking by Least-squares Fitting of Molecular Surface Patterns." J.Mol.Biol. 225: 849-858.
Bartlett, P. A., et al. (1989). "CAVEAT: A Program to Facilitate the Structure-Derived Design of Biologically Active Molecules." In Molecular Recognition in Chemical and Biological Problems, Special Pub., Royal Chem. Soc. 78: 82-196.
Berge, S. M., et al. (1977). "Pharmaceutical salts." J Pharm Sci 66(1): 1-19.
Bohm, H.-J. (1992). "The Computer Program LUDI: A New Method for the De Novo Design of Enzyme Inhibitors." J. Computer-Aided Molecular Design 6: 61-78.
Bonnelye, E., et al. (2002). "Estrogen receptor-related receptor alpha impinges on the estrogen axis in bone: potential function in osteoporosis." Endocrinology 143(9): 3658-70.
Bonnelye, E., et al. (2001). "The orphan nuclear estrogen receptor-related receptor alpha (ERRalpha) is expressed throughout osteoblast differentiation and regulates bone formation in vitro." J Cell Biol 153(5): 971-84.
Bonnelye, E., et al. (1997). "The ERR-1 orphan receptor is a transcriptional activator expressed during bone development." Mol Endocrinol 11(7): 905-16.

(Continued)

*Primary Examiner* — Suzanne M Noakes
(74) *Attorney, Agent, or Firm* — Andrea Jo Kamage

(57) ABSTRACT

The crystal structure of the ligand binding domain of ERR-α in complex with a ligand that forms a reversible thioether bond to Cys325 of ERR-α, methods to measure dissociation rates for ligands that form reversible covalent bonds, and methods to design ligands that form reversible covalent bonds for use as modulators of ERR-α activity are disclosed. The crystal structure and methods provide a novel molecular mechanism for modulation of the activity of ERR-α and provide the basis for rational drug design to obtain potent specific ligands for use as modulators of the activity of this new drug target.

2 Claims, 2 Drawing Sheets

OTHER PUBLICATIONS

Brunger, A. T., et al. (1998). "Crystallography & NME system: A new software suite for macromolecular structure determination." Acta Crystallogr D Biol Crystallogr 54(Pt 5): 905-21.

Cohen, N., J. Blaney, et al. (1990). "Molecular Modeling Software and Methods for Medicinal Chemistry." J. Med. Chem. 33: 883-894.

Emsley, P. and K. Cowtan (2004). "Coot: model-building tools for molecular graphics." Acta Crystallogr D Biol Crystallogr 60(Pt 12 Pt 1): 2126-32.

Fry, D. W., et al. (1998). "Specific, irreversible inactivation of the epidermal growth factor receptor and erbB2, by a new class of tyrosine kinase inhibitor." Proc Natl Acad Sci U S A 95(20): 12022-7.

Giguere, V. (1999). "Orphan nuclear receptors: from gene to function." Endocr Rev 20(5): 689-725.

Giguere, V. (2002). "To ERR in the estrogen pathway." Trends Endocrinol Metab 13(5): 220-5.

Giguere, V., et al. (1988). "Identification of a new class of steroid hormone receptors." Nature 331(6151): 91-4.

Goodford, P. J. (1985). "A Computational Procedure for Determining Energetically Favorable Binding Sites on Biologically Important Macromolecules." J. Med. Chem. 28: 849-857.

Goodsell, D. S. and A. J. Olsen (1990). "Automated Docking of Substrates to Proteins by Simulated Annealing." Proteins: Structure. Function, and Genetics 8: 195-202.

Gould, P. L. (1986). "Salt selection for basic drugs." International Journal of Pharmaceutics 33(1-3): 201-217.

Grundy, S. M., et al. (2004). "Definition of metabolic syndrome: Report of the National Heart, Lung, and Blood Institute/American Heart Association conference on scientific issues related to definition." Circulation 109(3): 433-8.

Henikoff, J. G. (1992). "Amino acid substitution matrices from protein blocks." Proc. Natl. Acad. Sci. USA(89): 10915-10919.

Hong, H., et al. (1999). "Hormone-independent transcriptional activation and coactivator binding by novel orphan nuclear receptor ERR3." J Biol Chem 274(32): 22618-26.

Jones, P. L. and Y. B. Shi (2003). "N-CoR-HDAC corepressor complexes: roles in transcriptional regulation by nuclear hormone receptors." Curr Top Microbiol Immunol 274: 237-68.

Jones, T. A., et al. (1991). "Improved methods for building protein models in electron density maps and the location of errors in these models." Acta Crystallogr A 47 ( Pt 2): 110-9.

Kalgutkar, A. S., et al. (1998). "Aspirin-like molecules that covalently inactivate cyclooxygenase-2." Science 280(5367): 1268-70.

Kallen, J., et al. (2007). "Crystal structure of human estrogen-related receptor alpha in complex with a synthetic inverse agonist reveals its novel molecular mechanism." J Biol Chem 282(32): 23231-9.

Kallen, J., et al. (2004). "Evidence for ligand-independent transcriptional activation of the human estrogen-related receptor alpha (ERRalpha): crystal structure of ERRalpha ligand binding domain in complex with peroxisome proliferator-activated receptor coactivator-1alpha." J Biol Chem 279(47): 49330-7.

Kamei, Y., et al. (2003). "PPARgamma coactivator 1beta/ERR ligand 1 is an ERR protein ligand, whose expression induces a high-energy expenditure and antagonizes obesity." Proc Natl Acad Sci U S A 100(21): 12378-83.

Karlin, S. and S. F. Altschul (1990). "Methods for assessing the statistical significance of molecular sequence features by using general scoring schemes." Proc. Natl. Acad. Sci. USA 87: 2264-2268.

Klostermeier, D. and D. P. Millar (2001). "Time-resolved fluorescence resonance energy transfer: a versatile tool for the analysis of nucleic acids." Biopolymers 61(3): 159-79.

Korach, K. S. (1994). "Insights from the study of animals lacking functional estrogen receptor." Science 266(5190): 1524-7.

Kraus, R. J., et al. (2002). "Estrogen-related receptor alpha 1 actively antagonizes estrogen receptor-regulated transcription in MCF-7 mammary cells." J Biol Chem 277(27): 24826-34.

Kuntz, I. D., et al. (1982). "A geometric approach to macromolecule-ligand interactions." J Mol Biol 161(2): 269-88.

Lipinski, C., et al. (1997). "Experimental and computational approaches to estimate solubility and permeability in drug discovery and development settings " Advanced Drug Delivery Reviews 23(1-3): 3-25.

Luo, J., et al. (2003). "Reduced fat mass in mice lacking orphan nuclear receptor estrogen-related receptor alpha." Mol Cell Biol 23(22): 7947-56.

Luo, Y., et al. (2006). "Inhibitors and inactivators of protein arginine deiminase 4: functional and structural characterization." Biochemistry 45(39): 11727-36.

Martin, Y. C. (1992). "3D Database Searching in Drug Design." J. Med. Chem. 35: 2145-2154.

Matteucci and J. Caruthers, "Synthesis of Deoxyoligucleotdies on a Polymer Support", (1981). J. Am. Chem. Soc. 103(3): 185-3191.

McKenna, N. J., et al. (1999). "Nuclear receptor coregulators: cellular and molecular biology." Endocr Rev 20(3): 321-44.

Meng, E. C., et al. (1992). "Automated docking with grid-based energy evaluation." J. Comp. Chem. 13: 505-524.

Miranker, A. and M. Karplus (1991). "Functionality Maps of Binding Sites: A Multiple Copy Simultaneous Search Method." Proteins: Structure, Function and Genetics 11: 29-34.

Navia, M. A. and M. A. Murcko (1992). "The Use of Structural Information in Drug Design." Current Opinions in Structural Biology 2: 202-210.

Nishibata, Y. and A. Rai (1991). "Automatic creation of drug candidate structures based on receptor structure. Starting point for artificial lead generation." Tetrahedron 47: 8985-8990.

Norton, P. A. and J. M. Coffin (1985). "Bacterial beta-galactosidase as a marker of Rous sarcoma virus gene expression and replication." Mol Cell Biol 5(2): 281-90.

Olefsky, J. M. (2001). "Nuclear receptor minireview series." J Biol Chem 276(40): 36863-4.

Pacifici, R. (1996). "Estrogen, cytokines, and pathogenesis of postmenopausal osteoporosis." J Bone Miner Res 11(8): 1043-51.

Pantoliano, M. W., et al. (2001). "High-density miniaturized thermal shift assays as a general strategy for drug discovery." J Biomol Screen 6(6): 429-40.

Pojer, F., et al. (2006). "Structural basis for the design of potent and species-specific inhibitors of 3-hydroxy-3-methylglutaryl CoA synthases." Proc Natl Acad Sci USA 103(31): 11491-6.

Rochette-Egly, C., et al. (1997). "Stimulation of RAR alpha activation function Af-1 through binding to the general transcription factor TFIIH and phosphorylation by CDK7." Cell 90(1): 97-107.

Rochette-Egly, C., et al. (1992). "Retinoic acid receptor-beta: immunodetection and phosphorylation on tyrosine residues." Mol Endocrinol 6(12): 2197-209.

Rotstein, S. H. and M. A. Murcko (1993). "GroupBuild: a fragment-based method for de novo drug design." J Med Chem 36(12): 1700-10.

Schirmer, A., et al. (2006). "Targeted covalent inactivation of protein kinases by resorcylic acid lactone polyketides." Proc Natl Acad Sci U S A 103(11): 4234-9.

Shiraki, T., et al. (2005). "Alpha,beta-unsaturated ketone is a core moiety of natural ligands for covalent binding to peroxisome proliferator-activated receptor gamma." J Biol Chem 280(14): 14145-53.

Sladek, R., et al. (1997). "The orphan nuclear receptor estrogen-related receptor alpha is a transcriptional regulator of the human medium-chain acyl coenzyme a dehydrogenase gene." Mol Cell Biol 17(9): 5400-9.

Sumi, D. and L. J. Ignarro (2003). "Estrogen-related receptor alpha 1 up-regulates endothelial nitric oxide synthase expression." Proc Natl Acad Sci U S A 100(24): 14451-6.

Travis, J. (1993). "Proteins and Organic Solvents Make an Eye-Opening Mix." Science 262: 1374.

Turner, R. T., et al. (1994). "Skeletal effects of estrogen." Endocr Rev 15(3): 275-300.

Vega, R. B. and D. P. Kelly (1997). "A role for estrogen-related receptor alpha in the control of mitochondrial fatty acid beta-oxidation during brown adipocyte differentiation." J Biol Chem 272(50): 31693-9.

Windahl, S. H., et al. (1999). "Increased cortical bone mineral content but unchanged trabecular bone mineral density in female ERbeta(-/-) mice." J Clin Invest 104(7): 895-901.

Wood, E. R., et al. (2008). "6-Ethynylthieno[3,2-d]- and 6-ethynylthieno[2,3-d]pyrimidin-4-anilines as tunable covalent modifiers of ErbB kinases." Proc Nati Acad Sci U S A 105(8): 2773-8.

Wurtz, J. M., et al. (1996). "A canonical structure for the ligand-binding domain of nuclear receptors." Nat Struct Biol 3(1): 87-94.

Xu, H. E., et al. (2002). "Structural basis for antagonist-mediated recruitment of nuclear co-repressors by PPARalpha." Nature 415(6873): 813-7.

Zhang, Z. and C. T. Teng (2000). "Estrogen receptor-related receptor alpha 1 interacts with coactivator and constitutively activates the estrogen response elements of the human lactoferrin gene." J Biol Chem 275(27): 20837-46.

\* cited by examiner

CO-CRYSTALLIZATION OF ERR-α WITH A LIGAND THAT FORMS A REVERSIBLE COVALENT BOND

CROSS REFERENCE TO RELATED APPLICATIONS

This application is a divisional application of U.S. Ser. No. 12/850,076, filed Aug. 4, 2010, which application claims priority from U.S. Patent Application No. 61/232,977, filed Aug. 11, 2009, all of which are hereby incorporated by reference in their entirety.

TECHNICAL FIELD

The present invention generally pertains to the fields of protein crystallization, X-ray diffraction analysis, three-dimensional structural determination, molecular modeling, and structure based rational drug design. The present invention provides a crystallized form of Estrogen Related Receptor alpha (ERR-α) in complex with a ligand that forms a thioether bond in the ligand binding pocket (LBP), methods to measure dissociation rates for ligands that form reversible covalent bonds, and methods to design ligands that form reversible covalent bonds for use as modulators of ERR-α activity.

BACKGROUND OF THE INVENTION

Various publications, which may include patents, published applications, technical articles and scholarly articles, are cited throughout the specification in parentheses, and full citations of each may be found at the end of the specification. Each of these cited publications is incorporated by reference herein, in its entirety.

Nuclear receptors are members of a superfamily of transcription factors. The members of this family share structural similarities and regulate a diverse set of biological effects (Olefsky 2001). Ligands activate or repress these transcription factors that control genes involved in metabolism, differentiation and reproduction (Laudet and Gronmeyer 2002). Presently, the human genome project has identified about 48 members for this family and cognate ligands have been identified for about 28 of them (Giguere 1999). This protein family is composed of modular structural domains that can be interchanged within the members of the family without loss of function. A typical nuclear receptor contains a hypervariable N-terminus, a conserved DNA binding domain (DBD), a hinge region, and a conserved ligand binding domain (LBD). The function of the DBD is targeting of the receptor to specific DNA sequences (nuclear hormone response elements or NREs). The function of the LBD is recognition of its cognate ligand. Within the sequence of the nuclear receptor there are regions involved in transcriptional activation. The AF-1 domain is situated at the N-terminus and constitutively activates transcription (Rochette-Egly, Gaub et al. 1992; Rochette-Egly, Adam et al. 1997), while the AF-2 domain is embedded within the LBD and its transcriptional activation is ligand dependent (Wurtz, Bourguet et al. 1996). Nuclear receptors can exist as monomers, homodimers or heterodimers and bind to direct or inverted nucleotide repeats (Aranda and Pascual 2001; Laudet and Gronmeyer 2002).

The members of this family exist either in an activated or repressed basal biological state. The basic mechanism of gene activation involves ligand dependent exchange of co-regulatory proteins. These co-regulatory proteins are referred to as co-activators or co-repressors (McKenna, Lanz et al. 1999). A nuclear receptor in the repressed state is bound to its DNA response element and is associated with co-repressor proteins that recruit histone de-acetylases (HDACs) (Jones and Shi 2003). In the presence of an agonist there is an exchange of co-repressors with co-activators that in turn recruit transcription factors that assemble into an ATP dependent chromatin-remodeling complex. Histones are hyper-acetylated, causing the nucleosome to unfold, and repression is alleviated. The AF-2 domain acts as the ligand dependent molecular switch for the exchange of co-regulatory proteins. In the presence of an agonist the AF-2 domain undergoes a conformational transition and presents a surface on the LBD for interaction with co-activator proteins. In the absence of an agonist or in the presence of an antagonist the AF-2 domain presents a surface that promotes interactions with co-repressor proteins. The interaction surfaces on the LBD for both co-activators, and co-repressors overlap and provide a conserved molecular mechanism for gene activation or repression that is shared by the members of this family of transcription factors (Xu, Stanley et al. 2002).

Natural ligands that modulate the biological activity of nuclear receptors have been identified for only approximately one half of known nuclear receptors. Receptors for which no natural ligand has been identified are termed "orphan receptors". The discovery of ligands or compounds that interact with an orphan receptor will accelerate the understanding of the role of the nuclear receptors in physiology and disease and facilitate the pursuit of new therapeutic approaches. A subclass of these receptors, for which no natural ligands have been identified, is the estrogen related receptors (ERRs).

Estrogen Related Receptor alpha (ERR-α), also known as ERR-1, is an orphan receptor and was the first to be identified of the three members of the estrogen receptor related subfamily of orphan nuclear receptors (ERR-α, β, γ). The ERR subfamily is closely related to the estrogen receptors (ER-α and ER-β). ERR-α and ERR-β were first isolated by a low stringency hybridization screen (Giguere, Yang et al. 1988) followed later with the discovery of ERR-γ (Hong, Yang et al. 1999). The ERRs and ERs share sequence similarity with the highest homology observed in their DBDs, approximately 60%, and all interact with the classical DNA estrogen response element. Recent biochemical evidence suggested that the ERRs and ERs share co-regulator proteins and also target genes, including pS2, lactoferin, aromatase, and osteopontin (Hong, Yang et al. 1999; Zhang and Teng 2000; Giguere 2002; Kraus, Ariazi et al. 2002). It has been suggested that one of the main functions of ERRs is to regulate the response of estrogen responsive genes. The effects of the steroid hormone estrogen are primarily mediated in the breast, bone and endometrium, so it is reasonable to believe that compounds that interact with ERRs may find use for the treatment of bone related disease, breast cancer, and other diseases related to the reproduction system.

For example, it has been shown that ERR-α is present in both normal and cancerous breast tissue (Ariazi, Clark et al. 2002). It has also been reported that the main function of ERR-α in normal breast tissue is that of a repressor for estrogen responsive genes. In breast cancers or cell lines that are non-estrogen responsive (ER-α negative), ERR-α has been reported to be in an activated state (Ariazi, Clark et al. 2002). Therefore compounds that interact with ERR-α may be useful agents for the treatment of breast cancer that is ER-α negative and non-responsive to classical anti-estrogenic therapy, or may be used as an adjunct agent for anti-estrogen responsive breast cancers. These agents may act as antagonists by reducing the biological activity of ERR-α in these particular tissues.

Regarding bone related diseases, many post-menopausal women experience osteoporosis, a condition that has been clearly associated with a reduction of estrogen production. For example, it has been shown that reduction of estrogen levels results in increased bone loss (Turner, Riggs et al. 1994). It has also been shown that administration of estrogens to postmenopausal patients with osteoporosis has an anabolic effect on bone development (Pacifici 1996). The molecular mechanism linking estrogen receptors to bone loss is not well understood, however, since ER-α and ER-β knock-out animals have only minor skeletal defects (Korach 1994; Windahl, Vidal et al. 1999). With regard to ERR-α in bone, ERR-α expression has been shown to be regulated by estrogen (Bonnelye, Vanacker et al. 1997; Bonnelye, Merdad et al. 2001) and ERR-α expression is known to be maintained throughout stages of osteoblast differentiation. Furthermore, over-expression of ERR-α in rat calvaria osteoblasts, an accepted model of bone differentiation, resulted in an increase of bone nodule formation and treatment of rat calvaria osteoblasts with ERR-α antisense results in a decrease of bone nodule formation. ERR-α also regulates osteopontin, a protein believed to be involved in bone matrix formation. Therefore, compounds that modulate ERR-α by increasing its activity may have an anabolic effect for the regeneration of bone density and provide a benefit over current approaches that prevent bone loss. Such compounds may enhance the activity of the receptor by enhancing the association of the receptor with proteins that increase its activity or improve the stability of the receptor or by increasing the intracellular concentrations of the receptor and consequently increasing its activity. Conversely, with respect to bone diseases that are a result of abnormal bone growth, compounds that interact with ERR-α and decrease its biological activity may provide a benefit for the treatment of these diseases by retarding bone growth. Antagonism of the association of the receptor with co-activator proteins decreases the activity of the receptor.

ERR-α is also present in cardiac, adipose, and muscle tissue and forms a transcriptionally active complex with the PGC-1 co-activator family, which are co-activators implicated in energy homeostasis, mitochondria biogenesis, hepatic gluconeogenesis and in the regulation of genes involved in fatty acid beta-oxidation (Kamei, Ohizumi et al. 2003). ERR-α regulates the expression of medium chain acyl-CoA dehydrogenase (MCAD) through interactions with its promoter. MCAD is a gene involved in the initial reaction in fatty acid beta-oxidation. It is believed that in the adipose tissue, ERR-α regulates energy expenditure through the regulation of MCAD (Sladek, Bader et al. 1997; Vega and Kelly 1997). In antisense experiments in rat calvaria osteoblasts, in addition to the inhibition of bone nodule formation, there was an increase in adipocyte differentiation markers including aP2 and PPAR-γ (Bonnelye, Kung et al. 2002). An ERR-α knockout model has been described that exhibited reduced fat mass relative to the wild type. DNA chip analysis indicated that the ERR-α knockout mice have an alteration in the expression levels of genes involved in adipogenesis and energy metabolism (Luo, Sladek et al. 2003). More recently it has been shown that ERR-α regulates the expression of endothelial nitric oxide synthase, a gene that has a protective mechanism against arteriosclerosis (Sumi and Ignarro 2003). The biochemical evidence supports the involvement of ERR-α in metabolic homeostasis and differentiation of cells into adipocytes. Therefore, compounds interacting with ERR-α may affect energy homeostasis and provide a benefit for the treatment of obesity and metabolic syndrome related disease indications, including arteriosclerosis and diabetes (Grundy, Brewer et al. 2004).

Lion Bioscience AG disclosed the use of certain pyrazole derivatives as antagonists of ERR-α for treating cancer, osteoporosis, obesity, lipid disorders and cardiovascular disorders and for regulating fertility (US20060148876). Still other small molecules were also disclosed as ERR-α modulators (US20060014812; US20080221179).

There is a continuing need for new ERR-α inverse agonists that may find use in the treatment of conditions including but not limited to bone-related disease, bone formation, breast cancer (including those unresponsive to anti-estrogen therapy), cartilage formation, cartilage injury, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, repetitive stress injury, periodontal disease, chronic inflammatory airway disease, chronic bronchitis, chronic obstructive pulmonary disease, metabolic syndrome, obesity, disorders of energy homeostasis, diabetes, lipid disorders, cardiovascular disorders, artherosclerosis, hyperglycemia, elevated blood glucose level, and insulin resistance.

X-ray crystal structures provide powerful tools for the rational design of ligands that can function as active agents for biologically important targets. The first crystal structure solved for ERR-α was a complex of the ERR-α ligand binding domain and a coactivator peptide from peroxisome proliferator-activated receptor coactivator-1 (PGC-1) (Kallen, Schlaeppi et al. 2004). The structure revealed that the putative ligand binding pocket (LBP) of ERR-α is almost completely occupied by side chains, in particular with the bulky side chain of Phe328. The crystal structure of ERR-α in a transcriptionally active conformation, in the absence of a ligand, provided evidence for ligand-independent transcriptional activation by ERR-α. A second ERR-α crystal structure was solved with the ligand binding domain of ERR-α (containing a C325S mutation) in complex with an inverse agonist bound in the ligand binding pocket (LBP). The C325S mutation was introduced to reduce biochemical instability problems during purification and crystallization that were determined to be associated with cysteine oxidation. (Kallen, Lattmann et al. 2007). The structure revealed a dramatic conformational change in the ERR-α LBP which created the necessary space for the ligand to bind. Due to the C325S mutation in the LBP, however, the structure left unresolved the importance of the Cys325 in designing ligands for use as modulators of ERR-α activity.

It has been shown that certain ligands form a covalent bond to a cysteine residue in the peroxisome proliferator-activated receptor (PPAR) ligand binding domain through a Michael addition, and that covalent binding is required for PPAR activation by the ligands (Shiraki, Kamiya et al. 2005). Covalent binding has also been demonstrated in a number of different drugs for a variety of drug targets. A few examples are briefly included below. It was proposed that targeted covalent inactivation of a variety of protein kinases may hold promise for developing treatments for a number of different diseases (US20060079494; Fry, Bridges et al. 1998; Schirmer, Kennedy et al. 2006; Wood, Shewchuk et al. 2008). Covalent binding was also demonstrated for potent and species-specific inhibitors of 3-hydroxy-3-methylglutaryl CoA synthases ((Pojer, Ferrer et al. 2006). It was shown that F-amidine and Cl-amidine irreversibly inactivate protein arginine deiminase 4 (PAD4) in a calcium-dependent manner via the specific modification of Cys645, an active site residue that is critical for catalysis. A growing body of evidence supports a role for PAD4 in the onset and progression of rheumatoid arthritis, a chronic autoimmune disorder. It was concluded that the covalent binding compounds may be useful as potential lead compounds for the treatment of rheumatoid arthritis (Luo, Arita et al. 2006). Even the unique properties of aspirin, the ubiquitous nonsteroidal anti-inflammatory drug, derive from its ability to covalently modify cyclooxygenases, COX-1 and COX-2, the in vivo targets for its action (Kalgutkar, Crews et al. 1998).

The present invention provides a crystallized form of a complex of the ERR-α ligand binding domain (ERR-α-LBD) with a ligand that forms a thioether bond to Cys325 of ERR-α. The diffraction pattern of the crystal is of sufficient resolution so that the three-dimensional structure of ERR-α can be determined at atomic resolution, ligand-binding sites on ERR-α can be identified, and the interactions of ligands with specific amino acid residues of ERR-α can be modeled and used to design ligands that can function as active agents. The assay methods of the present invention can be used to measure dissociation rates for ligands that form reversible covalent bonds and can function as active agents. Thus, the three-dimensional structure of the complex of the ERR-α ligand binding domain (ERR-α-LBD) with a ligand that forms a thioether bond to Cys325 and the assay methods of the present invention have applications to the design and biological characterization of ligands that function as modulators of ERR-α activity. Such ligands may be useful for treating, ameliorating, preventing or inhibiting the progression of disease states, disorders and conditions that are mediated by ERR-α activity.

SUMMARY OF THE INVENTION

According to a first aspect of the present invention, there is provided a method of producing and using three-dimensional structure information derived from the crystal structure of a complex of Estrogen Related Receptor alpha (ERR-α) and Compound 1.

The present invention also includes specific crystallization conditions to obtain crystals of the complex of ERR-α and Compound 1. The crystals are subsequently used to obtain a 3-dimensional structure of the complex using X-ray crystallography. The obtained data is used for rational drug discovery with the aim to design ligands that are modulators of ERR-α a activity.

The present invention includes a crystal comprising ERR-α, or a fragment, or target structural motif or derivative thereof, and a ligand, wherein the ligand forms a thioether bond to Cys325 of ERR-α.

In another embodiment, the present invention comprises a crystal of ERR-α and a ligand, wherein said ligand forms a thioether bond to Cys325 of ERR-α, the crystal having a spacegroup of P6522.

In yet another embodiment, the present invention comprises a crystal of ERR-α and a ligand, wherein said ligand forms a thioether bond to Cys325 of ERR-α, the crystal with a unit cell having dimensions of about a=b=103.007 and c=110.017.

In another aspect of the invention, the invention includes a computer system comprising: (a) a database stored on a computer readable storage medium, the database containing information on the three dimensional structure of a crystal comprising ERR-α, or a fragment or a target structural motif or derivative thereof, and a ligand, wherein said ligand that forms a thioether bond to Cys325 of ERR-α; and, (b) a user interface to view the information.

Further included in the present invention is a method of identifying a modulator of ERR-α activity, comprising: (a) employing the three dimensional structure of ERR-α cocrystallized with a ligand that forms a thioether bond to Cys325 of ERR-α; and, (b) designing or selecting said modulator of ERR-α activity, thereby identifying the modulator of ERR-α activity.

The invention comprises a method of locating the attachment site of a modulator of ERR-α activity, comprising: (a.) contacting human ERR-α with the ligand; (b.) cocrystallizing human ERR-α with the ligand; (c.) obtaining X-ray diffraction data for a complex of ERR-α and the ligand; (d.) obtaining X-ray diffraction data for a crystal of ERR-α without the ligand; (e.) subtracting the X-ray diffraction data obtained in step (c) from the X-ray diffraction data obtained in step (d) to obtain the difference in the X-ray diffraction data; (f.) obtaining phases that correspond to X-ray diffraction data obtained in step (c); (g.) utilizing the phases obtained in step (f) and the difference in the X-ray diffraction data obtained in step (e) to compute a difference Fourier image of the ligand; and, (h.) locating the attachment site of the ligand to ERR-α based on the computations obtained in step (g).

The invention additionally comprises a method for solving the crystal structure of a complex comprising an ERR-α polypeptide and a ligand that forms a thioether bond with Cys325 of ERR-α, comprising: (a) contacting the ERR-α polypeptide with said ligand in a suitable solution comprising ammonium sulfate, Pipes pH 6.5 and Na-thiocyanate; (b) crystallizing said resulting complex of the ERR-α polypeptide and the ligand from said solution; and, (c) solving the crystal structure of the complex of the ERR-α polypeptide and the ligand.

The invention includes a method for identifying a potential modulator of ERR-α activity, comprising: (a) using a three dimensional structure of the complex of ERR-α and a ligand that forms a thioether bond with Cys325 of ERR-α as defined by atomic coordinates according to Table 6; (b) replacing one or more ERR-α amino acids in said three-dimensional structure with a different amino acid to produce a modified ERR-α; (c) using said three-dimensional structure to design or select said potential modulator of ERR-α activity; (d) synthesizing said potential modulator; and, (e) contacting said potential modulator with said modified ERR-α and determining the ability of said potential modulator to affect said ERR-α activity. Also included in the invention is a modulator of ERR-α identified by the method.

In another embodiment, the present invention provides a method to measure the dissociation rate for a ligand that forms a reversible covalent bond with a protein, comprising the steps of: (a) measuring by LC/MS a mass for the protein, a mass for a first ligand that forms a reversible covalent bond with the protein, and a mass for a competing second ligand that forms a reversible covalent bond with the protein, wherein the competing second ligand has a different mass than the first ligand; (b) mixing the protein and the first ligand in a solution with the first ligand in molar excess of the protein; (c) incubating the protein and the first ligand in the solution to allow for a protein:first ligand complex to form; (d) removing an aliquot of the solution and measuring by LC/MS the mass for the protein:first ligand complex; (e) adding molar excess of the competing second ligand to the solution containing the protein:first ligand complex; (f) removing aliquots of the solution at time 0 and at regular intervals; (g) measuring the time-dependent change in the mass of the protein:first ligand complex; and, (h) determining the dissociation rate for the first ligand; thereby measuring the dissociation rate of a ligand that forms a reversible covalent bond with a protein.

The present invention further provides a method to measure the dissociation rate for a ligand that forms a reversible covalent bond with a protein, wherein the reversible covalent bond is a thioether bond to a cysteine (Cys).

The present invention also provides a method to measure the dissociation rate for a ligand that forms a reversible covalent bond with a protein, wherein the protein comprises Estrogen Related Receptor alpha (ERR-α) and the ligand that forms a thioether bond to Cys325 of ERR-α.

In its many embodiments, the present invention provides methods to identify novel ligands that may find use as modulators of ERR-α activity, for example, ligands that function as inverse agonists of ERR-α and form a thioether bond with Cys325 of ERR-α, pharmaceutical compositions comprising one or more such ligands, methods of preparing pharmaceutical compositions comprising one or more such ligands, and methods of treatment, prevention, inhibition or amelioration of one or more diseases associated with ERR-α activity using such ligands or pharmaceutical compositions containing such ligands.

Another aspect of the present invention features a pharmaceutical composition comprising at least one ligand that forms a thioether bond with Cys325 of ERR-α and at least one pharmaceutically acceptable carrier.

The present invention also features a method of treating a subject suffering from or diagnosed with a disease, disorder, or condition mediated by ERR-α activity, comprising administering to the subject a therapeutically effective amount of at least one ligand that forms a thioether bond with Cys325 of ERR-α. Such disease, disorder, or condition can include bone-related disease, bone formation, breast cancer (including those unresponsive to anti-estrogen therapy), cartilage formation, cartilage injury, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, repetitive stress injury, periodontal disease, chronic inflammatory airway disease, chronic bronchitis, chronic obstructive pulmonary disease, metabolic syndrome, obesity, disorders of energy homeostasis, diabetes, lipid disorders, cardiovascular disorders, artherosclerosis, hyperglycemia, elevated blood glucose level, and insulin resistance. The therapeutically effective amount of the ligand that forms a thioether bond with Cys325 of ERR-α can be from about 0.1 mg/day to about 5000 mg/day for an average human.

The present invention further includes a method of treating a subject suffering from or diagnosed with a disease, disorder, or medical condition mediated by Estrogen Related Receptor alpha (ERR-α) activity, comprising administering to the subject an effective amount to treat the disease, disorder, or medical condition, a ligand that forms a thioether bond to Cys325 of ERR-α, or a pharmaceutically acceptable salt, pharmaceutically acceptable prodrug, or pharmaceutically active metabolite thereof, wherein the disease, disorder, or medical condition is selected from the group consisting of: bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, repetitive stress injury, periodontal disease, chronic inflammatory airway disease, chronic bronchitis, chronic obstructive pulmonary disease, breast cancer, metabolic syndrome, obesity, disorders of energy homeostasis, diabetes, lipid disorders, cardiovascular disorders, and artherosclerosis.

The present invention provides a method of treating a subject suffering from or diagnosed with a disease, disorder, or medical condition mediated by ERR-α activity, comprising administering to the subject a pharmaceutical composition comprising: (a) an effective amount of a pharmaceutical agent to treat the disease, disorder, or medical condition, said pharmaceutical agent comprising a ligand that forms a thioether bond to Cys325 of ERR-α and pharmaceutically acceptable salts, pharmaceutically acceptable prodrugs, and pharmaceutically active metabolites of said compounds; and, (b) a pharmaceutically acceptable excipient, wherein the disease, disorder, or medical condition is bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, repetitive stress injury, periodontal disease, chronic inflammatory airway disease, chronic bronchitis, chronic obstructive pulmonary disease, breast cancer, metabolic syndrome, obesity, energy disorder, homeostasis, diabetes, lipid disorder, cardiovascular disorder, or artherosclerosis.

Additional embodiments and advantages of the invention will become apparent from the detailed discussion, schemes, examples, and claims below.

BRIEF DESCRIPTION OF THE DRAWINGS

A preferred embodiment of the present invention will now be described, by way of an example only, with reference to the accompanying drawings wherein.

DEFINITIONS

Figure 1A:
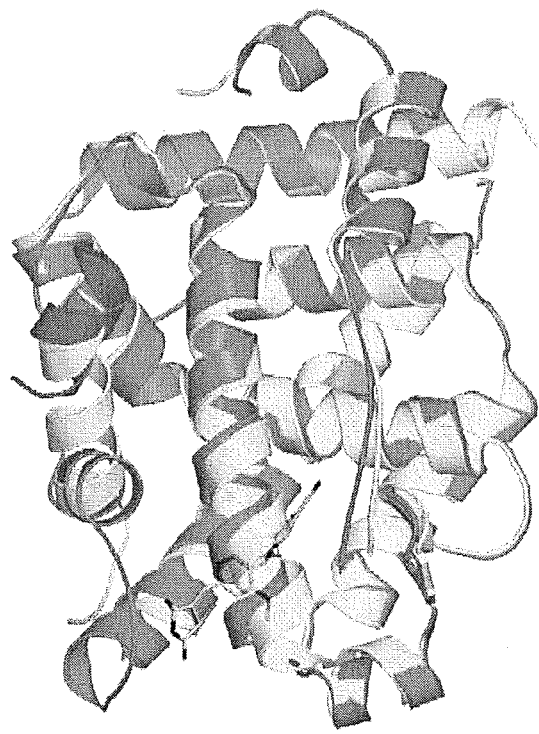
FIG. 1: A. Shown is a ribbon representation of an overlay of the complex of ERR-α and PGC1-α onto the complex of ERR-α and Compound 1. The ERR-α protein of the complex of ERR-α and Compound 1 is depicted in green with Compound 1 depicted in cyan. The complex of ERR-α and PGC1-α is shown in magenta with the PGC1-α peptide in red. B. Shown is a stick model representation of an overlay of complex of ERR-α and PGC1-α onto the complex of ERR-α and Compound 1.

As is generally the case in biotechnology and chemistry, the description of the present invention has required the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which this invention belongs. Definitions for other terms may also appear elsewhere herein. However, the definitions provided here and elsewhere herein should always be considered in determining the intended scope and meaning of the defined terms. Although any methods and materials similar or equivalent to those described herein can be used in the practice of the present invention, the preferred methods and materials are described.

The term "comprising" means "including principally, but not necessarily solely". Furthermore, variations of the word "comprising", such as "comprise" and "comprises", have correspondingly varied meanings.

As used herein, the terms "containing", "having" and "including" are used in their open, non-limiting sense.

As used herein, "sequence" means the linear order in which monomers occur in a polymer, for example, the order of amino acids in a polypeptide or the order of nucleotides in a polynucleotide.

The terms "polypeptide", "protein", and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide", "protein", and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by the codons of genes may also be included in a polypeptide.

As used herein, a protein or nucleic acid molecule is said to be "isolated" when the protein or nucleic acid molecule is substantially separated from contaminants from the source of the protein or nucleic acid.

As used herein, the term "native protein" refers to a protein comprising an amino acid sequence identical to that of a protein isolated from its natural source or organism.

As used herein, the term "amino acids" refers to the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyl-glutamic acid, arginine, ornithine, and lysine. Unless specifically indicated, all amino acids are referred to in this application are in the L-form.

As used herein, the term "nonnatural amino acids" refers to amino acids that are not naturally found in proteins. For example, selenomethionine.

As used herein, the term "positively charged amino acid" includes any amino acids having a positively charged side chain under normal physiological conditions. Examples of positively charged naturally occurring amino acids are arginine, lysine, and histidine.

As used herein, the term "negatively charged amino acid" includes any amino acids having a negatively charged side chains under normal physiological conditions. Examples of negatively charged naturally occurring amino acids are aspartic acid and glutamic acid.

As used herein, the term "hydrophobic amino acid" includes any amino acids having an uncharged, nonpolar side chain that is relatively insoluble in water. Examples of naturally occurring hydrophobic amino acids are alanine, leucine, isoleucine, valine, proline, phenylalanine, tryptophan, and methionine.

As used herein, the term "hydrophilic amino acid" refers to any amino acids having an uncharged, polar side chain that is relatively soluble in water. Examples of naturally occurring hydrophilic amino acids are serine, threonine, tyrosine, asparagine, glutamine and cysteine.

As used herein, "nucleic acid" is defined as RNA or DNA that encodes a protein or peptide as defined herein, or is complementary to nucleic acid sequence encoding such peptides, or hybridizes to such nucleic acid and remains stably bound to it under appropriate stringency conditions. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

The term "oligonucleotide" or "oligo" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

The term "high stringency" as used herein refers to the conditions under which two nucleic acids may be hybridized, and may include, for example, the concentration of salts and/or detergents in a solution, the temperature of a solution that is used during the hybridization of the two nucleic acids and time period of the hybridization. Accordingly, the term "high stringency" as used herein refers to conditions in a solution that are conducive to hybridization of two nucleic acids only where such nucleic acids share a high degree of complementarity. The degree of complementarity may include, but not be limited to, a range of from about 90% to 100%. Thus, "high stringency" conditions may involve, but are not limited to, the use of a varying temperature and a buffer comprising various concentrations of detergents, salts, and divalent cations.

As used herein, "vector" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term "activity" refers to an activity exerted by ERR-α as determined in vivo or in vitro, according to standard techniques. Examples of such activity include, but are not limited to, direct activity such as the ability to bind to a ligand or an analog thereof, changes in transcriptional activity, changes in the levels of genes or gene products that are regulated directly or indirectly by ERR-α activity, changes in enzymatic activity for protein whose expression may be affected directly or indirectly by ERR-α activity, or functional changes of cell physiology that result from changes in ERR-α activity.

The term "high-throughput assay" or "high-throughput screening" refers to assay designs that allow easy screening of multiple samples simultaneously and/or in rapid succession, and may include the capacity for robotic manipulation. Another desired feature of high-throughput assays is an assay design that is optimized to reduce reagent usage, or minimize the number of manipulations in order to achieve the analysis desired. Examples of high-throughput assay formats include, but are not limited to, formats that utilize 96-well, 384-well, and 1536-well plates, or "lab on a chip" microchannel chips used for liquid handling experiments. It is well known by those in the art that as miniaturization of plastic molds and liquid handling devices are advanced, or as improved assay devices are designed, greater numbers of samples can be processed using the forms of the present invention. Any high-throughput screening may be utilized to test new compounds, which are identified or designed for their ability to interact with ERR-α. For general information on high-throughput screening see, for example, (Devlin (editor) 1998); and U.S. Pat. No. 5,763,263.

By the term "selecting" or "select" compounds it is intended to encompass both (a) choosing compounds from a group previously unknown to be modulators of a protein complex or interacting protein members thereof and (b) testing compounds that are known to be capable of binding, or modulating the functions and activities of, a protein complex or interacting protein members thereof. The compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes, and derivatives, mimetics and analogs thereof. Preferably, they are small organic compounds, i.e., those having a molecular weight of no greater than 10,000 daltons, more preferably less than 5,000 daltons.

As used herein, the term "atomic coordinates" or "structure coordinates" refers to mathematical coordinates that describe the positions of atoms in crystals of ERR-α in Protein Data Bank (PDB) format, including X, Y, Z and B, for each atom. The diffraction data obtained from the crystals are used to calculate an electron density map of the repeating unit of the crystal. The electron density maps may be used to establish the positions (i.e. coordinates X, Y and Z) of the individual atoms within the crystal. Those of skill in the art understand that a set of structure coordinates determined by X-ray crystallography is not without standard error. For the purpose of this invention, any set of structure coordinates for a complex of ERR-α and a ligand that forms a thioether bond to Cys325 of ERR-α from any source having a root mean square deviation of non-hydrogen atoms of less than about 1.5 Å when superimposed on the non-hydrogen atom positions of the corresponding atomic coordinates of Table 6 are considered substantially identical or homologous. In a more preferred embodiment, any set of structure coordinates for a complex of ERR-α and a ligand that forms a thioether bond to Cys325 of ERR-α from any source having a root mean square deviation of non-hydrogen atoms of less than about 0.75 Å when superimposed on the non-hydrogen atom positions of the corresponding atomic coordinates of Table 6 are considered substantially identical or homologous.

The term "atom type" refers to the chemical element whose coordinates are measured. The abbreviations in column 3 of Table 6 identifies the element.

The terms "X," "Y" and "Z" refer to the crystallographically-defined atomic position of the element measured with respect to the chosen crystallographic origin. The term "B" refers to a thermal factor that measures the mean variation of an atom's position with respect to its average position.

As used herein, the term "crystal" refers to any three-dimensional ordered array of molecules that diffracts X-rays.

As used herein, the term "carrier" in a composition refers to a diluent, adjuvant, excipient, or vehicle with which the product is mixed.

As used herein, the term "composition" refers to the combining of distinct elements or ingredients to form a whole. A composition comprises more than one element or ingredient. For the purposes of this invention, a composition will often, but not always comprise a carrier.

As used herein, "ERR-α" is used to mean a protein obtained as a result of expression of human Estrogen Related Receptor alpha. Within the meaning of this term, it will be understood that human ERR-α encompasses all proteins encoded by Estrogen Related Receptor alpha, mutants thereof, conservative amino acid substitutions, alternative splice proteins thereof, and phosphorylated proteins thereof. Additionally, as used herein, it will be understood that the term "ERR-α" includes human Estrogen Related Receptor alpha and homologues from other animals. As an example, ERR-α includes the protein comprising SEQ ID NO:1 and variants thereof comprising at least about 70% amino acid sequence identity to SEQ ID NO:1, or preferably 80%, 85%, 90% and 95% sequence identity to SEQ ID NO:1, or more preferably, at least about 95% or more sequence identity to SEQ ID NO:1.

As used herein, the term "SAR", an abbreviation for Structure-Activity Relationships, collectively refers to the structure-activity/structure property relationships pertaining to the relationship(s) between a compound's activity/properties and its chemical structure.

As used herein, the term "molecular structure" refers to the three dimensional arrangement of molecules of a particular compound or complex of molecules (e.g., the three dimensional structure of a complex of ERR-α and a that ligand that forms a thioether bond to Cys325 of ERR-α).

As used herein, the term "molecular modeling" refers to the use of computational methods, preferably computer assisted methods, to draw realistic models of what molecules look like and to make predictions about structure activity relationships of ligands. The methods used in molecular modeling range from molecular graphics to computational chemistry.

As used herein, the term "molecular model" refers to the three dimensional arrangement of the atoms of a molecule connected by covalent bonds or the three dimensional arrangement of the atoms of a complex comprising more than one molecule, e.g., a protein:ligand complex.

As used herein, the term "molecular graphics" refers to three dimensional (3D) representations of the molecules; for instance, a 3D representation produced using computer assisted computational methods.

As used herein, "computer readable medium" refers to any medium, which can be read and accessed directly by a computer. Such media include, but are not limited to: magnetic storage media, such as floppy discs, hard disc storage media, and magnetic tape; optical storage media such as optical discs or CD-ROM; electrical storage media such as RAM and ROM; and hybrids of these categories such as magnetic/optical storage media.

As used herein, "recorded" refers to a process for storing information on computer readable media. A skilled artisan can readily adopt any of the presently known methods for recording information on computer readable media to generate compositions comprising an amino acid sequence and/or atomic coordinate/X-ray diffraction data information of the present invention.

As used herein, "a computer-based system" refers to the hardware means, software means, and data storage means used to analyze the sequence and/or X-ray diffraction data of the present invention. The minimum hardware means of the computer-based systems of the present invention comprises a central processing unit (CPU), input means, output means, and data storage means. A skilled artisan can readily appreciate which of the currently available computer-based systems are suitable for use in the present invention. A visualization device, such as a monitor, is optionally provided to visualize structure data.

As stated above, the computer-based systems of the present invention comprise a data storage means having stored therein sequence and/or atomic coordinate/X-ray diffraction data of the present invention and the necessary hardware means and software means for supporting and implementing an analysis means. As used herein, "data storage means" refers to memory which can store sequence or atomic coordinate/X-ray diffraction data of the present invention, or a memory access means which can access manufactures having recorded thereon the sequence or X-ray data of the present invention.

As used herein, "search means" or "analysis means" refers to one or more programs which are implemented on the computer-based system to compare a target sequence or target structural motif with the sequence or X-ray data stored within the data storage means. Search means are used to identify fragments or regions of a protein which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses can be adapted for use in the present computer-based systems.

As used herein, "a target structural motif", or "target motif", refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymatic active sites, inhibitor binding sites, structural subdomains, epitopes, functional domains and signal sequences. Similar motifs are known for RNA. A variety of structural formats for the input and output means can be used to input and output the information in the computer-based systems of the present invention.

As used herein, the term "computational chemistry" refers to calculations of the physical and chemical properties of the molecules.

As used herein, the term "molecular replacement" refers to a method that involves generating a preliminary model of a crystal of a complex of ERR-α and a ligand that forms a thioether bond to Cys325 of ERR-α whose coordinates are unknown, by orienting and positioning the atomic coordinates described in the present invention so as best to account for the observed diffraction pattern of the unknown crystal. Phases can then be calculated from this model and combined with the observed amplitudes to give an approximate Fourier synthesis of the structure whose coordinates are unknown. (Rossmann 1972).

As used herein, the term "homolog" refers to the ERR-α protein molecule or the nucleic acid molecule which encodes the protein, or a functional domain from said protein from a first source having at least about 70% or 75% sequence identity, or at least about 80% sequence identity, or more preferably at least about 85% sequence identity, or even more preferably at least about 90% sequence identity, and most preferably at least about 95%, 97% or 99% sequence identity, with the amino acid sequence of the protein, the encoding nucleic acid molecule, or any functional domain thereof, from a second source. The second source may be a version of the molecule from the first source that has been genetically altered by any available means to change the primary amino acid or nucleotide sequence or may be from the same or a different species than that of the first source.

As used herein, the term "active site" refers to regions on ERR-α or a structural motif of ERR-α that are directly involved in the function or activity of human ERR-α.

As used herein, the terms "binding site" or "binding pocket" refer to a region of human ERR-α or a molecular complex comprising ERR-α that, as a result of the primary amino acid sequence of human ERR-α and/or its three-dimensional shape, favourably associates with another chemical entity or compound including ligands, cofactors, inhibitors, or other types of modulators. For the purpose of this invention, any active site, binding site or binding pocket defined by a set of structure coordinates for a complex of ERR-α or a homolog of ERR-α and a ligand that forms a thioether bond to Cys325 of ERR-α or a homolog of ERR-α from any source having a root mean square deviation of non-hydrogen atoms of less than about 1.5 Å when superimposed on the non-hydrogen atom positions of the corresponding atomic coordinates of Table 6 are considered substantially identical or homologous. In a more preferred embodiment, any set of structure coordinates for a complex of ERR-α or a homolog of ERR-α and a ligand that forms a thioether bond to Cys325 of ERR-α or a homolog of ERR-α from any source having a root mean square deviation of non-hydrogen atoms of less than about 0.75 Å when superimposed on the non-hydrogen atom positions of the corresponding atomic coordinates of Table 6 are considered substantially identical or homologous.

The term "root mean square deviation" means the square root of the arithmetic mean of the squares of the deviations from the mean.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as carbon).

As used herein, the term "conjugated system" refers to more than two double bonds adjacent to each other, in which electrons are completely delocalized with the entire system. This also includes aromatic residues.

As used herein, the term "aromatic residue" refers to amino acids with side chains having a delocalized conjugated system. Examples of aromatic residues are phenylalanine, tryptophan, and tyrosine.

As used herein, the phrase "inhibiting the binding" refers to preventing or reducing the direct or indirect association of one or more molecules, peptides, proteins, enzymes, or receptors, or preventing or reducing the normal activity of one or more molecules, peptides, proteins, enzymes or receptors, e.g., preventing or reducing the direct or indirect association with human ERR-α.

As used herein, the term "competitive inhibitor" refers to inhibitors that bind to human ERR-α at active site, thus directly competing with a substrate or ligand. Competitive inhibition may, in some instances, be reversed completely by increasing the substrate or ligand concentration.

As used herein, the term "uncompetitive inhibitor" refers to one that inhibits the functional activity of human ERR-α by binding to a different site than does its substrate(s).

As used herein, the term "non-competitive inhibitor" refers to one that can bind to either the free or bound form of ERR-α. Those of skill in the art may identify inhibitors as competitive, uncompetitive, or non-competitive by computer fitting enzyme kinetic data using standard methods. See, for example, (Segel 1975).

The term "inverse agonist" as used herein refers to compounds or substances that have the ability to decrease the constitutive level of receptor activation in the absence of an agonist instead of only blocking the activation induced by agonist binding at the receptor.

As used herein, the term "R or S-isomer" refers to two possible stereoisomers of a chiral carbon according to the Cahn-Ingold-Prelog system adopted by International Union of Pure and Applied Chemistry (IUPAC). Each group attached to the chiral carbon is first assigned to a preference or priority a, b, c, or d on the basis of the atomic number of the atom that is directly attached to the chiral carbon. The group with the highest atomic number is given the highest preference a, the group with next highest atomic number is given the next highest preference b, and so on. The group with the lowest preference (d) is then directed away from the viewer. If the trace of a path from a to b to c is counter clockwise, the isomer is designated (S); in the opposite direction, clockwise, the isomer is designated (R).

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

As used herein, the term "chiral center" refers to a carbon atom to which four different groups are attached.

As used herein, the term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

As used herein, the term "racemic" refers to a mixture of equal parts of enantiomers and which is optically active.

As used herein, the term "resolution" refers to the separation or concentration or depletion of one of the two enantiomeric forms of a molecule. In the context of this application. The term "resolution" also refers to the amount of detail, which can be resolved by the diffraction experiment. Or in other terms, since the inherent disorder of a protein crystal diffraction pattern fades away at some diffraction angle theta$_{max}$, the corresponding distance d$_{min}$ of the reciprocal lattices is determined by Bragg's law. In practice in protein crystallography it is usual to quote the nominal resolution of a protein electron density in terms of d$_{min}$, the minimum lattice distance to which data is included in the calculation of the map.

As used herein, the term "ligand" refers to any molecule, or chemical entity, which binds with or to ERR-α, a subunit of ERR-α, a domain of ERR-α, a target structural motif of ERR-α, or a fragment of ERR-α. Thus, ligands include, but are not limited to, modulators of ERR-α activity such as small molecule inhibitors, small molecule agonists, and small molecule inverse agonists, for example.

As used herein, the term "small molecule inhibitor" refers to ligands useful in the present invention having the ability to modulate a measurable amount of ERR-α activity. In addition to small organic molecules, peptides, antibodies, cyclic peptides and peptidomimetics are contemplated as being useful in the disclosed methods. Preferred inhibitors and modulators are small molecules, preferably less than 10,000 daltons, and more preferably less than 5,000 daltons.

As used herein the terms "bind", "binding", "bond", or "bonded" when used in reference to the association of atoms, molecules, or chemical groups, refer to any physical contact or association of two or more atoms, molecules, or chemical groups.

As used herein, the terms "covalent bond" or "valence bond" refer to a chemical bond between two atoms in a molecule created by the sharing of electrons, usually in pairs, by the bonded atoms.

As used herein, "noncovalent bond" refers to an interaction between atoms and/or molecules that does not involve the formation of a covalent bond between them.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Metabolic disorders, diseases, or conditions include, but are not limited to, diabetes, obesity, and associated symptoms or complications thereof. They include such conditions as IDDM (insulin-dependent diabetes mellitus), NIDDM (non insulin-dependent diabetes mellitus), IGT (Impaired Glucose Tolerance), IFG (Impaired Fasting Glucose), Syndrome X (or Metabolic Syndrome), hyperglycemia, elevated blood glucose level, and insulin resistance. A condition such as IGT or IFG is also known as a "prediabetic condition" or "prediabetic state".

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to non-toxic pharmaceutically acceptable salts (Berge, Bighley et al. 1977; Gould 1986). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

DETAILED DESCRIPTION OF ILLUSTRATIVE EMBODIMENTS

It is to be understood at the outset, that the figures and examples provided herein are to exemplify, and not to limit the invention and its various embodiments.

The present invention includes a crystal comprising a complex of Estrogen Related Receptor alpha (ERR-α), or a fragment, or target structural motif or derivative thereof, and a ligand, wherein the ligand that forms a thioether bond to Cys325 of ERR-α. In a preferred embodiment, the fragment or derivative thereof is a peptide comprising SEQ ID NO:2. In another preferred embodiment, the ligand is Compound 1, or derivatives thereof. In highly preferred embodiment, the crystal has a spacegroup of P6522. In another highly preferred embodiment, the crystal comprises a unit cell consisting of about a=b=103.007 and c=110.017. In yet another highly preferred embodiment, the crystal comprises a complex of SEQ ID NO:2 and Compound 1 comprising an atomic structure characterized by the coordinates of Table 6.

The present invention also includes a crystal comprising a complex of ERR-α and a ligand that forms a thioether bond to Cys325 of ERR-α, in which ERR-α comprises a peptide having at least 95% sequence identity to SEQ ID NO:2.

In another aspect of the invention, the invention includes a computer system comprising: (a) a database stored on a computer readable storage medium containing information on the three dimensional structure of a crystal comprising a complex of ERR-α, or a fragment or a target structural motif or derivative thereof, and a ligand, wherein the ligand that forms a thioether bond to Cys325 of ERR-α; and, (b) a user interface to view the information. In one embodiment, the information comprises diffraction data obtained from a crystal comprising a complex of SEQ ID NO:2 and a ligand that forms a thioether bond to Cys325 of ERR-α. In a preferred embodiment, the information comprises diffraction data obtained from a crystal comprising a complex of SEQ ID NO:2 and Compound 1, or derivatives thereof. In a highly preferred embodiment, the information comprises diffraction data characterized by the coordinates of Table 6.

In another embodiment, the information comprises an electron density map of a crystal form comprising a complex of SEQ ID NO:2 and a ligand that forms a thioether bond to SEQ ID NO:2. In a preferred embodiment, the information comprises an electron density map of a crystal comprising a complex of SEQ ID NO:2 and Compound 1, or derivatives thereof. In a highly preferred embodiment, the information comprises an electron density map derived from the structure coordinates of Table 6, or homologous structure coordinates comprising a root mean square deviation of non-hydrogen atoms of less than about 1.5 Å when superimposed on the non-hydrogen atom positions of the corresponding atomic coordinates of Table 6. In a preferred embodiment, the information comprises structure coordinates comprising a root mean square deviation of non-hydrogen atoms of less than about 0.75 Å when superimposed on the non-hydrogen atom positions of the corresponding atomic coordinates of Table 6.

The present invention also includes a method of evaluating the potential of a ligand to modulate the activity of ERR-α comprising the steps of: (a) exposing ERR-α to the ligand; and (b) detecting the formation of a thioether bond to Cys325 of ERR-α, thereby evaluating the potential of the ligand to modulate the activity of ERR-α. In one embodiment of the method of the invention described above, the ligand is a virtual compound. In another embodiment the present invention includes a method of evaluating the potential of a ligand to modulate the activity of ERR-α comprising the steps of: (a) comparing the atomic structure of the ligand to the three dimensional structure of a complex of ERR-α and a ligand that forms a thioether bond to Cys325 of ERR-α; and, (b) using the information obtained in step (a) to determine if the ligand could form a thioether bond to Cys325 of ERR-α, thereby evaluating the potential of the ligand to modulate the activity of ERR-α. In a different embodiment the present invention includes a method of evaluating the potential of a ligand to modulate the activity of ERR-α comprising the steps of: (a) comparing the atomic structure of the ligand to the three dimensional structure of a complex of ERR-α and a ligand that forms a thioether bond to Cys325 of ERR-α, wherein the comparing comprises employing a computational means to perform a fitting operation between the ligand and a binding site of ERR-α, wherein the binding site is defined by structure coordinates for Cys325 according to Table 6; and, (b) using the information obtained in step (a) to determine if the ligand could form a thioether bond to Cys325 of ERR-α, thereby evaluating the potential of the ligand to modulate the activity of ERR-α. In a highly preferred embodiment, the present invention includes a method of evaluating the potential of a ligand to modulate the activity of ERR-α comprising the steps of: (a) exposing the ligand to crystalline SEQ ID NO:2; (b) detecting the formation of a thioether bond to Cys325 of ERR-α by determining the three dimensional structure of the complex of SEQ ID NO:2 and the ligand that formed a thioether bond to SEQ ID NO:2; thereby evaluating the potential of the ligand to modulate the activity of ERR-α. In a preferred embodiment, the ligand modulates the activity of ERR-α by functioning as an inverse agonist of ERR-α.

The present invention includes a method of identifying a ligand with the ability to modulate the activity of ERR-α, comprising the step of; (a) using the three dimensional structure of ERR-α cocrystallized with a small molecule that forms a thioether bond to Cys325 of ERR-α to design or select said ligand; (b) designing or selecting said ligand; thereby identifying a ligand with the ability to modulate the activity of ERR-α. In one embodiment, the three dimensional structure corresponds to the atomic structure characterized by the coordinates of Table 6, or similar structure coordinates comprising a root mean square deviation of non-hydrogen atoms of less than about 1.5 Å when superimposed on the non-hydrogen atom positions of the corresponding atomic coordinates of Table 6. In a different embodiment, the method described above further comprises the steps of: (c) synthesizing the ligand; and (d) contacting the ligand with ERR-α. In a preferred embodiment, the ligand is an inverse agonist of ERR-α.

The instant invention comprises a method of locating the attachment site of a small molecule ligand that modulates the activity of ERR-α, comprising the steps of: (a) obtaining X-ray diffraction data for a crystal of ERR-α; (b) obtaining X-ray diffraction data for a complex of ERR-α and small molecule ligand that forms a thioether bond to Cys325 of ERR-α; (c) subtracting the X-ray diffraction data obtained in step (a) from the X-ray diffraction data obtained in step (b) to obtain the difference in the X-ray diffraction data; (d) obtaining phases that correspond to X-ray diffraction data obtained in step (a); (e) utilizing the phases obtained in step (d) and the difference in the X-ray diffraction data obtained in step (c) to compute a difference Fourier image of the small molecule ligand; and, (f) locating the attachment site of the small molecule ligand to ERR-α based on the computations obtained in step (e). In a preferred embodiment, the small molecule ligand is an inverse agonist of ERR-α and the attachment site is Cys325 of ERR-α.

In another aspect of the present invention, the invention includes a method for the production of a crystal complex comprising an ERR-α polypeptide and a ligand that forms a thioether bond to Cys325 of ERR-α, comprising the steps of: (a) contacting the ERR-α polypeptide with said ligand in a suitable solution comprising ammonium sulfate, Pipes pH 6.5 and Na-thiocyanate; and, (b) crystallizing said resulting complex of ERR-α polypeptide and the ligand from said solution. In one embodiment, the ERR-α polypeptide is a polypeptide SEQ ID NO:2. In a preferred embodiment, the ligand is Compound 1, or a derivative thereof.

The invention further includes a method for the production of a crystal comprising a complex of ERR-α and a ligand that forms a thioether bond to Cys325 of ERR-α, wherein the ligand is a small molecule ligand that functions as an inverse agonist of ERR-α, comprising the steps of: (a) contacting and ERR-α polypeptide with said ligand; and, (b) cocrystallizing the polypeptide comprising SEQ ID NO:2 with the ligand; thereby producing the crystal comprising a complex of ERR-α and the ligand that forms the thioether bond to Cys325 of ERR-α.

The invention includes a method for identifying a ligand that functions as an inverse agonist of ERR-α comprising the steps of: (a) using a three dimensional structure of the complex of ERR-α and Compound 1, as defined by atomic coordinates according to Table 6; (b) replacing one or more ERR-α amino acids in said three-dimensional structure with a different amino acid to produce a modified ERR-α; (c) using said three-dimensional structure to design or select said ligand; (d) synthesizing said ligand; and, (e) contacting said ligand with said modified ERR-α in an assay designed to test the ability of the ligand to modulate the activity of ERR-α or said modified ERR-α. In another embodiment, the ligand identified in the method described above is selected from a database. In a preferred embodiment, the ligand identified in the method described above is designed de novo. In another preferred embodiment, the ligand identified in the method described above is designed from a known inverse agonist or other type of modulator.

Engineered Forms and Fragments

Engineered forms of ERR-α or fragments thereof, for instance engineered forms or fragments comprising active sites defined by two or more amino acids may be prepared by any available means including synthetic or recombinant means. Such fragments may then be used in the assays as described herein, for example, but not limited to, high-throughput assays to detect interactions between prospective ligands and the active site within the fragment.

For recombinant expression or production of the forms or fragments of the invention, nucleic acid molecules encoding the form or fragment may be prepared. Nucleic acid molecules encoding engineered forms or fragments of the invention may differ in sequence because of the degeneracy in the genetic code or may differ in sequence as they encode proteins or protein fragments that differ in amino acid sequence. Homology or sequence identity between two or more such nucleic acid molecules is determined by BLAST (Basic Local Alignment Search Tool) analysis using the algorithm employed by the programs blastp, blastn, blastx, tblastn and tblastx (Karlin and Altschul 1990) and (Altschul 1993), fully incorporated by reference, which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see (Altschul, Boguski et al. 1994) which is fully incorporated by reference. The search parameters for histogram, descriptions, alignments, expect (i.e., the statistical significance threshold for reporting matches against database sequences), cutoff, matrix and filter are at the default settings. For a discussion of default scoring matrix used by blastp, blastx, tblastn, and tblastx, see (Henikoff 1992).

The encoding nucleic acid molecules of the present invention or fragments thereof (i.e., synthetic oligonucleotides) and those that are used as probes or specific primers for polymerase chain reaction (PCR) or to synthesize gene sequences encoding proteins of the invention can easily be synthesized by chemical techniques, for example, the phosphotriester method of (Matteucci and Caruthers 1981) or using automated synthesis methods. In addition, larger DNA segments can readily be prepared by well-known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art-known labels to obtain a labeled encoding nucleic acid molecule.

The present invention further provides recombinant DNA molecules (rDNA) that contain a coding sequence for a protein or protein fragment as described herein. As used herein, an rDNA molecule is a DNA molecule that has been subjected to molecular manipulation. Methods for generating rDNA molecules are well known in the art, for example, see (Sambrook, Fritsch et al. 1989). In the preferred rDNA molecules, a coding DNA sequence is operably linked to expression control sequences and/or vector sequences.

The choice of vector and expression control sequences to which one of the protein encoding sequences of the present invention is operably linked depends directly, as is well known in the art, on the functional properties desired (e.g., protein expression, and the host cell to be transformed). A vector of the present invention may be capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

The present invention further provides host cells transformed with a nucleic acid molecule that encodes a protein or protein fragment of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, insect, yeast, and mammalian cells. Preferred eukaryotic host cells include *Spodoptera frugiperda* (Sf9 or Sf21) insect cells.

Transformed host cells of the invention may be cultured under conditions that allow the production of the recombinant protein. Optionally the recombinant protein is isolated from the medium or from the cells; recovery and purification of the protein may not be necessary in some instances where some impurities may be tolerated.

Kits may also be prepared with any of the above described nucleic acid molecules, proteins, protein fragments, vector and/or host cells optionally packaged with the reagents needed for a specific assay, such as those described above. In such kits, the protein, protein fragments, or other reagents may be attached to a solid support, such as glass or plastic beads.

High-Throughput Assays

Compound identification methods can be performed using conventional laboratory assay formats or in high-throughput assays, including, but not limited to, those described below.

Immunoassays are a group of techniques used for the measurement of specific biochemical substances, commonly at low concentrations in complex mixtures such as biological fluids. The assays depend upon suitably prepared and selected antibodies with specificity and high affinity for their complementary antigens. A substance to be measured must, of necessity, be antigenic, either an immunogenic macromolecule or a haptenic small molecule. To each sample a known limited amount of specific antibody is added and the fraction of the antigen combining with it, often expressed as the bound:free ratio, is estimated by quantifying the signal from the antibody. Quantification can be achieved with a number of readily identifiable labels and used for various types of assays, including, but not limited to, radioisotopes for radioimmunoassays (RIA), fluorescent molecules for fluoroimmunoassays (FIA), stable free radicals for spin immunoassays, chemiluminescent molecules for chemiluminescent immunoassays (CLIA), colloidal gold particles for immunogold assays, and enzymes for enzyme-linked immunosorbent assays (ELISA).

A common immunoassay format is the ELISA, which avoids the hazards of radiochemicals and the expense of fluorescence detection systems. Instead, an ELISA is a form of quantitative immunoassay based on the use of antibodies (or antigens) that may be linked to an insoluble carrier surface, which is then used to "capture" the relevant antigen (or antibody) the test solution. The antigen-antibody complex is then detected by measuring the activity of an appropriate enzyme that can be covalently attached to the capture antigen (or antibody) or to a subsequent "detection" antibody (or antigen). For more information on ELISA techniques, see, for example, (Crowther 1995); (Kemeny (editor) and Challacombe (editor) 1988), (Kemeny 1991), and (Ishikawa 1999).

Colorimetric assays for enzymes are methods of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically. Standard colorimetric assays of beta-galactosidase enzymatic activity are well known to those skilled in the art, see for example, (Norton and Coffin 1985). A colorimetric assay can be performed on whole cell lysates using O-nitrophenyl-beta-D-galacto-pyranoside (ONPG, Sigma) as the substrate in a standard colorimetric beta-galactosidase assay (Sambrook, Fritsch et al. 1989). Automated colorimetric assays are also available for the detection of beta-galactosidase activity, as described in U.S. Pat. No. 5,733,720.

Enzymatic substrates that become fluorescent after being acted upon by an enzyme generally are well known. Such fluorescent substrates typically have two components that are bound to one another through, for example, a covalent chemical bond. One component is a fluorescent molecule that is capable of fluorescing by first accepting light energy and then emitting light energy. The other component is an entity that prevents the fluorescent molecule from accepting or emitting light energy when the two components are covalently bound to one another. In the presence of an appropriate enzyme, the enzyme cleaves the covalent bond between the two components and separates one component from the other to permit the fluorescent molecule to accept and emit light energy. In other words, the enzyme frees the fluorescent molecule and allows it to fluoresce. Ideally, fluorescent substrates should be soluble and stable in aqueous buffers, should have a high affinity for the enzymes that act upon them, and should yield a strong signal upon enzymatic action (U.S. Pat. No. 5,998, 593A).

Detecting fluorescence emitted from the fluorescent component of a fluorescent enzyme substrate is typically achieved in two steps. The fluorescent molecule is first excited with light energy and subsequently the fluorescence emitted from the fluorescent component is then detected. Generally, fluorescent molecules can be excited with light energy from, for example, a laser or another suitable light source. Fluorescence is detected with a device designed to detect light energy of a wavelength that is emitted by the fluorescent molecule. Such excitation and emission detection systems generally are designed to operate at particular wavelength ranges (U.S. Pat. No. 5,998,593A).

Time-resolved Fluorescence resonance energy transfer (TR-FRET) unites TRF (Time-Resolved Fluorescence) and FRET (Fluorescence Resonance Energy Transfer) principles. This combination brings together the low background benefits of TRF with the homogeneous assay format of FRET. Time-resolved fluorometry (TRF) takes advantage of the unique properties of the rare earth elements called lanthanides. Specifically, lanthanides have large Stoke's shifts and extremely long emission half-lives compared to more traditional fluorophores. The commonly used lanthanides in TRF assays are samarium (Sm), europium (Eu), terbium (Tb), and dysprosium (Dy). Lanthanides are complexed with organic moieties that harvest light and transfer it to the lanthanide through intramolecular processes. FRET uses two fluorophores, a donor and an acceptor. Excitation of the donor by an energy source (e.g. flash lamp or fluorometer laser) triggers an energy transfer to the acceptor if they are within a given proximity to each other. The acceptor in turn emits light at its given wavelength. Because of this energy transfer, molecular interactions between biomolecules can be assessed by coupling each partner with a fluorescent label and detecting the level of energy transfer. More importantly acceptor emissions, as a measure of energy transfer, can be detected without the need to separate bound from unbound assay components (Klostermeier and Millar 2001).

Thermofluor® assays detect small changes in the intrinsic melting temperature of proteins based on binding of ligands. Compounds that interact preferentially with the native form of the protein will increase the $T_m$, the temperature at which half of the protein is unfolded (Pantoliano, Petrella et al. 2001). The technique monitors changes in the fluorescent intensity of dyes such as 1-anilinonaphthalene-8-sulfonic acid (1,8-ANS). The fluorescent dyes are quenched in aqueous environments but increase in fluorescence on binding to the hydrophobic core of denatured proteins.

Modeling the Three-Dimensional Structure of ERR-α

The atomic coordinate data provided in Table 6, or the coordinate data derived from homologous proteins may be used to build a three-dimensional model of ERR-α. Any available computational methods may be used to build the three dimensional model. As a starting point, the X-ray diffraction pattern obtained from the assemblage of the molecules or atoms in a crystalline version of ERR-α or an ERR-α homolog can be used to build an electron density map using tools well known to those skilled in the art of crystallography and X-ray diffraction techniques. Additional phase information extracted either from the diffraction data and available in the published literature and/or from supplementing experiments may then be used to complete the reconstruction.

For basic concepts and procedures of collecting, analyzing, and utilizing X-ray diffraction data for the construction of electron densities see, for example, (Campbell 1984), (Cantor and Schimmel 1980), (Brunger 1993), (Woolfson 1997), (Drenth 1999), (Tsirelson and Ozerov 1996), and U.S. Pat. Nos. 5,942,428A; 6,037,117A; 5,200,910A; and 5,365,456A, each of which is herein specifically incorporated by reference in their entirety.

For basic information on molecular modeling, see, for example, (Schlecht 1998); (Gans, Amann et al. 1996); (Cohen (editor) 1996); and (Smith 1996). U.S. patents which provide detailed information on molecular modeling include U.S. Pat. Nos. 4,906,122A; 5,030,103A; 5,583,973A; 5,612,894A; 5,994,503A; 6,071,700A; 6,075,014A; 6,075,123A; 6,080, 576A; 6,093,573A, each of which are incorporated by reference herein in their entirety.

Methods of Using the Atomic Coordinates to Identify and Design Ligands of Interest The atomic coordinates of the invention, such as those described in Table 6, or coordinates substantially identical to or homologous to those of Table 6 may be used with any available methods to prepare three dimensional models of ERR-α as well as to identify and design ERR-α ligands, inhibitors, antagonists, agonist, or inverse agonist molecules. Such a method provides the amino acid sequence and/or X-ray diffraction data in a form which allows a skilled artisan to analyze and molecular model the three-dimensional structure of ERR-α or related molecules, including a subdomain thereof.

For instance, three-dimensional modeling may be performed using the experimentally determined coordinates derived from X-ray diffraction patterns, such as those in Table 6, for example, wherein such modeling includes, but is not limited to, drawing pictures of the actual structures, building physical models of the actual structures, and determining the structures of related subunits and ERR-α:ligand and ERR-α subunit:ligand complexes using the coordinates. Such molecular modeling can utilize known X-ray diffraction molecular modeling algorithms or molecular modeling software to generate atomic coordinates corresponding to the three-dimensional structure of ERR-α.

As described above, molecular modeling involves the use of computational methods, preferably computer assisted methods, to build realistic models of molecules that are identifiably related in sequence to the known crystal structure. It also involves modeling new small molecules bound to ERR-α starting with the structures of ERR-α and or ERR-α complexed with known ligands or other molecules. The methods utilized in ligand modeling range from molecular graphics (i.e., 3D representations) to computational chemistry (i.e., calculations of the physical and chemical properties) to make predictions about the binding of ligands or activities of ligands; to design new ligands; and to predict novel molecules, including ligands such as drugs, for chemical synthesis, collectively referred to as rational drug design.

One approach to rational drug design is to search for known molecular structures that might bind to an active site. Using molecular modeling, rational drug design programs can look at a range of different molecular structures of drugs that may fit into the active site of an enzyme, and by moving them in a three-dimensional environment it can be decided which structures actually fit the site well.

An alternative but related rational drug design approach starts with the known structure of a complex with a small molecule ligand and models modifications of that small molecule in an effort to make additional favourable interactions with ERR-α.

The present invention includes the use of molecular and computer modeling techniques to design and select and design ligands, such as small molecule ligands that act as agonists, antagonists, inverse agonists or other therapeutic agents that interact with ERR-α. For example, the invention as herein described includes the design of ligands that act as modulators of at least one ERR-α function by binding to all, or a portion of, the active sites or other regions of ERR-α. In a preferred embodiment, the ligand binds to Cys325 of ERR-α. In another preferred embodiment the ligand is an inverse agonist. Similarly, agents that modulate at least one function of ERR-α, whether or not it is bound to another chemical entity, may be designed using the atomic coordinates of ERR-α or complexes comprising ERR-α of this invention.

The atomic coordinates of the present invention also provide the needed information to probe a crystal of ERR-α with molecules composed of a variety of different chemical features to determine optimal sites for interaction between candidate modulators of ERR-α activity and ERR-α. For example, high resolution X-ray diffraction data collected from crystals saturated with solvent allows the determination of where each type of solvent molecule sticks. Small molecules that bind to those sites can then be designed and synthesized and tested for their ability to modulate activity (Travis 1993).

The present invention also includes methods for computationally screening small molecule databases and libraries for chemical entities, agents, ligands, or compounds that can bind in whole, or in part, to ERR-α. In this screening, the quality of fit of such entities or compounds to the binding site or sites may be judged either by shape complementarity or by estimated interaction energy (Meng, Shoichet et al. 1992).

The design of ligands that bind to, promote or inhibit the functional activity of ERR-α according to this invention generally involves consideration of two factors. First, the compound must be capable of physically and structurally associating with ERR-α. In addition to the covalent interaction described herein, non-covalent molecular interactions important in the association of ERR-α with the ligand include hydrogen bonding, van der Waals and hydrophobic interactions. Second, the ligand must be able to assume a conformation that allows it to associate with ERR-α. Although certain portions of the ligand may not directly participate in the association with ERR-α, those portions may still influence the overall conformation of the molecule. This, in turn, may have a significant impact on binding affinities, therapeutic efficacy, drug-like qualities and potency of the ligand. Such conformational requirements include the overall three-dimensional structure and orientation of the ligand in relation to all or a portion of the active site or other region of ERR-α, or the spacing between functional groups of a ligand comprising several chemical entities that directly interact with ERR-α.

The potential, predicted, agonist, antagonist, inverse agonist, or binding effect of a ligand or other compound on ERR-α may be analyzed prior to its actual synthesis and testing by the use of computer modeling techniques. If the theoretical structure of the given ligand suggests insufficient interaction and association between it and ERR-α, synthesis and testing of the ligand may be obviated. If computer modeling indicates a strong interaction, however, the molecule may then be synthesized and tested for its ability to interact with ERR-α. In this manner, synthesis of inoperative ligand may be avoided. In some cases, inactive ligands are synthesized predicted on modeling and then tested to develop a SAR (structure-activity relationship) for compounds interacting with a specific region of ERR-α.

One skilled in the art may use one of several methods to screen chemical entities, fragments, compounds, or other agents for use as ligands based on their ability to associate with ERR-α and more particularly their ability to associate with the individual binding pockets or active sites of ERR-α. This process may begin by visual inspection of, for example, the active site on the computer screen based on the atomic coordinates of ERR-α or ERR-α complexed with a ligand. Selected chemical entities, compounds, or agents may then be positioned in a variety of orientations, or docked within an individual binding pocket of ERR-α. Docking may be accomplished using software such as QUANTA, available from Accelrys, Inc., San Diego, Calif.; and SYBYL, available for Tripos, St. Louis, Mo.; followed by energy minimization and molecular dynamics with standard molecular mechanics forcefields, such as CHARMm; available from Accelrys, Inc., San Diego, Calif.; and AMBER, University of California, San Francisco.

Specialized computer programs may also assist in the process of selecting chemical entities. These include but are not limited to: GRID (Goodford 1985), available from Oxford University, Oxford, UK); MCSS (Miranker and Karplus 1991), available from Molecular Simulations, Burlington, Mass.; AUTODOCK (Goodsell and Olsen 1990), available from Scripps Research Institute, La Jolla, Calif.; and DOCK (Kuntz, Blaney et al. 1982), available from University of California, San Francisco, Calif.

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand-binding site and suggest ligands with complementary steric properties.

Once suitable chemical entities, compounds, or agents have been selected as potential ligands, they can be assembled into a single ligand, compound, antagonist (inhibitor), agonist (activator), or inverse agonist. Assembly may proceed by visual inspection of the relationship of the fragments to each other on the three-dimensional image. This may be followed by manual model building using software such as QUANTA or SYBYL.

Useful programs to aid in connecting the individual chemical entities, compounds, or agents include but are not limited to: CAVEAT (Bartlett, Shea et al. 1989); 3D Database systems such as MACCS-3D (Martin 1992), available from MDL Information Systems, San Leandro, Calif.; and HOOK, available from Molecular Simulations, Burlington, Mass.

Several methodologies for searching three-dimensional databases to test pharmacophore hypotheses and select compounds for screening are available. These include the program CAVEAT (Bacon and Moult 1992). For instance, CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding.

Instead of proceeding to build an inhibitor, activator, agonist, antagonist, or inverse agonist of ERR-α in a step-wise fashion, one chemical entity at a time as described above, such ligands may be designed as a whole or "de novo" using either an empty active site or optionally including some portion(s) of a known molecule(s). These methods include: LUDI (Bohm 1992), available from Biosym Technologies, San Diego, Calif.; LEGEND (Nishibata and Itai 1991), available from Molecular Simulations, Burlington, Mass.; and LeapFrog, available from Tripos Associates, St. Louis, Mo., USA.

For example, the program LUDI can determine a list of interaction sites into which to place both hydrogen bonding and hydrophobic fragments. LUDI then uses a library of linkers to connect up to four different interaction sites into fragments. Then smaller "bridging" groups such as —CH2- and —COO— are used to connect these fragments. For the enzyme DHFR, the placements of key functional groups in the well-known inhibitor methotrexate were reproduced by LUDI. See also, (Rotstein and Murcko 1993).

Other molecular modeling techniques may also be employed in accordance with this invention. See, e.g., (Cohen, Blaney et al. 1990). See also, (Navia and Murcko 1992).

Once a ligand has been designed or selected by the above methods, the affinity with which that ligand may bind or associate with ERR-α may be tested and optimized by computational evaluation and/or by testing biological activity after synthesizing the compound. Ligands may interact with the ERR-α in more than one conformation that is similar in overall binding energy. In those cases, the deformation energy of binding is taken to be the difference between the energy of the free ligand and the average energy of the conformations observed when the ligand binds to ERR-α.

A ligand designed or selected as binding or associating with ERR-α may be further computationally optimized so that in its bound state it would preferably lack repulsive electrostatic interaction with ERR-α. Such non-complementary (e.g., electrostatic) interactions include repulsive charge-charge, dipole-dipole and charge-dipole interactions. Specifically, the sum of all electrostatic interactions between the compound and ERR-α when the compound is bound, preferably make a neutral or favourable contribution to the enthalpy of binding. Weak binding compounds will also be designed by these methods so as to determine SAR.

Specific computer software is available in the art to evaluate compound deformation energy and electrostatic interaction. Examples of programs designed for such uses include: Gaussian 92, revision C (Frisch, Trucks et al. 1992); AMBER, University of California, San Francisco; QUANTA and CHARMm, available from Accelrys, Inc., San Diego, Calif.; and Insight II/Discover, from Biosysm Technologies Inc., San Diego, Calif., USA. Other hardware systems and software packages will be known to those skilled in the art.

Once a ligand that associates with ERR-α has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted ligands may then be analyzed for efficiency of fit to ERR-α by the same computer methods described in detail, above.

Use of Homology Structure Modeling to Design Ligands with Modulated Binding or Activity to ERR-α.

The present invention includes the use of the atomic coordinates and structures of ERR-α complexed with a ligand that forms a thioether bond to Cys325 of ERR-α to design modifications to starting ligands and derivatives thereof that will bind more tightly or interact more specifically to the target enzyme.

The structure of a complex between the ERR-α and the starting ligand can be used to guide the modification of that ligand to produce new ligands that have other desirable properties for applicable industrial and other uses (e.g., as pharmaceuticals), such as chemical stability, solubility or membrane permeability. (Lipinski, Lombardo et al. 1997).

Binding ligands, that act as agonists, antagonists, or inverse agonists and such that are known in the art can be diffused into or soaked with the stabilized crystals of ERR-α to form a complex for collecting X-ray diffraction data. Alternatively, ligands known and unknown in the art can be cocrystallized with ERR-α by mixing the ligand with ERR-α before crystallization.

To produce custom high affinity and very specific compounds, the structure of ERR-α can be compared to the structure of a selected non-targeted molecule and a hybrid constructed by changing the structure of residues at the binding site for a ligand for the residues at the same positions of the non-target molecule. The process whereby this modeling is achieved is referred to as homology structure modeling. This is done computationally by removing the side chains from the molecule or target of known structure and replacing them with the side chains of the unknown structure put in sterically plausible positions. In this way it can be understood how the shapes of the active site cavities of the targeted and non-targeted molecules differ. This process, therefore, provides information concerning how a bound ligand can be chemically altered in order to produce compounds that will bind tightly and specifically to the desired target but will simultaneously be sterically prevented from binding to the non-targeted molecule. Likewise, knowledge of portions of the bound ligands that are facing to the solvent would allow introduction of other functional groups for additional pharmaceutical purposes. The use of homology structure modeling to design ligands that bind more tightly to the target enzyme than to the non-target enzyme has wide spread applicability.

Databases and Computer Systems

An amino acid sequence or nucleotide sequence of ERR-α and/or X-ray diffraction data, useful for computer molecular modeling of ERR-α or a portion thereof, can be provided in a variety of mediums to facilitate use thereof. In one application of this embodiment, databases comprising data pertaining to X-ray diffraction data for a complex of ERR-α and a ligand that forms a thioether bond with Cys325 of ERR-α, or at least one ERR-α subdomain thereof, is recorded on computer readable medium. A skilled artisan can readily appreciate how any of the presently known computer readable media can be used to create a manufacture comprising computer readable medium having recorded thereon data pertaining to X-ray diffraction data of the present invention.

A variety of data storage structures are available to a skilled artisan for creating a computer readable medium having recorded thereon an amino acid sequence and/or atomic coordinate/X-ray diffraction data of the present invention. The choice of the data storage structure will generally be based on the means chosen to access the stored information. In addition, a variety of data processor programs and formats can be used to store the sequence and X-ray data information of the present invention on computer readable media. The sequence information can be represented in a word processing text file, formatted in commercially-available software such as Word-Perfect and MICROSOFT Word, or represented in the form of an ASCII file, stored in a database application, such as DB2, Sybase, Oracle, or the like. A skilled artisan can readily adapt any number of dataprocessor structuring formats (e.g., text file or database) in order to obtain computer readable media having recorded thereon the information of the present invention.

By providing computer readable media having sequence and/or atomic coordinates based on X-ray diffraction data, a skilled artisan can routinely access the sequence and atomic coordinate or X-ray diffraction data to model a related molecule, a subdomain, mimetic, or a ligand thereof. Computer algorithms are publicly and commercially available which allow a skilled artisan to access this data provided in a computer readable medium and analyze it for molecular modeling and/or RDD (rational drug design). See, e.g., (Mary Ann Liebert (Publishers) 1995).

The present invention further provides systems, particularly computer-based systems, which contain the sequence and/or diffraction data described herein. Such systems are designed to do structure determination and RDD for ERR-α or at least one subdomain thereof. Non-limiting examples are microcomputer workstations available from Silicon Graphics Incorporated and Sun Microsystems running UNIX based, Windows NT or IBM OS/2 operating systems.

A variety of comparing means can also be used to compare a target sequence or target motif with the data storage means to identify structural motifs or electron density maps derived in part from the atomic coordinate/X-ray diffraction data. A skilled artisan can readily recognize that any one of the publicly available computer modeling programs can be used as the search means for the computer-based systems of the present invention.

Integrated Procedures which Utilize the Present Invention

Molecular modeling is provided by the present invention for rational drug design (RDD) of mimetics and ligands that form a thioether bond with Cys325 of ERR-α. As described above, the drug design paradigm uses computer-modeling programs to determine potential mimetics and ligands which are expected to interact with sites on the protein. The potential mimetics or ligands are then screened for activity and/or binding and/or interaction. For ERR-α-related mimetics or ligands, screening methods can be selected from assays for at least one biological activity of ERR-α.

Thus, the tools and methodologies provided by the present invention may be used in procedures for identifying and designing ligands which bind in desirable ways with the target. Such procedures utilize an iterative process whereby ligands are synthesized, tested and characterized. New ligands can be designed based on the information gained in the testing and characterization of the initial ligands and then such newly identified ligands can themselves be tested and characterized. This series of processes may be repeated as many times as necessary to obtain ligands with the desirable binding properties.

The following steps (1-7) serve as an example of the overall procedure:

1. A biological activity of a target is selected.
2. A ligand is identified that appears to be in some way associated with the chosen biological activity (e.g., the ligand may be an agonist, antagonist, or inverse agonist of a known activity). The activity of the ligand may be tested by in vivo and/or in vitro methods. A ligand of the present invention can be, but is not limited to, at least one selected from a lipid, a nucleic acid, a compound, a protein, an element, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention. Suitable compounds are then tested for activities in relationship to the target. Complexes between ERR-α and ligands are made either by co-crystallization or more commonly by diffusing the ligand into the crystal. X-ray diffraction data from the crystal complex are measured and a difference electron density map is calculated. This process provides the precise location of the bound ligand on the target molecule. The difference Fourier is calculated using measure diffraction amplitudes and the phases of these reflections calculated from the coordinates.
3. Using the methods of the present invention, X-ray crystallography is utilized to create electron density maps and/or molecular models of the interaction of the ligand with the target molecule. The entry of the coordinates of the target into the computer programs discussed above results in the calculation of most probable structure of the macromolecule. These structures are combined and refined by additional calculations using such programs to determine the probable or actual three-dimensional structure of the target including potential or actual active or binding sites of ligands. Such molecular modeling (and related) programs useful for rational drug design of ligands or mimetics are also provided by the present invention.
4. The electron density maps and/or molecular models obtained in Step 3 are compared to the electron density maps and/or molecular models of a non-ligand containing target and the observed/calculated differences are used to specifically locate the binding of the ligand on the target or subunit.
5. Modeling tools, such as computational chemistry and computer modeling, are used to adjust or modify the structure of the ligand so that it can make additional or different interactions with the target. The ligand design uses computer-modeling programs which calculate how different molecules interact with the various sites of the target, subunit, or a fragment thereof. Thus, this procedure determines potential ligands or ligand mimetics.
6. The newly designed ligand from Step 5 can be tested for its biological activity using appropriate in vivo or in vitro tests, including but not limited to the high-throughput screening methods discussed above. The potential ligands or mimetics are then screened for activity relating to ERR-α, or at least a fragment thereof. Such screening methods are selected from assays for at least one biological activity of the native target. The resulting ligands or mimetics, provided by methods of the present invention, are useful for treating, screening or preventing diseases in animals, such as mammals (including humans).
7. Of course, each of the above steps can be modified as desired by those of skill in the art so as to refine the procedure for the particular goal in mind. Also, additional X-ray diffraction data may be collected on ERR-α, ERR-α/ligand complexes, ERR-α structural target motifs and ERR-α subunit/ligand complexes at any step or phase of the procedure. Such additional diffraction data can be used to reconstruct electron density maps and molecular models, which may further assist in the design and selection of ligands with the desirable binding attributes.

It is to be understood that the present invention is considered to include stereoisomers as well as optical isomers, e.g., mixtures of enantiomers as well as individual enantiomers and diastereomers, which arise as a consequence of structural asymmetry in selected compounds, ligands or mimetics of the present series.

Some of the ligands disclosed or discovered by the methods herein may contain one or more asymmetric centers and thus give rise to enantiomers, diastereomers, and other stereoisomeric forms. The present invention is also meant to encompass all such possible forms as well as their racemic and resolved forms and mixtures thereof. When the ligands described or discovered herein contain olefinic double bonds or other centers of geometric asymmetry, and unless otherwise specified, it is intended to include both E and Z geometric isomers. All tautomers are intended to be encompassed by the present invention as well.

EXAMPLES

Without further description, it is believed that one of ordinary skill in the art can, using the preceding description and the following illustrative examples, make and utilize the present invention and practice the claimed methods. The following working examples therefore, specifically point out preferred embodiments of the present invention, and are not to be construed as limiting in any way the remainder of the disclosure.

Protein Cloning, Expression and Purification

The ligand binding domain of human ERR-α (amino acids 290-519 of Swiss-Prot P11474, SEQ ID NO:1) was subcloned into pDEST (Novagen) to produce a construct with a PreScission protease cleavage site for cleavage of an included N-terminal His tag (SEQ ID NO:2). The plasmid was co-transfected with linearized baculovirus DNA into *Spodoptera frugiperda* (Sf9) insect cells and the baculovirus was amplified and purified from plaques from a titer $1-2\times10^8$ pfu/mL. Sf9 cells were maintained in ESF 921 media (Expression Systems. LLC, Woodland, Calif.) and grown in 2 L Erlenmeyer flasks at 27° C. The insect cells at a cell density of $1.5\times10^6$ cells/mL were infected with the baculovirus at a multiplicity of infection (MOI) of 1. Cells were harvested 3 days post-infection by centrifugation at 1200×g, rinsed with PBS supplemented with protease inhibitors and stored at −80° C. until further use. Expression level of the protein was confirmed by Western blots using anti-His antibody.

For purification, the cells containing recombinant human ERR-α were suspended in 25 mM Tris-HCl, pH 8.0, 0.5 M NaCl, 10 mM imidazole, 0.6 mM PMSF, 10 mM β-mercaptoethanol (buffer A) supplemented with Complete Protease Inhibitor Cocktail (Roche). The suspension was sonicated using Branson-450 sonicator and clarified by centrifugation at 100,000×g for 1 hour. The supernatant was applied onto 5 ml Ni-NTA column (QIAGEN) pre-equilibrated in buffer A. The column was washed with 10 column volumes of 50 mM imidazole in buffer A, and developed by 250 mM imidazole in buffer A. The elution fractions containing ERR-α were pooled and dialyzed O/N against 25 mM Tris-HCl, pH 8.0, 50 mM NaCl, 5 mM dithiothreitol (buffer B). After dialysis, the protein was loaded on MonoQ 10/10 (GE Healthcare) and the column was developed by 50-1000 mM linear gradient of NaCl in buffer B. The ERR-α was eluted at about 300 mM NaCl and its purity was greater than 95% as judged by SDS-PAGE. Finally, the ERR-α was concentrated to 17 mg/ml at 2× molar access of the Compound 1, and delivered for crystallization in 25 mM Tris-HCl, pH 8.0, 0.3 M NaCl, 5 mM dithiothreitol.

Crystallization and Data Collection

Using a hanging drop vapor diffusion method, crystals formed at 277° K in a drop solution containing a 1:1 ratio of the solution of the ERR-α protein and Compound 1 complex and a solution containing 1.4 M ammonium sulfate, 100 mM Pipes pH 6.5 and 200 mM Na-thiocyanate. The drop was suspended over a the same solution used to make the drop, the solution containing 1.4 M ammonium sulfate, 100 mM Pipes pH 6.5 and 200 mM Na-thiocyanate.

The crystals were transferred to a cryoprotectant solution containing 1.4 M ammonium sulfate, 100 mM Pipes pH 6.5, 200 mM Na-thiocyanate and 25% glycerol. The crystals were then mounted and quickly frozen by immersion in liquid nitrogen. X-ray diffraction data to a resolution of 2.0 Å were collected on a Bruker AXS Proteum 6000 detector. Diffraction data was indexed, integrated and scaled using the Proteum Processing Program suite from Bruker AXS. Under these conditions, the crystals belong to the P6522 space group, with unit cell parameters a=b=103, c=110 Å, α=β=90 and γ=120. The structure was determined by molecular replacement with CNX (Brunger, Adams et al. 1998) using the crystal structure of ERR-α in complex with the peroxisome proliferator-activated receptor coactivator-1 (PGC1-α, pdb id 1XB7) as the search model (Kallen, Schlaeppi et al. 2004). Model building was done using the program O (Jones, Zou et al. 1991) and Coot (Emsley and Cowtan 2004). Refinement and map calculations were carried out using PHENIX (Adams, Grosse-Kunstleve et al. 2002). The final structure was refined to an Rfactor of 21.1 and Rfree of 24.9. Inspection of the electron density map revealed that Compound 1 bound between helices 3 and 11 of ERR-α.

TABLE 1

Crystal and Refinement Parameters

| Parameter | BPA |
| --- | --- |
| Unit cell, Å | a = b = 103.007 |
|  | c = 110.017 |
| Resolution, Å | 2 |
| Completeness, % | 99.92 |
| Rmerge[¥], % | 10 (44.6) |
| $<I>/<\sigma_I>$ | 8.20 (2.18) |
| Rfactor[#], % | 21.1 |
| Rfree[¶], % | 24.9 |

Values in parenthesis refer to the highest resolution shell
[¥]$R_{merge} = \Sigma_{hkl}\Sigma_I(|I_I - <I>|/<I>)$, where $I_I$ is an individual intensity measurement and $<I>$ is the average intensity for this reflection, with summation over all data.
[#]Rfactor = Σ||F$_o$| − |F$_c$||/Σ|F$_o$|.
[¶]10% of the total reflections withheld.

X-Ray Structure Discussion

Figure 1B:
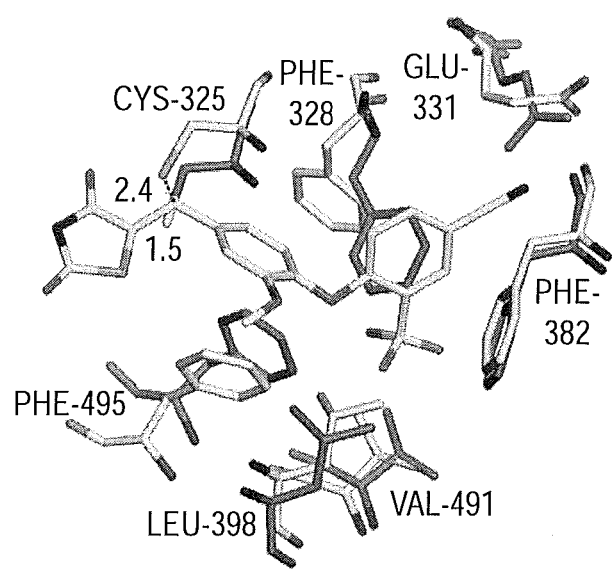
Figure 2A:
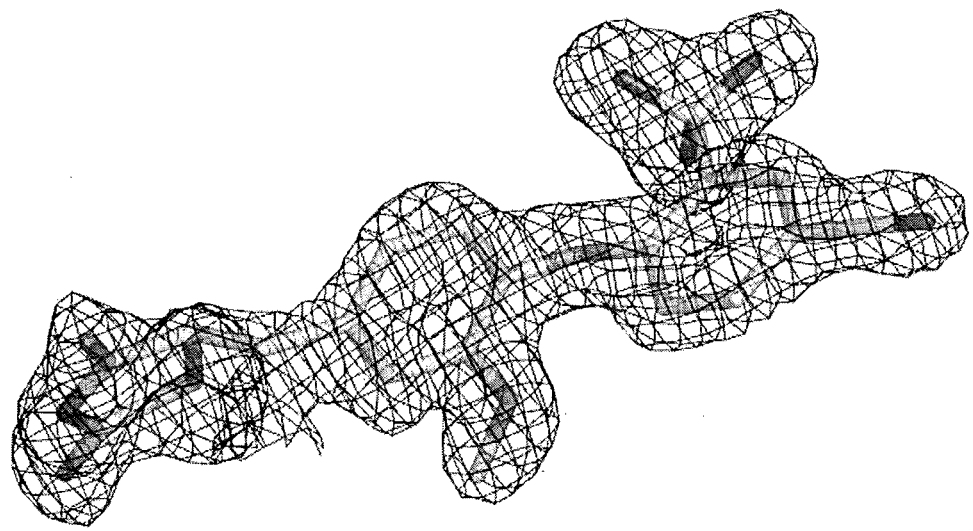
FIG. 2: A. Shown is a 2fofc map calculated to 1.6 σ around Compound 1. B. Shown is a sulfur anomalous map calculated to 3.5 σ, that validates the correct orientation of the thiazole of Compound 1 and Cys325 of ERR-α.
Figure 2B:
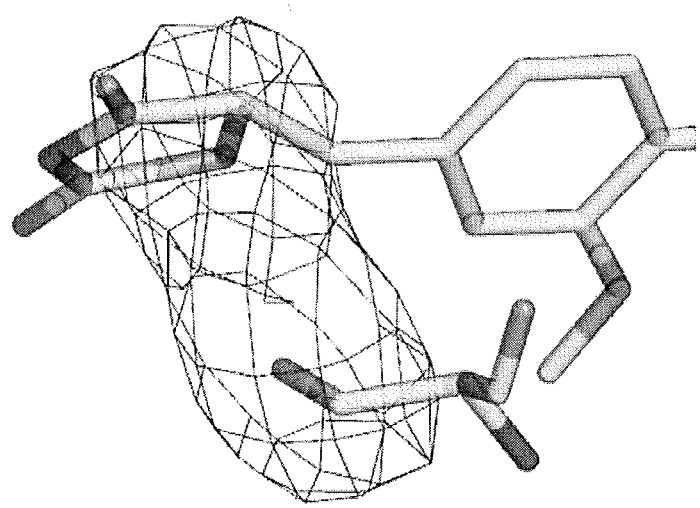

A comparison between the crystal structure of the complex of ERR-α and Compound 1 and the previously determined crystal structure of the complex of ERR-α and PGC1-α showed conserved arrangement of secondary structural elements throughout most of the structure (FIG. 1A). The excellent data quality obtained from the complex of ERR-α and Compound 1 allowed unambiguous placement of Compound 1 in the electron density (FIG. 2A). The positions of the sulfurs of Cys325 and the thiazole of Compound 1 were validated by the calculation of a sulfur anomalous map (FIG. 2B). Anomalous signal from all other cysteines and methionines throughout the protein were also observed. Secondary structure rearrangement upon Compound 1 binding included the displacement of helix 11 and helix 12. The side chains of residues F328 and F495 must move to accommodate the ligand as shown on FIG. 1B. The structure of the complex of ERR-α and Compound 1 also showed helix 12 occupying the position of the activation peptide. Some shifting was also observed on helix 3 and its side chains to make room for Compound 1 and maximize its interactions with helix 12.

ERR-α Covalent Modification

Inspection of the binding site and protein-ligand interactions revealed Compound 1 binding covalently to the protein by a thioether bond between the carbon C5 of the Compound 1 and the sulfur from Cys325. The distance between the sulfur of Cys325 and carbon C6 is 2.44 Å, consistent with a covalent bond. The double bond between C6 and C7 of the Compound 1 must reduce in order to allow C6 to covalently link the protein. A measurement of this distance is 1.55 Å, consistent with a carbon-carbon single bond distance and evidence that covalent modification occurred.

Other Interactions Observed and to be Explored

The hydrophobic pocket of ERR-α presents a few polar groups within H-bond distance to Compound 1 that could be explored in further optimization to develop additional ligands. These residues include E331, R372, F382-carbonyl and L324-carbonyl (Table 2). The carbonyl of F382 hydrogen bonds (3.41 Å) with N2 in the cyano. The carbons C13 and C14 of the 3-Trifluoromethyl-benzonitrile are close enough to the carbonyl of L324 that an H-donor substitution would take advantage of the proximity to this residue. The cyano group of Compound 1 is 3.2 Å from R372, another proton donor. Substituting the cyano with an electronegative atom could potentially optimize this part of the molecule.

TABLE 2

List of contacts between ERR-α and Compound 1 within a distance of 3.5 Å

| Source atoms | | | | target atoms | | | distance Å |
|---|---|---|---|---|---|---|---|
| Leu | 324A | CB | ... | Lig | 1I | O02 | ... | 3.42 |
| Leu | 324A | O  | ... | Lig | 1I | C19 | ... | 3.28 |
| Cys | 325A | CB | ... | Lig | 1I | C06 | ... | 3.36 |
| Cys | 325A | SG | ... | Lig | 1I | C07 | ... | 2.94 |
|     |      |    | ... | Lig | 1I | C12 | ... | 3.48 |
|     |      |    | ... | Lig | 1I | C05 | ... | 3.15 |
|     |      |    | ... | Lig | 1I | C06 | ... | 2.44 |
|     |      |    | ... | Lig | 1I | C04 | ... | 3.24 |
| Phe | 328A | CG | ... | Lig | 1I | C14 | ... | 3.40 |
|     |      |    | ... | Lig | 1I | C15 | ... | 3.17 |
| Phe | 328A | CD1 | ... | Lig | 1I | C14 | ... | 3.39 |

TABLE 2-continued

List of contacts between ERR-α and Compound 1 within a distance of 3.5 Å

| Source atoms | | | | target atoms | | | distance Å |
|---|---|---|---|---|---|---|---|
| Phe | 328A | CD2 | ... | Lig | 1I | C15 | ... | 3.33 |
| Glu | 331A | CG  | ... | Lig | 1I | N23 | ... | 3.29 |
| Arg | 372A | NH2 | ... | Lig | 1I | N23 | ... | 3.21 *** |
| Phe | 382A | O   | ... | Lig | 1I | N23 | ... | 3.41 * |
| Ala | 396A | O   | ... | Lig | 1I | C01 | ... | 3.27 |
| Leu | 398A | CD2 | ... | Lig | 1I | O02 | ... | 3.28 |
|     |      |     | ... | Lig | 1I | C01 | ... | 3.40 |
| Val | 491A | CG1 | ... | Lig | 1I | F27 | ... | 3.19 |
| Phe | 495A | CZ  | ... | Lig | 1I | C03 | ... | 3.33 |
|     |      |     | ... | Lig | 1I | C16 | ... | 3.19 |
|     |      |     | ... | Lig | 1I | O17 | ... | 3.33 |
| Met | 506A | CE  | ... | Lig | 1I | C14 | ... | 3.40 |
|     |      |     | ... | Lig | 1I | C15 | ... | 3.30 |

*** indicates strong hydrogen bonds

LC/MS Experiments

To monitor the kinetics of association and dissociation for ligands that formed a complex with ERR-α by forming a covalent bond to Cys325 of ERR-α, LC/MS detection was employed. LC analysis was performed on an Agilent 1100 LC system that was in line with an Agilent MSD TOF for mass detection. Software provided by the vendor was used to deconvolute the ESI positive ion quadrupole time-of-flight spectra. To measure association rates, typically a 1 μM ERR-α solution was mixed with an equal volume of a 2 μM ligand solution. 20 uL aliquots of the mixed solutions were removed at time zero and at regular defined time intervals and diluted out in 100 μL of a 0.1% TFA, 10% $CH_3CN$ solution to quench the reaction. 50 μL samples of the diluted analyte were processed on the LC/MS instrument. Similarly, for determination of the dissociation rates, the mixed solutions of ERR-α and the ligand were first equilibrated up to one hour to allow formation of the complex. At time 0, a 20-fold excess of a competing ligand (Compound 2) was added and aliquots were removed and processed as described for the association rate experiments. Final concentrations for the ligand, ERR-α, and the competing ligand were 1 μM, 0.5 μM, and 20 μM, respectively. All experiments were carried out in buffer containing 25 mM HEPES, pH 7.9, 200 mM KCl and 3% DMSO at 37° C.

For the apo form of ERR-α, a mass of 27042 was detected, corresponding to an amino acid sequence where the initiator methionine is cleaved followed by N-terminal acetylation. This is the "Expected Mass" shown in Table 3. When the ERR-α protein was incubated with a ligand that formed a covalent bond to Cys325 of ERR-α, there was a time dependent increase in the mass of the protein equal to the mass of the compound+1 amu (Table 3).

TABLE 3

Observed mass changes for 2 ligands that formed a complex with ERR-α

| Compound Structure | Compound Number | Expected Mass (daltons) | Observed Mass (daltons) | Mass Difference (daltons) | Ligand Mass (daltons) |
|---|---|---|---|---|---|
| (structure) | Compound 1 | 27042 | 27461 | 419 | 420.0392 |
| (structure) | Compound 2 | 27042 | 27494 | 452 | 453.0494 |

The progress of the reaction was expressed as a fraction of the integrated areas observed for the expected mass (27042 amu) and observed mass (27042+compound amu−1) with the following expression:

$$\text{progress of reaction} = \frac{\text{area of observed mass}}{\text{area of observed mass} + \text{area of expected mass}}$$

Similarly for the experiments to measure dissociation rates, incubation of a complex of ERR-α and a ligand with the competing ligand resulted in a time dependent change in the mass of the complex of ERR-α and the ligand, equal to the mass difference of the ligand and the competing ligand. To standardize the experiments to measure dissociation rates for different ligands, the same competing ligand (Compound 2) was used in all experiments. The progress of the reaction was also expressed as a fraction of the area observed for the complex of ERR-α and the competing ligand over the sum of total area for the complex of ERR-α with the ligand and the complex of ERR-α with the competing ligand.

Association and dissociation rates for ligands were determined by fitting fractional values obtained for the progress of the reaction as a function of time using a single exponential equation $$\text{progress of reaction} = e^{-kt}$$

where k is the apparent rate constant. For the dissociation experiments, the reaction is assumed to be first order and dissociation rates, $k_d$, are expressed as $s^{-1}$. For the association rates, $k^a$, the reaction is assumed to be second order and the rates are expressed as $M^{-1}s^{-1}$ by dividing the apparent rate constants by the concentration of the protein determined by experimental conditions (Table 4). Apparent half-lives ($t_{0.5}$) were calculated using the equation:

$$t_{0.5} = \frac{0.693}{k_d}$$

TABLE 4

Kinetic rate constants for ligands that formed a complex with ERR-α

Dissociation rates determined with 20-fold excess Compound 2 as a competing ligand

| Compound Structure | Compound Number | $k_a$ $M^{-1}s^{-1}$ | $k_d$ $s^{-1}$ |
|---|---|---|---|
| (structure) | Compound 1 | 6600 | $1.10 \times 10^{-5}$ |

TABLE 4-continued

Kinetic rate constants for ligands that formed a complex with ERR-α
Dissociation rates determined with 20-fold excess Compound 2 as a competing ligand

| Compound Structure | Compound Number | $k_a$ $M^{-1}s^{-1}$ | $k_d$ $s^{-1}$ |
|---|---|---|---|
| (structure) | Compound 3 | Not Determined | $1.53 \times 10^{-5}$ |
| (structure) | Compound 4 | Not Determined | $2.19 \times 10^{-5}$ |
| (structure) | Compound 5 | Not Determined | $2.05 \times 10^{-5}$ |

TR-FRET Assay

Time-resolved Fluorescence resonance energy transfer (TR-FRET) experiments were performed to examine the functional activity of the ERR-α ligands. The components of this homogeneous secondary assay included: the purified ERR-α protein (SEQ ID NO:2), a GST-labeled-hSRC2 co-activator polypeptide, and a fluorescent donor/acceptor pair from CIS bio international htrf/bioassays (Bedford, Mass.) using both an α-GST Europium Cryptate (Eu) label and an α$^6$His-XL665 (allophycocyanin) fluorophore.

For TR-FRET measurements, the reaction was buffered in 25 mM Tris pH 8, 2.5 mM Hepes, 20 mM KCl, 1 mM DTT, and 0.05 mg/mL BSA (-lipids). The final concentrations of reagents were 6 nM of ERR-α protein, 6 nM GST-SRC-2 peptide, 30 nM Eu cryptate, and 7.5 nM XL665. Reactions were allowed to reach equilibrium at 25° C. for 4-18 hours before collecting data on the Analyst from LJL Biosystems (Molecular Devices Sunnyvale, Calif.). As a time-resolved method, the samples were excited at 340 nM and emission was collected for 1 ms at both 615 and 665 nm with delays of 400 and 75 μs, respectively. Dose response curves were fitted using a hyperbolic equation and the data reported in Table 5 is the average of three independent experiments.

TABLE 5

EC50 values determined by TR-FRET measurements

| Compound Structure | Compound Number | EC50 (nM) |
|---|---|---|
| (structure: 4-cyano-2-trifluoromethylphenoxy-methoxybenzylidene-thiazolidinedione) | Compound 1 | 54 |
| (structure: methyl 4-(2-methoxy-4-((2,4-dioxothiazolidin-5-ylidene)methyl)phenoxy)-3-(trifluoromethyl)benzoate) | Compound 2 | 11 |

TABLE 6

Coordinates for crystal structure of the complex of ERR-α and Compound 1

| | | | | | | | | | | | | |
|---|---|---|---|---|---|---|---|---|---|---|---|---|
| CRYST1 | 103.007 | 103.007 | 110.017 | 90.00 | 90.00 | 120.00 | P 65 2 2 | | | | | |
| SCALE1 | | 0.009708 | 0.005605 | 0.000000 | | 0.00000 | | | | | | |
| SCALE2 | | 0.000000 | 0.011210 | 0.000000 | | 0.00000 | | | | | | |
| SCALE3 | | 0.000000 | 0.000000 | 0.009090 | | 0.00000 | | | | | | |
| ATOM | 1 | CB | HIS | A | 280 | 22.940 | 21.391 | 17.566 | 1.00 | 25.58 | A | C |
| ATOM | 2 | CG | HIS | A | 280 | 21.544 | 21.696 | 17.118 | 1.00 | 23.84 | A | C |
| ATOM | 3 | CD2 | HIS | A | 280 | 20.344 | 21.364 | 17.648 | 1.00 | 24.17 | A | C |
| ATOM | 4 | ND1 | HIS | A | 280 | 21.271 | 22.448 | 15.990 | 1.00 | 28.34 | A | N |
| ATOM | 5 | CE1 | HIS | A | 280 | 19.963 | 22.557 | 15.845 | 1.00 | 27.40 | A | C |
| ATOM | 6 | NE2 | HIS | A | 280 | 19.375 | 21.909 | 16.837 | 1.00 | 27.33 | A | N |
| ATOM | 7 | C | HIS | A | 280 | 25.289 | 20.755 | 16.965 | 1.00 | 21.27 | A | C |
| ATOM | 8 | O | HIS | A | 280 | 25.430 | 19.936 | 17.872 | 1.00 | 17.88 | A | O |
| ATOM | 9 | N | HIS | A | 280 | 23.397 | 19.993 | 15.595 | 1.00 | 34.65 | A | N |
| ATOM | 10 | CA | HIS | A | 280 | 23.905 | 21.085 | 16.419 | 1.00 | 25.98 | A | C |
| ATOM | 11 | N | HIS | A | 281 | 26.308 | 21.409 | 16.420 | 1.00 | 19.22 | A | N |
| ATOM | 12 | CA | HIS | A | 281 | 27.685 | 21.080 | 16.764 | 1.00 | 19.90 | A | C |
| ATOM | 13 | CB | HIS | A | 281 | 28.556 | 21.123 | 15.518 | 1.00 | 18.01 | A | C |
| ATOM | 14 | CG | HIS | A | 281 | 28.150 | 20.134 | 14.477 | 1.00 | 24.32 | A | C |
| ATOM | 15 | CD2 | HIS | A | 281 | 27.629 | 18.889 | 14.587 | 1.00 | 25.01 | A | C |
| ATOM | 16 | ND1 | HIS | A | 281 | 28.249 | 20.389 | 13.125 | 1.00 | 31.11 | A | N |
| ATOM | 17 | CE1 | HIS | A | 281 | 27.819 | 19.338 | 12.450 | 1.00 | 27.61 | A | C |
| ATOM | 18 | NE2 | HIS | A | 281 | 27.440 | 18.414 | 13.314 | 1.00 | 27.91 | A | N |
| ATOM | 19 | C | HIS | A | 281 | 28.279 | 21.970 | 17.855 | 1.00 | 22.70 | A | C |
| ATOM | 20 | O | HIS | A | 281 | 29.413 | 21.744 | 18.294 | 1.00 | 13.09 | A | O |
| ATOM | 21 | N | LEU | A | 282 | 27.514 | 22.980 | 18.270 | 1.00 | 16.02 | A | N |
| ATOM | 22 | CA | LEU | A | 282 | 27.905 | 23.856 | 19.367 | 1.00 | 14.99 | A | C |
| ATOM | 23 | CB | LEU | A | 282 | 28.083 | 23.045 | 20.650 | 1.00 | 15.69 | A | C |
| ATOM | 24 | CG | LEU | A | 282 | 26.922 | 22.138 | 21.057 | 1.00 | 16.92 | A | C |
| ATOM | 25 | CD1 | LEU | A | 282 | 27.340 | 21.212 | 22.192 | 1.00 | 20.99 | A | C |
| ATOM | 26 | CD2 | LEU | A | 282 | 25.730 | 22.971 | 21.460 | 1.00 | 19.45 | A | C |
| ATOM | 27 | C | LEU | A | 282 | 29.184 | 24.642 | 19.076 | 1.00 | 15.48 | A | C |
| ATOM | 28 | O | LEU | A | 282 | 29.837 | 25.139 | 19.998 | 1.00 | 13.42 | A | O |
| ATOM | 29 | N | GLU | A | 283 | 29.537 | 24.772 | 17.801 | 1.00 | 11.87 | A | N |
| ATOM | 30 | CA | GLU | A | 283 | 30.759 | 25.485 | 17.443 | 1.00 | 13.95 | A | C |
| ATOM | 31 | CB | GLU | A | 283 | 31.047 | 25.331 | 15.956 | 1.00 | 20.90 | A | C |
| ATOM | 32 | CG | GLU | A | 283 | 31.088 | 23.869 | 15.523 | 1.00 | 23.92 | A | C |
| ATOM | 33 | CD | GLU | A | 283 | 32.328 | 23.537 | 14.729 | 1.00 | 28.45 | A | C |
| ATOM | 34 | OE1 | GLU | A | 283 | 33.070 | 22.625 | 15.149 | 1.00 | 35.17 | A | O |
| ATOM | 35 | OE2 | GLU | A | 283 | 32.570 | 24.191 | 13.693 | 1.00 | 36.58 | A | O |
| ATOM | 36 | C | GLU | A | 283 | 30.776 | 26.966 | 17.847 | 1.00 | 14.78 | A | C |
| ATOM | 37 | O | GLU | A | 283 | 31.844 | 27.555 | 18.007 | 1.00 | 11.19 | A | O |
| ATOM | 38 | N | VAL | A | 284 | 29.606 | 27.568 | 18.022 | 1.00 | 12.37 | A | N |
| ATOM | 39 | CA | VAL | A | 284 | 29.553 | 28.968 | 18.444 | 1.00 | 14.42 | A | C |
| ATOM | 40 | CB | VAL | A | 284 | 28.104 | 29.518 | 18.479 | 1.00 | 16.39 | A | C |
| ATOM | 41 | CG1 | VAL | A | 284 | 27.339 | 28.954 | 19.674 | 1.00 | 12.80 | A | C |
| ATOM | 42 | CG2 | VAL | A | 284 | 28.125 | 31.046 | 18.510 | 1.00 | 14.14 | A | C |
| ATOM | 43 | C | VAL | A | 284 | 30.245 | 29.204 | 19.801 | 1.00 | 16.08 | A | C |
| ATOM | 44 | O | VAL | A | 284 | 30.691 | 30.316 | 20.090 | 1.00 | 16.22 | A | O |

TABLE 6-continued

Coordinates for crystal structure of the complex of ERR-α and Compound 1

| ATOM | 45 | N | LEU | A | 285 | 30.350 | 28.164 | 20.626 | 1.00 | 12.98 | A | N |
|---|---|---|---|---|---|---|---|---|---|---|---|---|
| ATOM | 46 | CA | LEU | A | 285 | 31.010 | 28.301 | 21.924 | 1.00 | 13.92 | A | C |
| ATOM | 47 | CB | LEU | A | 285 | 30.747 | 27.086 | 22.808 | 1.00 | 12.78 | A | C |
| ATOM | 48 | CG | LEU | A | 285 | 29.316 | 26.963 | 23.325 | 1.00 | 13.18 | A | C |
| ATOM | 49 | CD1 | LEU | A | 285 | 29.133 | 25.636 | 24.037 | 1.00 | 11.18 | A | C |
| ATOM | 50 | CD2 | LEU | A | 285 | 28.979 | 28.122 | 24.237 | 1.00 | 14.27 | A | C |
| ATOM | 51 | C | LEU | A | 285 | 32.516 | 28.566 | 21.806 | 1.00 | 14.98 | A | C |
| ATOM | 52 | O | LEU | A | 285 | 33.149 | 29.045 | 22.749 | 1.00 | 14.98 | A | O |
| ATOM | 53 | N | PHE | A | 286 | 33.086 | 28.265 | 20.644 | 1.00 | 16.74 | A | N |
| ATOM | 54 | CA | PHE | A | 286 | 34.484 | 28.594 | 20.389 | 1.00 | 11.61 | A | C |
| ATOM | 55 | CB | PHE | A | 286 | 35.096 | 27.627 | 19.366 | 1.00 | 11.98 | A | C |
| ATOM | 56 | CG | PHE | A | 286 | 35.234 | 26.203 | 19.868 | 1.00 | 11.57 | A | C |
| ATOM | 57 | CD1 | PHE | A | 286 | 34.572 | 25.160 | 19.235 | 1.00 | 10.35 | A | C |
| ATOM | 58 | CD2 | PHE | A | 286 | 36.020 | 25.913 | 20.969 | 1.00 | 11.94 | A | C |
| ATOM | 59 | CE1 | PHE | A | 286 | 34.695 | 23.845 | 19.693 | 1.00 | 9.95 | A | C |
| ATOM | 60 | CE2 | PHE | A | 286 | 36.156 | 24.598 | 21.430 | 1.00 | 9.44 | A | C |
| ATOM | 61 | CZ | PHE | A | 286 | 35.486 | 23.568 | 20.788 | 1.00 | 8.04 | A | C |
| ATOM | 62 | C | PHE | A | 286 | 34.663 | 30.055 | 19.935 | 1.00 | 17.58 | A | C |
| ATOM | 63 | O | PHE | A | 286 | 35.774 | 30.580 | 19.949 | 1.00 | 15.23 | A | O |
| ATOM | 64 | N | GLN | A | 287 | 33.570 | 30.719 | 19.561 | 1.00 | 18.72 | A | N |
| ATOM | 65 | CA | GLN | A | 287 | 33.680 | 32.084 | 19.048 | 1.00 | 23.71 | A | C |
| ATOM | 66 | CB | GLN | A | 287 | 32.472 | 32.466 | 18.178 | 1.00 | 25.11 | A | C |
| ATOM | 67 | CG | GLN | A | 287 | 32.869 | 33.179 | 16.866 | 1.00 | 39.90 | A | C |
| ATOM | 68 | CD | GLN | A | 287 | 32.064 | 34.458 | 16.570 | 1.00 | 40.35 | A | C |
| ATOM | 69 | OE1 | GLN | A | 287 | 30.893 | 34.587 | 16.942 | 1.00 | 28.44 | A | O |
| ATOM | 70 | NE2 | GLN | A | 287 | 32.704 | 35.408 | 15.892 | 1.00 | 40.81 | A | N |
| ATOM | 71 | C | GLN | A | 287 | 33.869 | 33.116 | 20.152 | 1.00 | 25.99 | A | C |
| ATOM | 72 | O | GLN | A | 287 | 34.713 | 34.007 | 20.048 | 1.00 | 34.52 | A | O |
| ATOM | 73 | N | GLY | A | 288 | 33.087 | 33.015 | 21.213 | 1.00 | 18.89 | A | N |
| ATOM | 74 | CA | GLY | A | 288 | 33.075 | 34.089 | 22.191 | 1.00 | 33.22 | A | C |
| ATOM | 75 | C | GLY | A | 288 | 34.224 | 34.056 | 23.181 | 1.00 | 35.28 | A | C |
| ATOM | 76 | O | GLY | A | 288 | 35.141 | 33.240 | 23.057 | 1.00 | 32.12 | A | O |
| ATOM | 77 | N | PRO | A | 289 | 34.210 | 34.983 | 24.149 | 1.00 | 34.30 | A | N |
| ATOM | 78 | CD | PRO | A | 289 | 33.796 | 36.396 | 24.046 | 1.00 | 29.11 | A | C |
| ATOM | 79 | CA | PRO | A | 289 | 34.948 | 34.726 | 25.386 | 1.00 | 27.66 | A | C |
| ATOM | 80 | CB | PRO | A | 289 | 34.369 | 35.771 | 26.335 | 1.00 | 28.11 | A | C |
| ATOM | 81 | CG | PRO | A | 289 | 34.161 | 36.971 | 25.414 | 1.00 | 31.29 | A | C |
| ATOM | 82 | C | PRO | A | 289 | 34.675 | 33.299 | 25.881 | 1.00 | 22.34 | A | C |
| ATOM | 83 | O | PRO | A | 289 | 33.582 | 32.759 | 25.687 | 1.00 | 15.25 | A | O |
| ATOM | 84 | N | VAL | A | 290 | 35.679 | 32.702 | 26.510 | 1.00 | 19.05 | A | N |
| ATOM | 85 | CA | VAL | A | 290 | 35.700 | 31.267 | 26.788 | 1.00 | 15.83 | A | C |
| ATOM | 86 | CB | VAL | A | 290 | 37.109 | 30.846 | 27.208 | 1.00 | 11.51 | A | C |
| ATOM | 87 | CG1 | VAL | A | 290 | 37.480 | 31.530 | 28.509 | 1.00 | 13.50 | A | C |
| ATOM | 88 | CG2 | VAL | A | 290 | 37.207 | 29.330 | 27.339 | 1.00 | 13.64 | A | C |
| ATOM | 89 | C | VAL | A | 290 | 34.728 | 30.851 | 27.891 | 1.00 | 15.39 | A | C |
| ATOM | 90 | O | VAL | A | 290 | 34.453 | 29.662 | 28.101 | 1.00 | 11.02 | A | O |
| ATOM | 91 | N | ASN | A | 291 | 34.196 | 31.834 | 28.600 | 1.00 | 13.40 | A | N |
| ATOM | 92 | CA | ASN | A | 291 | 33.413 | 31.533 | 29.789 | 1.00 | 14.32 | A | C |
| ATOM | 93 | CB | ASN | A | 291 | 33.294 | 32.797 | 30.618 | 1.00 | 25.98 | A | C |
| ATOM | 94 | CG | ASN | A | 291 | 34.657 | 33.480 | 30.786 | 1.00 | 42.18 | A | C |
| ATOM | 95 | OD1 | ASN | A | 291 | 35.463 | 33.076 | 31.641 | 1.00 | 33.92 | A | O |
| ATOM | 96 | ND2 | ASN | A | 291 | 34.949 | 34.469 | 29.922 | 1.00 | 23.39 | A | N |
| ATOM | 97 | C | ASN | A | 291 | 32.080 | 30.835 | 29.497 | 1.00 | 14.00 | A | C |
| ATOM | 98 | O | ASN | A | 291 | 31.573 | 30.069 | 30.323 | 1.00 | 13.69 | A | O |
| ATOM | 99 | N | ALA | A | 292 | 31.541 | 31.058 | 28.302 | 1.00 | 12.59 | A | N |
| ATOM | 100 | CA | ALA | A | 292 | 30.354 | 30.331 | 27.867 | 1.00 | 12.77 | A | C |
| ATOM | 101 | CB | ALA | A | 292 | 29.745 | 30.981 | 26.628 | 1.00 | 12.55 | A | C |
| ATOM | 102 | C | ALA | A | 292 | 30.698 | 28.860 | 27.597 | 1.00 | 12.45 | A | C |
| ATOM | 103 | O | ALA | A | 292 | 29.909 | 27.967 | 27.891 | 1.00 | 10.66 | A | O |
| ATOM | 104 | N | LEU | A | 293 | 31.875 | 28.618 | 27.024 | 1.00 | 12.65 | A | N |
| ATOM | 105 | CA | LEU | A | 293 | 32.311 | 27.256 | 26.729 | 1.00 | 11.33 | A | C |
| ATOM | 106 | CB | LEU | A | 293 | 33.588 | 27.260 | 25.876 | 1.00 | 7.25 | A | C |
| ATOM | 107 | CG | LEU | A | 293 | 34.298 | 25.897 | 25.723 | 1.00 | 9.88 | A | C |
| ATOM | 108 | CD1 | LEU | A | 293 | 33.352 | 24.814 | 25.182 | 1.00 | 9.87 | A | C |
| ATOM | 109 | CD2 | LEU | A | 293 | 35.543 | 26.019 | 24.847 | 1.00 | 10.09 | A | C |
| ATOM | 110 | C | LEU | A | 293 | 32.538 | 26.507 | 28.037 | 1.00 | 8.89 | A | C |
| ATOM | 111 | O | LEU | A | 293 | 32.065 | 25.387 | 28.214 | 1.00 | 9.23 | A | O |
| ATOM | 112 | N | VAL | A | 294 | 33.258 | 27.147 | 28.953 | 1.00 | 8.15 | A | N |
| ATOM | 113 | CA | VAL | A | 294 | 33.529 | 26.570 | 30.262 | 1.00 | 12.41 | A | C |
| ATOM | 114 | CB | VAL | A | 294 | 34.406 | 27.505 | 31.126 | 1.00 | 10.83 | A | C |
| ATOM | 115 | CG1 | VAL | A | 294 | 34.342 | 27.088 | 32.582 | 1.00 | 11.13 | A | C |
| ATOM | 116 | CG2 | VAL | A | 294 | 35.843 | 27.502 | 30.623 | 1.00 | 8.98 | A | C |
| ATOM | 117 | C | VAL | A | 294 | 32.234 | 26.263 | 31.014 | 1.00 | 12.48 | A | C |
| ATOM | 118 | O | VAL | A | 294 | 32.106 | 25.209 | 31.622 | 1.00 | 10.18 | A | O |
| ATOM | 119 | N | SER | A | 295 | 31.284 | 27.194 | 30.981 | 1.00 | 10.91 | A | N |
| ATOM | 120 | CA | SER | A | 295 | 29.997 | 26.974 | 31.625 | 1.00 | 9.45 | A | C |
| ATOM | 121 | CB | SER | A | 295 | 29.096 | 28.212 | 31.499 | 1.00 | 14.43 | A | C |
| ATOM | 122 | OG | SER | A | 295 | 27.744 | 27.897 | 31.806 | 1.00 | 20.43 | A | O |

TABLE 6-continued

Coordinates for crystal structure of the complex of ERR-α and Compound 1

| ATOM | 123 | C   | SER | A | 295 | 29.325 | 25.750 | 31.023 | 1.00 | 12.36 A | C |
| ---- | --- | --- | --- | - | --- | ------ | ------ | ------ | ---- | ------- | - |
| ATOM | 124 | O   | SER | A | 295 | 28.736 | 24.939 | 31.739 | 1.00 | 10.39 A | O |
| ATOM | 125 | N   | HIS | A | 296 | 29.425 | 25.605 | 29.706 | 1.00 | 11.75 A | N |
| ATOM | 126 | CA  | HIS | A | 296 | 28.855 | 24.439 | 29.035 | 1.00 | 10.68 A | C |
| ATOM | 127 | CB  | HIS | A | 296 | 28.941 | 24.582 | 27.517 | 1.00 | 9.76 A  | C |
| ATOM | 128 | CG  | HIS | A | 296 | 28.506 | 23.361 | 26.772 | 1.00 | 10.90 A | C |
| ATOM | 129 | CD2 | HIS | A | 296 | 29.187 | 22.254 | 26.392 | 1.00 | 10.88 A | C |
| ATOM | 130 | ND1 | HIS | A | 296 | 27.209 | 23.180 | 26.326 | 1.00 | 12.76 A | N |
| ATOM | 131 | CE1 | HIS | A | 296 | 27.118 | 22.020 | 25.703 | 1.00 | 14.01 A | C |
| ATOM | 132 | NE2 | HIS | A | 296 | 28.304 | 21.437 | 25.726 | 1.00 | 14.24 A | N |
| ATOM | 133 | C   | HIS | A | 296 | 29.523 | 23.132 | 29.476 | 1.00 | 11.92 A | C |
| ATOM | 134 | O   | HIS | A | 296 | 28.847 | 22.141 | 29.761 | 1.00 | 11.60 A | O |
| ATOM | 135 | N   | LEU | A | 297 | 30.847 | 23.120 | 29.531 | 1.00 | 9.35 A  | N |
| ATOM | 136 | CA  | LEU | A | 297 | 31.553 | 21.917 | 29.972 | 1.00 | 10.01 A | C |
| ATOM | 137 | CB  | LEU | A | 297 | 33.061 | 22.123 | 29.911 | 1.00 | 9.01 A  | C |
| ATOM | 138 | CG  | LEU | A | 297 | 33.553 | 22.379 | 28.495 | 1.00 | 7.69 A  | C |
| ATOM | 139 | CD1 | LEU | A | 297 | 35.024 | 22.708 | 28.538 | 1.00 | 5.55 A  | C |
| ATOM | 140 | CD2 | LEU | A | 297 | 33.246 | 21.150 | 27.637 | 1.00 | 6.97 A  | C |
| ATOM | 141 | C   | LEU | A | 297 | 31.169 | 21.520 | 31.384 | 1.00 | 10.36 A | C |
| ATOM | 142 | O   | LEU | A | 297 | 31.045 | 20.336 | 31.691 | 1.00 | 10.64 A | O |
| ATOM | 143 | N   | LEU | A | 298 | 30.994 | 22.513 | 32.251 | 1.00 | 10.74 A | N |
| ATOM | 144 | CA  | LEU | A | 298 | 30.614 | 22.245 | 33.629 | 1.00 | 12.52 A | C |
| ATOM | 145 | CB  | LEU | A | 298 | 30.658 | 23.524 | 34.468 | 1.00 | 10.34 A | C |
| ATOM | 146 | CG  | LEU | A | 298 | 32.041 | 24.076 | 34.815 | 1.00 | 12.08 A | C |
| ATOM | 147 | CD1 | LEU | A | 298 | 31.920 | 25.418 | 35.555 | 1.00 | 8.73 A  | C |
| ATOM | 148 | CD2 | LEU | A | 298 | 32.841 | 23.076 | 35.640 | 1.00 | 9.28 A  | C |
| ATOM | 149 | C   | LEU | A | 298 | 29.232 | 21.588 | 33.682 | 1.00 | 10.48 A | C |
| ATOM | 150 | O   | LEU | A | 298 | 29.018 | 20.646 | 34.450 | 1.00 | 10.70 A | O |
| ATOM | 151 | N   | VAL | A | 299 | 28.311 | 22.066 | 32.849 | 1.00 | 10.43 A | N |
| ATOM | 152 | CA  | VAL | A | 299 | 26.954 | 21.499 | 32.789 | 1.00 | 12.43 A | C |
| ATOM | 153 | CB  | VAL | A | 299 | 26.000 | 22.363 | 31.927 | 1.00 | 15.42 A | C |
| ATOM | 154 | CG1 | VAL | A | 299 | 24.746 | 21.569 | 31.528 | 1.00 | 11.39 A | C |
| ATOM | 155 | CG2 | VAL | A | 299 | 25.613 | 23.630 | 32.668 | 1.00 | 16.30 A | C |
| ATOM | 156 | C   | VAL | A | 299 | 26.914 | 20.046 | 32.293 | 1.00 | 12.64 A | C |
| ATOM | 157 | O   | VAL | A | 299 | 26.206 | 19.223 | 32.852 | 1.00 | 11.54 A | O |
| ATOM | 158 | N   | VAL | A | 300 | 27.670 | 19.734 | 31.246 | 1.00 | 13.30 A | N |
| ATOM | 159 | CA  | VAL | A | 300 | 27.618 | 18.398 | 30.646 | 1.00 | 13.01 A | C |
| ATOM | 160 | CB  | VAL | A | 300 | 28.052 | 18.407 | 29.165 | 1.00 | 13.09 A | C |
| ATOM | 161 | CG1 | VAL | A | 300 | 27.198 | 19.369 | 28.359 | 1.00 | 13.58 A | C |
| ATOM | 162 | CG2 | VAL | A | 300 | 29.516 | 18.770 | 29.050 | 1.00 | 11.79 A | C |
| ATOM | 163 | C   | VAL | A | 300 | 28.481 | 17.387 | 31.407 | 1.00 | 14.75 A | C |
| ATOM | 164 | O   | VAL | A | 300 | 28.515 | 16.209 | 31.069 | 1.00 | 12.75 A | O |
| ATOM | 165 | N   | GLU | A | 301 | 29.191 | 17.861 | 32.422 | 1.00 | 14.54 A | N |
| ATOM | 166 | CA  | GLU | A | 301 | 29.901 | 16.974 | 33.325 | 1.00 | 15.49 A | C |
| ATOM | 167 | CB  | GLU | A | 301 | 30.595 | 17.793 | 34.410 | 1.00 | 13.73 A | C |
| ATOM | 168 | CG  | GLU | A | 301 | 31.478 | 17.003 | 35.356 | 1.00 | 18.04 A | C |
| ATOM | 169 | CD  | GLU | A | 301 | 32.572 | 16.200 | 34.658 | 1.00 | 14.78 A | C |
| ATOM | 170 | OE1 | GLU | A | 301 | 33.082 | 15.260 | 35.292 | 1.00 | 16.40 A | O |
| ATOM | 171 | OE2 | GLU | A | 301 | 32.929 | 16.494 | 33.496 | 1.00 | 13.16 A | O |
| ATOM | 172 | C   | GLU | A | 301 | 28.886 | 16.004 | 33.931 | 1.00 | 19.75 A | C |
| ATOM | 173 | O   | GLU | A | 301 | 27.857 | 16.426 | 34.455 | 1.00 | 20.35 A | O |
| ATOM | 174 | N   | PRO | A | 302 | 29.169 | 14.698 | 33.850 | 1.00 | 17.66 A | N |
| ATOM | 175 | CD  | PRO | A | 302 | 30.417 | 14.127 | 33.304 | 1.00 | 14.23 A | C |
| ATOM | 176 | CA  | PRO | A | 302 | 28.245 | 13.671 | 34.349 | 1.00 | 19.35 A | C |
| ATOM | 177 | CB  | PRO | A | 302 | 29.059 | 12.380 | 34.237 | 1.00 | 19.40 A | C |
| ATOM | 178 | CG  | PRO | A | 302 | 30.105 | 12.673 | 33.178 | 1.00 | 19.78 A | C |
| ATOM | 179 | C   | PRO | A | 302 | 27.834 | 13.888 | 35.801 | 1.00 | 19.84 A | C |
| ATOM | 180 | O   | PRO | A | 302 | 28.633 | 14.369 | 36.608 | 1.00 | 18.01 A | O |
| ATOM | 181 | N   | GLU | A | 303 | 26.595 | 13.527 | 36.129 | 1.00 | 24.87 A | N |
| ATOM | 182 | CA  | GLU | A | 303 | 26.127 | 13.587 | 37.513 | 1.00 | 34.74 A | C |
| ATOM | 183 | CB  | GLU | A | 303 | 24.637 | 13.246 | 37.601 | 1.00 | 31.77 A | C |
| ATOM | 184 | CG  | GLU | A | 303 | 23.731 | 14.164 | 36.791 | 1.00 | 46.93 A | C |
| ATOM | 185 | CD  | GLU | A | 303 | 23.742 | 15.601 | 37.287 | 1.00 | 48.48 A | C |
| ATOM | 186 | OE1 | GLU | A | 303 | 24.025 | 15.820 | 38.486 | 1.00 | 53.83 A | O |
| ATOM | 187 | OE2 | GLU | A | 303 | 23.459 | 16.510 | 36.475 | 1.00 | 51.75 A | O |
| ATOM | 188 | C   | GLU | A | 303 | 26.913 | 12.594 | 38.359 | 1.00 | 28.66 A | C |
| ATOM | 189 | O   | GLU | A | 303 | 27.459 | 11.623 | 37.837 | 1.00 | 18.80 A | O |
| ATOM | 190 | N   | LYS | A | 304 | 26.968 | 12.830 | 39.663 | 1.00 | 27.38 A | N |
| ATOM | 191 | CA  | LYS | A | 304 | 27.639 | 11.894 | 40.552 | 1.00 | 28.05 A | C |
| ATOM | 192 | CB  | LYS | A | 304 | 27.673 | 12.425 | 41.986 | 1.00 | 30.61 A | C |
| ATOM | 193 | CG  | LYS | A | 304 | 27.340 | 13.898 | 42.124 | 1.00 | 41.26 A | C |
| ATOM | 194 | CD  | LYS | A | 304 | 28.151 | 14.772 | 41.174 | 1.00 | 46.02 A | C |
| ATOM | 195 | CE  | LYS | A | 304 | 27.391 | 16.062 | 40.869 | 1.00 | 50.74 A | C |
| ATOM | 196 | NZ  | LYS | A | 304 | 25.928 | 15.791 | 40.674 | 1.00 | 44.82 A | N |
| ATOM | 197 | C   | LYS | A | 304 | 26.906 | 10.554 | 40.493 | 1.00 | 26.57 A | C |
| ATOM | 198 | O   | LYS | A | 304 | 25.678 | 10.508 | 40.464 | 1.00 | 26.65 A | O |
| ATOM | 199 | N   | LEU | A | 305 | 27.657 | 9.462  | 40.442 | 1.00 | 24.73 A | N |
| ATOM | 200 | CA  | LEU | A | 305 | 27.040 | 8.143  | 40.446 | 1.00 | 23.98 A | C |

TABLE 6-continued

Coordinates for crystal structure of the complex of ERR-α and Compound 1

| ATOM | 201 | CB | LEU | A | 305 | 27.729 | 7.207 | 39.453 | 1.00 | 25.79 | A | C |
|---|---|---|---|---|---|---|---|---|---|---|---|---|
| ATOM | 202 | CG | LEU | A | 305 | 27.617 | 7.530 | 37.961 | 1.00 | 26.42 | A | C |
| ATOM | 203 | CD1 | LEU | A | 305 | 28.192 | 6.385 | 37.146 | 1.00 | 21.98 | A | C |
| ATOM | 204 | CD2 | LEU | A | 305 | 26.175 | 7.793 | 37.568 | 1.00 | 27.99 | A | C |
| ATOM | 205 | C | LEU | A | 305 | 27.099 | 7.542 | 41.838 | 1.00 | 23.16 | A | C |
| ATOM | 206 | O | LEU | A | 305 | 28.014 | 7.834 | 42.616 | 1.00 | 23.56 | A | O |
| ATOM | 207 | N | TYR | A | 306 | 26.110 | 6.713 | 42.151 | 1.00 | 22.53 | A | N |
| ATOM | 208 | CA | TYR | A | 306 | 26.143 | 5.911 | 43.365 | 1.00 | 26.89 | A | C |
| ATOM | 209 | CB | TYR | A | 306 | 24.880 | 6.128 | 44.198 | 1.00 | 27.79 | A | C |
| ATOM | 210 | CG | TYR | A | 306 | 24.844 | 7.508 | 44.794 | 1.00 | 31.63 | A | C |
| ATOM | 211 | CD1 | TYR | A | 306 | 24.342 | 8.585 | 44.071 | 1.00 | 29.49 | A | C |
| ATOM | 212 | CE1 | TYR | A | 306 | 24.334 | 9.854 | 44.603 | 1.00 | 32.64 | A | C |
| ATOM | 213 | CD2 | TYR | A | 306 | 25.356 | 7.746 | 46.061 | 1.00 | 33.55 | A | C |
| ATOM | 214 | CE2 | TYR | A | 306 | 25.351 | 9.008 | 46.604 | 1.00 | 36.28 | A | C |
| ATOM | 215 | CZ | TYR | A | 306 | 24.841 | 10.060 | 45.874 | 1.00 | 42.00 | A | C |
| ATOM | 216 | OH | TYR | A | 306 | 24.839 | 11.320 | 46.426 | 1.00 | 52.73 | A | O |
| ATOM | 217 | C | TYR | A | 306 | 26.320 | 4.448 | 42.998 | 1.00 | 26.38 | A | C |
| ATOM | 218 | O | TYR | A | 306 | 25.511 | 3.882 | 42.274 | 1.00 | 22.90 | A | O |
| ATOM | 219 | N | ALA | A | 307 | 27.398 | 3.850 | 43.488 | 1.00 | 23.02 | A | N |
| ATOM | 220 | CA | ALA | A | 307 | 27.699 | 2.460 | 43.198 | 1.00 | 24.52 | A | C |
| ATOM | 221 | CB | ALA | A | 307 | 29.188 | 2.218 | 43.325 | 1.00 | 22.08 | A | C |
| ATOM | 222 | C | ALA | A | 307 | 26.920 | 1.488 | 44.091 | 1.00 | 27.85 | A | C |
| ATOM | 223 | O | ALA | A | 307 | 26.705 | 0.338 | 43.719 | 1.00 | 27.89 | A | O |
| ATOM | 224 | N | MET | A | 308 | 26.505 | 1.945 | 45.267 | 1.00 | 29.84 | A | N |
| ATOM | 225 | CA | MET | A | 308 | 25.797 | 1.076 | 46.208 | 1.00 | 39.93 | A | C |
| ATOM | 226 | CB | MET | A | 308 | 26.185 | 1.413 | 47.654 | 1.00 | 33.82 | A | C |
| ATOM | 227 | CG | MET | A | 308 | 27.682 | 1.467 | 47.915 | 1.00 | 34.50 | A | C |
| ATOM | 228 | SD | MET | A | 308 | 28.540 | −0.093 | 47.616 | 1.00 | 42.64 | A | S |
| ATOM | 229 | CE | MET | A | 308 | 30.221 | 0.421 | 47.935 | 1.00 | 45.56 | A | C |
| ATOM | 230 | C | MET | A | 308 | 24.274 | 1.148 | 46.059 | 1.00 | 39.26 | A | C |
| ATOM | 231 | O | MET | A | 308 | 23.726 | 2.189 | 45.691 | 1.00 | 44.59 | A | O |
| ATOM | 232 | N | PRO | A | 309 | 23.589 | 0.030 | 46.348 | 1.00 | 50.14 | A | N |
| ATOM | 233 | CD | PRO | A | 309 | 24.235 | −1.277 | 46.579 | 1.00 | 48.34 | A | C |
| ATOM | 234 | CA | PRO | A | 309 | 22.124 | −0.058 | 46.414 | 1.00 | 47.55 | A | C |
| ATOM | 235 | CB | PRO | A | 309 | 21.898 | −1.375 | 47.155 | 1.00 | 49.88 | A | C |
| ATOM | 236 | CG | PRO | A | 309 | 23.069 | −2.217 | 46.766 | 1.00 | 58.07 | A | C |
| ATOM | 237 | C | PRO | A | 309 | 21.516 | 1.091 | 47.217 | 1.00 | 52.44 | A | C |
| ATOM | 238 | O | PRO | A | 309 | 21.952 | 1.339 | 48.347 | 1.00 | 50.51 | A | O |
| ATOM | 239 | N | LEU | A | 317 | 25.154 | −4.678 | 48.314 | 1.00 | 52.79 | A | N |
| ATOM | 240 | CA | LEU | A | 317 | 25.358 | −5.964 | 48.977 | 1.00 | 51.70 | A | C |
| ATOM | 241 | CB | LEU | A | 317 | 24.020 | −6.568 | 49.438 | 1.00 | 56.53 | A | C |
| ATOM | 242 | CG | LEU | A | 317 | 22.702 | −6.226 | 48.722 | 1.00 | 59.14 | A | C |
| ATOM | 243 | CD1 | LEU | A | 317 | 22.266 | −4.787 | 49.001 | 1.00 | 58.56 | A | C |
| ATOM | 244 | CD2 | LEU | A | 317 | 22.757 | −6.501 | 47.218 | 1.00 | 52.71 | A | C |
| ATOM | 245 | C | LEU | A | 317 | 26.145 | −6.955 | 48.110 | 1.00 | 44.57 | A | C |
| ATOM | 246 | O | LEU | A | 317 | 26.440 | −8.073 | 48.538 | 1.00 | 45.10 | A | O |
| ATOM | 247 | N | LEU | A | 318 | 26.484 | −6.532 | 46.895 | 1.00 | 41.57 | A | N |
| ATOM | 248 | CA | LEU | A | 318 | 27.298 | −7.340 | 45.993 | 1.00 | 31.89 | A | C |
| ATOM | 249 | CB | LEU | A | 318 | 27.230 | −6.782 | 44.573 | 1.00 | 29.81 | A | C |
| ATOM | 250 | CG | LEU | A | 318 | 25.911 | −6.909 | 43.816 | 1.00 | 32.72 | A | C |
| ATOM | 251 | CD1 | LEU | A | 318 | 25.977 | −6.147 | 42.503 | 1.00 | 26.20 | A | C |
| ATOM | 252 | CD2 | LEU | A | 318 | 25.595 | −8.371 | 43.573 | 1.00 | 35.10 | A | C |
| ATOM | 253 | C | LEU | A | 318 | 28.749 | −7.350 | 46.456 | 1.00 | 26.04 | A | C |
| ATOM | 254 | O | LEU | A | 318 | 29.186 | −6.435 | 47.152 | 1.00 | 22.04 | A | O |
| ATOM | 255 | N | PRO | A | 319 | 29.503 | −8.394 | 46.079 | 1.00 | 23.87 | A | N |
| ATOM | 256 | CD | PRO | A | 319 | 29.055 | −9.610 | 45.383 | 1.00 | 21.16 | A | C |
| ATOM | 257 | CA | PRO | A | 319 | 30.942 | −8.415 | 46.362 | 1.00 | 18.87 | A | C |
| ATOM | 258 | CB | PRO | A | 319 | 31.398 | −9.751 | 45.765 | 1.00 | 18.38 | A | C |
| ATOM | 259 | CG | PRO | A | 319 | 30.160 | −10.570 | 45.651 | 1.00 | 20.01 | A | C |
| ATOM | 260 | C | PRO | A | 319 | 31.641 | −7.244 | 45.651 | 1.00 | 17.27 | A | C |
| ATOM | 261 | O | PRO | A | 319 | 31.106 | −6.692 | 44.686 | 1.00 | 16.55 | A | O |
| ATOM | 262 | N | ALA | A | 320 | 32.823 | −6.875 | 46.130 | 1.00 | 17.00 | A | N |
| ATOM | 263 | CA | ALA | A | 320 | 33.549 | −5.723 | 45.601 | 1.00 | 19.01 | A | C |
| ATOM | 264 | CB | ALA | A | 320 | 34.920 | −5.614 | 46.257 | 1.00 | 16.56 | A | C |
| ATOM | 265 | C | ALA | A | 320 | 33.690 | −5.741 | 44.081 | 1.00 | 16.68 | A | C |
| ATOM | 266 | O | ALA | A | 320 | 33.388 | −4.749 | 43.415 | 1.00 | 15.58 | A | O |
| ATOM | 267 | N | VAL | A | 321 | 34.157 | −6.860 | 43.536 | 1.00 | 13.60 | A | N |
| ATOM | 268 | CA | VAL | A | 321 | 34.378 | −6.951 | 42.093 | 1.00 | 16.13 | A | C |
| ATOM | 269 | CB | VAL | A | 321 | 34.927 | −8.323 | 41.674 | 1.00 | 15.02 | A | C |
| ATOM | 270 | CG1 | VAL | A | 321 | 35.190 | −8.336 | 40.180 | 1.00 | 15.96 | A | C |
| ATOM | 271 | CG2 | VAL | A | 321 | 36.197 | −8.633 | 42.435 | 1.00 | 22.36 | A | C |
| ATOM | 272 | C | VAL | A | 321 | 33.112 | −6.670 | 41.287 | 1.00 | 16.45 | A | C |
| ATOM | 273 | O | VAL | A | 321 | 33.146 | −5.947 | 40.287 | 1.00 | 15.37 | A | O |
| ATOM | 274 | N | ALA | A | 322 | 31.997 | −7.243 | 41.732 | 1.00 | 15.98 | A | N |
| ATOM | 275 | CA | ALA | A | 322 | 30.734 | −7.140 | 41.010 | 1.00 | 14.85 | A | C |
| ATOM | 276 | CB | ALA | A | 322 | 29.700 | −8.085 | 41.622 | 1.00 | 15.22 | A | C |
| ATOM | 277 | C | ALA | A | 322 | 30.213 | −5.708 | 41.008 | 1.00 | 15.26 | A | C |
| ATOM | 278 | O | ALA | A | 322 | 29.718 | −5.212 | 40.002 | 1.00 | 15.54 | A | O |

TABLE 6-continued

Coordinates for crystal structure of the complex of ERR-α and Compound 1

| ATOM | 279 | N | THR | A | 323 | 30.327 | −5.059 | 42.154 | 1.00 | 15.80 | A | N |
|---|---|---|---|---|---|---|---|---|---|---|---|---|
| ATOM | 280 | CA | THR | A | 323 | 29.934 | −3.669 | 42.309 | 1.00 | 14.87 | A | C |
| ATOM | 281 | CB | THR | A | 323 | 30.219 | −3.211 | 43.745 | 1.00 | 14.02 | A | C |
| ATOM | 282 | OG1 | THR | A | 323 | 29.453 | −4.027 | 44.643 | 1.00 | 16.97 | A | O |
| ATOM | 283 | CG2 | THR | A | 323 | 29.872 | −1.734 | 43.946 | 1.00 | 16.94 | A | C |
| ATOM | 284 | C | THR | A | 323 | 30.703 | −2.799 | 41.326 | 1.00 | 14.96 | A | C |
| ATOM | 285 | O | THR | A | 323 | 30.121 | −1.995 | 40.605 | 1.00 | 15.71 | A | O |
| ATOM | 286 | N | LEU | A | 324 | 32.015 | −2.983 | 41.281 | 1.00 | 14.81 | A | N |
| ATOM | 287 | CA | LEU | A | 324 | 32.862 | −2.206 | 40.385 | 1.00 | 13.95 | A | C |
| ATOM | 288 | CB | LEU | A | 324 | 34.334 | −2.495 | 40.671 | 1.00 | 11.37 | A | C |
| ATOM | 289 | CG | LEU | A | 324 | 34.922 | −1.806 | 41.899 | 1.00 | 8.98 | A | C |
| ATOM | 290 | CD1 | LEU | A | 324 | 36.314 | −2.336 | 42.199 | 1.00 | 13.92 | A | C |
| ATOM | 291 | CD2 | LEU | A | 324 | 34.972 | −0.307 | 41.664 | 1.00 | 11.73 | A | C |
| ATOM | 292 | C | LEU | A | 324 | 32.519 | −2.471 | 38.915 | 1.00 | 14.54 | A | C |
| ATOM | 293 | O | LEU | A | 324 | 32.516 | −1.550 | 38.097 | 1.00 | 13.87 | A | O |
| ATOM | 294 | N | CYS | A | 325 | 32.215 | −3.722 | 38.585 | 1.00 | 12.55 | A | N |
| ATOM | 295 | CA | CYS | A | 325 | 31.795 | −4.067 | 37.226 | 1.00 | 14.33 | A | C |
| ATOM | 296 | CB | CYS | A | 325 | 31.543 | −5.568 | 37.097 | 1.00 | 16.72 | A | C |
| ATOM | 297 | SG | CYS | A | 325 | 33.027 | −6.555 | 37.110 | 1.00 | 14.65 | A | S |
| ATOM | 298 | C | CYS | A | 325 | 30.528 | −3.328 | 36.822 | 1.00 | 18.79 | A | C |
| ATOM | 299 | O | CYS | A | 325 | 30.468 | −2.717 | 35.749 | 1.00 | 14.81 | A | O |
| ATOM | 300 | N | ASP | A | 326 | 29.508 | −3.412 | 37.674 | 1.00 | 12.37 | A | N |
| ATOM | 301 | CA | ASP | A | 326 | 28.272 | −2.685 | 37.437 | 1.00 | 15.44 | A | C |
| ATOM | 302 | CB | ASP | A | 326 | 27.289 | −2.893 | 38.588 | 1.00 | 19.76 | A | C |
| ATOM | 303 | CG | ASP | A | 326 | 26.718 | −4.296 | 38.619 | 1.00 | 22.47 | A | C |
| ATOM | 304 | OD1 | ASP | A | 326 | 26.885 | −5.044 | 37.628 | 1.00 | 22.18 | A | O |
| ATOM | 305 | OD2 | ASP | A | 326 | 26.098 | −4.648 | 39.642 | 1.00 | 30.32 | A | O |
| ATOM | 306 | C | ASP | A | 326 | 28.544 | −1.196 | 37.272 | 1.00 | 16.07 | A | C |
| ATOM | 307 | O | ASP | A | 326 | 28.000 | −0.554 | 36.375 | 1.00 | 19.73 | A | O |
| ATOM | 308 | N | LEU | A | 327 | 29.376 | −0.641 | 38.148 | 1.00 | 10.96 | A | N |
| ATOM | 309 | CA | LEU | A | 327 | 29.697 | 0.781 | 38.070 | 1.00 | 13.98 | A | C |
| ATOM | 310 | CB | LEU | A | 327 | 30.617 | 1.197 | 39.216 | 1.00 | 10.97 | A | C |
| ATOM | 311 | CG | LEU | A | 327 | 31.149 | 2.627 | 39.141 | 1.00 | 14.38 | A | C |
| ATOM | 312 | CD1 | LEU | A | 327 | 30.006 | 3.646 | 39.117 | 1.00 | 14.70 | A | C |
| ATOM | 313 | CD2 | LEU | A | 327 | 32.116 | 2.901 | 40.291 | 1.00 | 10.90 | A | C |
| ATOM | 314 | C | LEU | A | 327 | 30.350 | 1.087 | 36.725 | 1.00 | 15.52 | A | C |
| ATOM | 315 | O | LEU | A | 327 | 29.987 | 2.059 | 36.054 | 1.00 | 11.65 | A | O |
| ATOM | 316 | N | PHE | A | 328 | 31.296 | 0.232 | 36.327 | 1.00 | 13.97 | A | N |
| ATOM | 317 | CA | PHE | A | 328 | 32.035 | 0.417 | 35.080 | 1.00 | 11.13 | A | C |
| ATOM | 318 | CB | PHE | A | 328 | 33.014 | −0.733 | 34.869 | 1.00 | 8.54 | A | C |
| ATOM | 319 | CG | PHE | A | 328 | 34.070 | −0.453 | 33.842 | 1.00 | 13.15 | A | C |
| ATOM | 320 | CD1 | PHE | A | 328 | 34.124 | −1.181 | 32.664 | 1.00 | 12.18 | A | C |
| ATOM | 321 | CD2 | PHE | A | 328 | 35.027 | 0.529 | 34.063 | 1.00 | 11.71 | A | C |
| ATOM | 322 | CE1 | PHE | A | 328 | 35.110 | −0.934 | 31.729 | 1.00 | 15.78 | A | C |
| ATOM | 323 | CE2 | PHE | A | 328 | 36.021 | 0.779 | 33.127 | 1.00 | 11.74 | A | C |
| ATOM | 324 | CZ | PHE | A | 328 | 36.062 | 0.053 | 31.960 | 1.00 | 12.05 | A | C |
| ATOM | 325 | C | PHE | A | 328 | 31.119 | 0.534 | 33.870 | 1.00 | 13.77 | A | C |
| ATOM | 326 | O | PHE | A | 328 | 31.327 | 1.393 | 33.018 | 1.00 | 12.07 | A | O |
| ATOM | 327 | N | ASP | A | 329 | 30.116 | −0.341 | 33.790 | 1.00 | 12.95 | A | N |
| ATOM | 328 | CA | ASP | A | 329 | 29.178 | −0.326 | 32.671 | 1.00 | 14.28 | A | C |
| ATOM | 329 | CB | ASP | A | 329 | 28.108 | −1.415 | 32.826 | 1.00 | 14.85 | A | C |
| ATOM | 330 | CG | ASP | A | 329 | 28.660 | −2.817 | 32.617 | 1.00 | 20.42 | A | C |
| ATOM | 331 | OD1 | ASP | A | 329 | 28.069 | −3.780 | 33.149 | 1.00 | 21.88 | A | O |
| ATOM | 332 | OD2 | ASP | A | 329 | 29.685 | −2.955 | 31.925 | 1.00 | 16.14 | A | O |
| ATOM | 333 | C | ASP | A | 329 | 28.504 | 1.030 | 32.560 | 1.00 | 13.17 | A | C |
| ATOM | 334 | O | ASP | A | 329 | 28.339 | 1.559 | 31.466 | 1.00 | 11.47 | A | O |
| ATOM | 335 | N | ARG | A | 330 | 28.120 | 1.590 | 33.701 | 1.00 | 10.93 | A | N |
| ATOM | 336 | CA | ARG | A | 330 | 27.460 | 2.887 | 33.720 | 1.00 | 13.26 | A | C |
| ATOM | 337 | CB | ARG | A | 330 | 26.799 | 3.122 | 35.080 | 1.00 | 13.70 | A | C |
| ATOM | 338 | CG | ARG | A | 330 | 25.816 | 2.014 | 35.444 | 1.00 | 17.68 | A | C |
| ATOM | 339 | CD | ARG | A | 330 | 24.756 | 2.507 | 36.396 | 1.00 | 27.55 | A | C |
| ATOM | 340 | NE | ARG | A | 330 | 25.282 | 2.632 | 37.745 | 1.00 | 31.14 | A | N |
| ATOM | 341 | CZ | ARG | A | 330 | 24.938 | 3.588 | 38.598 | 1.00 | 25.26 | A | C |
| ATOM | 342 | NH1 | ARG | A | 330 | 24.067 | 4.524 | 38.242 | 1.00 | 21.90 | A | N |
| ATOM | 343 | NH2 | ARG | A | 330 | 25.477 | 3.609 | 39.806 | 1.00 | 22.06 | A | N |
| ATOM | 344 | C | ARG | A | 330 | 28.423 | 4.023 | 33.361 | 1.00 | 14.84 | A | C |
| ATOM | 345 | O | ARG | A | 330 | 28.032 | 4.983 | 32.690 | 1.00 | 11.00 | A | O |
| ATOM | 346 | N | GLU | A | 331 | 29.681 | 3.902 | 33.792 | 1.00 | 11.85 | A | N |
| ATOM | 347 | CA | GLU | A | 331 | 30.709 | 4.885 | 33.443 | 1.00 | 13.26 | A | C |
| ATOM | 348 | CB | GLU | A | 331 | 32.029 | 4.589 | 34.170 | 1.00 | 11.64 | A | C |
| ATOM | 349 | CG | GLU | A | 331 | 32.103 | 5.126 | 35.592 | 1.00 | 12.18 | A | C |
| ATOM | 350 | CD | GLU | A | 331 | 32.073 | 6.653 | 35.651 | 1.00 | 20.62 | A | C |
| ATOM | 351 | OE1 | GLU | A | 331 | 32.694 | 7.311 | 34.774 | 1.00 | 17.66 | A | O |
| ATOM | 352 | OE2 | GLU | A | 331 | 31.433 | 7.191 | 36.583 | 1.00 | 17.88 | A | O |
| ATOM | 353 | C | GLU | A | 331 | 30.965 | 4.914 | 31.945 | 1.00 | 12.27 | A | C |
| ATOM | 354 | O | GLU | A | 331 | 31.266 | 5.956 | 31.385 | 1.00 | 12.04 | A | O |
| ATOM | 355 | N | ILE | A | 332 | 30.857 | 3.763 | 31.294 | 1.00 | 10.67 | A | N |
| ATOM | 356 | CA | ILE | A | 332 | 31.077 | 3.701 | 29.855 | 1.00 | 11.62 | A | C |

TABLE 6-continued

Coordinates for crystal structure of the complex of ERR-α and Compound 1

| ATOM | 357 | CB | ILE | A | 332 | 31.096 | 2.243 | 29.353 | 1.00 | 13.91 | A | C |
|---|---|---|---|---|---|---|---|---|---|---|---|---|
| ATOM | 358 | CG2 | ILE | A | 332 | 30.640 | 2.172 | 27.900 | 1.00 | 10.95 | A | C |
| ATOM | 359 | CG1 | ILE | A | 332 | 32.511 | 1.666 | 29.509 | 1.00 | 14.60 | A | C |
| ATOM | 360 | CD1 | ILE | A | 332 | 32.546 | 0.170 | 29.645 | 1.00 | 18.15 | A | C |
| ATOM | 361 | C | ILE | A | 332 | 30.019 | 4.497 | 29.100 | 1.00 | 13.24 | A | C |
| ATOM | 362 | O | ILE | A | 332 | 30.331 | 5.281 | 28.199 | 1.00 | 12.76 | A | O |
| ATOM | 363 | N | VAL | A | 333 | 28.764 | 4.287 | 29.472 | 1.00 | 10.95 | A | N |
| ATOM | 364 | CA | VAL | A | 333 | 27.645 | 4.956 | 28.823 | 1.00 | 11.00 | A | C |
| ATOM | 365 | CB | VAL | A | 333 | 26.314 | 4.429 | 29.398 | 1.00 | 12.69 | A | C |
| ATOM | 366 | CG1 | VAL | A | 333 | 25.144 | 5.332 | 28.999 | 1.00 | 12.65 | A | C |
| ATOM | 367 | CG2 | VAL | A | 333 | 26.093 | 2.977 | 28.961 | 1.00 | 8.88 | A | C |
| ATOM | 368 | C | VAL | A | 333 | 27.748 | 6.462 | 29.043 | 1.00 | 13.15 | A | C |
| ATOM | 369 | O | VAL | A | 333 | 27.651 | 7.259 | 28.111 | 1.00 | 15.58 | A | O |
| ATOM | 370 | N | VAL | A | 334 | 27.962 | 6.837 | 30.292 | 1.00 | 9.75 | A | N |
| ATOM | 371 | CA | VAL | A | 334 | 28.130 | 8.229 | 30.667 | 1.00 | 14.02 | A | C |
| ATOM | 372 | CB | VAL | A | 334 | 28.333 | 8.336 | 32.183 | 1.00 | 18.06 | A | C |
| ATOM | 373 | CG1 | VAL | A | 334 | 28.975 | 9.645 | 32.540 | 1.00 | 17.29 | A | C |
| ATOM | 374 | CG2 | VAL | A | 334 | 26.984 | 8.151 | 32.906 | 1.00 | 18.35 | A | C |
| ATOM | 375 | C | VAL | A | 334 | 29.298 | 8.892 | 29.926 | 1.00 | 13.50 | A | C |
| ATOM | 376 | O | VAL | A | 334 | 29.203 | 10.046 | 29.502 | 1.00 | 13.96 | A | O |
| ATOM | 377 | N | THR | A | 335 | 30.393 | 8.159 | 29.760 | 1.00 | 9.79 | A | N |
| ATOM | 378 | CA | THR | A | 335 | 31.543 | 8.670 | 29.018 | 1.00 | 10.99 | A | C |
| ATOM | 379 | CB | THR | A | 335 | 32.732 | 7.690 | 29.082 | 1.00 | 11.18 | A | C |
| ATOM | 380 | OG1 | THR | A | 335 | 33.184 | 7.579 | 30.434 | 1.00 | 10.57 | A | O |
| ATOM | 381 | CG2 | THR | A | 335 | 33.886 | 8.174 | 28.209 | 1.00 | 11.31 | A | C |
| ATOM | 382 | C | THR | A | 335 | 31.179 | 8.962 | 27.555 | 1.00 | 11.10 | A | C |
| ATOM | 383 | O | THR | A | 335 | 31.510 | 10.014 | 27.021 | 1.00 | 9.77 | A | O |
| ATOM | 384 | N | ILE | A | 336 | 30.501 | 8.025 | 26.909 | 1.00 | 10.81 | A | N |
| ATOM | 385 | CA | ILE | A | 336 | 30.071 | 8.215 | 25.524 | 1.00 | 14.82 | A | C |
| ATOM | 386 | CB | ILE | A | 336 | 29.448 | 6.912 | 24.942 | 1.00 | 13.32 | A | C |
| ATOM | 387 | CG2 | ILE | A | 336 | 28.903 | 7.161 | 23.559 | 1.00 | 15.67 | A | C |
| ATOM | 388 | CG1 | ILE | A | 336 | 30.503 | 5.798 | 24.891 | 1.00 | 12.25 | A | C |
| ATOM | 389 | CD1 | ILE | A | 336 | 29.933 | 4.390 | 24.730 | 1.00 | 12.52 | A | C |
| ATOM | 390 | C | ILE | A | 336 | 29.109 | 9.417 | 25.363 | 1.00 | 16.41 | A | C |
| ATOM | 391 | O | ILE | A | 336 | 29.286 | 10.248 | 24.468 | 1.00 | 16.31 | A | O |
| ATOM | 392 | N | SER | A | 337 | 28.107 | 9.518 | 26.234 | 1.00 | 15.70 | A | N |
| ATOM | 393 | CA | SER | A | 337 | 27.155 | 10.641 | 26.181 | 1.00 | 14.63 | A | C |
| ATOM | 394 | CB | SER | A | 337 | 26.061 | 10.483 | 27.243 | 1.00 | 16.35 | A | C |
| ATOM | 395 | OG | SER | A | 337 | 25.234 | 9.375 | 26.964 | 1.00 | 24.14 | A | O |
| ATOM | 396 | C | SER | A | 337 | 27.863 | 11.973 | 26.403 | 1.00 | 13.85 | A | C |
| ATOM | 397 | O | SER | A | 337 | 27.557 | 12.985 | 25.755 | 1.00 | 11.00 | A | O |
| ATOM | 398 | N | TRP | A | 338 | 28.801 | 11.969 | 27.343 | 1.00 | 12.03 | A | N |
| ATOM | 399 | CA | TRP | A | 338 | 29.598 | 13.152 | 27.607 | 1.00 | 12.03 | A | C |
| ATOM | 400 | CB | TRP | A | 338 | 30.587 | 12.906 | 28.741 | 1.00 | 10.09 | A | C |
| ATOM | 401 | CG | TRP | A | 338 | 31.618 | 13.982 | 28.844 | 1.00 | 10.22 | A | C |
| ATOM | 402 | CD2 | TRP | A | 338 | 32.943 | 13.960 | 28.287 | 1.00 | 9.82 | A | C |
| ATOM | 403 | CE2 | TRP | A | 338 | 33.558 | 15.177 | 28.629 | 1.00 | 11.66 | A | C |
| ATOM | 404 | CE3 | TRP | A | 338 | 33.661 | 13.018 | 27.538 | 1.00 | 6.42 | A | C |
| ATOM | 405 | CD1 | TRP | A | 338 | 31.492 | 15.180 | 29.477 | 1.00 | 11.24 | A | C |
| ATOM | 406 | NE1 | TRP | A | 338 | 32.654 | 15.904 | 29.357 | 1.00 | 8.68 | A | N |
| ATOM | 407 | CZ2 | TRP | A | 338 | 34.864 | 15.487 | 28.241 | 1.00 | 6.65 | A | C |
| ATOM | 408 | CZ3 | TRP | A | 338 | 34.954 | 13.324 | 27.157 | 1.00 | 7.40 | A | C |
| ATOM | 409 | CH2 | TRP | A | 338 | 35.544 | 14.551 | 27.511 | 1.00 | 6.61 | A | C |
| ATOM | 410 | C | TRP | A | 338 | 30.335 | 13.602 | 26.347 | 1.00 | 13.94 | A | C |
| ATOM | 411 | O | TRP | A | 338 | 30.237 | 14.766 | 25.954 | 1.00 | 11.68 | A | O |
| ATOM | 412 | N | ALA | A | 339 | 31.055 | 12.680 | 25.709 | 1.00 | 8.94 | A | N |
| ATOM | 413 | CA | ALA | A | 339 | 31.832 | 13.020 | 24.517 | 1.00 | 10.09 | A | C |
| ATOM | 414 | CB | ALA | A | 339 | 32.538 | 11.796 | 23.980 | 1.00 | 10.38 | A | C |
| ATOM | 415 | C | ALA | A | 339 | 30.996 | 13.667 | 23.413 | 1.00 | 13.70 | A | C |
| ATOM | 416 | O | ALA | A | 339 | 31.460 | 14.594 | 22.737 | 1.00 | 14.16 | A | O |
| ATOM | 417 | N | LYS | A | 340 | 29.778 | 13.167 | 23.223 | 1.00 | 11.98 | A | N |
| ATOM | 418 | CA | LYS | A | 340 | 28.912 | 13.636 | 22.149 | 1.00 | 16.41 | A | C |
| ATOM | 419 | CB | LYS | A | 340 | 27.699 | 12.722 | 21.980 | 1.00 | 18.59 | A | C |
| ATOM | 420 | CG | LYS | A | 340 | 28.020 | 11.284 | 21.593 | 1.00 | 24.43 | A | C |
| ATOM | 421 | CD | LYS | A | 340 | 26.735 | 10.496 | 21.338 | 1.00 | 29.74 | A | C |
| ATOM | 422 | CE | LYS | A | 340 | 27.014 | 9.017 | 21.127 | 1.00 | 40.34 | A | C |
| ATOM | 423 | NZ | LYS | A | 340 | 25.806 | 8.261 | 20.678 | 1.00 | 43.59 | A | N |
| ATOM | 424 | C | LYS | A | 340 | 28.437 | 15.051 | 22.425 | 1.00 | 16.65 | A | C |
| ATOM | 425 | O | LYS | A | 340 | 28.010 | 15.752 | 21.517 | 1.00 | 16.11 | A | O |
| ATOM | 426 | N | SER | A | 341 | 28.512 | 15.469 | 23.684 | 1.00 | 16.51 | A | N |
| ATOM | 427 | CA | SER | A | 341 | 28.101 | 16.817 | 24.058 | 1.00 | 13.10 | A | C |
| ATOM | 428 | CB | SER | A | 341 | 27.380 | 16.791 | 25.405 | 1.00 | 18.40 | A | C |
| ATOM | 429 | OG | SER | A | 341 | 28.309 | 16.806 | 26.473 | 1.00 | 17.08 | A | O |
| ATOM | 430 | C | SER | A | 341 | 29.264 | 17.815 | 24.102 | 1.00 | 13.99 | A | C |
| ATOM | 431 | O | SER | A | 341 | 29.082 | 18.974 | 24.473 | 1.00 | 13.97 | A | O |
| ATOM | 432 | N | ILE | A | 342 | 30.459 | 17.370 | 23.733 | 1.00 | 11.84 | A | N |
| ATOM | 433 | CA | ILE | A | 342 | 31.611 | 18.272 | 23.703 | 1.00 | 11.35 | A | C |
| ATOM | 434 | CB | ILE | A | 342 | 32.942 | 17.492 | 23.793 | 1.00 | 12.73 | A | C |

TABLE 6-continued

Coordinates for crystal structure of the complex of ERR-α and Compound 1

| ATOM | 435 | CG2 | ILE | A | 342 | 34.133 | 18.398 | 23.481 | 1.00 | 8.77 | A | C |
| --- | --- | --- | --- | --- | --- | --- | --- | --- | --- | --- | --- | --- |
| ATOM | 436 | CG1 | ILE | A | 342 | 33.085 | 16.849 | 25.177 | 1.00 | 10.78 | A | C |
| ATOM | 437 | CD1 | ILE | A | 342 | 33.057 | 17.843 | 26.338 | 1.00 | 8.36 | A | C |
| ATOM | 438 | C | ILE | A | 342 | 31.588 | 19.109 | 22.428 | 1.00 | 12.44 | A | C |
| ATOM | 439 | O | ILE | A | 342 | 31.644 | 18.560 | 21.326 | 1.00 | 12.27 | A | O |
| ATOM | 440 | N | PRO | A | 343 | 31.500 | 20.446 | 22.569 | 1.00 | 10.97 | A | N |
| ATOM | 441 | CD | PRO | A | 343 | 31.567 | 21.224 | 23.817 | 1.00 | 11.85 | A | C |
| ATOM | 442 | CA | PRO | A | 343 | 31.417 | 21.310 | 21.387 | 1.00 | 13.07 | A | C |
| ATOM | 443 | CB | PRO | A | 343 | 31.726 | 22.696 | 21.951 | 1.00 | 9.91 | A | C |
| ATOM | 444 | CG | PRO | A | 343 | 31.279 | 22.636 | 23.361 | 1.00 | 11.17 | A | C |
| ATOM | 445 | C | PRO | A | 343 | 32.465 | 20.925 | 20.350 | 1.00 | 13.44 | A | C |
| ATOM | 446 | O | PRO | A | 343 | 33.624 | 20.748 | 20.708 | 1.00 | 11.20 | A | O |
| ATOM | 447 | N | GLY | A | 344 | 32.057 | 20.779 | 19.094 | 1.00 | 12.03 | A | N |
| ATOM | 448 | CA | GLY | A | 344 | 32.991 | 20.523 | 18.015 | 1.00 | 15.36 | A | C |
| ATOM | 449 | C | GLY | A | 344 | 33.218 | 19.048 | 17.734 | 1.00 | 15.61 | A | C |
| ATOM | 450 | O | GLY | A | 344 | 33.613 | 18.681 | 16.633 | 1.00 | 19.51 | A | O |
| ATOM | 451 | N | PHE | A | 345 | 32.964 | 18.203 | 18.728 | 1.00 | 14.84 | A | N |
| ATOM | 452 | CA | PHE | A | 345 | 33.097 | 16.762 | 18.553 | 1.00 | 17.20 | A | C |
| ATOM | 453 | CB | PHE | A | 345 | 32.775 | 16.010 | 19.852 | 1.00 | 15.51 | A | C |
| ATOM | 454 | CG | PHE | A | 345 | 33.184 | 14.558 | 19.823 | 1.00 | 13.59 | A | C |
| ATOM | 455 | CD1 | PHE | A | 345 | 34.528 | 14.207 | 19.821 | 1.00 | 10.15 | A | C |
| ATOM | 456 | CD2 | PHE | A | 345 | 32.230 | 13.549 | 19.773 | 1.00 | 16.53 | A | C |
| ATOM | 457 | CE1 | PHE | A | 345 | 34.925 | 12.885 | 19.786 | 1.00 | 9.99 | A | C |
| ATOM | 458 | CE2 | PHE | A | 345 | 32.620 | 12.208 | 19.732 | 1.00 | 17.15 | A | C |
| ATOM | 459 | CZ | PHE | A | 345 | 33.973 | 11.882 | 19.734 | 1.00 | 11.80 | A | C |
| ATOM | 460 | C | PHE | A | 345 | 32.224 | 16.241 | 17.411 | 1.00 | 18.58 | A | C |
| ATOM | 461 | O | PHE | A | 345 | 32.676 | 15.432 | 16.591 | 1.00 | 17.81 | A | O |
| ATOM | 462 | N | SER | A | 346 | 30.983 | 16.720 | 17.356 | 1.00 | 16.25 | A | N |
| ATOM | 463 | CA | SER | A | 346 | 30.014 | 16.280 | 16.352 | 1.00 | 22.10 | A | C |
| ATOM | 464 | CB | SER | A | 346 | 28.613 | 16.774 | 16.717 | 1.00 | 18.82 | A | C |
| ATOM | 465 | OG | SER | A | 346 | 28.364 | 16.578 | 18.098 | 1.00 | 37.90 | A | O |
| ATOM | 466 | C | SER | A | 346 | 30.359 | 16.768 | 14.953 | 1.00 | 23.07 | A | C |
| ATOM | 467 | O | SER | A | 346 | 29.811 | 16.280 | 13.965 | 1.00 | 25.31 | A | O |
| ATOM | 468 | N | SER | A | 347 | 31.248 | 17.748 | 14.869 | 1.00 | 19.61 | A | N |
| ATOM | 469 | CA | SER | A | 347 | 31.689 | 18.245 | 13.574 | 1.00 | 25.27 | A | C |
| ATOM | 470 | CB | SER | A | 347 | 32.466 | 19.553 | 13.728 | 1.00 | 21.25 | A | C |
| ATOM | 471 | OG | SER | A | 347 | 31.626 | 20.577 | 14.238 | 1.00 | 30.98 | A | O |
| ATOM | 472 | C | SER | A | 347 | 32.540 | 17.202 | 12.853 | 1.00 | 25.20 | A | C |
| ATOM | 473 | O | SER | A | 347 | 32.556 | 17.149 | 11.622 | 1.00 | 25.78 | A | O |
| ATOM | 474 | N | LEU | A | 348 | 33.245 | 16.374 | 13.621 | 1.00 | 19.70 | A | N |
| ATOM | 475 | CA | LEU | A | 348 | 34.041 | 15.293 | 13.045 | 1.00 | 21.27 | A | C |
| ATOM | 476 | CB | LEU | A | 348 | 34.843 | 14.585 | 14.131 | 1.00 | 16.81 | A | C |
| ATOM | 477 | CG | LEU | A | 348 | 35.806 | 15.435 | 14.948 | 1.00 | 15.92 | A | C |
| ATOM | 478 | CD1 | LEU | A | 348 | 36.394 | 14.596 | 16.085 | 1.00 | 13.54 | A | C |
| ATOM | 479 | CD2 | LEU | A | 348 | 36.900 | 16.001 | 14.058 | 1.00 | 17.60 | A | C |
| ATOM | 480 | C | LEU | A | 348 | 33.146 | 14.275 | 12.334 | 1.00 | 19.87 | A | C |
| ATOM | 481 | O | LEU | A | 348 | 31.978 | 14.102 | 12.696 | 1.00 | 16.45 | A | O |
| ATOM | 482 | N | SER | A | 349 | 33.683 | 13.603 | 11.321 | 1.00 | 18.80 | A | N |
| ATOM | 483 | CA | SER | A | 349 | 32.906 | 12.557 | 10.664 | 1.00 | 21.86 | A | C |
| ATOM | 484 | CB | SER | A | 349 | 33.727 | 11.867 | 9.588 | 1.00 | 18.54 | A | C |
| ATOM | 485 | OG | SER | A | 349 | 34.814 | 11.173 | 10.177 | 1.00 | 20.71 | A | O |
| ATOM | 486 | C | SER | A | 349 | 32.511 | 11.541 | 11.717 | 1.00 | 21.03 | A | C |
| ATOM | 487 | O | SER | A | 349 | 33.231 | 11.345 | 12.701 | 1.00 | 18.54 | A | O |
| ATOM | 488 | N | LEU | A | 350 | 31.369 | 10.897 | 11.519 | 1.00 | 21.90 | A | N |
| ATOM | 489 | CA | LEU | A | 350 | 30.916 | 9.885 | 12.451 | 1.00 | 18.97 | A | C |
| ATOM | 490 | CB | LEU | A | 350 | 29.696 | 9.157 | 11.888 | 1.00 | 30.73 | A | C |
| ATOM | 491 | CG | LEU | A | 350 | 28.662 | 8.614 | 12.878 | 1.00 | 36.96 | A | C |
| ATOM | 492 | CD1 | LEU | A | 350 | 27.966 | 7.389 | 12.287 | 1.00 | 37.93 | A | C |
| ATOM | 493 | CD2 | LEU | A | 350 | 29.300 | 8.266 | 14.214 | 1.00 | 34.80 | A | C |
| ATOM | 494 | C | LEU | A | 350 | 32.052 | 8.895 | 12.687 | 1.00 | 21.31 | A | C |
| ATOM | 495 | O | LEU | A | 350 | 32.319 | 8.485 | 13.820 | 1.00 | 21.06 | A | O |
| ATOM | 496 | N | SER | A | 351 | 32.727 | 8.524 | 11.606 | 1.00 | 22.72 | A | N |
| ATOM | 497 | CA | SER | A | 351 | 33.810 | 7.554 | 11.675 | 1.00 | 22.26 | A | C |
| ATOM | 498 | CB | SER | A | 351 | 34.395 | 7.318 | 10.279 | 1.00 | 18.71 | A | C |
| ATOM | 499 | OG | SER | A | 351 | 35.400 | 6.319 | 10.318 | 1.00 | 27.66 | A | O |
| ATOM | 500 | C | SER | A | 351 | 34.909 | 8.020 | 12.633 | 1.00 | 21.66 | A | C |
| ATOM | 501 | O | SER | A | 351 | 35.372 | 7.257 | 13.487 | 1.00 | 22.40 | A | O |
| ATOM | 502 | N | ASP | A | 352 | 35.329 | 9.273 | 12.487 | 1.00 | 20.12 | A | N |
| ATOM | 503 | CA | ASP | A | 352 | 36.377 | 9.809 | 13.348 | 1.00 | 20.76 | A | C |
| ATOM | 504 | CB | ASP | A | 352 | 36.919 | 11.128 | 12.801 | 1.00 | 16.76 | A | C |
| ATOM | 505 | CG | ASP | A | 352 | 37.887 | 10.915 | 11.663 | 1.00 | 21.88 | A | C |
| ATOM | 506 | OD1 | ASP | A | 352 | 38.283 | 11.902 | 11.011 | 1.00 | 20.77 | A | O |
| ATOM | 507 | OD2 | ASP | A | 352 | 38.255 | 9.744 | 11.428 | 1.00 | 23.51 | A | O |
| ATOM | 508 | C | ASP | A | 352 | 35.920 | 9.957 | 14.794 | 1.00 | 17.01 | A | C |
| ATOM | 509 | O | ASP | A | 352 | 36.711 | 9.775 | 15.711 | 1.00 | 16.19 | A | O |
| ATOM | 510 | N | GLN | A | 353 | 34.646 | 10.278 | 15.000 | 1.00 | 16.91 | A | N |
| ATOM | 511 | CA | GLN | A | 353 | 34.130 | 10.387 | 16.359 | 1.00 | 15.73 | A | C |
| ATOM | 512 | CB | GLN | A | 353 | 32.641 | 10.740 | 16.362 | 1.00 | 13.27 | A | C |

TABLE 6-continued

Coordinates for crystal structure of the complex of ERR-α and Compound 1

| ATOM | 513 | CG | GLN | A | 353 | 32.348 | 12.177 | 15.972 | 1.00 | 15.41 | A | C |
|---|---|---|---|---|---|---|---|---|---|---|---|---|
| ATOM | 514 | CD | GLN | A | 353 | 30.863 | 12.462 | 15.838 | 1.00 | 21.44 | A | C |
| ATOM | 515 | OE1 | GLN | A | 353 | 30.071 | 12.178 | 16.740 | 1.00 | 21.89 | A | O |
| ATOM | 516 | NE2 | GLN | A | 353 | 30.482 | 13.041 | 14.710 | 1.00 | 18.96 | A | N |
| ATOM | 517 | C | GLN | A | 353 | 34.352 | 9.063 | 17.059 | 1.00 | 15.88 | A | C |
| ATOM | 518 | O | GLN | A | 353 | 34.815 | 9.015 | 18.199 | 1.00 | 12.23 | A | O |
| ATOM | 519 | N | MET | A | 354 | 34.036 | 7.983 | 16.355 | 1.00 | 14.37 | A | N |
| ATOM | 520 | CA | MET | A | 354 | 34.132 | 6.660 | 16.936 | 1.00 | 19.04 | A | C |
| ATOM | 521 | CB | MET | A | 354 | 33.385 | 5.632 | 16.080 | 1.00 | 20.68 | A | C |
| ATOM | 522 | CG | MET | A | 354 | 31.897 | 5.925 | 15.985 | 1.00 | 24.71 | A | C |
| ATOM | 523 | SD | MET | A | 354 | 30.898 | 4.500 | 15.531 | 1.00 | 38.54 | A | S |
| ATOM | 524 | CE | MET | A | 354 | 31.689 | 3.994 | 14.005 | 1.00 | 31.83 | A | C |
| ATOM | 525 | C | MET | A | 354 | 35.586 | 6.269 | 17.128 | 1.00 | 16.32 | A | C |
| ATOM | 526 | O | MET | A | 354 | 35.942 | 5.699 | 18.160 | 1.00 | 18.95 | A | O |
| ATOM | 527 | N | SER | A | 355 | 36.423 | 6.585 | 16.142 | 1.00 | 13.80 | A | N |
| ATOM | 528 | CA | SER | A | 355 | 37.845 | 6.277 | 16.223 | 1.00 | 15.36 | A | C |
| ATOM | 529 | CB | SER | A | 355 | 38.560 | 6.625 | 14.915 | 1.00 | 17.70 | A | C |
| ATOM | 530 | OG | SER | A | 355 | 38.448 | 5.579 | 13.968 | 1.00 | 22.38 | A | O |
| ATOM | 531 | C | SER | A | 355 | 38.501 | 7.024 | 17.381 | 1.00 | 17.93 | A | C |
| ATOM | 532 | O | SER | A | 355 | 39.274 | 6.442 | 18.140 | 1.00 | 12.93 | A | O |
| ATOM | 533 | N | VAL | A | 356 | 38.203 | 8.316 | 17.502 | 1.00 | 14.09 | A | N |
| ATOM | 534 | CA | VAL | A | 356 | 38.685 | 9.100 | 18.634 | 1.00 | 12.55 | A | C |
| ATOM | 535 | CB | VAL | A | 356 | 38.212 | 10.568 | 18.552 | 1.00 | 13.35 | A | C |
| ATOM | 536 | CG1 | VAL | A | 356 | 38.440 | 11.283 | 19.877 | 1.00 | 10.53 | A | C |
| ATOM | 537 | CG2 | VAL | A | 356 | 38.939 | 11.291 | 17.425 | 1.00 | 11.16 | A | C |
| ATOM | 538 | C | VAL | A | 356 | 38.239 | 8.459 | 19.956 | 1.00 | 14.87 | A | C |
| ATOM | 539 | O | VAL | A | 356 | 39.069 | 8.152 | 20.810 | 1.00 | 10.80 | A | O |
| ATOM | 540 | N | LEU | A | 357 | 36.935 | 8.227 | 20.110 | 1.00 | 10.72 | A | N |
| ATOM | 541 | CA | LEU | A | 357 | 36.415 | 7.661 | 21.351 | 1.00 | 12.32 | A | C |
| ATOM | 542 | CB | LEU | A | 357 | 34.893 | 7.520 | 21.308 | 1.00 | 12.78 | A | C |
| ATOM | 543 | CG | LEU | A | 357 | 34.108 | 8.645 | 21.976 | 1.00 | 11.28 | A | C |
| ATOM | 544 | CD1 | LEU | A | 357 | 32.621 | 8.466 | 21.750 | 1.00 | 18.76 | A | C |
| ATOM | 545 | CD2 | LEU | A | 357 | 34.411 | 8.681 | 23.453 | 1.00 | 9.57 | A | C |
| ATOM | 546 | C | LEU | A | 357 | 37.036 | 6.317 | 21.735 | 1.00 | 13.32 | A | C |
| ATOM | 547 | O | LEU | A | 357 | 37.326 | 6.085 | 22.907 | 1.00 | 11.76 | A | O |
| ATOM | 548 | N | GLN | A | 358 | 37.218 | 5.431 | 20.760 | 1.00 | 11.69 | A | N |
| ATOM | 549 | CA | GLN | A | 358 | 37.777 | 4.110 | 21.035 | 1.00 | 13.23 | A | C |
| ATOM | 550 | CB | GLN | A | 358 | 37.778 | 3.236 | 19.779 | 1.00 | 12.80 | A | C |
| ATOM | 551 | CG | GLN | A | 358 | 36.419 | 2.692 | 19.387 | 1.00 | 18.19 | A | C |
| ATOM | 552 | CD | GLN | A | 358 | 36.487 | 1.830 | 18.140 | 1.00 | 25.29 | A | C |
| ATOM | 553 | OE1 | GLN | A | 358 | 36.213 | 2.299 | 17.034 | 1.00 | 28.13 | A | O |
| ATOM | 554 | NE2 | GLN | A | 358 | 36.872 | 0.566 | 18.310 | 1.00 | 21.86 | A | N |
| ATOM | 555 | C | GLN | A | 358 | 39.191 | 4.186 | 21.580 | 1.00 | 12.85 | A | C |
| ATOM | 556 | O | GLN | A | 358 | 39.637 | 3.287 | 22.294 | 1.00 | 12.84 | A | O |
| ATOM | 557 | N | SER | A | 359 | 39.900 | 5.255 | 21.238 | 1.00 | 10.05 | A | N |
| ATOM | 558 | CA | SER | A | 359 | 41.311 | 5.370 | 21.601 | 1.00 | 12.66 | A | C |
| ATOM | 559 | CB | SER | A | 359 | 42.083 | 6.109 | 20.498 | 1.00 | 12.37 | A | C |
| ATOM | 560 | OG | SER | A | 359 | 41.674 | 7.476 | 20.416 | 1.00 | 15.00 | A | O |
| ATOM | 561 | C | SER | A | 359 | 41.571 | 6.040 | 22.960 | 1.00 | 11.14 | A | C |
| ATOM | 562 | O | SER | A | 359 | 42.627 | 5.833 | 23.558 | 1.00 | 14.86 | A | O |
| ATOM | 563 | N | VAL | A | 360 | 40.622 | 6.837 | 23.445 | 1.00 | 10.02 | A | N |
| ATOM | 564 | CA | VAL | A | 360 | 40.826 | 7.593 | 24.683 | 1.00 | 9.96 | A | C |
| ATOM | 565 | CB | VAL | A | 360 | 40.961 | 9.101 | 24.402 | 1.00 | 9.66 | A | C |
| ATOM | 566 | CG1 | VAL | A | 360 | 42.199 | 9.374 | 23.604 | 1.00 | 11.91 | A | C |
| ATOM | 567 | CG2 | VAL | A | 360 | 39.701 | 9.616 | 23.693 | 1.00 | 8.37 | A | C |
| ATOM | 568 | C | VAL | A | 360 | 39.721 | 7.445 | 25.728 | 1.00 | 7.98 | A | C |
| ATOM | 569 | O | VAL | A | 360 | 39.781 | 8.071 | 26.780 | 1.00 | 9.05 | A | O |
| ATOM | 570 | N | TRP | A | 361 | 38.702 | 6.643 | 25.458 | 1.00 | 6.77 | A | N |
| ATOM | 571 | CA | TRP | A | 361 | 37.628 | 6.538 | 26.434 | 1.00 | 11.30 | A | C |
| ATOM | 572 | CB | TRP | A | 361 | 36.540 | 5.553 | 25.989 | 1.00 | 9.72 | A | C |
| ATOM | 573 | CG | TRP | A | 361 | 36.968 | 4.123 | 25.981 | 1.00 | 9.75 | A | C |
| ATOM | 574 | CD2 | TRP | A | 361 | 36.840 | 3.183 | 27.055 | 1.00 | 9.74 | A | C |
| ATOM | 575 | CE2 | TRP | A | 361 | 37.364 | 1.958 | 26.604 | 1.00 | 9.82 | A | C |
| ATOM | 576 | CE3 | TRP | A | 361 | 36.320 | 3.261 | 28.353 | 1.00 | 11.35 | A | C |
| ATOM | 577 | CD1 | TRP | A | 361 | 37.548 | 3.449 | 24.950 | 1.00 | 12.73 | A | C |
| ATOM | 578 | NE1 | TRP | A | 361 | 37.797 | 2.144 | 25.317 | 1.00 | 10.44 | A | N |
| ATOM | 579 | CZ2 | TRP | A | 361 | 37.391 | 0.817 | 27.403 | 1.00 | 11.49 | A | C |
| ATOM | 580 | CZ3 | TRP | A | 361 | 36.344 | 2.125 | 29.145 | 1.00 | 13.49 | A | C |
| ATOM | 581 | CH2 | TRP | A | 361 | 36.876 | 0.921 | 28.666 | 1.00 | 11.95 | A | C |
| ATOM | 582 | C | TRP | A | 361 | 38.146 | 6.189 | 27.834 | 1.00 | 7.33 | A | C |
| ATOM | 583 | O | TRP | A | 361 | 37.613 | 6.674 | 28.830 | 1.00 | 8.33 | A | O |
| ATOM | 584 | N | MET | A | 362 | 39.183 | 5.364 | 27.914 | 1.00 | 6.24 | A | N |
| ATOM | 585 | CA | MET | A | 362 | 39.702 | 4.959 | 29.222 | 1.00 | 7.37 | A | C |
| ATOM | 586 | CB | MET | A | 362 | 40.655 | 3.756 | 29.121 | 1.00 | 7.77 | A | C |
| ATOM | 587 | CG | MET | A | 362 | 41.207 | 3.268 | 30.483 | 1.00 | 9.27 | A | C |
| ATOM | 588 | SD | MET | A | 362 | 39.931 | 2.656 | 31.630 | 1.00 | 10.13 | A | S |
| ATOM | 589 | CE | MET | A | 362 | 39.582 | 1.052 | 30.898 | 1.00 | 8.76 | A | C |
| ATOM | 590 | C | MET | A | 362 | 40.380 | 6.136 | 29.915 | 1.00 | 7.87 | A | C |

TABLE 6-continued

Coordinates for crystal structure of the complex of ERR-α and Compound 1

| ATOM | 591 | O   | MET | A | 362 | 40.265 | 6.291  | 31.131 | 1.00 | 8.80  | A | O |
|------|-----|-----|-----|---|-----|--------|--------|--------|------|-------|---|---|
| ATOM | 592 | N   | GLU | A | 363 | 41.073 | 6.965  | 29.135 | 1.00 | 6.62  | A | N |
| ATOM | 593 | CA  | GLU | A | 363 | 41.684 | 8.189  | 29.656 | 1.00 | 10.64 | A | C |
| ATOM | 594 | CB  | GLU | A | 363 | 42.429 | 8.949  | 28.549 | 1.00 | 6.65  | A | C |
| ATOM | 595 | CG  | GLU | A | 363 | 43.655 | 8.232  | 28.003 | 1.00 | 9.31  | A | C |
| ATOM | 596 | CD  | GLU | A | 363 | 44.474 | 9.106  | 27.056 | 1.00 | 14.27 | A | C |
| ATOM | 597 | OE1 | GLU | A | 363 | 45.155 | 8.533  | 26.175 | 1.00 | 13.30 | A | O |
| ATOM | 598 | OE2 | GLU | A | 363 | 44.439 | 10.357 | 27.186 | 1.00 | 10.35 | A | O |
| ATOM | 599 | C   | GLU | A | 363 | 40.630 | 9.106  | 30.281 | 1.00 | 6.33  | A | C |
| ATOM | 600 | O   | GLU | A | 363 | 40.801 | 9.623  | 31.389 | 1.00 | 5.31  | A | O |
| ATOM | 601 | N   | VAL | A | 364 | 39.548 | 9.332  | 29.551 | 1.00 | 5.93  | A | N |
| ATOM | 602 | CA  | VAL | A | 364 | 38.477 | 10.177 | 30.064 | 1.00 | 5.96  | A | C |
| ATOM | 603 | CB  | VAL | A | 364 | 37.344 | 10.308 | 29.028 | 1.00 | 6.40  | A | C |
| ATOM | 604 | CG1 | VAL | A | 364 | 36.125 | 10.998 | 29.644 | 1.00 | 6.59  | A | C |
| ATOM | 605 | CG2 | VAL | A | 364 | 37.847 | 11.058 | 27.775 | 1.00 | 7.12  | A | C |
| ATOM | 606 | C   | VAL | A | 364 | 37.941 | 9.589  | 31.381 | 1.00 | 7.64  | A | C |
| ATOM | 607 | O   | VAL | A | 364 | 37.817 | 10.284 | 32.400 | 1.00 | 7.59  | A | O |
| ATOM | 608 | N   | LEU | A | 365 | 37.636 | 8.300  | 31.351 | 1.00 | 6.22  | A | N |
| ATOM | 609 | CA  | LEU | A | 365 | 37.075 | 7.609  | 32.506 | 1.00 | 7.44  | A | C |
| ATOM | 610 | CB  | LEU | A | 365 | 36.830 | 6.139  | 32.150 | 1.00 | 8.63  | A | C |
| ATOM | 611 | CG  | LEU | A | 365 | 35.820 | 5.378  | 33.005 | 1.00 | 9.53  | A | C |
| ATOM | 612 | CD1 | LEU | A | 365 | 35.258 | 4.207  | 32.225 | 1.00 | 9.09  | A | C |
| ATOM | 613 | CD2 | LEU | A | 365 | 36.462 | 4.913  | 34.308 | 1.00 | 10.31 | A | C |
| ATOM | 614 | C   | LEU | A | 365 | 38.017 | 7.710  | 33.702 | 1.00 | 8.08  | A | C |
| ATOM | 615 | O   | LEU | A | 365 | 37.618 | 8.119  | 34.797 | 1.00 | 5.69  | A | O |
| ATOM | 616 | N   | VAL | A | 366 | 39.276 | 7.342  | 33.482 | 1.00 | 8.82  | A | N |
| ATOM | 617 | CA  | VAL | A | 366 | 40.279 | 7.382  | 34.538 | 1.00 | 6.69  | A | C |
| ATOM | 618 | CB  | VAL | A | 366 | 41.636 | 6.800  | 34.055 | 1.00 | 9.23  | A | C |
| ATOM | 619 | CG1 | VAL | A | 366 | 42.792 | 7.367  | 34.875 | 1.00 | 6.28  | A | C |
| ATOM | 620 | CG2 | VAL | A | 366 | 41.600 | 5.285  | 34.145 | 1.00 | 8.23  | A | C |
| ATOM | 621 | C   | VAL | A | 366 | 40.467 | 8.791  | 35.099 | 1.00 | 6.44  | A | C |
| ATOM | 622 | O   | VAL | A | 366 | 40.662 | 8.976  | 36.307 | 1.00 | 6.79  | A | O |
| ATOM | 623 | N   | LEU | A | 367 | 40.409 | 9.795  | 34.234 | 1.00 | 6.54  | A | N |
| ATOM | 624 | CA  | LEU | A | 367 | 40.563 | 11.167 | 34.720 | 1.00 | 8.51  | A | C |
| ATOM | 625 | CB  | LEU | A | 367 | 40.660 | 12.164 | 33.558 | 1.00 | 5.56  | A | C |
| ATOM | 626 | CG  | LEU | A | 367 | 40.932 | 13.612 | 33.982 | 1.00 | 8.69  | A | C |
| ATOM | 627 | CD1 | LEU | A | 367 | 42.249 | 13.685 | 34.727 | 1.00 | 3.58  | A | C |
| ATOM | 628 | CD2 | LEU | A | 367 | 40.947 | 14.545 | 32.763 | 1.00 | 7.76  | A | C |
| ATOM | 629 | C   | LEU | A | 367 | 39.405 | 11.527 | 35.667 | 1.00 | 6.52  | A | C |
| ATOM | 630 | O   | LEU | A | 367 | 39.588 | 12.243 | 36.643 | 1.00 | 7.03  | A | O |
| ATOM | 631 | N   | GLY | A | 368 | 38.215 | 11.026 | 35.375 | 1.00 | 4.77  | A | N |
| ATOM | 632 | CA  | GLY | A | 368 | 37.083 | 11.211 | 36.270 | 1.00 | 10.05 | A | C |
| ATOM | 633 | C   | GLY | A | 368 | 37.357 | 10.643 | 37.654 | 1.00 | 8.34  | A | C |
| ATOM | 634 | O   | GLY | A | 368 | 37.161 | 11.322 | 38.667 | 1.00 | 9.15  | A | O |
| ATOM | 635 | N   | VAL | A | 369 | 37.816 | 9.395  | 37.697 | 1.00 | 8.95  | A | N |
| ATOM | 636 | CA  | VAL | A | 369 | 38.204 | 8.743  | 38.959 | 1.00 | 9.48  | A | C |
| ATOM | 637 | CB  | VAL | A | 369 | 38.794 | 7.345  | 38.713 | 1.00 | 5.72  | A | C |
| ATOM | 638 | CG1 | VAL | A | 369 | 39.399 | 6.780  | 40.010 | 1.00 | 5.85  | A | C |
| ATOM | 639 | CG2 | VAL | A | 369 | 37.728 | 6.385  | 38.121 | 1.00 | 8.99  | A | C |
| ATOM | 640 | C   | VAL | A | 369 | 39.237 | 9.564  | 39.744 | 1.00 | 7.51  | A | C |
| ATOM | 641 | O   | VAL | A | 369 | 39.108 | 9.766  | 40.953 | 1.00 | 6.01  | A | O |
| ATOM | 642 | N   | ALA | A | 370 | 40.268 | 10.026 | 39.049 | 1.00 | 7.55  | A | N |
| ATOM | 643 | CA  | ALA | A | 370 | 41.318 | 10.818 | 39.689 | 1.00 | 6.33  | A | C |
| ATOM | 644 | CB  | ALA | A | 370 | 42.427 | 11.110 | 38.699 | 1.00 | 5.48  | A | C |
| ATOM | 645 | C   | ALA | A | 370 | 40.704 | 12.118 | 40.210 | 1.00 | 9.15  | A | C |
| ATOM | 646 | O   | ALA | A | 370 | 40.992 | 12.568 | 41.321 | 1.00 | 6.32  | A | O |
| ATOM | 647 | N   | GLN | A | 371 | 39.830 | 12.695 | 39.394 | 1.00 | 8.46  | A | N |
| ATOM | 648 | CA  | GLN | A | 371 | 39.153 | 13.936 | 39.721 | 1.00 | 9.76  | A | C |
| ATOM | 649 | CB  | GLN | A | 371 | 38.249 | 14.342 | 38.544 | 1.00 | 11.97 | A | C |
| ATOM | 650 | CG  | GLN | A | 371 | 36.838 | 14.762 | 38.941 | 1.00 | 21.47 | A | C |
| ATOM | 651 | CD  | GLN | A | 371 | 36.865 | 16.064 | 39.645 | 1.00 | 20.86 | A | C |
| ATOM | 652 | OE1 | GLN | A | 371 | 37.842 | 16.799 | 39.527 | 1.00 | 30.40 | A | O |
| ATOM | 653 | NE2 | GLN | A | 371 | 35.812 | 16.372 | 40.394 | 1.00 | 24.96 | A | N |
| ATOM | 654 | C   | GLN | A | 371 | 38.361 | 13.805 | 41.027 | 1.00 | 10.44 | A | C |
| ATOM | 655 | O   | GLN | A | 371 | 38.427 | 14.670 | 41.897 | 1.00 | 10.03 | A | O |
| ATOM | 656 | N   | ARG | A | 372 | 37.611 | 12.718 | 41.173 | 1.00 | 9.65  | A | N |
| ATOM | 657 | CA  | ARG | A | 372 | 36.831 | 12.524 | 42.397 | 1.00 | 11.43 | A | C |
| ATOM | 658 | CB  | ARG | A | 372 | 35.792 | 11.410 | 42.217 | 1.00 | 10.17 | A | C |
| ATOM | 659 | CG  | ARG | A | 372 | 34.853 | 11.627 | 41.045 | 1.00 | 7.35  | A | C |
| ATOM | 660 | CD  | ARG | A | 372 | 33.726 | 10.590 | 41.008 | 1.00 | 10.71 | A | C |
| ATOM | 661 | NE  | ARG | A | 372 | 34.136 | 9.296  | 40.466 | 1.00 | 9.30  | A | N |
| ATOM | 662 | CZ  | ARG | A | 372 | 34.323 | 9.048  | 39.169 | 1.00 | 14.09 | A | C |
| ATOM | 663 | NH1 | ARG | A | 372 | 34.162 | 10.017 | 38.266 | 1.00 | 9.78  | A | N |
| ATOM | 664 | NH2 | ARG | A | 372 | 34.678 | 7.828  | 38.766 | 1.00 | 11.35 | A | N |
| ATOM | 665 | C   | ARG | A | 372 | 37.726 | 12.229 | 43.610 | 1.00 | 11.57 | A | C |
| ATOM | 666 | O   | ARG | A | 372 | 37.304 | 12.384 | 44.753 | 1.00 | 10.98 | A | O |
| ATOM | 667 | N   | SER | A | 373 | 38.965 | 11.818 | 43.357 | 1.00 | 6.73  | A | N |
| ATOM | 668 | CA  | SER | A | 373 | 39.870 | 11.431 | 44.433 | 1.00 | 8.65  | A | C |

TABLE 6-continued

Coordinates for crystal structure of the complex of ERR-α and Compound 1

| ATOM | 669 | CB | SER | A | 373 | 40.807 | 10.302 | 43.969 | 1.00 | 10.24 | A | C |
|---|---|---|---|---|---|---|---|---|---|---|---|---|
| ATOM | 670 | OG | SER | A | 373 | 40.073 | 9.218 | 43.415 | 1.00 | 9.92 | A | O |
| ATOM | 671 | C | SER | A | 373 | 40.697 | 12.597 | 44.973 | 1.00 | 9.36 | A | C |
| ATOM | 672 | O | SER | A | 373 | 41.357 | 12.465 | 46.010 | 1.00 | 8.35 | A | O |
| ATOM | 673 | N | LEU | A | 374 | 40.663 | 13.738 | 44.283 | 1.00 | 9.32 | A | N |
| ATOM | 674 | CA | LEU | A | 374 | 41.542 | 14.853 | 44.649 | 1.00 | 10.69 | A | C |
| ATOM | 675 | CB | LEU | A | 374 | 41.402 | 16.046 | 43.684 | 1.00 | 10.73 | A | C |
| ATOM | 676 | CG | LEU | A | 374 | 41.741 | 15.856 | 42.195 | 1.00 | 10.64 | A | C |
| ATOM | 677 | CD1 | LEU | A | 374 | 41.658 | 17.182 | 41.464 | 1.00 | 9.35 | A | C |
| ATOM | 678 | CD2 | LEU | A | 374 | 43.107 | 15.230 | 41.985 | 1.00 | 9.59 | A | C |
| ATOM | 679 | C | LEU | A | 374 | 41.424 | 15.321 | 46.110 | 1.00 | 8.24 | A | C |
| ATOM | 680 | O | LEU | A | 374 | 42.433 | 15.642 | 46.721 | 1.00 | 9.80 | A | O |
| ATOM | 681 | N | PRO | A | 375 | 40.203 | 15.379 | 46.668 | 1.00 | 8.86 | A | N |
| ATOM | 682 | CD | PRO | A | 375 | 38.887 | 15.308 | 46.014 | 1.00 | 14.08 | A | C |
| ATOM | 683 | CA | PRO | A | 375 | 40.105 | 15.902 | 48.043 | 1.00 | 13.75 | A | C |
| ATOM | 684 | CB | PRO | A | 375 | 38.609 | 16.215 | 48.207 | 1.00 | 14.41 | A | C |
| ATOM | 685 | CG | PRO | A | 375 | 38.065 | 16.291 | 46.810 | 1.00 | 17.04 | A | C |
| ATOM | 686 | C | PRO | A | 375 | 40.542 | 14.898 | 49.106 | 1.00 | 14.57 | A | C |
| ATOM | 687 | O | PRO | A | 375 | 40.662 | 15.248 | 50.286 | 1.00 | 11.98 | A | O |
| ATOM | 688 | N | LEU | A | 376 | 40.797 | 13.666 | 48.687 | 1.00 | 11.24 | A | N |
| ATOM | 689 | CA | LEU | A | 376 | 41.072 | 12.597 | 49.627 | 1.00 | 10.05 | A | C |
| ATOM | 690 | CB | LEU | A | 376 | 40.369 | 11.310 | 49.175 | 1.00 | 11.85 | A | C |
| ATOM | 691 | CG | LEU | A | 376 | 38.855 | 11.445 | 48.930 | 1.00 | 13.18 | A | C |
| ATOM | 692 | CD1 | LEU | A | 376 | 38.250 | 10.148 | 48.377 | 1.00 | 11.14 | A | C |
| ATOM | 693 | CD2 | LEU | A | 376 | 38.122 | 11.868 | 50.205 | 1.00 | 9.73 | A | C |
| ATOM | 694 | C | LEU | A | 376 | 42.578 | 12.397 | 49.740 | 1.00 | 14.10 | A | C |
| ATOM | 695 | O | LEU | A | 376 | 43.341 | 12.984 | 48.982 | 1.00 | 12.26 | A | O |
| ATOM | 696 | N | GLN | A | 377 | 43.007 | 11.594 | 50.706 | 1.00 | 14.87 | A | N |
| ATOM | 697 | CA | GLN | A | 377 | 44.416 | 11.276 | 50.833 | 1.00 | 16.83 | A | C |
| ATOM | 698 | CB | GLN | A | 377 | 44.982 | 11.782 | 52.160 | 1.00 | 24.46 | A | C |
| ATOM | 699 | CG | GLN | A | 377 | 46.275 | 11.063 | 52.563 | 1.00 | 33.92 | A | C |
| ATOM | 700 | CD | GLN | A | 377 | 47.085 | 11.817 | 53.618 | 1.00 | 54.60 | A | C |
| ATOM | 701 | OE1 | GLN | A | 377 | 47.531 | 11.237 | 54.614 | 1.00 | 48.37 | A | O |
| ATOM | 702 | NE2 | GLN | A | 377 | 47.281 | 13.116 | 53.397 | 1.00 | 60.36 | A | N |
| ATOM | 703 | C | GLN | A | 377 | 44.637 | 9.776 | 50.700 | 1.00 | 15.47 | A | C |
| ATOM | 704 | O | GLN | A | 377 | 44.196 | 8.996 | 51.539 | 1.00 | 15.74 | A | O |
| ATOM | 705 | N | ASP | A | 378 | 45.316 | 9.384 | 49.628 | 1.00 | 15.96 | A | N |
| ATOM | 706 | CA | ASP | A | 378 | 45.640 | 7.982 | 49.382 | 1.00 | 19.65 | A | C |
| ATOM | 707 | CB | ASP | A | 378 | 46.539 | 7.443 | 50.485 | 1.00 | 14.84 | A | C |
| ATOM | 708 | CG | ASP | A | 378 | 47.819 | 8.233 | 50.614 | 1.00 | 20.81 | A | C |
| ATOM | 709 | OD1 | ASP | A | 378 | 48.295 | 8.436 | 51.751 | 1.00 | 28.90 | A | O |
| ATOM | 710 | OD2 | ASP | A | 378 | 48.344 | 8.669 | 49.574 | 1.00 | 22.14 | A | O |
| ATOM | 711 | C | ASP | A | 378 | 44.386 | 7.132 | 49.262 | 1.00 | 14.53 | A | C |
| ATOM | 712 | O | ASP | A | 378 | 44.368 | 5.974 | 49.665 | 1.00 | 16.70 | A | O |
| ATOM | 713 | N | GLU | A | 379 | 43.340 | 7.724 | 48.705 | 1.00 | 13.21 | A | N |
| ATOM | 714 | CA | GLU | A | 379 | 42.102 | 7.009 | 48.482 | 1.00 | 12.77 | A | C |
| ATOM | 715 | CB | GLU | A | 379 | 41.055 | 7.413 | 49.514 | 1.00 | 12.81 | A | C |
| ATOM | 716 | CG | GLU | A | 379 | 41.411 | 7.010 | 50.937 | 1.00 | 20.07 | A | C |
| ATOM | 717 | CD | GLU | A | 379 | 40.271 | 7.258 | 51.907 | 1.00 | 20.55 | A | C |
| ATOM | 718 | OE1 | GLU | A | 379 | 39.800 | 8.412 | 52.001 | 1.00 | 19.77 | A | O |
| ATOM | 719 | OE2 | GLU | A | 379 | 39.841 | 6.292 | 52.570 | 1.00 | 30.93 | A | O |
| ATOM | 720 | C | GLU | A | 379 | 41.587 | 7.303 | 47.092 | 1.00 | 13.51 | A | C |
| ATOM | 721 | O | GLU | A | 379 | 41.897 | 8.344 | 46.510 | 1.00 | 12.64 | A | O |
| ATOM | 722 | N | LEU | A | 380 | 40.786 | 6.379 | 46.578 | 1.00 | 14.16 | A | N |
| ATOM | 723 | CA | LEU | A | 380 | 40.207 | 6.486 | 45.251 | 1.00 | 11.49 | A | C |
| ATOM | 724 | CB | LEU | A | 380 | 40.681 | 5.314 | 44.388 | 1.00 | 13.39 | A | C |
| ATOM | 725 | CG | LEU | A | 380 | 42.194 | 5.232 | 44.123 | 1.00 | 8.17 | A | C |
| ATOM | 726 | CD1 | LEU | A | 380 | 42.589 | 3.869 | 43.547 | 1.00 | 9.15 | A | C |
| ATOM | 727 | CD2 | LEU | A | 380 | 42.647 | 6.373 | 43.205 | 1.00 | 6.52 | A | C |
| ATOM | 728 | C | LEU | A | 380 | 38.682 | 6.488 | 45.367 | 1.00 | 14.12 | A | C |
| ATOM | 729 | O | LEU | A | 380 | 38.086 | 5.537 | 45.882 | 1.00 | 10.80 | A | O |
| ATOM | 730 | N | ALA | A | 381 | 38.062 | 7.575 | 44.910 | 1.00 | 11.42 | A | N |
| ATOM | 731 | CA | ALA | A | 381 | 36.608 | 7.705 | 44.926 | 1.00 | 11.52 | A | C |
| ATOM | 732 | CB | ALA | A | 381 | 36.194 | 9.155 | 45.184 | 1.00 | 6.66 | A | C |
| ATOM | 733 | C | ALA | A | 381 | 36.053 | 7.231 | 43.601 | 1.00 | 9.79 | A | C |
| ATOM | 734 | O | ALA | A | 381 | 35.817 | 8.023 | 42.682 | 1.00 | 9.06 | A | O |
| ATOM | 735 | N | PHE | A | 382 | 35.869 | 5.928 | 43.492 | 1.00 | 10.68 | A | N |
| ATOM | 736 | CA | PHE | A | 382 | 35.320 | 5.356 | 42.276 | 1.00 | 12.09 | A | C |
| ATOM | 737 | CB | PHE | A | 382 | 35.382 | 3.826 | 42.332 | 1.00 | 10.44 | A | C |
| ATOM | 738 | CG | PHE | A | 382 | 36.769 | 3.279 | 42.138 | 1.00 | 11.39 | A | C |
| ATOM | 739 | CD1 | PHE | A | 382 | 37.560 | 2.945 | 43.230 | 1.00 | 10.96 | A | C |
| ATOM | 740 | CD2 | PHE | A | 382 | 37.295 | 3.133 | 40.867 | 1.00 | 10.93 | A | C |
| ATOM | 741 | CE1 | PHE | A | 382 | 38.843 | 2.444 | 43.054 | 1.00 | 13.01 | A | C |
| ATOM | 742 | CE2 | PHE | A | 382 | 38.584 | 2.637 | 40.677 | 1.00 | 12.78 | A | C |
| ATOM | 743 | CZ | PHE | A | 382 | 39.360 | 2.293 | 41.771 | 1.00 | 12.04 | A | C |
| ATOM | 744 | C | PHE | A | 382 | 33.907 | 5.870 | 42.048 | 1.00 | 11.39 | A | C |
| ATOM | 745 | O | PHE | A | 382 | 33.460 | 5.984 | 40.912 | 1.00 | 10.81 | A | O |
| ATOM | 746 | N | ALA | A | 383 | 33.223 | 6.200 | 43.144 | 1.00 | 10.40 | A | N |

TABLE 6-continued

Coordinates for crystal structure of the complex of ERR-α and Compound 1

| ATOM | 747 | CA | ALA | A | 383 | 31.893 | 6.791 | 43.090 | 1.00 | 17.44 | A | C |
|---|---|---|---|---|---|---|---|---|---|---|---|---|
| ATOM | 748 | CB | ALA | A | 383 | 30.828 | 5.728 | 42.837 | 1.00 | 16.71 | A | C |
| ATOM | 749 | C | ALA | A | 383 | 31.629 | 7.510 | 44.401 | 1.00 | 17.54 | A | C |
| ATOM | 750 | O | ALA | A | 383 | 32.380 | 7.349 | 45.362 | 1.00 | 15.38 | A | O |
| ATOM | 751 | N | GLU | A | 384 | 30.561 | 8.302 | 44.433 | 1.00 | 23.55 | A | N |
| ATOM | 752 | CA | GLU | A | 384 | 30.194 | 9.043 | 45.637 | 1.00 | 30.68 | A | C |
| ATOM | 753 | CB | GLU | A | 384 | 28.766 | 9.588 | 45.507 | 1.00 | 36.59 | A | C |
| ATOM | 754 | CG | GLU | A | 384 | 28.405 | 10.665 | 46.521 | 1.00 | 41.29 | A | C |
| ATOM | 755 | CD | GLU | A | 384 | 29.191 | 11.950 | 46.313 | 1.00 | 51.97 | A | C |
| ATOM | 756 | OE1 | GLU | A | 384 | 29.494 | 12.288 | 45.145 | 1.00 | 51.70 | A | O |
| ATOM | 757 | OE2 | GLU | A | 384 | 29.505 | 12.622 | 47.319 | 1.00 | 45.08 | A | O |
| ATOM | 758 | C | GLU | A | 384 | 30.310 | 8.147 | 46.872 | 1.00 | 27.66 | A | C |
| ATOM | 759 | O | GLU | A | 384 | 30.874 | 8.542 | 47.891 | 1.00 | 30.68 | A | O |
| ATOM | 760 | N | ASP | A | 385 | 29.808 | 6.924 | 46.748 | 1.00 | 24.97 | A | N |
| ATOM | 761 | CA | ASP | A | 385 | 29.681 | 6.007 | 47.873 | 1.00 | 22.29 | A | C |
| ATOM | 762 | CB | ASP | A | 385 | 28.237 | 5.513 | 47.949 | 1.00 | 28.50 | A | C |
| ATOM | 763 | CG | ASP | A | 385 | 27.782 | 4.867 | 46.654 | 1.00 | 28.92 | A | C |
| ATOM | 764 | OD1 | ASP | A | 385 | 26.674 | 4.293 | 46.625 | 1.00 | 31.32 | A | O |
| ATOM | 765 | OD2 | ASP | A | 385 | 28.540 | 4.938 | 45.658 | 1.00 | 23.99 | A | O |
| ATOM | 766 | C | ASP | A | 385 | 30.595 | 4.794 | 47.748 | 1.00 | 25.57 | A | C |
| ATOM | 767 | O | ASP | A | 385 | 30.310 | 3.739 | 48.311 | 1.00 | 26.40 | A | O |
| ATOM | 768 | N | LEU | A | 386 | 31.686 | 4.927 | 47.005 | 1.00 | 21.78 | A | N |
| ATOM | 769 | CA | LEU | A | 386 | 32.617 | 3.820 | 46.859 | 1.00 | 19.10 | A | C |
| ATOM | 770 | CB | LEU | A | 386 | 32.269 | 2.984 | 45.624 | 1.00 | 17.20 | A | C |
| ATOM | 771 | CG | LEU | A | 386 | 33.230 | 1.865 | 45.204 | 1.00 | 24.05 | A | C |
| ATOM | 772 | CD1 | LEU | A | 386 | 33.784 | 1.113 | 46.396 | 1.00 | 21.63 | A | C |
| ATOM | 773 | CD2 | LEU | A | 386 | 32.560 | 0.908 | 44.215 | 1.00 | 20.24 | A | C |
| ATOM | 774 | C | LEU | A | 386 | 34.045 | 4.351 | 46.810 | 1.00 | 18.71 | A | C |
| ATOM | 775 | O | LEU | A | 386 | 34.524 | 4.809 | 45.772 | 1.00 | 12.82 | A | O |
| ATOM | 776 | N | VAL | A | 387 | 34.703 | 4.299 | 47.960 | 1.00 | 17.48 | A | N |
| ATOM | 777 | CA | VAL | A | 387 | 36.012 | 4.904 | 48.153 | 1.00 | 15.69 | A | C |
| ATOM | 778 | CB | VAL | A | 387 | 35.944 | 6.009 | 49.215 | 1.00 | 16.36 | A | C |
| ATOM | 779 | CG1 | VAL | A | 387 | 37.351 | 6.457 | 49.605 | 1.00 | 16.49 | A | C |
| ATOM | 780 | CG2 | VAL | A | 387 | 35.077 | 7.178 | 48.734 | 1.00 | 16.54 | A | C |
| ATOM | 781 | C | VAL | A | 387 | 36.943 | 3.839 | 48.683 | 1.00 | 15.82 | A | C |
| ATOM | 782 | O | VAL | A | 387 | 36.677 | 3.260 | 49.735 | 1.00 | 19.22 | A | O |
| ATOM | 783 | N | LEU | A | 388 | 38.029 | 3.577 | 47.963 | 1.00 | 15.55 | A | N |
| ATOM | 784 | CA | LEU | A | 388 | 38.949 | 2.501 | 48.318 | 1.00 | 15.32 | A | C |
| ATOM | 785 | CB | LEU | A | 388 | 38.951 | 1.439 | 47.222 | 1.00 | 13.11 | A | C |
| ATOM | 786 | CG | LEU | A | 388 | 37.621 | 0.784 | 46.870 | 1.00 | 14.26 | A | C |
| ATOM | 787 | CD1 | LEU | A | 388 | 37.802 | −0.144 | 45.667 | 1.00 | 14.40 | A | C |
| ATOM | 788 | CD2 | LEU | A | 388 | 37.074 | 0.023 | 48.078 | 1.00 | 15.81 | A | C |
| ATOM | 789 | C | LEU | A | 388 | 40.371 | 3.016 | 48.479 | 1.00 | 17.45 | A | C |
| ATOM | 790 | O | LEU | A | 388 | 40.804 | 3.883 | 47.722 | 1.00 | 15.60 | A | O |
| ATOM | 791 | N | ASP | A | 389 | 41.095 | 2.485 | 49.462 | 1.00 | 14.27 | A | N |
| ATOM | 792 | CA | ASP | A | 389 | 42.524 | 2.740 | 49.552 | 1.00 | 15.01 | A | C |
| ATOM | 793 | CB | ASP | A | 389 | 43.023 | 2.770 | 51.007 | 1.00 | 15.97 | A | C |
| ATOM | 794 | CG | ASP | A | 389 | 42.771 | 1.461 | 51.762 | 1.00 | 22.33 | A | C |
| ATOM | 795 | OD1 | ASP | A | 389 | 43.057 | 1.432 | 52.979 | 1.00 | 23.29 | A | O |
| ATOM | 796 | OD2 | ASP | A | 389 | 42.291 | 0.469 | 51.165 | 1.00 | 19.43 | A | O |
| ATOM | 797 | C | ASP | A | 389 | 43.231 | 1.676 | 48.730 | 1.00 | 14.30 | A | C |
| ATOM | 798 | O | ASP | A | 389 | 42.579 | 0.846 | 48.097 | 1.00 | 16.58 | A | O |
| ATOM | 799 | N | GLU | A | 390 | 44.553 | 1.698 | 48.726 | 1.00 | 15.09 | A | N |
| ATOM | 800 | CA | GLU | A | 390 | 45.310 | 0.770 | 47.895 | 1.00 | 16.00 | A | C |
| ATOM | 801 | CB | GLU | A | 390 | 46.806 | 0.987 | 48.094 | 1.00 | 18.13 | A | C |
| ATOM | 802 | CG | GLU | A | 390 | 47.643 | 0.358 | 47.027 | 1.00 | 22.46 | A | C |
| ATOM | 803 | CD | GLU | A | 390 | 49.077 | 0.826 | 47.065 | 1.00 | 27.40 | A | C |
| ATOM | 804 | OE1 | GLU | A | 390 | 49.333 | 1.960 | 47.543 | 1.00 | 28.62 | A | O |
| ATOM | 805 | OE2 | GLU | A | 390 | 49.944 | 0.055 | 46.604 | 1.00 | 27.35 | A | O |
| ATOM | 806 | C | GLU | A | 390 | 44.941 | −0.688 | 48.183 | 1.00 | 21.66 | A | C |
| ATOM | 807 | O | GLU | A | 390 | 44.725 | −1.478 | 47.260 | 1.00 | 20.71 | A | O |
| ATOM | 808 | N | GLU | A | 391 | 44.861 | −1.037 | 49.464 | 1.00 | 19.04 | A | N |
| ATOM | 809 | CA | GLU | A | 391 | 44.582 | −2.411 | 49.859 | 1.00 | 24.03 | A | C |
| ATOM | 810 | CB | GLU | A | 391 | 44.797 | −2.592 | 51.359 | 1.00 | 27.75 | A | C |
| ATOM | 811 | CG | GLU | A | 391 | 46.261 | −2.509 | 51.758 | 1.00 | 38.64 | A | C |
| ATOM | 812 | CD | GLU | A | 391 | 46.483 | −2.757 | 53.241 | 1.00 | 57.74 | A | C |
| ATOM | 813 | OE1 | GLU | A | 391 | 45.488 | −2.768 | 54.003 | 1.00 | 48.08 | A | O |
| ATOM | 814 | OE2 | GLU | A | 391 | 47.659 | −2.940 | 53.638 | 1.00 | 53.93 | A | O |
| ATOM | 815 | C | GLU | A | 391 | 43.177 | −2.833 | 49.481 | 1.00 | 20.44 | A | C |
| ATOM | 816 | O | GLU | A | 391 | 42.947 | −3.981 | 49.100 | 1.00 | 19.46 | A | O |
| ATOM | 817 | N | GLY | A | 392 | 42.240 | −1.900 | 49.592 | 1.00 | 15.59 | A | N |
| ATOM | 818 | CA | GLY | A | 392 | 40.868 | −2.148 | 49.198 | 1.00 | 18.72 | A | C |
| ATOM | 819 | C | GLY | A | 392 | 40.736 | −2.367 | 47.699 | 1.00 | 16.46 | A | C |
| ATOM | 820 | O | GLY | A | 392 | 39.908 | −3.167 | 47.257 | 1.00 | 13.18 | A | O |
| ATOM | 821 | N | ALA | A | 393 | 41.542 | −1.656 | 46.912 | 1.00 | 13.40 | A | N |
| ATOM | 822 | CA | ALA | A | 393 | 41.533 | −1.835 | 45.461 | 1.00 | 12.07 | A | C |
| ATOM | 823 | CB | ALA | A | 393 | 42.354 | −0.746 | 44.771 | 1.00 | 12.61 | A | C |
| ATOM | 824 | C | ALA | A | 393 | 42.075 | −3.215 | 45.109 | 1.00 | 14.92 | A | C |

TABLE 6-continued

Coordinates for crystal structure of the complex of ERR-α and Compound 1

| ATOM | 825 | O | ALA | A | 393 | 41.496 | −3.938 | 44.297 | 1.00 | 12.11 | A | O |
|---|---|---|---|---|---|---|---|---|---|---|---|---|
| ATOM | 826 | N | ARG | A | 394 | 43.189 | −3.568 | 45.735 | 1.00 | 11.42 | A | N |
| ATOM | 827 | CA | ARG | A | 394 | 43.808 | −4.863 | 45.531 | 1.00 | 15.97 | A | C |
| ATOM | 828 | CB | ARG | A | 394 | 45.048 | −4.967 | 46.421 | 1.00 | 17.24 | A | C |
| ATOM | 829 | CG | ARG | A | 394 | 46.048 | −6.024 | 46.019 | 1.00 | 25.58 | A | C |
| ATOM | 830 | CD | ARG | A | 394 | 47.479 | −5.481 | 46.137 | 1.00 | 29.11 | A | C |
| ATOM | 831 | NE | ARG | A | 394 | 47.679 | −4.667 | 47.336 | 1.00 | 27.07 | A | N |
| ATOM | 832 | CZ | ARG | A | 394 | 48.580 | −3.691 | 47.427 | 1.00 | 33.82 | A | C |
| ATOM | 833 | NH1 | ARG | A | 394 | 49.349 | −3.399 | 46.385 | 1.00 | 34.86 | A | N |
| ATOM | 834 | NH2 | ARG | A | 394 | 48.706 | −2.995 | 48.553 | 1.00 | 29.51 | A | N |
| ATOM | 835 | C | ARG | A | 394 | 42.798 | −5.969 | 45.848 | 1.00 | 16.73 | A | C |
| ATOM | 836 | O | ARG | A | 394 | 42.657 | −6.933 | 45.099 | 1.00 | 18.65 | A | O |
| ATOM | 837 | N | ALA | A | 395 | 42.074 | −5.807 | 46.947 | 1.00 | 14.18 | A | N |
| ATOM | 838 | CA | ALA | A | 395 | 41.106 | −6.812 | 47.372 | 1.00 | 16.13 | A | C |
| ATOM | 839 | CB | ALA | A | 395 | 40.716 | −6.597 | 48.845 | 1.00 | 12.32 | A | C |
| ATOM | 840 | C | ALA | A | 395 | 39.871 | −6.799 | 46.480 | 1.00 | 19.06 | A | C |
| ATOM | 841 | O | ALA | A | 395 | 39.083 | −7.750 | 46.481 | 1.00 | 16.59 | A | O |
| ATOM | 842 | N | ALA | A | 396 | 39.702 | −5.725 | 45.710 | 1.00 | 14.54 | A | N |
| ATOM | 843 | CA | ALA | A | 396 | 38.552 | −5.624 | 44.812 | 1.00 | 12.53 | A | C |
| ATOM | 844 | CB | ALA | A | 396 | 37.994 | −4.197 | 44.802 | 1.00 | 15.65 | A | C |
| ATOM | 845 | C | ALA | A | 396 | 38.891 | −6.081 | 43.394 | 1.00 | 13.40 | A | C |
| ATOM | 846 | O | ALA | A | 396 | 38.122 | −5.859 | 42.465 | 1.00 | 18.31 | A | O |
| ATOM | 847 | N | GLY | A | 397 | 40.049 | −6.708 | 43.235 | 1.00 | 14.85 | A | N |
| ATOM | 848 | CA | GLY | A | 397 | 40.434 | −7.296 | 41.965 | 1.00 | 14.90 | A | C |
| ATOM | 849 | C | GLY | A | 397 | 41.245 | −6.398 | 41.037 | 1.00 | 17.60 | A | C |
| ATOM | 850 | O | GLY | A | 397 | 41.512 | −6.772 | 39.897 | 1.00 | 16.08 | A | O |
| ATOM | 851 | N | LEU | A | 398 | 41.654 | −5.229 | 41.527 | 1.00 | 15.81 | A | N |
| ATOM | 852 | CA | LEU | A | 398 | 42.314 | −4.220 | 40.690 | 1.00 | 14.58 | A | C |
| ATOM | 853 | CB | LEU | A | 398 | 41.949 | −2.815 | 41.184 | 1.00 | 10.85 | A | C |
| ATOM | 854 | CG | LEU | A | 398 | 40.461 | −2.478 | 41.075 | 1.00 | 9.27 | A | C |
| ATOM | 855 | CD1 | LEU | A | 398 | 40.122 | −1.134 | 41.713 | 1.00 | 10.67 | A | C |
| ATOM | 856 | CD2 | LEU | A | 398 | 40.066 | −2.479 | 39.620 | 1.00 | 14.03 | A | C |
| ATOM | 857 | C | LEU | A | 398 | 43.837 | −4.377 | 40.629 | 1.00 | 16.08 | A | C |
| ATOM | 858 | O | LEU | A | 398 | 44.545 | −3.537 | 40.046 | 1.00 | 14.37 | A | O |
| ATOM | 859 | N | GLY | A | 399 | 44.339 | −5.445 | 41.234 | 1.00 | 12.30 | A | N |
| ATOM | 860 | CA | GLY | A | 399 | 45.766 | −5.699 | 41.253 | 1.00 | 11.79 | A | C |
| ATOM | 861 | C | GLY | A | 399 | 46.505 | −4.499 | 41.804 | 1.00 | 14.14 | A | C |
| ATOM | 862 | O | GLY | A | 399 | 46.197 | −4.021 | 42.899 | 1.00 | 15.51 | A | O |
| ATOM | 863 | N | GLU | A | 400 | 47.465 | −3.996 | 41.037 | 1.00 | 12.60 | A | N |
| ATOM | 864 | CA | GLU | A | 400 | 48.245 | −2.836 | 41.455 | 1.00 | 13.99 | A | C |
| ATOM | 865 | CB | GLU | A | 400 | 49.720 | −3.026 | 41.096 | 1.00 | 17.29 | A | C |
| ATOM | 866 | CG | GLU | A | 400 | 50.402 | −4.170 | 41.847 | 1.00 | 23.15 | A | C |
| ATOM | 867 | CD | GLU | A | 400 | 50.218 | −4.061 | 43.350 | 1.00 | 25.72 | A | C |
| ATOM | 868 | OE1 | GLU | A | 400 | 49.736 | −5.038 | 43.959 | 1.00 | 31.69 | A | O |
| ATOM | 869 | OE2 | GLU | A | 400 | 50.535 | −2.996 | 43.921 | 1.00 | 30.47 | A | O |
| ATOM | 870 | C | GLU | A | 400 | 47.726 | −1.537 | 40.842 | 1.00 | 12.72 | A | C |
| ATOM | 871 | O | GLU | A | 400 | 48.413 | −0.514 | 40.876 | 1.00 | 11.57 | A | O |
| ATOM | 872 | N | LEU | A | 401 | 46.525 | −1.574 | 40.269 | 1.00 | 11.68 | A | N |
| ATOM | 873 | CA | LEU | A | 401 | 45.950 | −0.373 | 39.679 | 1.00 | 11.44 | A | C |
| ATOM | 874 | CB | LEU | A | 401 | 44.642 | −0.668 | 38.940 | 1.00 | 10.03 | A | C |
| ATOM | 875 | CG | LEU | A | 401 | 44.742 | −1.526 | 37.678 | 1.00 | 10.87 | A | C |
| ATOM | 876 | CD1 | LEU | A | 401 | 43.359 | −1.748 | 37.072 | 1.00 | 10.54 | A | C |
| ATOM | 877 | CD2 | LEU | A | 401 | 45.694 | −0.902 | 36.671 | 1.00 | 10.80 | A | C |
| ATOM | 878 | C | LEU | A | 401 | 45.725 | 0.672 | 40.767 | 1.00 | 14.90 | A | C |
| ATOM | 879 | O | LEU | A | 401 | 45.772 | 1.877 | 40.504 | 1.00 | 12.23 | A | O |
| ATOM | 880 | N | GLY | A | 402 | 45.478 | 0.211 | 41.989 | 1.00 | 11.10 | A | N |
| ATOM | 881 | CA | GLY | A | 402 | 45.332 | 1.123 | 43.105 | 1.00 | 8.33 | A | C |
| ATOM | 882 | C | GLY | A | 402 | 46.511 | 2.077 | 43.160 | 1.00 | 12.05 | A | C |
| ATOM | 883 | O | GLY | A | 402 | 46.341 | 3.296 | 43.220 | 1.00 | 9.18 | A | O |
| ATOM | 884 | N | ALA | A | 403 | 47.715 | 1.520 | 43.103 | 1.00 | 10.25 | A | N |
| ATOM | 885 | CA | ALA | A | 403 | 48.929 | 2.322 | 43.156 | 1.00 | 12.95 | A | C |
| ATOM | 886 | CB | ALA | A | 403 | 50.162 | 1.424 | 43.288 | 1.00 | 11.24 | A | C |
| ATOM | 887 | C | ALA | A | 403 | 49.055 | 3.223 | 41.926 | 1.00 | 10.76 | A | C |
| ATOM | 888 | O | ALA | A | 403 | 49.405 | 4.394 | 42.043 | 1.00 | 9.68 | A | O |
| ATOM | 889 | N | ALA | A | 404 | 48.764 | 2.677 | 40.750 | 1.00 | 8.99 | A | N |
| ATOM | 890 | CA | ALA | A | 404 | 48.915 | 3.427 | 39.501 | 1.00 | 10.80 | A | C |
| ATOM | 891 | CB | ALA | A | 404 | 48.695 | 2.509 | 38.303 | 1.00 | 10.92 | A | C |
| ATOM | 892 | C | ALA | A | 404 | 47.954 | 4.621 | 39.442 | 1.00 | 12.45 | A | C |
| ATOM | 893 | O | ALA | A | 404 | 48.324 | 5.740 | 39.052 | 1.00 | 9.31 | A | O |
| ATOM | 894 | N | LEU | A | 405 | 46.709 | 4.373 | 39.821 | 1.00 | 11.85 | A | N |
| ATOM | 895 | CA | LEU | A | 405 | 45.714 | 5.431 | 39.853 | 1.00 | 8.39 | A | C |
| ATOM | 896 | CB | LEU | A | 405 | 44.340 | 4.853 | 40.168 | 1.00 | 8.93 | A | C |
| ATOM | 897 | CG | LEU | A | 405 | 43.735 | 4.076 | 39.002 | 1.00 | 10.00 | A | C |
| ATOM | 898 | CD1 | LEU | A | 405 | 42.556 | 3.245 | 39.467 | 1.00 | 7.23 | A | C |
| ATOM | 899 | CD2 | LEU | A | 405 | 43.321 | 5.047 | 37.903 | 1.00 | 9.72 | A | C |
| ATOM | 900 | C | LEU | A | 405 | 46.097 | 6.515 | 40.860 | 1.00 | 9.64 | A | C |
| ATOM | 901 | O | LEU | A | 405 | 46.031 | 7.704 | 40.545 | 1.00 | 12.51 | A | O |
| ATOM | 902 | N | LEU | A | 406 | 46.512 | 6.115 | 42.058 | 1.00 | 9.03 | A | N |

TABLE 6-continued

Coordinates for crystal structure of the complex of ERR-α and Compound 1

| ATOM | 903 | CA | LEU | A | 406 | 46.928 | 7.092 | 43.072 | 1.00 | 12.76 | A | C |
|---|---|---|---|---|---|---|---|---|---|---|---|---|
| ATOM | 904 | CB | LEU | A | 406 | 47.231 | 6.417 | 44.415 | 1.00 | 11.94 | A | C |
| ATOM | 905 | CG | LEU | A | 406 | 46.008 | 5.984 | 45.225 | 1.00 | 13.22 | A | C |
| ATOM | 906 | CD1 | LEU | A | 406 | 46.413 | 5.086 | 46.393 | 1.00 | 11.84 | A | C |
| ATOM | 907 | CD2 | LEU | A | 406 | 45.236 | 7.212 | 45.705 | 1.00 | 9.96 | A | C |
| ATOM | 908 | C | LEU | A | 406 | 48.131 | 7.912 | 42.611 | 1.00 | 9.76 | A | C |
| ATOM | 909 | O | LEU | A | 406 | 48.287 | 9.070 | 42.989 | 1.00 | 11.41 | A | O |
| ATOM | 910 | N | GLN | A | 407 | 48.986 | 7.308 | 41.796 | 1.00 | 10.47 | A | N |
| ATOM | 911 | CA | GLN | A | 407 | 50.108 | 8.037 | 41.220 | 1.00 | 10.23 | A | C |
| ATOM | 912 | CB | GLN | A | 407 | 50.944 | 7.105 | 40.357 | 1.00 | 12.87 | A | C |
| ATOM | 913 | CG | GLN | A | 407 | 52.308 | 7.650 | 40.016 | 1.00 | 18.46 | A | C |
| ATOM | 914 | CD | GLN | A | 407 | 53.175 | 6.612 | 39.326 | 1.00 | 27.96 | A | C |
| ATOM | 915 | OE1 | GLN | A | 407 | 52.811 | 5.433 | 39.240 | 1.00 | 26.97 | A | O |
| ATOM | 916 | NE2 | GLN | A | 407 | 54.323 | 7.047 | 38.825 | 1.00 | 23.36 | A | N |
| ATOM | 917 | C | GLN | A | 407 | 49.596 | 9.204 | 40.373 | 1.00 | 10.26 | A | C |
| ATOM | 918 | O | GLN | A | 407 | 50.103 | 10.325 | 40.467 | 1.00 | 9.77 | A | O |
| ATOM | 919 | N | LEU | A | 408 | 48.584 | 8.931 | 39.551 | 1.00 | 9.23 | A | N |
| ATOM | 920 | CA | LEU | A | 408 | 47.954 | 9.964 | 38.729 | 1.00 | 8.47 | A | C |
| ATOM | 921 | CB | LEU | A | 408 | 46.860 | 9.351 | 37.839 | 1.00 | 7.74 | A | C |
| ATOM | 922 | CG | LEU | A | 408 | 46.445 | 10.000 | 36.513 | 1.00 | 8.05 | A | C |
| ATOM | 923 | CD1 | LEU | A | 408 | 44.963 | 9.764 | 36.197 | 1.00 | 4.98 | A | C |
| ATOM | 924 | CD2 | LEU | A | 408 | 46.787 | 11.473 | 36.412 | 1.00 | 6.46 | A | C |
| ATOM | 925 | C | LEU | A | 408 | 47.329 | 11.021 | 39.636 | 1.00 | 8.66 | A | C |
| ATOM | 926 | O | LEU | A | 408 | 47.501 | 12.218 | 39.414 | 1.00 | 9.51 | A | O |
| ATOM | 927 | N | VAL | A | 409 | 46.588 | 10.568 | 40.647 | 1.00 | 7.46 | A | N |
| ATOM | 928 | CA | VAL | A | 409 | 45.906 | 11.465 | 41.579 | 1.00 | 6.92 | A | C |
| ATOM | 929 | CB | VAL | A | 409 | 45.157 | 10.668 | 42.686 | 1.00 | 8.65 | A | C |
| ATOM | 930 | CG1 | VAL | A | 409 | 44.547 | 11.603 | 43.711 | 1.00 | 8.71 | A | C |
| ATOM | 931 | CG2 | VAL | A | 409 | 44.079 | 9.777 | 42.078 | 1.00 | 8.89 | A | C |
| ATOM | 932 | C | VAL | A | 409 | 46.880 | 12.448 | 42.227 | 1.00 | 11.22 | A | C |
| ATOM | 933 | O | VAL | A | 409 | 46.592 | 13.641 | 42.317 | 1.00 | 11.95 | A | O |
| ATOM | 934 | N | ARG | A | 410 | 48.031 | 11.941 | 42.672 | 1.00 | 8.64 | A | N |
| ATOM | 935 | CA | ARG | A | 410 | 49.041 | 12.766 | 43.329 | 1.00 | 11.83 | A | C |
| ATOM | 936 | CB | ARG | A | 410 | 50.168 | 11.894 | 43.909 | 1.00 | 11.23 | A | C |
| ATOM | 937 | CG | ARG | A | 410 | 49.743 | 11.103 | 45.159 | 1.00 | 15.02 | A | C |
| ATOM | 938 | CD | ARG | A | 410 | 50.939 | 10.572 | 45.932 | 1.00 | 13.71 | A | C |
| ATOM | 939 | NE | ARG | A | 410 | 51.751 | 9.649 | 45.136 | 1.00 | 16.06 | A | N |
| ATOM | 940 | CZ | ARG | A | 410 | 51.467 | 8.359 | 44.959 | 1.00 | 16.13 | A | C |
| ATOM | 941 | NH1 | ARG | A | 410 | 50.384 | 7.830 | 45.513 | 1.00 | 13.28 | A | N |
| ATOM | 942 | NH2 | ARG | A | 410 | 52.265 | 7.594 | 44.224 | 1.00 | 12.54 | A | N |
| ATOM | 943 | C | ARG | A | 410 | 49.615 | 13.804 | 42.378 | 1.00 | 11.91 | A | C |
| ATOM | 944 | O | ARG | A | 410 | 49.854 | 14.949 | 42.756 | 1.00 | 13.27 | A | O |
| ATOM | 945 | N | ARG | A | 411 | 49.818 | 13.402 | 41.129 | 1.00 | 12.33 | A | N |
| ATOM | 946 | CA | ARG | A | 411 | 50.325 | 14.314 | 40.103 | 1.00 | 12.23 | A | C |
| ATOM | 947 | CB | ARG | A | 411 | 50.560 | 13.530 | 38.808 | 1.00 | 13.09 | A | C |
| ATOM | 948 | CG | ARG | A | 411 | 51.193 | 14.305 | 37.701 | 1.00 | 14.85 | A | C |
| ATOM | 949 | CD | ARG | A | 411 | 52.703 | 14.473 | 37.877 | 1.00 | 10.64 | A | C |
| ATOM | 950 | NE | ARG | A | 411 | 53.121 | 15.589 | 37.036 | 1.00 | 9.23 | A | N |
| ATOM | 951 | CZ | ARG | A | 411 | 53.941 | 15.504 | 36.000 | 1.00 | 8.72 | A | C |
| ATOM | 952 | NH1 | ARG | A | 411 | 54.511 | 14.341 | 35.669 | 1.00 | 6.36 | A | N |
| ATOM | 953 | NH2 | ARG | A | 411 | 54.207 | 16.604 | 35.314 | 1.00 | 5.92 | A | N |
| ATOM | 954 | C | ARG | A | 411 | 49.362 | 15.497 | 39.890 | 1.00 | 11.17 | A | C |
| ATOM | 955 | O | ARG | A | 411 | 49.786 | 16.637 | 39.668 | 1.00 | 11.92 | A | O |
| ATOM | 956 | N | LEU | A | 412 | 48.065 | 15.234 | 39.990 | 1.00 | 9.22 | A | N |
| ATOM | 957 | CA | LEU | A | 412 | 47.065 | 16.289 | 39.841 | 1.00 | 12.80 | A | C |
| ATOM | 958 | CB | LEU | A | 412 | 45.737 | 15.707 | 39.365 | 1.00 | 8.02 | A | C |
| ATOM | 959 | CG | LEU | A | 412 | 45.759 | 15.057 | 37.988 | 1.00 | 10.32 | A | C |
| ATOM | 960 | CD1 | LEU | A | 412 | 44.492 | 14.244 | 37.774 | 1.00 | 6.91 | A | C |
| ATOM | 961 | CD2 | LEU | A | 412 | 45.905 | 16.118 | 36.906 | 1.00 | 10.21 | A | C |
| ATOM | 962 | C | LEU | A | 412 | 46.856 | 17.101 | 41.121 | 1.00 | 11.20 | A | C |
| ATOM | 963 | O | LEU | A | 412 | 46.626 | 18.310 | 41.066 | 1.00 | 14.93 | A | O |
| ATOM | 964 | N | GLN | A | 413 | 46.924 | 16.435 | 42.265 | 1.00 | 11.94 | A | N |
| ATOM | 965 | CA | GLN | A | 413 | 46.783 | 17.107 | 43.553 | 1.00 | 13.74 | A | C |
| ATOM | 966 | CB | GLN | A | 413 | 46.871 | 16.109 | 44.711 | 1.00 | 10.70 | A | C |
| ATOM | 967 | CG | GLN | A | 413 | 45.653 | 15.226 | 44.897 | 1.00 | 13.99 | A | C |
| ATOM | 968 | CD | GLN | A | 413 | 45.853 | 14.228 | 46.023 | 1.00 | 14.92 | A | C |
| ATOM | 969 | OE1 | GLN | A | 413 | 46.919 | 13.621 | 46.142 | 1.00 | 13.57 | A | O |
| ATOM | 970 | NE2 | GLN | A | 413 | 44.836 | 14.065 | 46.863 | 1.00 | 11.26 | A | N |
| ATOM | 971 | C | GLN | A | 413 | 47.878 | 18.145 | 43.722 | 1.00 | 12.17 | A | C |
| ATOM | 972 | O | GLN | A | 413 | 47.668 | 19.178 | 44.349 | 1.00 | 15.85 | A | O |
| ATOM | 973 | N | ALA | A | 414 | 49.051 | 17.867 | 43.163 | 1.00 | 11.15 | A | N |
| ATOM | 974 | CA | ALA | A | 414 | 50.180 | 18.793 | 43.255 | 1.00 | 11.85 | A | C |
| ATOM | 975 | CB | ALA | A | 414 | 51.428 | 18.168 | 42.634 | 1.00 | 12.32 | A | C |
| ATOM | 976 | C | ALA | A | 414 | 49.886 | 20.149 | 42.596 | 1.00 | 12.81 | A | C |
| ATOM | 977 | O | ALA | A | 414 | 50.496 | 21.152 | 42.944 | 1.00 | 13.14 | A | O |
| ATOM | 978 | N | LEU | A | 415 | 48.962 | 20.175 | 41.641 | 1.00 | 14.00 | A | N |
| ATOM | 979 | CA | LEU | A | 415 | 48.648 | 21.409 | 40.922 | 1.00 | 12.59 | A | C |
| ATOM | 980 | CB | LEU | A | 415 | 48.375 | 21.118 | 39.443 | 1.00 | 12.24 | A | C |

TABLE 6-continued

Coordinates for crystal structure of the complex of ERR-α and Compound 1

| ATOM | 981 | CG | LEU | A | 415 | 49.452 | 20.343 | 38.678 | 1.00 | 15.07 | A | C |
| --- | --- | --- | --- | --- | --- | --- | --- | --- | --- | --- | --- | --- |
| ATOM | 982 | CD1 | LEU | A | 415 | 49.027 | 20.137 | 37.238 | 1.00 | 13.21 | A | C |
| ATOM | 983 | CD2 | LEU | A | 415 | 50.800 | 21.055 | 38.760 | 1.00 | 11.85 | A | C |
| ATOM | 984 | C | LEU | A | 415 | 47.444 | 22.126 | 41.536 | 1.00 | 16.77 | A | C |
| ATOM | 985 | O | LEU | A | 415 | 47.148 | 23.279 | 41.191 | 1.00 | 10.65 | A | O |
| ATOM | 986 | N | ARG | A | 416 | 46.747 | 21.434 | 42.435 | 1.00 | 13.53 | A | N |
| ATOM | 987 | CA | ARG | A | 416 | 45.525 | 21.975 | 43.034 | 1.00 | 17.12 | A | C |
| ATOM | 988 | CB | ARG | A | 416 | 45.879 | 23.090 | 44.026 | 1.00 | 18.84 | A | C |
| ATOM | 989 | CG | ARG | A | 416 | 46.696 | 22.579 | 45.215 | 1.00 | 25.04 | A | C |
| ATOM | 990 | CD | ARG | A | 416 | 47.264 | 23.701 | 46.102 | 1.00 | 42.45 | A | C |
| ATOM | 991 | NE | ARG | A | 416 | 47.936 | 23.161 | 47.290 | 1.00 | 55.20 | A | N |
| ATOM | 992 | CZ | ARG | A | 416 | 48.633 | 23.882 | 48.170 | 1.00 | 58.48 | A | C |
| ATOM | 993 | NH1 | ARG | A | 416 | 48.764 | 25.195 | 48.013 | 1.00 | 57.23 | A | N |
| ATOM | 994 | NH2 | ARG | A | 416 | 49.204 | 23.289 | 49.215 | 1.00 | 47.79 | A | N |
| ATOM | 995 | C | ARG | A | 416 | 44.539 | 22.452 | 41.954 | 1.00 | 14.71 | A | C |
| ATOM | 996 | O | ARG | A | 416 | 44.260 | 23.636 | 41.819 | 1.00 | 17.79 | A | O |
| ATOM | 997 | N | LEU | A | 417 | 44.029 | 21.509 | 41.173 | 1.00 | 15.18 | A | N |
| ATOM | 998 | CA | LEU | A | 417 | 43.092 | 21.820 | 40.099 | 1.00 | 16.31 | A | C |
| ATOM | 999 | CB | LEU | A | 417 | 42.602 | 20.533 | 39.445 | 1.00 | 17.35 | A | C |
| ATOM | 1000 | CG | LEU | A | 417 | 43.236 | 20.062 | 38.146 | 1.00 | 21.89 | A | C |
| ATOM | 1001 | CD1 | LEU | A | 417 | 44.676 | 19.654 | 38.383 | 1.00 | 21.71 | A | C |
| ATOM | 1002 | CD2 | LEU | A | 417 | 42.422 | 18.910 | 37.580 | 1.00 | 19.02 | A | C |
| ATOM | 1003 | C | LEU | A | 417 | 41.864 | 22.559 | 40.604 | 1.00 | 22.00 | A | C |
| ATOM | 1004 | O | LEU | A | 417 | 41.407 | 22.331 | 41.724 | 1.00 | 21.62 | A | O |
| ATOM | 1005 | N | GLU | A | 418 | 41.319 | 23.437 | 39.771 | 1.00 | 15.35 | A | N |
| ATOM | 1006 | CA | GLU | A | 418 | 39.939 | 23.841 | 39.961 | 1.00 | 16.35 | A | C |
| ATOM | 1007 | CB | GLU | A | 418 | 39.744 | 25.318 | 39.699 | 1.00 | 19.89 | A | C |
| ATOM | 1008 | CG | GLU | A | 418 | 40.727 | 26.227 | 40.377 | 1.00 | 27.23 | A | C |
| ATOM | 1009 | CD | GLU | A | 418 | 40.787 | 27.541 | 39.662 | 1.00 | 33.21 | A | C |
| ATOM | 1010 | OE1 | GLU | A | 418 | 40.238 | 27.607 | 38.528 | 1.00 | 30.20 | A | O |
| ATOM | 1011 | OE2 | GLU | A | 418 | 41.378 | 28.490 | 40.217 | 1.00 | 45.03 | A | O |
| ATOM | 1012 | C | GLU | A | 418 | 39.096 | 23.053 | 38.975 | 1.00 | 15.57 | A | C |
| ATOM | 1013 | O | GLU | A | 418 | 39.609 | 22.506 | 37.994 | 1.00 | 12.20 | A | O |
| ATOM | 1014 | N | ARG | A | 419 | 37.796 | 23.024 | 39.226 | 1.00 | 12.89 | A | N |
| ATOM | 1015 | CA | ARG | A | 419 | 36.872 | 22.241 | 38.422 | 1.00 | 12.88 | A | C |
| ATOM | 1016 | CB | ARG | A | 419 | 35.471 | 22.342 | 39.028 | 1.00 | 12.88 | A | C |
| ATOM | 1017 | CG | ARG | A | 419 | 34.466 | 21.368 | 38.453 | 1.00 | 24.19 | A | C |
| ATOM | 1018 | CD | ARG | A | 419 | 33.216 | 21.347 | 39.314 | 1.00 | 24.82 | A | C |
| ATOM | 1019 | NE | ARG | A | 419 | 32.239 | 20.377 | 38.828 | 1.00 | 36.72 | A | N |
| ATOM | 1020 | CZ | ARG | A | 419 | 32.388 | 19.057 | 38.903 | 1.00 | 37.97 | A | C |
| ATOM | 1021 | NH1 | ARG | A | 419 | 33.485 | 18.527 | 39.439 | 1.00 | 33.99 | A | N |
| ATOM | 1022 | NH2 | ARG | A | 419 | 31.435 | 18.262 | 38.437 | 1.00 | 38.54 | A | N |
| ATOM | 1023 | C | ARG | A | 419 | 36.874 | 22.669 | 36.944 | 1.00 | 12.43 | A | C |
| ATOM | 1024 | O | ARG | A | 419 | 36.760 | 21.829 | 36.047 | 1.00 | 11.81 | A | O |
| ATOM | 1025 | N | GLU | A | 420 | 37.011 | 23.971 | 36.697 | 1.00 | 9.29 | A | N |
| ATOM | 1026 | CA | GLU | A | 420 | 37.087 | 24.502 | 35.333 | 1.00 | 8.71 | A | C |
| ATOM | 1027 | CB | GLU | A | 420 | 37.185 | 26.027 | 35.346 | 1.00 | 8.84 | A | C |
| ATOM | 1028 | CG | GLU | A | 420 | 35.932 | 26.745 | 35.786 | 1.00 | 8.55 | A | C |
| ATOM | 1029 | CD | GLU | A | 420 | 35.794 | 26.835 | 37.297 | 1.00 | 12.59 | A | C |
| ATOM | 1030 | OE1 | GLU | A | 420 | 34.795 | 27.428 | 37.761 | 1.00 | 16.63 | A | O |
| ATOM | 1031 | OE2 | GLU | A | 420 | 36.670 | 26.324 | 38.020 | 1.00 | 11.37 | A | O |
| ATOM | 1032 | C | GLU | A | 420 | 38.287 | 23.935 | 34.571 | 1.00 | 10.65 | A | C |
| ATOM | 1033 | O | GLU | A | 420 | 38.205 | 23.643 | 33.371 | 1.00 | 8.02 | A | O |
| ATOM | 1034 | N | GLU | A | 421 | 39.409 | 23.800 | 35.272 | 1.00 | 10.35 | A | N |
| ATOM | 1035 | CA | GLU | A | 421 | 40.617 | 23.285 | 34.653 | 1.00 | 9.75 | A | C |
| ATOM | 1036 | CB | GLU | A | 421 | 41.802 | 23.492 | 35.586 | 1.00 | 8.77 | A | C |
| ATOM | 1037 | CG | GLU | A | 421 | 42.093 | 24.953 | 35.830 | 1.00 | 11.31 | A | C |
| ATOM | 1038 | CD | GLU | A | 421 | 43.241 | 25.177 | 36.782 | 1.00 | 13.29 | A | C |
| ATOM | 1039 | OE1 | GLU | A | 421 | 43.246 | 24.571 | 37.875 | 1.00 | 13.11 | A | O |
| ATOM | 1040 | OE2 | GLU | A | 421 | 44.136 | 25.972 | 36.438 | 1.00 | 11.52 | A | O |
| ATOM | 1041 | C | GLU | A | 421 | 40.434 | 21.807 | 34.302 | 1.00 | 8.84 | A | C |
| ATOM | 1042 | O | GLU | A | 421 | 40.802 | 21.366 | 33.213 | 1.00 | 11.01 | A | O |
| ATOM | 1043 | N | TYR | A | 422 | 39.856 | 21.055 | 35.226 | 1.00 | 8.23 | A | N |
| ATOM | 1044 | CA | TYR | A | 422 | 39.553 | 19.650 | 34.995 | 1.00 | 8.38 | A | C |
| ATOM | 1045 | CB | TYR | A | 422 | 38.929 | 19.036 | 36.251 | 1.00 | 10.40 | A | C |
| ATOM | 1046 | CG | TYR | A | 422 | 38.035 | 17.840 | 36.016 | 1.00 | 9.57 | A | C |
| ATOM | 1047 | CD1 | TYR | A | 422 | 38.563 | 16.613 | 35.622 | 1.00 | 8.81 | A | C |
| ATOM | 1048 | CE1 | TYR | A | 422 | 37.731 | 15.497 | 35.426 | 1.00 | 8.70 | A | C |
| ATOM | 1049 | CD2 | TYR | A | 422 | 36.660 | 17.927 | 36.235 | 1.00 | 10.68 | A | C |
| ATOM | 1050 | CE2 | TYR | A | 422 | 35.826 | 16.829 | 36.050 | 1.00 | 13.62 | A | C |
| ATOM | 1051 | CZ | TYR | A | 422 | 36.363 | 15.616 | 35.646 | 1.00 | 12.55 | A | C |
| ATOM | 1052 | OH | TYR | A | 422 | 35.521 | 14.530 | 35.464 | 1.00 | 11.27 | A | O |
| ATOM | 1053 | C | TYR | A | 422 | 38.681 | 19.425 | 33.751 | 1.00 | 7.77 | A | C |
| ATOM | 1054 | O | TYR | A | 422 | 39.045 | 18.645 | 32.881 | 1.00 | 9.57 | A | O |
| ATOM | 1055 | N | VAL | A | 423 | 37.546 | 20.109 | 33.633 | 1.00 | 6.84 | A | N |
| ATOM | 1056 | CA | VAL | A | 423 | 36.706 | 19.885 | 32.453 | 1.00 | 7.87 | A | C |
| ATOM | 1057 | CB | VAL | A | 423 | 35.308 | 20.520 | 32.570 | 1.00 | 9.33 | A | C |
| ATOM | 1058 | CG1 | VAL | A | 423 | 34.537 | 19.908 | 33.750 | 1.00 | 10.97 | A | C |

TABLE 6-continued

Coordinates for crystal structure of the complex of ERR-α and Compound 1

| ATOM | 1059 | CG2 | VAL | A | 423 | 35.406 | 22.043 | 32.710 | 1.00 | 8.96 | A | C |
|---|---|---|---|---|---|---|---|---|---|---|---|---|
| ATOM | 1060 | C | VAL | A | 423 | 37.402 | 20.319 | 31.152 | 1.00 | 7.11 | A | C |
| ATOM | 1061 | O | VAL | A | 423 | 37.269 | 19.663 | 30.120 | 1.00 | 6.06 | A | O |
| ATOM | 1062 | N | LEU | A | 424 | 38.168 | 21.401 | 31.196 | 1.00 | 6.15 | A | N |
| ATOM | 1063 | CA | LEU | A | 424 | 38.894 | 21.818 | 30.002 | 1.00 | 6.24 | A | C |
| ATOM | 1064 | CB | LEU | A | 424 | 39.511 | 23.210 | 30.175 | 1.00 | 6.57 | A | C |
| ATOM | 1065 | CG | LEU | A | 424 | 38.531 | 24.389 | 30.072 | 1.00 | 8.76 | A | C |
| ATOM | 1066 | CD1 | LEU | A | 424 | 39.009 | 25.609 | 30.869 | 1.00 | 9.27 | A | C |
| ATOM | 1067 | CD2 | LEU | A | 424 | 38.270 | 24.763 | 28.620 | 1.00 | 9.39 | A | C |
| ATOM | 1068 | C | LEU | A | 424 | 39.954 | 20.772 | 29.644 | 1.00 | 8.74 | A | C |
| ATOM | 1069 | O | LEU | A | 424 | 40.070 | 20.355 | 28.486 | 1.00 | 5.94 | A | O |
| ATOM | 1070 | N | LEU | A | 425 | 40.701 | 20.328 | 30.651 | 1.00 | 6.82 | A | N |
| ATOM | 1071 | CA | LEU | A | 425 | 41.749 | 19.342 | 30.441 | 1.00 | 5.92 | A | C |
| ATOM | 1072 | CB | LEU | A | 425 | 42.475 | 19.065 | 31.748 | 1.00 | 6.23 | A | C |
| ATOM | 1073 | CG | LEU | A | 425 | 43.680 | 18.124 | 31.646 | 1.00 | 6.80 | A | C |
| ATOM | 1074 | CD1 | LEU | A | 425 | 44.758 | 18.748 | 30.761 | 1.00 | 6.80 | A | C |
| ATOM | 1075 | CD2 | LEU | A | 425 | 44.221 | 17.830 | 33.026 | 1.00 | 6.21 | A | C |
| ATOM | 1076 | C | LEU | A | 425 | 41.160 | 18.036 | 29.917 | 1.00 | 7.43 | A | C |
| ATOM | 1077 | O | LEU | A | 425 | 41.731 | 17.387 | 29.031 | 1.00 | 5.47 | A | O |
| ATOM | 1078 | N | LYS | A | 426 | 40.017 | 17.648 | 30.475 | 1.00 | 5.57 | A | N |
| ATOM | 1079 | CA | LYS | A | 426 | 39.379 | 16.406 | 30.067 | 1.00 | 7.09 | A | C |
| ATOM | 1080 | CB | LYS | A | 426 | 38.214 | 16.070 | 31.001 | 1.00 | 7.82 | A | C |
| ATOM | 1081 | CG | LYS | A | 426 | 37.478 | 14.810 | 30.614 | 1.00 | 6.77 | A | C |
| ATOM | 1082 | CD | LYS | A | 426 | 36.706 | 14.267 | 31.789 | 1.00 | 11.38 | A | C |
| ATOM | 1083 | CE | LYS | A | 426 | 35.480 | 15.104 | 32.087 | 1.00 | 9.60 | A | C |
| ATOM | 1084 | NZ | LYS | A | 426 | 34.510 | 14.302 | 32.900 | 1.00 | 14.46 | A | N |
| ATOM | 1085 | C | LYS | A | 426 | 38.919 | 16.462 | 28.609 | 1.00 | 6.38 | A | C |
| ATOM | 1086 | O | LYS | A | 426 | 39.111 | 15.515 | 27.841 | 1.00 | 7.93 | A | O |
| ATOM | 1087 | N | ALA | A | 427 | 38.307 | 17.575 | 28.229 | 1.00 | 7.50 | A | N |
| ATOM | 1088 | CA | ALA | A | 427 | 37.853 | 17.762 | 26.856 | 1.00 | 8.16 | A | C |
| ATOM | 1089 | CB | ALA | A | 427 | 37.090 | 19.081 | 26.719 | 1.00 | 5.44 | A | C |
| ATOM | 1090 | C | ALA | A | 427 | 39.053 | 17.730 | 25.921 | 1.00 | 7.13 | A | C |
| ATOM | 1091 | O | ALA | A | 427 | 39.004 | 17.133 | 24.842 | 1.00 | 5.94 | A | O |
| ATOM | 1092 | N | LEU | A | 428 | 40.139 | 18.361 | 26.360 | 1.00 | 7.29 | A | N |
| ATOM | 1093 | CA | LEU | A | 428 | 41.380 | 18.398 | 25.589 | 1.00 | 8.01 | A | C |
| ATOM | 1094 | CB | LEU | A | 428 | 42.397 | 19.339 | 26.245 | 1.00 | 6.63 | A | C |
| ATOM | 1095 | CG | LEU | A | 428 | 43.703 | 19.529 | 25.472 | 1.00 | 8.24 | A | C |
| ATOM | 1096 | CD1 | LEU | A | 428 | 43.417 | 20.011 | 24.046 | 1.00 | 9.06 | A | C |
| ATOM | 1097 | CD2 | LEU | A | 428 | 44.630 | 20.502 | 26.213 | 1.00 | 7.30 | A | C |
| ATOM | 1098 | C | LEU | A | 428 | 41.977 | 17.005 | 25.430 | 1.00 | 6.79 | A | C |
| ATOM | 1099 | O | LEU | A | 428 | 42.481 | 16.658 | 24.358 | 1.00 | 6.14 | A | O |
| ATOM | 1100 | N | ALA | A | 429 | 41.912 | 16.200 | 26.487 | 1.00 | 7.19 | A | N |
| ATOM | 1101 | CA | ALA | A | 429 | 42.415 | 14.836 | 26.411 | 1.00 | 5.65 | A | C |
| ATOM | 1102 | CB | ALA | A | 429 | 42.320 | 14.157 | 27.770 | 1.00 | 6.20 | A | C |
| ATOM | 1103 | C | ALA | A | 429 | 41.650 | 14.037 | 25.360 | 1.00 | 6.78 | A | C |
| ATOM | 1104 | O | ALA | A | 429 | 42.214 | 13.199 | 24.666 | 1.00 | 5.45 | A | O |
| ATOM | 1105 | N | LEU | A | 430 | 40.344 | 14.270 | 25.279 | 1.00 | 7.60 | A | N |
| ATOM | 1106 | CA | LEU | A | 430 | 39.530 | 13.624 | 24.264 | 1.00 | 8.00 | A | C |
| ATOM | 1107 | CB | LEU | A | 430 | 38.082 | 14.077 | 24.391 | 1.00 | 5.99 | A | C |
| ATOM | 1108 | CG | LEU | A | 430 | 37.151 | 13.694 | 23.237 | 1.00 | 10.42 | A | C |
| ATOM | 1109 | CD1 | LEU | A | 430 | 36.837 | 12.206 | 23.290 | 1.00 | 8.94 | A | C |
| ATOM | 1110 | CD2 | LEU | A | 430 | 35.858 | 14.522 | 23.295 | 1.00 | 10.83 | A | C |
| ATOM | 1111 | C | LEU | A | 430 | 40.046 | 13.986 | 22.876 | 1.00 | 8.39 | A | C |
| ATOM | 1112 | O | LEU | A | 430 | 40.214 | 13.114 | 22.019 | 1.00 | 7.76 | A | O |
| ATOM | 1113 | N | ALA | A | 431 | 40.307 | 15.276 | 22.672 | 1.00 | 5.46 | A | N |
| ATOM | 1114 | CA | ALA | A | 431 | 40.668 | 15.787 | 21.357 | 1.00 | 7.20 | A | C |
| ATOM | 1115 | CB | ALA | A | 431 | 40.371 | 17.277 | 21.269 | 1.00 | 7.30 | A | C |
| ATOM | 1116 | C | ALA | A | 431 | 42.126 | 15.534 | 21.032 | 1.00 | 6.17 | A | C |
| ATOM | 1117 | O | ALA | A | 431 | 42.556 | 15.760 | 19.911 | 1.00 | 7.37 | A | O |
| ATOM | 1118 | N | ASN | A | 432 | 42.891 | 15.084 | 22.019 | 1.00 | 6.25 | A | N |
| ATOM | 1119 | CA | ASN | A | 432 | 44.306 | 14.828 | 21.787 | 1.00 | 5.84 | A | C |
| ATOM | 1120 | CB | ASN | A | 432 | 45.172 | 15.339 | 22.934 | 1.00 | 5.42 | A | C |
| ATOM | 1121 | CG | ASN | A | 432 | 46.630 | 15.449 | 22.532 | 1.00 | 7.14 | A | C |
| ATOM | 1122 | OD1 | ASN | A | 432 | 46.932 | 15.864 | 21.414 | 1.00 | 7.76 | A | O |
| ATOM | 1123 | ND2 | ASN | A | 432 | 47.532 | 15.064 | 23.421 | 1.00 | 4.33 | A | N |
| ATOM | 1124 | C | ASN | A | 432 | 44.593 | 13.355 | 21.518 | 1.00 | 5.85 | A | C |
| ATOM | 1125 | O | ASN | A | 432 | 45.739 | 12.900 | 21.620 | 1.00 | 5.13 | A | O |
| ATOM | 1126 | N | SER | A | 433 | 43.535 | 12.622 | 21.192 | 1.00 | 6.01 | A | N |
| ATOM | 1127 | CA | SER | A | 433 | 43.640 | 11.238 | 20.740 | 1.00 | 8.50 | A | C |
| ATOM | 1128 | CB | SER | A | 433 | 42.285 | 10.768 | 20.217 | 1.00 | 7.80 | A | C |
| ATOM | 1129 | OG | SER | A | 433 | 42.441 | 9.759 | 19.228 | 1.00 | 10.95 | A | O |
| ATOM | 1130 | C | SER | A | 433 | 44.676 | 11.075 | 19.630 | 1.00 | 8.64 | A | C |
| ATOM | 1131 | O | SER | A | 433 | 44.811 | 11.936 | 18.762 | 1.00 | 9.43 | A | O |
| ATOM | 1132 | N | ASP | A | 434 | 45.395 | 9.959 | 19.653 | 1.00 | 6.22 | A | N |
| ATOM | 1133 | CA | ASP | A | 434 | 46.324 | 9.643 | 18.584 | 1.00 | 9.48 | A | C |
| ATOM | 1134 | CB | ASP | A | 434 | 47.749 | 9.555 | 19.131 | 1.00 | 7.92 | A | C |
| ATOM | 1135 | CG | ASP | A | 434 | 48.320 | 10.924 | 19.465 | 1.00 | 7.14 | A | C |
| ATOM | 1136 | OD1 | ASP | A | 434 | 48.600 | 11.186 | 20.660 | 1.00 | 5.12 | A | O |

TABLE 6-continued

Coordinates for crystal structure of the complex of ERR-α and Compound 1

| ATOM | 1137 | OD2 | ASP | A | 434 | 48.465 | 11.740 | 18.526 | 1.00 | 7.55 | A | O |
|---|---|---|---|---|---|---|---|---|---|---|---|---|
| ATOM | 1138 | C | ASP | A | 434 | 45.925 | 8.346 | 17.888 | 1.00 | 18.02 | A | C |
| ATOM | 1139 | O | ASP | A | 434 | 46.773 | 7.536 | 17.516 | 1.00 | 19.74 | A | O |
| ATOM | 1140 | N | SER | A | 435 | 44.623 | 8.148 | 17.721 | 1.00 | 17.08 | A | N |
| ATOM | 1141 | CA | SER | A | 435 | 44.125 | 6.960 | 17.038 | 1.00 | 17.65 | A | C |
| ATOM | 1142 | CB | SER | A | 435 | 42.602 | 7.017 | 16.905 | 1.00 | 18.23 | A | C |
| ATOM | 1143 | OG | SER | A | 435 | 42.142 | 6.004 | 16.025 | 1.00 | 23.32 | A | O |
| ATOM | 1144 | C | SER | A | 435 | 44.747 | 6.830 | 15.653 | 1.00 | 19.96 | A | C |
| ATOM | 1145 | O | SER | A | 435 | 44.768 | 7.787 | 14.876 | 1.00 | 14.76 | A | O |
| ATOM | 1146 | N | VAL | A | 436 | 45.231 | 5.631 | 15.347 | 1.00 | 25.14 | A | N |
| ATOM | 1147 | CA | VAL | A | 436 | 45.766 | 5.313 | 14.028 | 1.00 | 24.59 | A | C |
| ATOM | 1148 | CB | VAL | A | 436 | 46.382 | 3.908 | 14.030 | 1.00 | 25.48 | A | C |
| ATOM | 1149 | CG1 | VAL | A | 436 | 46.627 | 3.462 | 15.461 | 1.00 | 31.74 | A | C |
| ATOM | 1150 | CG2 | VAL | A | 436 | 45.454 | 2.927 | 13.349 | 1.00 | 29.48 | A | C |
| ATOM | 1151 | C | VAL | A | 436 | 44.687 | 5.364 | 12.935 | 1.00 | 24.11 | A | C |
| ATOM | 1152 | O | VAL | A | 436 | 44.997 | 5.484 | 11.747 | 1.00 | 27.48 | A | O |
| ATOM | 1153 | N | HIS | A | 437 | 43.423 | 5.286 | 13.341 | 1.00 | 23.04 | A | N |
| ATOM | 1154 | CA | HIS | A | 437 | 42.313 | 5.168 | 12.389 | 1.00 | 24.50 | A | C |
| ATOM | 1155 | CB | HIS | A | 437 | 41.287 | 4.159 | 12.904 | 1.00 | 22.95 | A | C |
| ATOM | 1156 | CG | HIS | A | 437 | 41.883 | 2.827 | 13.222 | 1.00 | 24.70 | A | C |
| ATOM | 1157 | CD2 | HIS | A | 437 | 42.096 | 2.204 | 14.405 | 1.00 | 27.02 | A | C |
| ATOM | 1158 | ND1 | HIS | A | 437 | 42.376 | 1.987 | 12.249 | 1.00 | 28.99 | A | N |
| ATOM | 1159 | CE1 | HIS | A | 437 | 42.850 | 0.891 | 12.817 | 1.00 | 35.30 | A | C |
| ATOM | 1160 | NE2 | HIS | A | 437 | 42.696 | 1.000 | 14.124 | 1.00 | 32.58 | A | N |
| ATOM | 1161 | C | HIS | A | 437 | 41.610 | 6.473 | 12.050 | 1.00 | 25.58 | A | C |
| ATOM | 1162 | O | HIS | A | 437 | 40.536 | 6.460 | 11.450 | 1.00 | 22.32 | A | O |
| ATOM | 1163 | N | ILE | A | 438 | 42.202 | 7.597 | 12.432 | 1.00 | 19.92 | A | N |
| ATOM | 1164 | CA | ILE | A | 438 | 41.607 | 8.892 | 12.119 | 1.00 | 20.49 | A | C |
| ATOM | 1165 | CB | ILE | A | 438 | 42.228 | 10.005 | 12.982 | 1.00 | 17.72 | A | C |
| ATOM | 1166 | CG2 | ILE | A | 438 | 41.957 | 11.381 | 12.366 | 1.00 | 19.00 | A | C |
| ATOM | 1167 | CG1 | ILE | A | 438 | 41.699 | 9.913 | 14.421 | 1.00 | 16.43 | A | C |
| ATOM | 1168 | CD1 | ILE | A | 438 | 42.615 | 10.586 | 15.455 | 1.00 | 18.54 | A | C |
| ATOM | 1169 | C | ILE | A | 438 | 41.764 | 9.218 | 10.632 | 1.00 | 22.78 | A | C |
| ATOM | 1170 | O | ILE | A | 438 | 42.867 | 9.151 | 10.091 | 1.00 | 26.18 | A | O |
| ATOM | 1171 | N | GLU | A | 439 | 40.666 | 9.570 | 9.970 | 1.00 | 21.53 | A | N |
| ATOM | 1172 | CA | GLU | A | 439 | 40.713 | 9.815 | 8.533 | 1.00 | 22.55 | A | C |
| ATOM | 1173 | CB | GLU | A | 439 | 39.501 | 9.194 | 7.836 | 1.00 | 25.78 | A | C |
| ATOM | 1174 | CG | GLU | A | 439 | 38.168 | 9.888 | 8.108 | 1.00 | 33.70 | A | C |
| ATOM | 1175 | CD | GLU | A | 439 | 36.984 | 9.020 | 7.693 | 1.00 | 40.85 | A | C |
| ATOM | 1176 | OE1 | GLU | A | 439 | 35.822 | 9.469 | 7.838 | 1.00 | 31.28 | A | O |
| ATOM | 1177 | OE2 | GLU | A | 439 | 37.227 | 7.882 | 7.227 | 1.00 | 34.29 | A | O |
| ATOM | 1178 | C | GLU | A | 439 | 40.868 | 11.291 | 8.159 | 1.00 | 23.80 | A | C |
| ATOM | 1179 | O | GLU | A | 439 | 41.462 | 11.614 | 7.133 | 1.00 | 23.54 | A | O |
| ATOM | 1180 | N | ASP | A | 440 | 40.334 | 12.185 | 8.984 | 1.00 | 24.35 | A | N |
| ATOM | 1181 | CA | ASP | A | 440 | 40.566 | 13.612 | 8.792 | 1.00 | 24.76 | A | C |
| ATOM | 1182 | CB | ASP | A | 440 | 39.250 | 14.377 | 8.680 | 1.00 | 20.26 | A | C |
| ATOM | 1183 | CG | ASP | A | 440 | 39.440 | 15.771 | 8.124 | 1.00 | 23.85 | A | C |
| ATOM | 1184 | OD1 | ASP | A | 440 | 40.601 | 16.240 | 8.067 | 1.00 | 26.74 | A | O |
| ATOM | 1185 | OD2 | ASP | A | 440 | 38.429 | 16.396 | 7.740 | 1.00 | 27.40 | A | O |
| ATOM | 1186 | C | ASP | A | 440 | 41.423 | 14.181 | 9.922 | 1.00 | 22.00 | A | C |
| ATOM | 1187 | O | ASP | A | 440 | 40.906 | 14.710 | 10.910 | 1.00 | 18.34 | A | O |
| ATOM | 1188 | N | ALA | A | 441 | 42.734 | 14.073 | 9.755 | 1.00 | 17.84 | A | N |
| ATOM | 1189 | CA | ALA | A | 441 | 43.681 | 14.430 | 10.805 | 1.00 | 22.82 | A | C |
| ATOM | 1190 | CB | ALA | A | 441 | 45.080 | 13.929 | 10.454 | 1.00 | 20.64 | A | C |
| ATOM | 1191 | C | ALA | A | 441 | 43.713 | 15.926 | 11.099 | 1.00 | 21.00 | A | C |
| ATOM | 1192 | O | ALA | A | 441 | 44.000 | 16.338 | 12.228 | 1.00 | 19.72 | A | O |
| ATOM | 1193 | N | GLU | A | 442 | 43.437 | 16.749 | 10.095 | 1.00 | 21.58 | A | N |
| ATOM | 1194 | CA | GLU | A | 442 | 43.464 | 18.184 | 10.343 | 1.00 | 20.04 | A | C |
| ATOM | 1195 | CB | GLU | A | 442 | 43.779 | 18.984 | 9.073 | 1.00 | 25.38 | A | C |
| ATOM | 1196 | CG | GLU | A | 442 | 42.633 | 19.175 | 8.106 | 1.00 | 39.10 | A | C |
| ATOM | 1197 | CD | GLU | A | 442 | 43.007 | 20.112 | 6.959 | 1.00 | 54.49 | A | C |
| ATOM | 1198 | OE1 | GLU | A | 442 | 43.856 | 19.725 | 6.123 | 1.00 | 61.64 | A | O |
| ATOM | 1199 | OE2 | GLU | A | 442 | 42.457 | 21.235 | 6.898 | 1.00 | 47.00 | A | O |
| ATOM | 1200 | C | GLU | A | 442 | 42.176 | 18.636 | 11.029 | 1.00 | 19.84 | A | C |
| ATOM | 1201 | O | GLU | A | 442 | 42.169 | 19.609 | 11.775 | 1.00 | 19.40 | A | O |
| ATOM | 1202 | N | ALA | A | 443 | 41.091 | 17.908 | 10.796 | 1.00 | 17.15 | A | N |
| ATOM | 1203 | CA | ALA | A | 443 | 39.840 | 18.207 | 11.476 | 1.00 | 18.23 | A | C |
| ATOM | 1204 | CB | ALA | A | 443 | 38.725 | 17.378 | 10.911 | 1.00 | 15.37 | A | C |
| ATOM | 1205 | C | ALA | A | 443 | 39.991 | 17.945 | 12.974 | 1.00 | 18.94 | A | C |
| ATOM | 1206 | O | ALA | A | 443 | 39.504 | 18.720 | 13.800 | 1.00 | 15.50 | A | O |
| ATOM | 1207 | N | VAL | A | 444 | 40.651 | 16.842 | 13.317 | 1.00 | 11.01 | A | N |
| ATOM | 1208 | CA | VAL | A | 444 | 40.915 | 16.534 | 14.714 | 1.00 | 14.83 | A | C |
| ATOM | 1209 | CB | VAL | A | 444 | 41.528 | 15.136 | 14.903 | 1.00 | 12.93 | A | C |
| ATOM | 1210 | CG1 | VAL | A | 444 | 41.880 | 14.916 | 16.372 | 1.00 | 12.78 | A | C |
| ATOM | 1211 | CG2 | VAL | A | 444 | 40.586 | 14.064 | 14.402 | 1.00 | 9.54 | A | C |
| ATOM | 1212 | C | VAL | A | 444 | 41.901 | 17.546 | 15.264 | 1.00 | 12.87 | A | C |
| ATOM | 1213 | O | VAL | A | 444 | 41.746 | 18.028 | 16.380 | 1.00 | 9.39 | A | O |
| ATOM | 1214 | N | GLU | A | 445 | 42.924 | 17.859 | 14.475 | 1.00 | 12.91 | A | N |

TABLE 6-continued

Coordinates for crystal structure of the complex of ERR-α and Compound 1

| ATOM | 1215 | CA | GLU | A | 445 | 43.889 | 18.861 | 14.891 | 1.00 | 14.38 | A | C |
|---|---|---|---|---|---|---|---|---|---|---|---|---|
| ATOM | 1216 | CB | GLU | A | 445 | 44.917 | 19.134 | 13.797 | 1.00 | 15.55 | A | C |
| ATOM | 1217 | CG | GLU | A | 445 | 45.958 | 20.144 | 14.205 | 1.00 | 16.05 | A | C |
| ATOM | 1218 | CD | GLU | A | 445 | 46.977 | 20.408 | 13.117 | 1.00 | 22.16 | A | C |
| ATOM | 1219 | OE1 | GLU | A | 445 | 48.173 | 20.152 | 13.352 | 1.00 | 22.61 | A | O |
| ATOM | 1220 | OE2 | GLU | A | 445 | 46.585 | 20.874 | 12.026 | 1.00 | 30.96 | A | O |
| ATOM | 1221 | C | GLU | A | 445 | 43.177 | 20.159 | 15.263 | 1.00 | 14.87 | A | C |
| ATOM | 1222 | O | GLU | A | 445 | 43.474 | 20.756 | 16.291 | 1.00 | 11.42 | A | O |
| ATOM | 1223 | N | GLN | A | 446 | 42.220 | 20.585 | 14.440 | 1.00 | 15.11 | A | N |
| ATOM | 1224 | CA | GLN | A | 446 | 41.568 | 21.860 | 14.695 | 1.00 | 17.36 | A | C |
| ATOM | 1225 | CB | GLN | A | 446 | 40.759 | 22.335 | 13.482 | 1.00 | 17.05 | A | C |
| ATOM | 1226 | CG | GLN | A | 446 | 39.275 | 22.058 | 13.571 | 1.00 | 31.52 | A | C |
| ATOM | 1227 | CD | GLN | A | 446 | 38.458 | 22.993 | 12.690 | 1.00 | 46.25 | A | C |
| ATOM | 1228 | OE1 | GLN | A | 446 | 38.992 | 23.634 | 11.774 | 1.00 | 40.21 | A | O |
| ATOM | 1229 | NE2 | GLN | A | 446 | 37.153 | 23.077 | 12.965 | 1.00 | 42.91 | A | N |
| ATOM | 1230 | C | GLN | A | 446 | 40.729 | 21.825 | 15.983 | 1.00 | 14.65 | A | C |
| ATOM | 1231 | O | GLN | A | 446 | 40.694 | 22.800 | 16.732 | 1.00 | 11.67 | A | O |
| ATOM | 1232 | N | LEU | A | 447 | 40.068 | 20.702 | 16.251 | 1.00 | 15.45 | A | N |
| ATOM | 1233 | CA | LEU | A | 447 | 39.338 | 20.556 | 17.511 | 1.00 | 11.38 | A | C |
| ATOM | 1234 | CB | LEU | A | 447 | 38.572 | 19.232 | 17.555 | 1.00 | 11.90 | A | C |
| ATOM | 1235 | CG | LEU | A | 447 | 37.819 | 18.964 | 18.863 | 1.00 | 13.32 | A | C |
| ATOM | 1236 | CD1 | LEU | A | 447 | 36.859 | 20.108 | 19.173 | 1.00 | 13.67 | A | C |
| ATOM | 1237 | CD2 | LEU | A | 447 | 37.072 | 17.637 | 18.795 | 1.00 | 10.35 | A | C |
| ATOM | 1238 | C | LEU | A | 447 | 40.298 | 20.644 | 18.700 | 1.00 | 12.43 | A | C |
| ATOM | 1239 | O | LEU | A | 447 | 40.036 | 21.361 | 19.667 | 1.00 | 10.76 | A | O |
| ATOM | 1240 | N | ARG | A | 448 | 41.407 | 19.906 | 18.619 | 1.00 | 8.12 | A | N |
| ATOM | 1241 | CA | ARG | A | 448 | 42.438 | 19.912 | 19.664 | 1.00 | 8.60 | A | C |
| ATOM | 1242 | CB | ARG | A | 448 | 43.599 | 19.002 | 19.264 | 1.00 | 9.77 | A | C |
| ATOM | 1243 | CG | ARG | A | 448 | 44.710 | 18.863 | 20.299 | 1.00 | 7.47 | A | C |
| ATOM | 1244 | CD | ARG | A | 448 | 46.029 | 18.548 | 19.600 | 1.00 | 6.92 | A | C |
| ATOM | 1245 | NE | ARG | A | 448 | 45.902 | 17.399 | 18.710 | 1.00 | 11.60 | A | N |
| ATOM | 1246 | CZ | ARG | A | 448 | 46.486 | 17.295 | 17.517 | 1.00 | 12.15 | A | C |
| ATOM | 1247 | NH1 | ARG | A | 448 | 47.233 | 18.285 | 17.030 | 1.00 | 10.50 | A | N |
| ATOM | 1248 | NH2 | ARG | A | 448 | 46.305 | 16.203 | 16.795 | 1.00 | 9.94 | A | N |
| ATOM | 1249 | C | ARG | A | 448 | 42.965 | 21.328 | 19.893 | 1.00 | 13.39 | A | C |
| ATOM | 1250 | O | ARG | A | 448 | 43.060 | 21.790 | 21.034 | 1.00 | 13.33 | A | O |
| ATOM | 1251 | N | GLU | A | 449 | 43.305 | 22.019 | 18.805 | 1.00 | 9.29 | A | N |
| ATOM | 1252 | CA | GLU | A | 449 | 43.770 | 23.403 | 18.904 | 1.00 | 13.30 | A | C |
| ATOM | 1253 | CB | GLU | A | 449 | 44.149 | 23.959 | 17.526 | 1.00 | 12.75 | A | C |
| ATOM | 1254 | CG | GLU | A | 449 | 45.549 | 23.575 | 17.075 | 1.00 | 15.91 | A | C |
| ATOM | 1255 | CD | GLU | A | 449 | 45.780 | 23.844 | 15.599 | 1.00 | 22.96 | A | C |
| ATOM | 1256 | OE1 | GLU | A | 449 | 44.906 | 24.470 | 14.956 | 1.00 | 24.52 | A | O |
| ATOM | 1257 | OE2 | GLU | A | 449 | 46.831 | 23.420 | 15.076 | 1.00 | 17.98 | A | O |
| ATOM | 1258 | C | GLU | A | 449 | 42.758 | 24.326 | 19.579 | 1.00 | 10.98 | A | C |
| ATOM | 1259 | O | GLU | A | 449 | 43.137 | 25.171 | 20.393 | 1.00 | 10.65 | A | O |
| ATOM | 1260 | N | ALA | A | 450 | 41.480 | 24.175 | 19.233 | 1.00 | 8.22 | A | N |
| ATOM | 1261 | CA | ALA | A | 450 | 40.443 | 25.042 | 19.779 | 1.00 | 9.95 | A | C |
| ATOM | 1262 | CB | ALA | A | 450 | 39.093 | 24.815 | 19.062 | 1.00 | 9.97 | A | C |
| ATOM | 1263 | C | ALA | A | 450 | 40.288 | 24.828 | 21.277 | 1.00 | 10.41 | A | C |
| ATOM | 1264 | O | ALA | A | 450 | 40.073 | 25.778 | 22.022 | 1.00 | 11.91 | A | O |
| ATOM | 1265 | N | LEU | A | 451 | 40.379 | 23.579 | 21.723 | 1.00 | 10.66 | A | N |
| ATOM | 1266 | CA | LEU | A | 451 | 40.256 | 23.296 | 23.151 | 1.00 | 7.86 | A | C |
| ATOM | 1267 | CB | LEU | A | 451 | 39.934 | 21.824 | 23.389 | 1.00 | 9.13 | A | C |
| ATOM | 1268 | CG | LEU | A | 451 | 38.504 | 21.519 | 22.934 | 1.00 | 8.28 | A | C |
| ATOM | 1269 | CD1 | LEU | A | 451 | 38.276 | 20.030 | 22.816 | 1.00 | 11.12 | A | C |
| ATOM | 1270 | CD2 | LEU | A | 451 | 37.507 | 22.162 | 23.895 | 1.00 | 6.01 | A | C |
| ATOM | 1271 | C | LEU | A | 451 | 41.492 | 23.736 | 23.926 | 1.00 | 10.55 | A | C |
| ATOM | 1272 | O | LEU | A | 451 | 41.385 | 24.208 | 25.058 | 1.00 | 10.13 | A | O |
| ATOM | 1273 | N | HIS | A | 452 | 42.664 | 23.594 | 23.310 | 1.00 | 7.71 | A | N |
| ATOM | 1274 | CA | HIS | A | 452 | 43.884 | 24.095 | 23.917 | 1.00 | 11.17 | A | C |
| ATOM | 1275 | CB | HIS | A | 452 | 45.099 | 23.727 | 23.064 | 1.00 | 9.18 | A | C |
| ATOM | 1276 | CG | HIS | A | 452 | 46.396 | 24.236 | 23.603 | 1.00 | 10.33 | A | C |
| ATOM | 1277 | CD2 | HIS | A | 452 | 46.807 | 24.462 | 24.874 | 1.00 | 11.74 | A | C |
| ATOM | 1278 | ND1 | HIS | A | 452 | 47.453 | 24.585 | 22.789 | 1.00 | 13.92 | A | N |
| ATOM | 1279 | CE1 | HIS | A | 452 | 48.464 | 24.997 | 23.538 | 1.00 | 13.80 | A | C |
| ATOM | 1280 | NE2 | HIS | A | 452 | 48.099 | 24.933 | 24.804 | 1.00 | 12.48 | A | N |
| ATOM | 1281 | C | HIS | A | 452 | 43.787 | 25.615 | 24.099 | 1.00 | 10.62 | A | C |
| ATOM | 1282 | O | HIS | A | 452 | 44.086 | 26.132 | 25.174 | 1.00 | 10.48 | A | O |
| ATOM | 1283 | N | GLU | A | 453 | 43.362 | 26.324 | 23.055 | 1.00 | 11.13 | A | N |
| ATOM | 1284 | CA | GLU | A | 453 | 43.245 | 27.783 | 23.135 | 1.00 | 13.13 | A | C |
| ATOM | 1285 | CB | GLU | A | 453 | 42.901 | 28.386 | 21.768 | 1.00 | 15.88 | A | C |
| ATOM | 1286 | CG | GLU | A | 453 | 42.436 | 29.856 | 21.810 | 1.00 | 26.46 | A | C |
| ATOM | 1287 | CD | GLU | A | 453 | 43.584 | 30.868 | 21.927 | 1.00 | 37.28 | A | C |
| ATOM | 1288 | OE1 | GLU | A | 453 | 43.306 | 32.047 | 22.253 | 1.00 | 40.62 | A | O |
| ATOM | 1289 | OE2 | GLU | A | 453 | 44.758 | 30.491 | 21.693 | 1.00 | 33.52 | A | O |
| ATOM | 1290 | C | GLU | A | 453 | 42.214 | 28.185 | 24.193 | 1.00 | 12.79 | A | C |
| ATOM | 1291 | O | GLU | A | 453 | 42.394 | 29.172 | 24.904 | 1.00 | 9.59 | A | O |
| ATOM | 1292 | N | ALA | A | 454 | 41.139 | 27.404 | 24.301 | 1.00 | 10.51 | A | N |

TABLE 6-continued

Coordinates for crystal structure of the complex of ERR-α and Compound 1

| ATOM | 1293 | CA | ALA | A | 454 | 40.165 | 27.600 | 25.366 | 1.00 | 10.72 | A | C |
|------|------|-----|-----|---|-----|--------|--------|--------|------|-------|---|---|
| ATOM | 1294 | CB | ALA | A | 454 | 39.044 | 26.560 | 25.273 | 1.00 | 9.25 | A | C |
| ATOM | 1295 | C | ALA | A | 454 | 40.846 | 27.534 | 26.732 | 1.00 | 10.67 | A | C |
| ATOM | 1296 | O | ALA | A | 454 | 40.652 | 28.403 | 27.568 | 1.00 | 10.84 | A | O |
| ATOM | 1297 | N | LEU | A | 455 | 41.640 | 26.492 | 26.964 | 1.00 | 10.88 | A | N |
| ATOM | 1298 | CA | LEU | A | 455 | 42.345 | 26.353 | 28.236 | 1.00 | 8.61 | A | C |
| ATOM | 1299 | CB | LEU | A | 455 | 43.221 | 25.088 | 28.250 | 1.00 | 7.42 | A | C |
| ATOM | 1300 | CG | LEU | A | 455 | 44.127 | 24.857 | 29.472 | 1.00 | 8.75 | A | C |
| ATOM | 1301 | CD1 | LEU | A | 455 | 43.341 | 24.897 | 30.782 | 1.00 | 6.63 | A | C |
| ATOM | 1302 | CD2 | LEU | A | 455 | 44.913 | 23.547 | 29.352 | 1.00 | 6.89 | A | C |
| ATOM | 1303 | C | LEU | A | 455 | 43.200 | 27.588 | 28.504 | 1.00 | 9.40 | A | C |
| ATOM | 1304 | O | LEU | A | 455 | 43.184 | 28.138 | 29.607 | 1.00 | 7.99 | A | O |
| ATOM | 1305 | N | LEU | A | 456 | 43.950 | 28.012 | 27.487 | 1.00 | 10.89 | A | N |
| ATOM | 1306 | CA | LEU | A | 456 | 44.818 | 29.186 | 27.583 | 1.00 | 11.72 | A | C |
| ATOM | 1307 | CB | LEU | A | 456 | 45.549 | 29.396 | 26.254 | 1.00 | 14.86 | A | C |
| ATOM | 1308 | CG | LEU | A | 456 | 47.032 | 29.041 | 26.111 | 1.00 | 21.47 | A | C |
| ATOM | 1309 | CD1 | LEU | A | 456 | 47.549 | 28.219 | 27.269 | 1.00 | 14.74 | A | C |
| ATOM | 1310 | CD2 | LEU | A | 456 | 47.300 | 28.348 | 24.772 | 1.00 | 17.27 | A | C |
| ATOM | 1311 | C | LEU | A | 456 | 44.028 | 30.450 | 27.921 | 1.00 | 12.19 | A | C |
| ATOM | 1312 | O | LEU | A | 456 | 44.414 | 31.229 | 28.800 | 1.00 | 10.93 | A | O |
| ATOM | 1313 | N | GLU | A | 457 | 42.928 | 30.656 | 27.202 | 1.00 | 9.66 | A | N |
| ATOM | 1314 | CA | GLU | A | 457 | 42.117 | 31.845 | 27.399 | 1.00 | 11.10 | A | C |
| ATOM | 1315 | CB | GLU | A | 457 | 41.012 | 31.938 | 26.348 | 1.00 | 13.16 | A | C |
| ATOM | 1316 | CG | GLU | A | 457 | 41.526 | 32.147 | 24.927 | 1.00 | 16.72 | A | C |
| ATOM | 1317 | CD | GLU | A | 457 | 40.403 | 32.205 | 23.888 | 1.00 | 29.59 | A | C |
| ATOM | 1318 | OE1 | GLU | A | 457 | 40.717 | 32.236 | 22.676 | 1.00 | 30.94 | A | O |
| ATOM | 1319 | OE2 | GLU | A | 457 | 39.213 | 32.220 | 24.280 | 1.00 | 26.23 | A | O |
| ATOM | 1320 | C | GLU | A | 457 | 41.523 | 31.823 | 28.795 | 1.00 | 11.37 | A | C |
| ATOM | 1321 | O | GLU | A | 457 | 41.504 | 32.846 | 29.478 | 1.00 | 11.20 | A | O |
| ATOM | 1322 | N | TYR | A | 458 | 41.058 | 30.652 | 29.230 | 1.00 | 9.53 | A | N |
| ATOM | 1323 | CA | TYR | A | 458 | 40.542 | 30.536 | 30.591 | 1.00 | 14.47 | A | C |
| ATOM | 1324 | CB | TYR | A | 458 | 40.051 | 29.121 | 30.928 | 1.00 | 10.65 | A | C |
| ATOM | 1325 | CG | TYR | A | 458 | 39.702 | 29.013 | 32.400 | 1.00 | 14.28 | A | C |
| ATOM | 1326 | CD1 | TYR | A | 458 | 38.490 | 29.501 | 32.891 | 1.00 | 13.02 | A | C |
| ATOM | 1327 | CE1 | TYR | A | 458 | 38.179 | 29.425 | 34.242 | 1.00 | 16.48 | A | C |
| ATOM | 1328 | CD2 | TYR | A | 458 | 40.602 | 28.469 | 33.305 | 1.00 | 14.10 | A | C |
| ATOM | 1329 | CE2 | TYR | A | 458 | 40.305 | 28.393 | 34.654 | 1.00 | 16.20 | A | C |
| ATOM | 1330 | CZ | TYR | A | 458 | 39.095 | 28.872 | 35.117 | 1.00 | 18.51 | A | C |
| ATOM | 1331 | OH | TYR | A | 458 | 38.811 | 28.781 | 36.460 | 1.00 | 20.92 | A | O |
| ATOM | 1332 | C | TYR | A | 458 | 41.598 | 30.955 | 31.607 | 1.00 | 15.93 | A | C |
| ATOM | 1333 | O | TYR | A | 458 | 41.324 | 31.750 | 32.514 | 1.00 | 14.40 | A | O |
| ATOM | 1334 | N | GLU | A | 459 | 42.807 | 30.422 | 31.455 | 1.00 | 11.63 | A | N |
| ATOM | 1335 | CA | GLU | A | 459 | 43.875 | 30.716 | 32.401 | 1.00 | 13.04 | A | C |
| ATOM | 1336 | CB | GLU | A | 459 | 45.127 | 29.892 | 32.094 | 1.00 | 15.32 | A | C |
| ATOM | 1337 | CG | GLU | A | 459 | 44.930 | 28.394 | 32.295 | 1.00 | 12.08 | A | C |
| ATOM | 1338 | CD | GLU | A | 459 | 44.667 | 28.034 | 33.745 | 1.00 | 13.32 | A | C |
| ATOM | 1339 | OE1 | GLU | A | 459 | 44.650 | 28.942 | 34.606 | 1.00 | 15.61 | A | O |
| ATOM | 1340 | OE2 | GLU | A | 459 | 44.484 | 26.841 | 34.033 | 1.00 | 10.12 | A | O |
| ATOM | 1341 | C | GLU | A | 459 | 44.208 | 32.200 | 32.386 | 1.00 | 16.76 | A | C |
| ATOM | 1342 | O | GLU | A | 459 | 44.403 | 32.812 | 33.439 | 1.00 | 20.81 | A | O |
| ATOM | 1343 | N | ALA | A | 460 | 44.267 | 32.772 | 31.189 | 1.00 | 13.37 | A | N |
| ATOM | 1344 | CA | ALA | A | 460 | 44.658 | 34.167 | 31.022 | 1.00 | 18.22 | A | C |
| ATOM | 1345 | CB | ALA | A | 460 | 44.771 | 34.518 | 29.530 | 1.00 | 17.66 | A | C |
| ATOM | 1346 | C | ALA | A | 460 | 43.667 | 35.096 | 31.713 | 1.00 | 18.87 | A | C |
| ATOM | 1347 | O | ALA | A | 460 | 44.027 | 36.187 | 32.155 | 1.00 | 17.28 | A | O |
| ATOM | 1348 | N | GLY | A | 461 | 42.420 | 34.651 | 31.811 | 1.00 | 13.96 | A | N |
| ATOM | 1349 | CA | GLY | A | 461 | 41.367 | 35.480 | 32.359 | 1.00 | 17.50 | A | C |
| ATOM | 1350 | C | GLY | A | 461 | 41.030 | 35.266 | 33.824 | 1.00 | 24.82 | A | C |
| ATOM | 1351 | O | GLY | A | 461 | 40.097 | 35.888 | 34.326 | 1.00 | 24.71 | A | O |
| ATOM | 1352 | N | ARG | A | 462 | 41.761 | 34.392 | 34.516 | 1.00 | 27.99 | A | N |
| ATOM | 1353 | CA | ARG | A | 462 | 41.496 | 34.184 | 35.939 | 1.00 | 27.80 | A | C |
| ATOM | 1354 | CB | ARG | A | 462 | 42.321 | 33.033 | 36.529 | 1.00 | 27.47 | A | C |
| ATOM | 1355 | CG | ARG | A | 462 | 42.322 | 31.756 | 35.713 | 1.00 | 28.09 | A | C |
| ATOM | 1356 | CD | ARG | A | 462 | 41.902 | 30.549 | 36.550 | 1.00 | 30.71 | A | C |
| ATOM | 1357 | NE | ARG | A | 462 | 42.527 | 30.494 | 37.870 | 1.00 | 30.04 | A | N |
| ATOM | 1358 | CZ | ARG | A | 462 | 43.352 | 29.528 | 38.270 | 1.00 | 38.66 | A | C |
| ATOM | 1359 | NH1 | ARG | A | 462 | 43.661 | 28.534 | 37.447 | 1.00 | 27.12 | A | N |
| ATOM | 1360 | NH2 | ARG | A | 462 | 43.870 | 29.553 | 39.495 | 1.00 | 38.79 | A | N |
| ATOM | 1361 | C | ARG | A | 462 | 41.781 | 35.475 | 36.703 | 1.00 | 30.36 | A | C |
| ATOM | 1362 | O | ARG | A | 462 | 40.864 | 36.121 | 37.215 | 1.00 | 33.54 | A | O |
| ATOM | 1363 | N | GLY | A | 467 | 57.554 | 33.642 | 29.449 | 1.00 | 31.18 | | N |
| ATOM | 1364 | CA | GLY | A | 467 | 57.315 | 32.741 | 30.563 | 1.00 | 33.18 | | C |
| ATOM | 1365 | C | GLY | A | 467 | 55.889 | 32.770 | 31.090 | 1.00 | 43.87 | | C |
| ATOM | 1366 | O | GLY | A | 467 | 55.650 | 32.403 | 32.246 | 1.00 | 49.22 | | O |
| ATOM | 1367 | N | GLY | A | 468 | 54.950 | 33.187 | 30.235 | 1.00 | 44.36 | | N |
| ATOM | 1368 | CA | GLY | A | 468 | 53.550 | 33.393 | 30.594 | 1.00 | 38.41 | | C |
| ATOM | 1369 | C | GLY | A | 468 | 53.034 | 32.617 | 31.790 | 1.00 | 43.19 | | C |
| ATOM | 1370 | O | GLY | A | 468 | 53.016 | 31.399 | 31.761 | 1.00 | 42.24 | | O |

TABLE 6-continued

Coordinates for crystal structure of the complex of ERR-α and Compound 1

| ATOM | 1371 | O | ALA | A | 469 | 50.412 | 31.103 | 34.683 | 1.00 | 38.34 | | O |
|---|---|---|---|---|---|---|---|---|---|---|---|---|
| ATOM | 1372 | N | ALA | A | 469 | 52.606 | 33.327 | 32.837 | 1.00 | 57.57 | | N |
| ATOM | 1373 | CA | ALA | A | 469 | 52.127 | 32.699 | 34.077 | 1.00 | 47.79 | | C |
| ATOM | 1374 | C | ALA | A | 469 | 50.862 | 31.883 | 33.831 | 1.00 | 42.70 | | C |
| ATOM | 1375 | CB | ALA | A | 469 | 51.886 | 33.747 | 35.152 | 1.00 | 53.53 | | C |
| ATOM | 1376 | N | GLU | A | 470 | 50.286 | 32.077 | 32.652 | 1.00 | 49.90 | | N |
| ATOM | 1377 | CA | GLU | A | 470 | 49.229 | 31.206 | 32.173 | 1.00 | 44.12 | | C |
| ATOM | 1378 | C | GLU | A | 470 | 49.866 | 29.881 | 31.772 | 1.00 | 38.68 | | C |
| ATOM | 1379 | CB | GLU | A | 470 | 48.517 | 31.848 | 30.987 | 1.00 | 45.04 | | C |
| ATOM | 1380 | CG | GLU | A | 470 | 48.080 | 33.273 | 31.272 | 1.00 | 37.73 | | C |
| ATOM | 1381 | CD | GLU | A | 470 | 48.604 | 34.255 | 30.246 | 1.00 | 45.69 | | C |
| ATOM | 1382 | OE1 | GLU | A | 470 | 47.821 | 34.670 | 29.364 | 1.00 | 45.18 | | O |
| ATOM | 1383 | OE2 | GLU | A | 470 | 49.805 | 34.606 | 30.316 | 1.00 | 53.29 | | O |
| ATOM | 1384 | O | GLU | A | 470 | 49.187 | 29.035 | 31.176 | 1.00 | 22.49 | | O |
| ATOM | 1385 | N | ARG | A | 472 | 51.175 | 29.768 | 32.084 | 1.00 | 38.15 | A | N |
| ATOM | 1386 | CA | ARG | A | 472 | 52.000 | 28.538 | 32.163 | 1.00 | 28.98 | A | C |
| ATOM | 1387 | CB | ARG | A | 472 | 53.407 | 28.910 | 32.624 | 1.00 | 32.47 | A | C |
| ATOM | 1388 | CG | ARG | A | 472 | 53.960 | 28.048 | 33.758 | 1.00 | 28.83 | A | C |
| ATOM | 1389 | CD | ARG | A | 472 | 55.076 | 28.765 | 34.521 | 1.00 | 36.97 | A | C |
| ATOM | 1390 | NE | ARG | A | 472 | 54.552 | 29.761 | 35.457 | 1.00 | 49.68 | A | N |
| ATOM | 1391 | CZ | ARG | A | 472 | 55.221 | 30.835 | 35.875 | 1.00 | 48.56 | A | C |
| ATOM | 1392 | NH1 | ARG | A | 472 | 56.449 | 31.077 | 35.435 | 1.00 | 47.42 | A | N |
| ATOM | 1393 | NH2 | ARG | A | 472 | 54.654 | 31.679 | 36.727 | 1.00 | 57.24 | A | N |
| ATOM | 1394 | C | ARG | A | 472 | 51.460 | 27.528 | 33.167 | 1.00 | 22.66 | A | C |
| ATOM | 1395 | O | ARG | A | 472 | 51.953 | 26.385 | 33.296 | 1.00 | 15.82 | A | O |
| ATOM | 1396 | N | ARG | A | 473 | 50.483 | 27.992 | 33.924 | 1.00 | 12.06 | A | N |
| ATOM | 1397 | CA | ARG | A | 473 | 49.577 | 27.123 | 34.611 | 1.00 | 13.43 | A | C |
| ATOM | 1398 | CB | ARG | A | 473 | 48.402 | 27.962 | 35.118 | 1.00 | 14.06 | A | C |
| ATOM | 1399 | CG | ARG | A | 473 | 47.281 | 27.168 | 35.726 | 1.00 | 16.08 | A | C |
| ATOM | 1400 | CD | ARG | A | 473 | 47.744 | 26.481 | 36.985 | 1.00 | 14.45 | A | C |
| ATOM | 1401 | NE | ARG | A | 473 | 46.686 | 25.663 | 37.574 | 1.00 | 18.74 | A | N |
| ATOM | 1402 | CZ | ARG | A | 473 | 46.863 | 24.907 | 38.651 | 1.00 | 18.61 | A | C |
| ATOM | 1403 | NH1 | ARG | A | 473 | 48.060 | 24.882 | 39.231 | 1.00 | 13.30 | A | N |
| ATOM | 1404 | NH2 | ARG | A | 473 | 45.858 | 24.181 | 39.143 | 1.00 | 13.45 | A | N |
| ATOM | 1405 | C | ARG | A | 473 | 49.103 | 26.068 | 33.599 | 1.00 | 9.75 | A | C |
| ATOM | 1406 | O | ARG | A | 473 | 49.060 | 24.886 | 33.908 | 1.00 | 9.07 | A | O |
| ATOM | 1407 | N | ALA | A | 474 | 48.764 | 26.503 | 32.387 | 1.00 | 8.60 | A | N |
| ATOM | 1408 | CA | ALA | A | 474 | 48.233 | 25.602 | 31.357 | 1.00 | 12.29 | A | C |
| ATOM | 1409 | CB | ALA | A | 474 | 47.836 | 26.372 | 30.101 | 1.00 | 7.83 | A | C |
| ATOM | 1410 | C | ALA | A | 474 | 49.209 | 24.476 | 31.010 | 1.00 | 9.60 | A | C |
| ATOM | 1411 | O | ALA | A | 474 | 48.821 | 23.312 | 30.918 | 1.00 | 6.48 | A | O |
| ATOM | 1412 | N | GLY | A | 475 | 50.474 | 24.825 | 30.791 | 1.00 | 8.47 | A | N |
| ATOM | 1413 | CA | GLY | A | 475 | 51.472 | 23.820 | 30.478 | 1.00 | 6.70 | A | C |
| ATOM | 1414 | C | GLY | A | 475 | 51.596 | 22.777 | 31.579 | 1.00 | 7.84 | A | C |
| ATOM | 1415 | O | GLY | A | 475 | 51.806 | 21.594 | 31.308 | 1.00 | 6.38 | A | O |
| ATOM | 1416 | N | ARG | A | 476 | 51.470 | 23.207 | 32.830 | 1.00 | 7.27 | A | N |
| ATOM | 1417 | CA | ARG | A | 476 | 51.621 | 22.276 | 33.937 | 1.00 | 9.01 | A | C |
| ATOM | 1418 | CB | ARG | A | 476 | 51.709 | 23.000 | 35.285 | 1.00 | 10.28 | A | C |
| ATOM | 1419 | CG | ARG | A | 476 | 53.021 | 23.745 | 35.462 | 1.00 | 14.06 | A | C |
| ATOM | 1420 | CD | ARG | A | 476 | 53.149 | 24.466 | 36.810 | 1.00 | 13.23 | A | C |
| ATOM | 1421 | NE | ARG | A | 476 | 54.392 | 25.229 | 36.835 | 1.00 | 21.02 | A | N |
| ATOM | 1422 | CZ | ARG | A | 476 | 54.731 | 26.093 | 37.788 | 1.00 | 28.20 | A | C |
| ATOM | 1423 | NH1 | ARG | A | 476 | 53.917 | 26.303 | 38.812 | 1.00 | 24.66 | A | N |
| ATOM | 1424 | NH2 | ARG | A | 476 | 55.887 | 26.742 | 37.716 | 1.00 | 27.48 | A | N |
| ATOM | 1425 | C | ARG | A | 476 | 50.502 | 21.243 | 33.937 | 1.00 | 8.35 | A | C |
| ATOM | 1426 | O | ARG | A | 476 | 50.720 | 20.076 | 34.296 | 1.00 | 6.16 | A | O |
| ATOM | 1427 | N | LEU | A | 477 | 49.307 | 21.668 | 33.544 | 1.00 | 9.30 | A | N |
| ATOM | 1428 | CA | LEU | A | 477 | 48.212 | 20.713 | 33.384 | 1.00 | 8.69 | A | C |
| ATOM | 1429 | CB | LEU | A | 477 | 46.885 | 21.429 | 33.139 | 1.00 | 7.76 | A | C |
| ATOM | 1430 | CG | LEU | A | 477 | 46.513 | 22.531 | 34.142 | 1.00 | 11.82 | A | C |
| ATOM | 1431 | CD1 | LEU | A | 477 | 45.216 | 23.218 | 33.737 | 1.00 | 11.76 | A | C |
| ATOM | 1432 | CD2 | LEU | A | 477 | 46.399 | 21.973 | 35.540 | 1.00 | 9.57 | A | C |
| ATOM | 1433 | C | LEU | A | 477 | 48.526 | 19.755 | 32.229 | 1.00 | 5.56 | A | C |
| ATOM | 1434 | O | LEU | A | 477 | 48.350 | 18.551 | 32.362 | 1.00 | 6.17 | A | O |
| ATOM | 1435 | N | LEU | A | 478 | 49.007 | 20.294 | 31.109 | 1.00 | 6.20 | A | N |
| ATOM | 1436 | CA | LEU | A | 478 | 49.321 | 19.463 | 29.939 | 1.00 | 7.90 | A | C |
| ATOM | 1437 | CB | LEU | A | 478 | 49.795 | 20.297 | 28.739 | 1.00 | 6.55 | A | C |
| ATOM | 1438 | CG | LEU | A | 478 | 48.915 | 21.411 | 28.161 | 1.00 | 10.60 | A | C |
| ATOM | 1439 | CD1 | LEU | A | 478 | 49.393 | 21.834 | 26.750 | 1.00 | 6.64 | A | C |
| ATOM | 1440 | CD2 | LEU | A | 478 | 47.465 | 20.999 | 28.127 | 1.00 | 6.74 | A | C |
| ATOM | 1441 | C | LEU | A | 478 | 50.369 | 18.406 | 30.266 | 1.00 | 4.61 | A | C |
| ATOM | 1442 | O | LEU | A | 478 | 50.329 | 17.306 | 29.723 | 1.00 | 4.57 | A | O |
| ATOM | 1443 | N | LEU | A | 479 | 51.283 | 18.730 | 31.174 | 1.00 | 3.82 | A | N |
| ATOM | 1444 | CA | LEU | A | 479 | 52.391 | 17.824 | 31.474 | 1.00 | 6.73 | A | C |
| ATOM | 1445 | CB | LEU | A | 479 | 53.524 | 18.546 | 32.203 | 1.00 | 3.69 | A | C |
| ATOM | 1446 | CG | LEU | A | 479 | 54.400 | 19.457 | 31.336 | 1.00 | 6.62 | A | C |
| ATOM | 1447 | CD1 | LEU | A | 479 | 55.179 | 20.409 | 32.225 | 1.00 | 6.04 | A | C |
| ATOM | 1448 | CD2 | LEU | A | 479 | 55.350 | 18.640 | 30.461 | 1.00 | 6.42 | A | C |

TABLE 6-continued

Coordinates for crystal structure of the complex of ERR-α and Compound 1

| ATOM | 1449 | C   | LEU | A | 479 | 51.958 | 16.587 | 32.266 | 1.00 | 5.21 A  | C |
|------|------|-----|-----|---|-----|--------|--------|--------|------|---------|---|
| ATOM | 1450 | O   | LEU | A | 479 | 52.767 | 15.681 | 32.488 | 1.00 | 5.37 A  | O |
| ATOM | 1451 | N   | THR | A | 480 | 50.700 | 16.568 | 32.705 | 1.00 | 4.49 A  | N |
| ATOM | 1452 | CA  | THR | A | 480 | 50.142 | 15.393 | 33.371 | 1.00 | 5.19 A  | C |
| ATOM | 1453 | CB  | THR | A | 480 | 49.115 | 15.771 | 34.454 | 1.00 | 5.02 A  | C |
| ATOM | 1454 | OG1 | THR | A | 480 | 47.881 | 16.129 | 33.828 | 1.00 | 3.89 A  | O |
| ATOM | 1455 | CG2 | THR | A | 480 | 49.612 | 16.943 | 35.313 | 1.00 | 7.08 A  | C |
| ATOM | 1456 | C   | THR | A | 480 | 49.458 | 14.442 | 32.376 | 1.00 | 5.92 A  | C |
| ATOM | 1457 | O   | THR | A | 480 | 49.067 | 13.323 | 32.730 | 1.00 | 4.76 A  | O |
| ATOM | 1458 | N   | LEU | A | 481 | 49.315 | 14.879 | 31.131 | 1.00 | 4.99 A  | N |
| ATOM | 1459 | CA  | LEU | A | 481 | 48.643 | 14.053 | 30.132 | 1.00 | 6.38 A  | C |
| ATOM | 1460 | CB  | LEU | A | 481 | 48.323 | 14.876 | 28.879 | 1.00 | 4.09 A  | C |
| ATOM | 1461 | CG  | LEU | A | 481 | 47.263 | 15.959 | 29.112 | 1.00 | 6.36 A  | C |
| ATOM | 1462 | CD1 | LEU | A | 481 | 47.099 | 16.855 | 27.885 | 1.00 | 4.83 A  | C |
| ATOM | 1463 | CD2 | LEU | A | 481 | 45.928 | 15.311 | 29.503 | 1.00 | 6.78 A  | C |
| ATOM | 1464 | C   | LEU | A | 481 | 49.419 | 12.765 | 29.787 | 1.00 | 6.72 A  | C |
| ATOM | 1465 | O   | LEU | A | 481 | 48.823 | 11.723 | 29.508 | 1.00 | 7.93 A  | O |
| ATOM | 1466 | N   | PRO | A | 482 | 50.753 | 12.834 | 29.782 | 1.00 | 6.60 A  | N |
| ATOM | 1467 | CD  | PRO | A | 482 | 51.648 | 14.000 | 29.669 | 1.00 | 4.04 A  | C |
| ATOM | 1468 | CA  | PRO | A | 482 | 51.450 | 11.572 | 29.529 | 1.00 | 6.31 A  | C |
| ATOM | 1469 | CB  | PRO | A | 482 | 52.924 | 11.978 | 29.568 | 1.00 | 7.44 A  | C |
| ATOM | 1470 | CG  | PRO | A | 482 | 52.914 | 13.410 | 29.084 | 1.00 | 4.45 A  | C |
| ATOM | 1471 | C   | PRO | A | 482 | 51.135 | 10.516 | 30.590 | 1.00 | 7.02 A  | C |
| ATOM | 1472 | O   | PRO | A | 482 | 50.852 | 9.372  | 30.233 | 1.00 | 5.79 A  | O |
| ATOM | 1473 | N   | LEU | A | 483 | 51.167 | 10.886 | 31.867 | 1.00 | 6.14 A  | N |
| ATOM | 1474 | CA  | LEU | A | 483 | 50.840 | 9.928  | 32.915 | 1.00 | 7.66 A  | C |
| ATOM | 1475 | CB  | LEU | A | 483 | 51.102 | 10.501 | 34.317 | 1.00 | 5.49 A  | C |
| ATOM | 1476 | CG  | LEU | A | 483 | 50.748 | 9.589  | 35.501 | 1.00 | 6.58 A  | C |
| ATOM | 1477 | CD1 | LEU | A | 483 | 51.488 | 8.251  | 35.455 | 1.00 | 7.85 A  | C |
| ATOM | 1478 | CD2 | LEU | A | 483 | 50.984 | 10.286 | 36.848 | 1.00 | 8.45 A  | C |
| ATOM | 1479 | C   | LEU | A | 483 | 49.387 | 9.491  | 32.784 | 1.00 | 6.34 A  | C |
| ATOM | 1480 | O   | LEU | A | 483 | 49.050 | 8.338  | 33.068 | 1.00 | 6.26 A  | O |
| ATOM | 1481 | N   | LEU | A | 484 | 48.519 | 10.405 | 32.361 | 1.00 | 5.41 A  | N |
| ATOM | 1482 | CA  | LEU | A | 484 | 47.112 | 10.037 | 32.191 | 1.00 | 4.94 A  | C |
| ATOM | 1483 | CB  | LEU | A | 484 | 46.267 | 11.235 | 31.773 | 1.00 | 5.72 A  | C |
| ATOM | 1484 | CG  | LEU | A | 484 | 44.838 | 10.871 | 31.359 | 1.00 | 8.11 A  | C |
| ATOM | 1485 | CD1 | LEU | A | 484 | 44.121 | 10.158 | 32.516 | 1.00 | 7.42 A  | C |
| ATOM | 1486 | CD2 | LEU | A | 484 | 44.037 | 12.092 | 30.873 | 1.00 | 4.36 A  | C |
| ATOM | 1487 | C   | LEU | A | 484 | 46.958 | 8.894  | 31.179 | 1.00 | 8.10 A  | C |
| ATOM | 1488 | O   | LEU | A | 484 | 46.278 | 7.899  | 31.448 | 1.00 | 7.35 A  | O |
| ATOM | 1489 | N   | ARG | A | 485 | 47.600 | 9.034  | 30.019 | 1.00 | 8.09 A  | N |
| ATOM | 1490 | CA  | ARG | A | 485 | 47.514 | 8.009  | 28.978 | 1.00 | 5.79 A  | C |
| ATOM | 1491 | CB  | ARG | A | 485 | 48.158 | 8.485  | 27.668 | 1.00 | 5.19 A  | C |
| ATOM | 1492 | CG  | ARG | A | 485 | 47.974 | 7.494  | 26.509 | 1.00 | 8.17 A  | C |
| ATOM | 1493 | CD  | ARG | A | 485 | 48.363 | 8.079  | 25.151 | 1.00 | 7.22 A  | C |
| ATOM | 1494 | NE  | ARG | A | 485 | 47.455 | 9.129  | 24.704 | 1.00 | 8.05 A  | N |
| ATOM | 1495 | CZ  | ARG | A | 485 | 47.585 | 9.771  | 23.550 | 1.00 | 6.38 A  | C |
| ATOM | 1496 | NH1 | ARG | A | 485 | 48.588 | 9.466  | 22.733 | 1.00 | 9.41 A  | N |
| ATOM | 1497 | NH2 | ARG | A | 485 | 46.727 | 10.718 | 23.213 | 1.00 | 6.28 A  | N |
| ATOM | 1498 | C   | ARG | A | 485 | 48.126 | 6.682  | 29.445 | 1.00 | 9.91 A  | C |
| ATOM | 1499 | O   | ARG | A | 485 | 47.532 | 5.610  | 29.246 | 1.00 | 8.36 A  | O |
| ATOM | 1500 | N   | GLN | A | 486 | 49.297 | 6.766  | 30.077 | 1.00 | 6.47 A  | N |
| ATOM | 1501 | CA  | GLN | A | 486 | 49.983 | 5.605  | 30.642 | 1.00 | 7.15 A  | C |
| ATOM | 1502 | CB  | GLN | A | 486 | 51.280 | 6.043  | 31.325 | 1.00 | 8.50 A  | C |
| ATOM | 1503 | CG  | GLN | A | 486 | 52.116 | 4.889  | 31.885 | 1.00 | 13.05 A | C |
| ATOM | 1504 | CD  | GLN | A | 486 | 53.436 | 5.358  | 32.486 | 1.00 | 18.63 A | C |
| ATOM | 1505 | OE1 | GLN | A | 486 | 54.385 | 4.586  | 32.611 | 1.00 | 27.27 A | O |
| ATOM | 1506 | NE2 | GLN | A | 486 | 53.498 | 6.622  | 32.857 | 1.00 | 7.54 A  | N |
| ATOM | 1507 | C   | GLN | A | 486 | 49.105 | 4.868  | 31.662 | 1.00 | 8.58 A  | C |
| ATOM | 1508 | O   | GLN | A | 486 | 49.034 | 3.634  | 31.671 | 1.00 | 10.15 A | O |
| ATOM | 1509 | N   | THR | A | 487 | 48.458 | 5.629  | 32.533 | 1.00 | 6.57 A  | N |
| ATOM | 1510 | CA  | THR | A | 487 | 47.601 | 5.041  | 33.554 | 1.00 | 6.03 A  | C |
| ATOM | 1511 | CB  | THR | A | 487 | 47.020 | 6.102  | 34.508 | 1.00 | 6.25 A  | C |
| ATOM | 1512 | OG1 | THR | A | 487 | 48.089 | 6.869  | 35.083 | 1.00 | 6.80 A  | O |
| ATOM | 1513 | CG2 | THR | A | 487 | 46.222 | 5.451  | 35.628 | 1.00 | 6.92 A  | C |
| ATOM | 1514 | C   | THR | A | 487 | 46.474 | 4.262  | 32.885 | 1.00 | 8.30 A  | C |
| ATOM | 1515 | O   | THR | A | 487 | 46.188 | 3.136  | 33.284 | 1.00 | 8.08 A  | O |
| ATOM | 1516 | N   | ALA | A | 488 | 45.838 | 4.859  | 31.869 | 1.00 | 7.90 A  | N |
| ATOM | 1517 | CA  | ALA | A | 488 | 44.778 | 4.172  | 31.121 | 1.00 | 7.61 A  | C |
| ATOM | 1518 | CB  | ALA | A | 488 | 44.158 | 5.094  | 30.086 | 1.00 | 6.25 A  | C |
| ATOM | 1519 | C   | ALA | A | 488 | 45.268 | 2.874  | 30.462 | 1.00 | 9.70 A  | C |
| ATOM | 1520 | O   | ALA | A | 488 | 44.570 | 1.854  | 30.480 | 1.00 | 9.54 A  | O |
| ATOM | 1521 | N   | GLY | A | 489 | 46.467 | 2.915  | 29.881 | 1.00 | 9.15 A  | N |
| ATOM | 1522 | CA  | GLY | A | 489 | 47.078 | 1.724  | 29.316 | 1.00 | 8.13 A  | C |
| ATOM | 1523 | C   | GLY | A | 489 | 47.277 | 0.653  | 30.375 | 1.00 | 12.71 A | C |
| ATOM | 1524 | O   | GLY | A | 489 | 47.060 | −0.540 | 30.124 | 1.00 | 13.11 A | O |
| ATOM | 1525 | N   | LYS | A | 490 | 47.690 | 1.077  | 31.567 | 1.00 | 10.81 A | N |
| ATOM | 1526 | CA  | LYS | A | 490 | 47.919 | 0.151  | 32.674 | 1.00 | 11.63 A | C |

TABLE 6-continued

Coordinates for crystal structure of the complex of ERR-α and Compound 1

| ATOM | 1527 | CB  | LYS | A | 490 | 48.531 | 0.883   | 33.874 | 1.00 | 10.68 | A | C |
|------|------|-----|-----|---|-----|--------|---------|--------|------|-------|---|---|
| ATOM | 1528 | CG  | LYS | A | 490 | 50.058 | 1.014   | 33.831 | 1.00 | 12.15 | A | C |
| ATOM | 1529 | CD  | LYS | A | 490 | 50.520 | 2.108   | 34.780 | 1.00 | 18.49 | A | C |
| ATOM | 1530 | CE  | LYS | A | 490 | 51.784 | 1.723   | 35.538 | 1.00 | 27.57 | A | C |
| ATOM | 1531 | NZ  | LYS | A | 490 | 52.910 | 1.332   | 34.646 | 1.00 | 30.65 | A | N |
| ATOM | 1532 | C   | LYS | A | 490 | 46.617 | −0.539  | 33.080 | 1.00 | 10.40 | A | C |
| ATOM | 1533 | O   | LYS | A | 490 | 46.594 | −1.740  | 33.334 | 1.00 | 9.67  | A | O |
| ATOM | 1534 | N   | VAL | A | 491 | 45.531 | 0.227   | 33.136 | 1.00 | 10.22 | A | N |
| ATOM | 1535 | CA  | VAL | A | 491 | 44.227 | −0.336  | 33.474 | 1.00 | 9.82  | A | C |
| ATOM | 1536 | CB  | VAL | A | 491 | 43.143 | 0.759   | 33.568 | 1.00 | 12.35 | A | C |
| ATOM | 1537 | CG1 | VAL | A | 491 | 41.758 | 0.129   | 33.706 | 1.00 | 8.81  | A | C |
| ATOM | 1538 | CG2 | VAL | A | 491 | 43.435 | 1.709   | 34.740 | 1.00 | 8.17  | A | C |
| ATOM | 1539 | C   | VAL | A | 491 | 43.815 | −1.394  | 32.444 | 1.00 | 10.85 | A | C |
| ATOM | 1540 | O   | VAL | A | 491 | 43.376 | −2.493  | 32.802 | 1.00 | 10.60 | A | O |
| ATOM | 1541 | N   | LEU | A | 492 | 43.970 | −1.065  | 31.166 | 1.00 | 9.78  | A | N |
| ATOM | 1542 | CA  | LEU | A | 492 | 43.612 | −1.999  | 30.101 | 1.00 | 11.20 | A | C |
| ATOM | 1543 | CB  | LEU | A | 492 | 43.727 | −1.335  | 28.726 | 1.00 | 12.15 | A | C |
| ATOM | 1544 | CG  | LEU | A | 492 | 42.641 | −0.300  | 28.433 | 1.00 | 11.13 | A | C |
| ATOM | 1545 | CD1 | LEU | A | 492 | 43.057 | 0.656   | 27.331 | 1.00 | 14.47 | A | C |
| ATOM | 1546 | CD2 | LEU | A | 492 | 41.326 | −0.995  | 28.097 | 1.00 | 13.28 | A | C |
| ATOM | 1547 | C   | LEU | A | 492 | 44.474 | −3.257  | 30.166 | 1.00 | 12.71 | A | C |
| ATOM | 1548 | O   | LEU | A | 492 | 43.971 | −4.364  | 30.014 | 1.00 | 16.59 | A | O |
| ATOM | 1549 | N   | ALA | A | 493 | 45.769 | −3.081  | 30.406 | 1.00 | 10.68 | A | N |
| ATOM | 1550 | CA  | ALA | A | 493 | 46.692 | −4.211  | 30.481 | 1.00 | 15.18 | A | C |
| ATOM | 1551 | CB  | ALA | A | 493 | 48.133 | −3.719  | 30.642 | 1.00 | 10.48 | A | C |
| ATOM | 1552 | C   | ALA | A | 493 | 46.312 | −5.157  | 31.626 | 1.00 | 14.89 | A | C |
| ATOM | 1553 | O   | ALA | A | 493 | 46.390 | −6.382  | 31.488 | 1.00 | 14.30 | A | O |
| ATOM | 1554 | N   | HIS | A | 494 | 45.897 | −4.586  | 32.754 | 1.00 | 10.41 | A | N |
| ATOM | 1555 | CA  | HIS | A | 494 | 45.480 | −5.391  | 33.888 | 1.00 | 13.47 | A | C |
| ATOM | 1556 | CB  | HIS | A | 494 | 45.179 | −4.509  | 35.098 | 1.00 | 12.79 | A | C |
| ATOM | 1557 | CG  | HIS | A | 494 | 44.532 | −5.249  | 36.226 | 1.00 | 12.11 | A | C |
| ATOM | 1558 | CD2 | HIS | A | 494 | 43.241 | −5.341  | 36.606 | 1.00 | 10.14 | A | C |
| ATOM | 1559 | ND1 | HIS | A | 494 | 45.250 | −6.048  | 37.096 | 1.00 | 11.52 | A | N |
| ATOM | 1560 | CE1 | HIS | A | 494 | 44.418 | −6.583  | 37.975 | 1.00 | 14.57 | A | C |
| ATOM | 1561 | NE2 | HIS | A | 494 | 43.195 | −6.173  | 37.698 | 1.00 | 13.14 | A | N |
| ATOM | 1562 | C   | HIS | A | 494 | 44.265 | −6.276  | 33.562 | 1.00 | 16.47 | A | C |
| ATOM | 1563 | O   | HIS | A | 494 | 44.227 | −7.459  | 33.912 | 1.00 | 14.02 | A | O |
| ATOM | 1564 | N   | PHE | A | 495 | 43.268 | −5.710  | 32.894 | 1.00 | 13.66 | A | N |
| ATOM | 1565 | CA  | PHE | A | 495 | 42.062 | −6.481  | 32.619 | 1.00 | 13.58 | A | C |
| ATOM | 1566 | CB  | PHE | A | 495 | 40.850 | −5.571  | 32.440 | 1.00 | 14.70 | A | C |
| ATOM | 1567 | CG  | PHE | A | 495 | 40.357 | −4.976  | 33.729 | 1.00 | 16.86 | A | C |
| ATOM | 1568 | CD1 | PHE | A | 495 | 39.483 | −5.686  | 34.545 | 1.00 | 12.62 | A | C |
| ATOM | 1569 | CD2 | PHE | A | 495 | 40.778 | −3.719  | 34.137 | 1.00 | 10.12 | A | C |
| ATOM | 1570 | CE1 | PHE | A | 495 | 39.028 | −5.150  | 35.738 | 1.00 | 12.50 | A | C |
| ATOM | 1571 | CE2 | PHE | A | 495 | 40.329 | −3.169  | 35.334 | 1.00 | 12.02 | A | C |
| ATOM | 1572 | CZ  | PHE | A | 495 | 39.455 | −3.882  | 36.137 | 1.00 | 14.88 | A | C |
| ATOM | 1573 | C   | PHE | A | 495 | 42.233 | −7.448  | 31.448 | 1.00 | 16.82 | A | C |
| ATOM | 1574 | O   | PHE | A | 495 | 41.553 | −8.474  | 31.380 | 1.00 | 18.15 | A | O |
| ATOM | 1575 | N   | TYR | A | 496 | 43.156 | −7.139  | 30.542 | 1.00 | 12.11 | A | N |
| ATOM | 1576 | CA  | TYR | A | 496 | 43.447 | −8.055  | 29.447 | 1.00 | 21.15 | A | C |
| ATOM | 1577 | CB  | TYR | A | 496 | 44.001 | −7.313  | 28.225 | 1.00 | 19.88 | A | C |
| ATOM | 1578 | CG  | TYR | A | 496 | 42.926 | −6.834  | 27.275 | 1.00 | 21.34 | A | C |
| ATOM | 1579 | CD1 | TYR | A | 496 | 42.366 | −5.572  | 27.415 | 1.00 | 18.88 | A | C |
| ATOM | 1580 | CE1 | TYR | A | 496 | 41.379 | −5.127  | 26.560 | 1.00 | 25.39 | A | C |
| ATOM | 1581 | CD2 | TYR | A | 496 | 42.463 | −7.648  | 26.245 | 1.00 | 22.92 | A | C |
| ATOM | 1582 | CE2 | TYR | A | 496 | 41.469 | −7.212  | 25.376 | 1.00 | 23.95 | A | C |
| ATOM | 1583 | CZ  | TYR | A | 496 | 40.928 | −5.947  | 25.542 | 1.00 | 27.62 | A | C |
| ATOM | 1584 | OH  | TYR | A | 496 | 39.937 | −5.490  | 24.697 | 1.00 | 25.41 | A | O |
| ATOM | 1585 | C   | TYR | A | 496 | 44.414 | −9.151  | 29.879 | 1.00 | 21.85 | A | C |
| ATOM | 1586 | O   | TYR | A | 496 | 44.498 | −10.195 | 29.235 | 1.00 | 26.69 | A | O |
| ATOM | 1587 | N   | GLY | A | 497 | 45.130 | −8.914  | 30.972 | 1.00 | 14.30 | A | N |
| ATOM | 1588 | CA  | GLY | A | 497 | 46.203 | −9.806  | 31.386 | 1.00 | 24.56 | A | C |
| ATOM | 1589 | C   | GLY | A | 497 | 47.316 | −9.753  | 30.360 | 1.00 | 28.72 | A | C |
| ATOM | 1590 | O   | GLY | A | 497 | 47.077 | −9.386  | 29.212 | 1.00 | 38.25 | A | O |
| ATOM | 1591 | N   | VAL | A | 498 | 48.530 | −10.115 | 30.751 | 1.00 | 35.38 | A | N |
| ATOM | 1592 | CA  | VAL | A | 498 | 49.669 | −10.002 | 29.836 | 1.00 | 36.63 | A | C |
| ATOM | 1593 | CB  | VAL | A | 498 | 50.529 | −8.807  | 30.207 | 1.00 | 26.53 | A | C |
| ATOM | 1594 | CG1 | VAL | A | 498 | 49.830 | −7.521  | 29.770 | 1.00 | 26.24 | A | C |
| ATOM | 1595 | CG2 | VAL | A | 498 | 50.766 | −8.805  | 31.706 | 1.00 | 24.96 | A | C |
| ATOM | 1596 | C   | VAL | A | 498 | 50.533 | −11.263 | 29.748 | 1.00 | 30.44 | A | C |
| ATOM | 1597 | O   | VAL | A | 498 | 51.458 | −11.456 | 30.534 | 1.00 | 38.80 | A | O |
| ATOM | 1598 | N   | LEU | A | 500 | 49.353 | −10.929 | 26.127 | 1.00 | 33.40 | A | N |
| ATOM | 1599 | CA  | LEU | A | 500 | 48.100 | −10.165 | 26.188 | 1.00 | 44.11 | A | C |
| ATOM | 1600 | CB  | LEU | A | 500 | 48.125 | −9.002  | 25.197 | 1.00 | 39.34 | A | C |
| ATOM | 1601 | CG  | LEU | A | 500 | 47.232 | −7.801  | 25.526 | 1.00 | 42.26 | A | C |
| ATOM | 1602 | CD1 | LEU | A | 500 | 47.446 | −6.670  | 24.521 | 1.00 | 44.56 | A | C |
| ATOM | 1603 | CD2 | LEU | A | 500 | 45.773 | −8.205  | 25.568 | 1.00 | 41.57 | A | C |
| ATOM | 1604 | C   | LEU | A | 500 | 46.877 | −11.048 | 25.927 | 1.00 | 37.26 | A | C |

TABLE 6-continued

Coordinates for crystal structure of the complex of ERR-α and Compound 1

| ATOM | 1605 | O   | LEU | A | 500 | 46.350 | −11.085 | 24.817 | 1.00 | 41.98 | A | O |
| ---- | ---- | --- | --- | - | --- | ------ | ------- | ------ | ---- | ----- | - | - |
| ATOM | 1606 | N   | LYS | A | 501 | 46.408 | −11.718 | 26.972 | 1.00 | 36.58 |   | N |
| ATOM | 1607 | CA  | LYS | A | 501 | 45.471 | −12.830 | 26.831 | 1.00 | 36.70 |   | C |
| ATOM | 1608 | C   | LYS | A | 501 | 44.045 | −12.462 | 26.375 | 1.00 | 41.70 |   | C |
| ATOM | 1609 | CB  | LYS | A | 501 | 45.451 | −13.636 | 28.128 | 1.00 | 32.29 |   | C |
| ATOM | 1610 | CG  | LYS | A | 501 | 46.741 | −13.512 | 28.919 | 1.00 | 31.65 |   | C |
| ATOM | 1611 | CD  | LYS | A | 501 | 46.963 | −14.693 | 29.849 | 1.00 | 34.94 |   | C |
| ATOM | 1612 | CE  | LYS | A | 501 | 47.808 | −14.292 | 31.040 | 1.00 | 35.22 |   | C |
| ATOM | 1613 | NZ  | LYS | A | 501 | 47.184 | −13.159 | 31.794 | 1.00 | 42.32 |   | N |
| ATOM | 1614 | O   | LYS | A | 501 | 43.573 | −12.965 | 25.352 | 1.00 | 50.52 | A | O |
| ATOM | 1615 | N   | GLY | A | 502 | 43.360 | −11.599 | 27.123 | 1.00 | 35.42 | A | N |
| ATOM | 1616 | CA  | GLY | A | 502 | 42.014 | −11.182 | 26.756 | 1.00 | 33.73 | A | C |
| ATOM | 1617 | C   | GLY | A | 502 | 40.925 | −11.689 | 27.694 | 1.00 | 36.80 | A | C |
| ATOM | 1618 | O   | GLY | A | 502 | 39.788 | −11.933 | 27.271 | 1.00 | 32.83 | A | O |
| ATOM | 1619 | N   | LYS | A | 503 | 41.280 | −11.839 | 28.970 | 1.00 | 30.78 | A | N |
| ATOM | 1620 | CA  | LYS | A | 503 | 40.371 | −12.320 | 30.007 | 1.00 | 25.52 | A | C |
| ATOM | 1621 | CB  | LYS | A | 503 | 41.084 | −12.332 | 31.360 | 1.00 | 29.96 | A | C |
| ATOM | 1622 | CG  | LYS | A | 503 | 42.588 | −12.524 | 31.289 | 1.00 | 29.72 | A | C |
| ATOM | 1623 | CD  | LYS | A | 503 | 42.978 | −13.554 | 30.242 | 1.00 | 34.88 | A | C |
| ATOM | 1624 | CE  | LYS | A | 503 | 44.025 | −14.527 | 30.766 | 1.00 | 41.36 | A | C |
| ATOM | 1625 | NZ  | LYS | A | 503 | 43.476 | −15.895 | 31.017 | 1.00 | 40.90 | A | N |
| ATOM | 1626 | C   | LYS | A | 503 | 39.126 | −11.447 | 30.127 | 1.00 | 29.45 | A | C |
| ATOM | 1627 | O   | LYS | A | 503 | 38.002 | −11.949 | 30.216 | 1.00 | 24.86 | A | O |
| ATOM | 1628 | N   | VAL | A | 504 | 39.344 | −10.136 | 30.159 | 1.00 | 20.96 | A | N |
| ATOM | 1629 | CA  | VAL | A | 504 | 38.259 | −9.164  | 30.245 | 1.00 | 22.57 | A | C |
| ATOM | 1630 | CB  | VAL | A | 504 | 38.282 | −8.432  | 31.604 | 1.00 | 19.39 | A | C |
| ATOM | 1631 | CG1 | VAL | A | 504 | 37.049 | −7.538  | 31.765 | 1.00 | 17.76 | A | C |
| ATOM | 1632 | CG2 | VAL | A | 504 | 38.379 | −9.441  | 32.747 | 1.00 | 18.00 | A | C |
| ATOM | 1633 | C   | VAL | A | 504 | 38.451 | −8.151  | 29.117 | 1.00 | 25.25 | A | C |
| ATOM | 1634 | O   | VAL | A | 504 | 39.164 | −7.167  | 29.288 | 1.00 | 17.14 | A | O |
| ATOM | 1635 | N   | PRO | A | 505 | 37.826 | −8.402  | 27.955 | 1.00 | 23.29 | A | N |
| ATOM | 1636 | CD  | PRO | A | 505 | 36.804 | −9.435  | 27.732 | 1.00 | 27.39 | A | C |
| ATOM | 1637 | CA  | PRO | A | 505 | 38.097 | −7.649  | 26.729 | 1.00 | 26.92 | A | C |
| ATOM | 1638 | CB  | PRO | A | 505 | 37.585 | −8.583  | 25.615 | 1.00 | 26.04 | A | C |
| ATOM | 1639 | CG  | PRO | A | 505 | 37.043 | −9.809  | 26.305 | 1.00 | 28.68 | A | C |
| ATOM | 1640 | C   | PRO | A | 505 | 37.337 | −6.331  | 26.680 | 1.00 | 24.66 | A | C |
| ATOM | 1641 | O   | PRO | A | 505 | 36.324 | −6.232  | 25.990 | 1.00 | 27.19 | A | O |
| ATOM | 1642 | N   | MET | A | 506 | 37.840 | −5.324  | 27.381 | 1.00 | 21.86 | A | N |
| ATOM | 1643 | CA  | MET | A | 506 | 37.124 | −4.065  | 27.511 | 1.00 | 24.67 | A | C |
| ATOM | 1644 | CB  | MET | A | 506 | 37.805 | −3.170  | 28.543 | 1.00 | 18.93 | A | C |
| ATOM | 1645 | CG  | MET | A | 506 | 37.726 | −3.710  | 29.948 | 1.00 | 17.36 | A | C |
| ATOM | 1646 | SD  | MET | A | 506 | 38.577 | −2.617  | 31.094 | 1.00 | 17.41 | A | S |
| ATOM | 1647 | CE  | MET | A | 506 | 37.807 | −3.106  | 32.638 | 1.00 | 12.10 | A | C |
| ATOM | 1648 | C   | MET | A | 506 | 36.935 | −3.322  | 26.191 | 1.00 | 19.43 | A | C |
| ATOM | 1649 | O   | MET | A | 506 | 35.937 | −2.633  | 26.018 | 1.00 | 24.23 | A | O |
| ATOM | 1650 | N   | HIS | A | 507 | 37.885 | −3.452  | 25.267 | 1.00 | 19.93 | A | N |
| ATOM | 1651 | CA  | HIS | A | 507 | 37.756 | −2.793  | 23.967 | 1.00 | 22.77 | A | C |
| ATOM | 1652 | CB  | HIS | A | 507 | 38.996 | −3.001  | 23.085 | 1.00 | 22.56 | A | C |
| ATOM | 1653 | CG  | HIS | A | 507 | 40.195 | −2.221  | 23.527 | 1.00 | 31.95 | A | C |
| ATOM | 1654 | CD2 | HIS | A | 507 | 41.480 | −2.600  | 23.743 | 1.00 | 28.06 | A | C |
| ATOM | 1655 | ND1 | HIS | A | 507 | 40.149 | −0.865  | 23.784 | 1.00 | 30.42 | A | N |
| ATOM | 1656 | CE1 | HIS | A | 507 | 41.350 | −0.446  | 24.147 | 1.00 | 28.24 | A | C |
| ATOM | 1657 | NE2 | HIS | A | 507 | 42.175 | −1.482  | 24.129 | 1.00 | 29.68 | A | N |
| ATOM | 1658 | C   | HIS | A | 507 | 36.507 | −3.272  | 23.238 | 1.00 | 23.49 | A | C |
| ATOM | 1659 | O   | HIS | A | 507 | 35.763 | −2.467  | 22.686 | 1.00 | 21.54 | A | O |
| ATOM | 1660 | N   | LYS | A | 508 | 36.277 | −4.585  | 23.246 | 1.00 | 27.48 | A | N |
| ATOM | 1661 | CA  | LYS | A | 508 | 35.072 | −5.155  | 22.647 | 1.00 | 24.95 | A | C |
| ATOM | 1662 | CB  | LYS | A | 508 | 35.130 | −6.685  | 22.650 | 1.00 | 27.54 | A | C |
| ATOM | 1663 | CG  | LYS | A | 508 | 36.269 | −7.263  | 21.822 | 1.00 | 32.43 | A | C |
| ATOM | 1664 | CD  | LYS | A | 508 | 36.428 | −6.536  | 20.493 | 1.00 | 38.63 | A | C |
| ATOM | 1665 | CE  | LYS | A | 508 | 37.419 | −7.257  | 19.576 | 1.00 | 56.26 | A | C |
| ATOM | 1666 | NZ  | LYS | A | 508 | 36.847 | −8.519  | 18.995 | 1.00 | 43.16 | A | N |
| ATOM | 1667 | C   | LYS | A | 508 | 33.824 | −4.680  | 23.384 | 1.00 | 19.68 | A | C |
| ATOM | 1668 | O   | LYS | A | 508 | 32.864 | −4.220  | 22.764 | 1.00 | 20.81 | A | O |
| ATOM | 1669 | N   | LEU | A | 509 | 33.842 | −4.786  | 24.709 | 1.00 | 22.68 | A | N |
| ATOM | 1670 | CA  | LEU | A | 509 | 32.729 | −4.293  | 25.513 | 1.00 | 23.48 | A | C |
| ATOM | 1671 | CB  | LEU | A | 509 | 33.017 | −4.426  | 27.011 | 1.00 | 29.22 | A | C |
| ATOM | 1672 | CG  | LEU | A | 509 | 31.995 | −3.739  | 27.925 | 1.00 | 27.44 | A | C |
| ATOM | 1673 | CD1 | LEU | A | 509 | 30.694 | −4.517  | 27.936 | 1.00 | 31.92 | A | C |
| ATOM | 1674 | CD2 | LEU | A | 509 | 32.523 | −3.560  | 29.346 | 1.00 | 26.65 | A | C |
| ATOM | 1675 | C   | LEU | A | 509 | 32.431 | −2.837  | 25.173 | 1.00 | 24.41 | A | C |
| ATOM | 1676 | O   | LEU | A | 509 | 31.272 | −2.457  | 25.002 | 1.00 | 22.28 | A | O |
| ATOM | 1677 | N   | PHE | A | 510 | 33.474 | −2.016  | 25.081 | 1.00 | 22.66 | A | N |
| ATOM | 1678 | CA  | PHE | A | 510 | 33.257 | −0.608  | 24.770 | 1.00 | 20.66 | A | C |
| ATOM | 1679 | CB  | PHE | A | 510 | 34.547 | 0.218   | 24.864 | 1.00 | 18.70 | A | C |
| ATOM | 1680 | CG  | PHE | A | 510 | 34.325 | 1.688   | 24.627 | 1.00 | 15.17 | A | C |
| ATOM | 1681 | CD1 | PHE | A | 510 | 34.718 | 2.280   | 23.439 | 1.00 | 16.27 | A | C |
| ATOM | 1682 | CD2 | PHE | A | 510 | 33.676 | 2.460   | 25.572 | 1.00 | 13.01 | A | C |

TABLE 6-continued

Coordinates for crystal structure of the complex of ERR-α and Compound 1

| ATOM | 1683 | CE1 | PHE | A | 510 | 34.506 | 3.626 | 23.218 | 1.00 | 14.48 | A | C |
|---|---|---|---|---|---|---|---|---|---|---|---|---|
| ATOM | 1684 | CE2 | PHE | A | 510 | 33.454 | 3.812 | 25.355 | 1.00 | 14.61 | A | C |
| ATOM | 1685 | CZ | PHE | A | 510 | 33.870 | 4.392 | 24.177 | 1.00 | 13.05 | A | C |
| ATOM | 1686 | C | PHE | A | 510 | 32.634 | −0.438 | 23.385 | 1.00 | 20.14 | A | C |
| ATOM | 1687 | O | PHE | A | 510 | 31.661 | 0.295 | 23.222 | 1.00 | 20.24 | A | O |
| ATOM | 1688 | N | LEU | A | 511 | 33.204 | −1.115 | 22.394 | 1.00 | 21.94 | A | N |
| ATOM | 1689 | CA | LEU | A | 511 | 32.731 | −0.985 | 21.023 | 1.00 | 23.06 | A | C |
| ATOM | 1690 | CB | LEU | A | 511 | 33.535 | −1.890 | 20.082 | 1.00 | 25.37 | A | C |
| ATOM | 1691 | CG | LEU | A | 511 | 33.673 | −1.459 | 18.615 | 1.00 | 34.06 | A | C |
| ATOM | 1692 | CD1 | LEU | A | 511 | 34.020 | −2.650 | 17.729 | 1.00 | 28.40 | A | C |
| ATOM | 1693 | CD2 | LEU | A | 511 | 32.414 | −0.778 | 18.096 | 1.00 | 31.99 | A | C |
| ATOM | 1694 | C | LEU | A | 511 | 31.243 | −1.313 | 20.958 | 1.00 | 26.74 | A | C |
| ATOM | 1695 | O | LEU | A | 511 | 30.448 | −0.524 | 20.452 | 1.00 | 24.65 | A | O |
| ATOM | 1696 | N | ALA | A | 512 | 30.863 | −2.470 | 21.491 | 1.00 | 26.69 | A | N |
| ATOM | 1697 | CA | ALA | A | 512 | 29.465 | −2.880 | 21.465 | 1.00 | 26.91 | A | C |
| ATOM | 1698 | CB | ALA | A | 512 | 29.253 | −4.172 | 22.267 | 1.00 | 28.84 | A | C |
| ATOM | 1699 | C | ALA | A | 512 | 28.571 | −1.766 | 21.989 | 1.00 | 24.32 | A | C |
| ATOM | 1700 | O | ALA | A | 512 | 27.559 | −1.425 | 21.371 | 1.00 | 30.32 | A | O |
| ATOM | 1701 | N | MET | A | 513 | 28.943 | −1.185 | 23.123 | 1.00 | 25.97 | A | N |
| ATOM | 1702 | CA | MET | A | 513 | 28.152 | −0.093 | 23.681 | 1.00 | 25.35 | A | C |
| ATOM | 1703 | CB | MET | A | 513 | 28.581 | 0.220 | 25.112 | 1.00 | 24.25 | A | C |
| ATOM | 1704 | CG | MET | A | 513 | 27.689 | 1.245 | 25.812 | 1.00 | 40.53 | A | C |
| ATOM | 1705 | SD | MET | A | 513 | 25.908 | 0.887 | 25.704 | 1.00 | 55.43 | A | S |
| ATOM | 1706 | CE | MET | A | 513 | 25.865 | −0.783 | 26.356 | 1.00 | 42.48 | A | C |
| ATOM | 1707 | C | MET | A | 513 | 28.224 | 1.159 | 22.802 | 1.00 | 26.20 | A | C |
| ATOM | 1708 | O | MET | A | 513 | 27.236 | 1.875 | 22.651 | 1.00 | 23.76 | A | O |
| ATOM | 1709 | N | LEU | A | 514 | 29.391 | 1.412 | 22.216 | 1.00 | 26.08 | A | N |
| ATOM | 1710 | CA | LEU | A | 514 | 29.578 | 2.579 | 21.359 | 1.00 | 21.31 | A | C |
| ATOM | 1711 | CB | LEU | A | 514 | 31.034 | 2.677 | 20.896 | 1.00 | 21.48 | A | C |
| ATOM | 1712 | CG | LEU | A | 514 | 31.425 | 3.871 | 20.017 | 1.00 | 21.99 | A | C |
| ATOM | 1713 | CD1 | LEU | A | 514 | 31.241 | 5.194 | 20.748 | 1.00 | 18.65 | A | C |
| ATOM | 1714 | CD2 | LEU | A | 514 | 32.860 | 3.721 | 19.548 | 1.00 | 20.15 | A | C |
| ATOM | 1715 | C | LEU | A | 514 | 28.638 | 2.527 | 20.150 | 1.00 | 33.07 | A | C |
| ATOM | 1716 | O | LEU | A | 514 | 27.919 | 3.490 | 19.861 | 1.00 | 29.12 | A | O |
| ATOM | 1717 | N | GLU | A | 515 | 28.627 | 1.398 | 19.449 | 1.00 | 29.69 | A | N |
| ATOM | 1718 | CA | GLU | A | 515 | 27.820 | 1.303 | 18.236 | 1.00 | 34.79 | A | C |
| ATOM | 1719 | CB | GLU | A | 515 | 28.287 | 0.162 | 17.330 | 1.00 | 27.08 | A | C |
| ATOM | 1720 | CG | GLU | A | 515 | 28.131 | −1.216 | 17.909 | 1.00 | 34.33 | A | C |
| ATOM | 1721 | CD | GLU | A | 515 | 28.908 | −2.253 | 17.113 | 1.00 | 45.47 | A | C |
| ATOM | 1722 | OE1 | GLU | A | 515 | 28.620 | −3.463 | 17.265 | 1.00 | 45.27 | A | O |
| ATOM | 1723 | OE2 | GLU | A | 515 | 29.804 | −1.853 | 16.333 | 1.00 | 37.65 | A | O |
| ATOM | 1724 | C | GLU | A | 515 | 26.331 | 1.207 | 18.550 | 1.00 | 35.53 | A | C |
| ATOM | 1725 | O | GLU | A | 515 | 25.492 | 1.520 | 17.705 | 1.00 | 42.10 | A | O |
| ATOM | 1726 | N | ALA | A | 516 | 26.008 | 0.799 | 19.772 | 1.00 | 32.13 | A | N |
| ATOM | 1727 | CA | ALA | A | 516 | 24.622 | 0.784 | 20.218 | 1.00 | 33.03 | A | C |
| ATOM | 1728 | CB | ALA | A | 516 | 24.472 | −0.076 | 21.466 | 1.00 | 34.02 | A | C |
| ATOM | 1729 | C | ALA | A | 516 | 24.106 | 2.199 | 20.480 | 1.00 | 38.57 | A | C |
| ATOM | 1730 | O | ALA | A | 516 | 22.911 | 2.466 | 20.355 | 1.00 | 48.26 | A | O |
| ATOM | 1731 | N | MET | A | 517 | 25.006 | 3.105 | 20.848 | 1.00 | 32.86 | A | N |
| ATOM | 1732 | CA | MET | A | 517 | 24.610 | 4.465 | 21.197 | 1.00 | 31.72 | A | C |
| ATOM | 1733 | CB | MET | A | 517 | 25.393 | 4.965 | 22.410 | 1.00 | 33.83 | A | C |
| ATOM | 1734 | CG | MET | A | 517 | 25.069 | 4.231 | 23.696 | 1.00 | 29.31 | A | C |
| ATOM | 1735 | SD | MET | A | 517 | 26.141 | 4.719 | 25.059 | 1.00 | 25.19 | A | S |
| ATOM | 1736 | CE | MET | A | 517 | 25.473 | 6.322 | 25.501 | 1.00 | 14.42 | A | C |
| ATOM | 1737 | C | MET | A | 517 | 24.798 | 5.418 | 20.025 | 1.00 | 42.08 | A | C |
| ATOM | 1738 | O | MET | A | 517 | 24.006 | 6.338 | 19.829 | 1.00 | 45.81 | A | O |
| ATOM | 1739 | N | MET | A | 518 | 25.860 | 5.206 | 19.256 | 1.00 | 41.48 | A | N |
| ATOM | 1740 | CA | MET | A | 518 | 26.018 | 5.912 | 17.997 | 1.00 | 39.72 | A | C |
| ATOM | 1741 | CB | MET | A | 518 | 27.489 | 6.235 | 17.727 | 1.00 | 39.95 | A | C |
| ATOM | 1742 | CG | MET | A | 518 | 28.203 | 6.832 | 18.931 | 1.00 | 44.06 | A | C |
| ATOM | 1743 | SD | MET | A | 518 | 29.573 | 7.946 | 18.546 | 1.00 | 63.51 | A | S |
| ATOM | 1744 | CE | MET | A | 518 | 28.702 | 9.340 | 17.827 | 1.00 | 49.02 | A | C |
| ATOM | 1745 | C | MET | A | 518 | 25.441 | 5.022 | 16.906 | 1.00 | 50.39 | A | C |
| ATOM | 1746 | O | MET | A | 518 | 26.173 | 4.321 | 16.199 | 1.00 | 52.80 | A | O |
| ATOM | 1747 | OXT | MET | A | 518 | 24.217 | 4.974 | 16.732 | 1.00 | 47.23 | A | O |
| TER | | | | | | | | | | | | |
| ATOM | 1748 | C01 | LIG | I | 1 | 37.522 | −4.728 | 39.460 | 1.00 | 12.56 | | C |
| ATOM | 1749 | O02 | LIG | I | 1 | 37.054 | −3.524 | 38.870 | 1.00 | 14.30 | | O |
| ATOM | 1750 | C03 | LIG | I | 1 | 36.474 | −3.538 | 37.583 | 1.00 | 13.35 | | C |
| ATOM | 1751 | C04 | LIG | I | 1 | 35.646 | −4.655 | 37.126 | 1.00 | 10.90 | | C |
| ATOM | 1752 | C05 | LIG | I | 1 | 35.079 | −4.567 | 35.789 | 1.00 | 11.99 | | C |
| ATOM | 1753 | C06 | LIG | I | 1 | 34.301 | −5.743 | 35.190 | 1.00 | 15.90 | | C |
| ATOM | 1754 | C07 | LIG | I | 1 | 35.012 | −7.105 | 35.006 | 1.00 | 14.60 | | C |
| ATOM | 1755 | S08 | LIG | I | 1 | 36.198 | −7.696 | 35.939 | 1.00 | 13.68 | | S |
| ATOM | 1756 | C09 | LIG | I | 1 | 35.895 | −9.317 | 35.780 | 1.00 | 17.64 | | C |
| ATOM | 1757 | O10 | LIG | I | 1 | 36.416 | −10.222 | 36.357 | 1.00 | 14.32 | | O |
| ATOM | 1758 | N11 | LIG | I | 1 | 34.725 | −9.490 | 35.021 | 1.00 | 12.73 | | N |
| ATOM | 1759 | C12 | LIG | I | 1 | 34.332 | −8.183 | 34.331 | 1.00 | 17.51 | | C |

TABLE 6-continued

Coordinates for crystal structure of the complex of ERR-α and Compound 1

| ATOM | 1760 | O13 | LIG | I | 1 | 33.348 | −8.028 | 33.683 | 1.00 | 20.19 | | O |
|---|---|---|---|---|---|---|---|---|---|---|---|---|
| ATOM | 1761 | C14 | LIG | I | 1 | 35.303 | −3.438 | 34.907 | 1.00 | 12.47 | | C |
| ATOM | 1762 | C15 | LIG | I | 1 | 36.115 | −2.338 | 35.366 | 1.00 | 10.28 | | C |
| ATOM | 1763 | C16 | LIG | I | 1 | 36.685 | −2.398 | 36.691 | 1.00 | 11.90 | | C |
| ATOM | 1764 | O17 | LIG | I | 1 | 37.521 | −1.350 | 37.104 | 1.00 | 13.21 | | O |
| ATOM | 1765 | C18 | LIG | I | 1 | 36.799 | −0.147 | 37.216 | 1.00 | 11.32 | | C |
| ATOM | 1766 | C19 | LIG | I | 1 | 35.432 | −0.111 | 37.662 | 1.00 | 11.91 | | C |
| ATOM | 1767 | C20 | LIG | I | 1 | 34.813 | 1.167 | 37.834 | 1.00 | 11.63 | | C |
| ATOM | 1768 | C21 | LIG | I | 1 | 35.559 | 2.375 | 37.554 | 1.00 | 10.56 | | C |
| ATOM | 1769 | C22 | LIG | I | 1 | 34.900 | 3.739 | 37.733 | 1.00 | 13.19 | | C |
| ATOM | 1770 | N23 | LIG | I | 1 | 34.438 | 4.755 | 37.881 | 1.00 | 13.97 | | N |
| ATOM | 1771 | C24 | LIG | I | 1 | 36.919 | 2.329 | 37.109 | 1.00 | 10.60 | | C |
| ATOM | 1772 | C25 | LIG | I | 1 | 37.542 | 1.065 | 36.943 | 1.00 | 12.03 | | C |
| ATOM | 1773 | C26 | LIG | I | 1 | 38.985 | 0.930 | 36.412 | 1.00 | 11.68 | | C |
| ATOM | 1774 | F27 | LIG | I | 1 | 38.952 | 0.288 | 35.215 | 1.00 | 12.26 | | F |
| ATOM | 1775 | F28 | LIG | I | 1 | 39.754 | 0.151 | 37.225 | 1.00 | 11.10 | | F |
| ATOM | 1776 | F29 | LIG | I | 1 | 39.515 | 2.184 | 36.275 | 1.00 | 13.01 | | F |
| TER | | | | | | | | | | | | |
| ATOM | 1777 | O | HOH | W | 1 | 44.563 | 11.913 | 24.932 | 1.00 | 5.38 | W | O |
| ATOM | 1778 | O | HOH | W | 2 | 38.446 | 19.540 | 40.333 | 1.00 | 9.46 | W | O |
| ATOM | 1779 | O | HOH | W | 3 | 52.753 | 19.023 | 35.890 | 1.00 | 5.49 | W | O |
| ATOM | 1780 | O | HOH | W | 4 | 46.434 | 13.708 | 25.858 | 1.00 | 4.30 | W | O |
| ATOM | 1781 | O | HOH | W | 5 | 32.599 | 18.092 | 31.284 | 1.00 | 8.37 | W | O |
| ATOM | 1782 | O | HOH | W | 6 | 45.519 | 7.675 | 21.494 | 1.00 | 10.79 | W | O |
| ATOM | 1783 | O | HOH | W | 7 | 50.103 | 12.930 | 22.113 | 1.00 | 8.76 | W | O |
| ATOM | 1784 | O | HOH | W | 8 | 52.695 | 11.128 | 41.005 | 1.00 | 10.34 | W | O |
| ATOM | 1785 | O | HOH | W | 9 | 51.885 | 17.800 | 38.312 | 1.00 | 6.75 | W | O |
| ATOM | 1786 | O | HOH | W | 10 | 36.830 | 24.389 | 41.795 | 1.00 | 13.60 | W | O |
| ATOM | 1787 | O | HOH | W | 11 | 34.888 | 8.253 | 35.837 | 1.00 | 8.78 | W | O |
| ATOM | 1788 | O | HOH | W | 12 | 48.188 | 20.582 | 18.407 | 1.00 | 10.34 | W | O |
| ATOM | 1789 | O | HOH | W | 13 | 51.054 | 4.999 | 44.053 | 1.00 | 14.61 | W | O |
| ATOM | 1790 | O | HOH | W | 14 | 43.436 | 10.535 | 47.007 | 1.00 | 12.83 | W | O |
| ATOM | 1791 | O | HOH | W | 15 | 35.385 | 30.646 | 23.313 | 1.00 | 13.24 | W | O |
| ATOM | 1792 | O | HOH | W | 16 | 49.727 | 5.453 | 36.692 | 1.00 | 12.89 | W | O |
| ATOM | 1793 | O | HOH | W | 17 | 35.157 | 11.077 | 33.306 | 1.00 | 9.35 | W | O |
| ATOM | 1794 | O | HOH | W | 18 | 45.912 | −1.723 | 44.249 | 1.00 | 17.09 | W | O |
| ATOM | 1795 | O | HOH | W | 19 | 43.769 | −7.652 | 42.933 | 1.00 | 13.50 | W | O |
| ATOM | 1796 | O | HOH | W | 20 | 38.854 | 28.044 | 21.341 | 1.00 | 11.86 | W | O |
| ATOM | 1797 | O | HOH | W | 21 | 32.657 | 26.460 | 39.127 | 1.00 | 17.14 | W | O |
| ATOM | 1798 | O | HOH | W | 22 | 40.960 | 10.711 | 52.535 | 1.00 | 16.60 | W | O |
| ATOM | 1799 | O | HOH | W | 23 | 46.706 | 12.019 | 27.977 | 1.00 | 7.53 | W | O |
| ATOM | 1800 | O | HOH | W | 24 | 37.946 | 29.687 | 23.346 | 1.00 | 18.39 | W | O |
| ATOM | 1801 | O | HOH | W | 25 | 46.126 | 10.791 | 47.156 | 1.00 | 11.87 | W | O |
| ATOM | 1802 | O | HOH | W | 26 | 40.690 | 17.783 | 50.908 | 1.00 | 17.28 | W | O |
| ATOM | 1803 | O | HOH | W | 27 | 44.571 | 14.585 | 18.546 | 1.00 | 8.23 | W | O |
| ATOM | 1804 | O | HOH | W | 28 | 27.731 | 24.259 | 15.446 | 1.00 | 19.31 | W | O |
| ATOM | 1805 | O | HOH | W | 29 | 31.269 | 7.302 | 39.383 | 1.00 | 19.07 | W | O |
| ATOM | 1806 | O | HOH | W | 30 | 40.707 | 4.311 | 17.305 | 1.00 | 15.13 | W | O |
| ATOM | 1807 | O | HOH | W | 31 | 48.235 | 8.960 | 47.013 | 1.00 | 18.19 | W | O |
| ATOM | 1808 | O | HOH | W | 32 | 48.610 | 10.754 | 15.965 | 1.00 | 11.66 | W | O |
| ATOM | 1809 | O | HOH | W | 33 | 34.927 | 18.100 | 29.929 | 1.00 | 14.15 | W | O |
| ATOM | 1810 | O | HOH | W | 34 | 38.481 | 0.849 | 22.579 | 1.00 | 21.28 | W | O |
| ATOM | 1811 | O | HOH | W | 35 | 41.452 | 4.608 | 25.983 | 1.00 | 17.81 | W | O |
| ATOM | 1812 | O | HOH | W | 36 | 25.482 | 25.452 | 26.713 | 1.00 | 14.94 | W | O |
| ATOM | 1813 | O | HOH | W | 37 | 27.711 | 26.034 | 34.233 | 1.00 | 16.10 | W | O |
| ATOM | 1814 | O | HOH | W | 38 | 27.242 | 27.675 | 27.326 | 1.00 | 12.39 | W | O |
| ATOM | 1815 | O | HOH | W | 39 | 48.422 | 3.965 | 49.199 | 1.00 | 21.16 | W | O |
| ATOM | 1816 | O | HOH | W | 40 | 27.239 | 11.729 | 30.392 | 1.00 | 14.28 | W | O |
| ATOM | 1817 | O | HOH | W | 41 | 37.994 | 6.978 | 11.502 | 1.00 | 23.03 | W | O |
| ATOM | 1818 | O | HOH | W | 42 | 23.431 | 6.077 | 35.524 | 1.00 | 34.53 | W | O |
| ATOM | 1819 | O | HOH | W | 43 | 45.863 | 3.874 | 49.965 | 1.00 | 19.14 | W | O |
| ATOM | 1820 | O | HOH | W | 44 | 27.797 | −0.642 | 41.412 | 1.00 | 19.39 | W | O |
| ATOM | 1821 | O | HOH | W | 45 | 26.168 | 0.520 | 39.513 | 1.00 | 28.17 | W | O |
| ATOM | 1822 | O | HOH | W | 46 | 44.368 | 19.096 | 42.291 | 1.00 | 22.45 | W | O |
| ATOM | 1823 | O | HOH | W | 47 | 37.196 | 8.585 | 52.837 | 1.00 | 27.40 | W | O |
| ATOM | 1824 | O | HOH | W | 48 | 33.242 | 9.597 | 32.198 | 1.00 | 12.89 | W | O |
| ATOM | 1825 | O | HOH | W | 49 | 37.595 | −3.868 | 48.438 | 1.00 | 20.47 | W | O |
| ATOM | 1826 | O | HOH | W | 50 | 29.456 | 31.835 | 22.598 | 1.00 | 22.53 | W | O |
| ATOM | 1827 | O | HOH | W | 51 | 52.443 | −1.281 | 44.167 | 1.00 | 26.58 | W | O |
| ATOM | 1828 | O | HOH | W | 52 | 25.736 | 27.500 | 30.294 | 1.00 | 22.78 | W | O |
| ATOM | 1829 | O | HOH | W | 53 | 24.976 | 4.533 | 48.715 | 1.00 | 34.74 | W | O |
| ATOM | 1830 | O | HOH | W | 54 | 30.217 | 11.415 | 37.945 | 1.00 | 22.25 | W | O |
| ATOM | 1831 | O | HOH | W | 55 | 23.646 | 6.611 | 40.768 | 1.00 | 24.70 | W | O |
| ATOM | 1832 | O | HOH | W | 56 | 33.098 | 29.193 | 35.887 | 1.00 | 25.06 | W | O |
| ATOM | 1833 | O | HOH | W | 57 | 45.363 | 14.885 | 13.948 | 1.00 | 23.76 | W | O |
| ATOM | 1834 | O | HOH | W | 58 | 56.109 | 25.198 | 34.855 | 1.00 | 19.03 | W | O |
| ATOM | 1835 | O | HOH | W | 59 | 27.048 | 14.448 | 29.929 | 1.00 | 22.03 | W | O |
| ATOM | 1836 | O | HOH | W | 60 | 20.591 | 21.180 | 20.283 | 1.00 | 23.50 | W | O |

TABLE 6-continued

Coordinates for crystal structure of the complex of ERR-α and Compound 1

| ATOM | 1837 | O | HOH | W | 61 | 24.951 | 22.850 | 14.338 | 1.00 | 24.22 | W | O |
|---|---|---|---|---|---|---|---|---|---|---|---|---|
| ATOM | 1838 | O | HOH | W | 62 | 32.399 | 30.737 | 24.989 | 1.00 | 21.02 | W | O |
| ATOM | 1839 | O | HOH | W | 64 | 30.450 | 9.645 | 40.192 | 1.00 | 20.15 | W | O |
| ATOM | 1840 | O | HOH | W | 65 | 32.062 | 8.706 | 8.641 | 1.00 | 22.60 | W | O |
| ATOM | 1841 | O | HOH | W | 66 | 26.846 | 18.470 | 35.842 | 1.00 | 25.13 | W | O |
| ATOM | 1842 | O | HOH | W | 67 | 41.119 | 25.411 | 15.836 | 1.00 | 21.06 | W | O |
| ATOM | 1843 | O | HOH | W | 68 | 33.143 | 12.560 | 31.491 | 1.00 | 15.57 | W | O |
| ATOM | 1844 | O | HOH | W | 69 | 39.252 | −7.193 | 22.659 | 1.00 | 25.67 | W | O |
| ATOM | 1845 | O | HOH | W | 70 | 50.811 | 15.765 | 45.335 | 1.00 | 21.12 | W | O |
| ATOM | 1846 | O | HOH | W | 71 | 46.413 | 27.950 | 39.831 | 1.00 | 26.80 | W | O |
| ATOM | 1847 | O | HOH | W | 72 | 39.136 | 33.217 | 33.030 | 1.00 | 18.67 | W | O |
| ATOM | 1848 | O | HOH | W | 73 | 34.194 | 12.875 | 38.074 | 1.00 | 16.42 | W | O |
| ATOM | 1849 | O | HOH | W | 74 | 36.706 | −0.992 | 15.956 | 1.00 | 29.45 | W | O |
| ATOM | 1850 | O | HOH | W | 75 | 35.355 | 4.249 | 13.073 | 1.00 | 26.96 | W | O |
| ATOM | 1851 | O | HOH | W | 76 | 37.681 | 17.086 | 43.354 | 1.00 | 20.14 | W | O |
| ATOM | 1852 | O | HOH | W | 77 | 36.654 | −0.356 | 21.303 | 1.00 | 19.60 | W | O |
| ATOM | 1853 | O | HOH | W | 78 | 33.084 | 3.541 | 50.395 | 1.00 | 20.52 | W | O |
| ATOM | 1854 | O | HOH | W | 79 | 48.844 | 22.050 | 16.012 | 1.00 | 19.97 | W | O |
| ATOM | 1855 | O | HOH | W | 80 | 48.656 | −2.928 | 34.698 | 1.00 | 20.76 | W | O |
| ATOM | 1856 | O | HOH | W | 81 | 44.932 | 5.820 | 25.320 | 1.00 | 22.17 | W | O |
| ATOM | 1857 | O | HOH | W | 82 | 31.873 | −3.931 | 33.216 | 1.00 | 22.90 | W | O |
| ATOM | 1858 | O | HOH | W | 83 | 44.834 | −2.170 | 24.937 | 1.00 | 31.94 | W | O |
| ATOM | 1859 | O | HOH | W | 84 | 39.285 | 0.729 | 51.059 | 1.00 | 24.54 | W | O |
| ATOM | 1860 | O | HOH | W | 85 | 25.168 | −1.488 | 35.911 | 1.00 | 25.84 | W | O |
| ATOM | 1861 | O | HOH | W | 86 | 41.248 | −1.515 | 52.975 | 1.00 | 22.30 | W | O |
| ATOM | 1862 | O | HOH | W | 87 | 25.070 | 13.693 | 24.590 | 1.00 | 23.03 | W | O |
| ATOM | 1863 | O | HOH | W | 88 | 44.389 | −6.291 | 50.027 | 1.00 | 22.81 | W | O |
| ATOM | 1864 | O | HOH | W | 89 | 41.774 | 2.851 | 24.353 | 1.00 | 27.80 | W | O |
| ATOM | 1865 | O | HOH | W | 90 | 36.606 | 14.144 | 11.018 | 1.00 | 25.46 | W | O |
| ATOM | 1866 | O | HOH | W | 91 | 44.230 | 8.168 | 54.303 | 1.00 | 33.85 | W | O |
| ATOM | 1867 | O | HOH | W | 92 | 45.880 | 15.287 | 55.235 | 1.00 | 35.04 | W | O |
| ATOM | 1868 | O | HOH | W | 93 | 29.650 | 18.425 | 19.417 | 1.00 | 20.98 | W | O |
| ATOM | 1869 | O | HOH | W | 94 | 51.922 | 4.436 | 36.410 | 1.00 | 25.61 | W | O |
| ATOM | 1870 | O | HOH | W | 95 | 26.692 | 18.098 | 19.536 | 1.00 | 29.43 | W | O |
| ATOM | 1871 | O | HOH | W | 96 | 45.929 | −3.837 | 56.932 | 1.00 | 39.12 | W | O |
| ATOM | 1872 | O | HOH | W | 97 | 39.394 | 18.914 | 7.326 | 1.00 | 31.99 | W | O |
| ATOM | 1873 | O | HOH | W | 98 | 36.622 | 24.788 | 15.555 | 1.00 | 25.22 | W | O |
| ATOM | 1874 | O | HOH | W | 99 | 46.562 | 4.351 | 26.855 | 1.00 | 19.74 | W | O |
| ATOM | 1875 | O | HOH | W | 100 | 48.753 | 17.971 | 14.821 | 1.00 | 20.14 | W | O |
| ATOM | 1876 | O | HOH | W | 101 | 36.333 | 15.561 | 8.688 | 1.00 | 32.23 | W | O |
| ATOM | 1877 | O | HOH | W | 102 | 23.790 | 8.703 | 29.637 | 1.00 | 26.40 | W | O |
| ATOM | 1878 | O | HOH | W | 103 | 35.740 | 20.515 | 15.207 | 1.00 | 24.92 | W | O |
| ATOM | 1879 | O | HOH | W | 104 | 33.980 | −5.351 | 31.541 | 1.00 | 27.67 | W | O |
| ATOM | 1880 | O | HOH | W | 105 | 46.968 | 13.932 | 50.523 | 1.00 | 33.67 | W | O |
| ATOM | 1881 | O | HOH | W | 106 | 38.247 | 29.301 | 40.424 | 1.00 | 32.89 | W | O |
| ATOM | 1882 | O | HOH | W | 107 | 36.603 | 3.854 | 52.414 | 1.00 | 36.07 | W | O |
| ATOM | 1883 | O | HOH | W | 108 | 29.336 | −5.723 | 31.437 | 1.00 | 28.89 | W | O |
| ATOM | 1884 | O | HOH | W | 109 | 24.706 | −6.887 | 36.659 | 1.00 | 48.50 | W | O |
| ATOM | 1885 | O | HOH | W | 110 | 31.473 | 38.020 | 15.477 | 1.00 | 26.02 | W | O |
| ATOM | 1886 | O | HOH | W | 111 | 45.417 | 10.652 | 9.607 | 1.00 | 31.22 | W | O |
| ATOM | 1887 | O | HOH | W | 112 | 23.315 | 0.319 | 16.488 | 1.00 | 37.06 | W | O |
| ATOM | 1888 | O | HOH | W | 113 | 26.781 | 10.307 | 35.802 | 1.00 | 27.62 | W | O |
| ATOM | 1889 | O | HOH | W | 114 | 33.398 | 15.480 | 42.028 | 1.00 | 32.73 | W | O |
| ATOM | 1890 | O | HOH | W | 115 | 52.462 | 0.347 | 46.182 | 1.00 | 31.78 | W | O |
| ATOM | 1891 | O | HOH | W | 116 | 48.108 | −6.958 | 36.719 | 1.00 | 27.94 | W | O |
| ATOM | 1892 | O | HOH | W | 117 | 45.076 | 26.135 | 42.044 | 1.00 | 28.97 | W | O |
| ATOM | 1893 | O | HOH | W | 118 | 37.577 | 32.603 | 21.541 | 1.00 | 28.63 | W | O |
| ATOM | 1894 | O | HOH | W | 119 | 54.350 | 5.605 | 35.775 | 1.00 | 23.98 | W | O |
| ATOM | 1895 | O | HOH | W | 120 | 37.896 | 5.652 | 7.847 | 1.00 | 32.99 | W | O |
| ATOM | 1896 | O | HOH | W | 121 | 28.463 | −0.754 | 28.203 | 1.00 | 35.81 | W | O |
| ATOM | 1897 | O | HOH | W | 122 | 43.755 | 18.893 | 45.269 | 1.00 | 26.83 | W | O |
| ATOM | 1898 | O | HOH | W | 123 | 33.542 | 11.698 | 35.367 | 1.00 | 13.20 | W | O |
| ATOM | 1899 | O | HOH | W | 124 | 48.924 | −7.374 | 43.248 | 1.00 | 24.11 | W | O |
| ATOM | 1900 | O | HOH | W | 125 | 48.582 | −7.854 | 40.770 | 1.00 | 25.71 | W | O |
| ATOM | 1901 | O | HOH | W | 126 | 43.905 | −8.775 | 48.077 | 1.00 | 16.75 | W | O |
| ATOM | 1902 | O | HOH | W | 127 | 43.324 | −10.397 | 50.258 | 1.00 | 26.72 | W | O |
| ATOM | 1903 | O | HOH | W | 128 | 49.872 | 14.459 | 47.358 | 1.00 | 19.45 | W | O |
| ATOM | 1904 | O | HOH | W | 129 | 36.062 | 22.802 | 16.227 | 1.00 | 21.75 | W | O |
| ATOM | 1905 | O | HOH | W | 130 | 48.888 | 3.228 | 26.017 | 1.00 | 28.29 | W | O |
| TER | | | | | | | | | | | | |
| END | | | | | | | | | | | | |

REFERENCES

US Patents

U.S. Pat. No. 4,906,122A "Coupling for molecular models", Barrett E., Hui Yee K.
U.S. Pat. No. 5,030,103A "Dynamic molecular model", Buist P. H., Raffler Alois A.
U.S. Pat. No. 5,200,910A "Method for modelling the electron density of a crystal", Univ. Leland Stanford Junior.
U.S. Pat. No. 5,365,456A "Method for modelling the electron density of a crystal", Univ. Leland Stanford Junior.
U.S. Pat. No. 5,583,973A "Molecular modeling method and system", Univ. Boston.
U.S. Pat. No. 5,612,894A "System and method for molecular modeling utilizing a sensitivity factor", Wertz D. H.
U.S. Pat. No. 5,733,720 "Genetically engineered cell lines for detecting infectious herpesvirus and methods therefor", Univ. Washington.
U.S. Pat. No. 5,763,263 "Method and apparatus for producing position addressable combinatorial libraries", Dehlinger, P. J.
U.S. Pat. No. 5,942,428A "Crystals of the tyrosine kinase domain of non-insulin receptor tyrosine kinases", Sugen, Inc.
U.S. Pat. No. 5,994,503A "Nucleotide and protein sequences of lats genes and methods based thereon", Univ. Yale.
U.S. Pat. No. 5,998,593A "Fluorescent enzyme substrates", Abbott Laboratories.
U.S. Pat. No. 6,037,117A "Methods using the *Staphylococcus aureus* glycyl tRNA synthetase crystalline structure", SmithKline Beecham Corp.
U.S. Pat. No. 6,071,700A "Heterologous polypeptide production in the absence of nonsense-mediated MRNA decay functions", Univ. Massachusetts.
U.S. Pat. No. 6,075,014A "Inhibitors of β-lactamases and uses therefor", Univ. Northwestern.
U.S. Pat. No. 6,075,123A "Cyclin-C variants, and diagnostic and therapeutic uses thereof", St. Jude Childrens Res. Hospital.
U.S. Pat. No. 6,080,576A "Vectors for gene trapping and gene activation", Lexicon Genetics, Inc.
U.S. Pat. No. 6,093,573A "Three-dimensional structure of bactericidal/permeability-increasing protein (BPI)", Xoma, Univ. California.

US Patent Applications

US20060148876 "Nr3b1 nuclear receptor binding 3-substituted pyrazoles", Lion Bioscience AG.
US20080221179 "Substituted Phenoxy Aminothiazolones as estrogen related receptor-alpha modulators", Johnson & Johnson.
US20060014812 "Use of estrogen related receptor-modulating aryl ethers", Johnson & Johnson.
US20060079494 "Specific kinase inhibitors", Kosan Biosciences, Inc.

Other References

Adams, P. D., R. W. Grosse-Kunstleve, et al. (2002). "PHENIX: building new software for automated crystallographic structure determination." *Acta Crystallogr D Biol Crystallogr* 58(Pt 11): 1948-54.
Altschul, S. F. (1993). "A protein alignment scoring system sensitive at all evolutionary distances." *J. Mol. Evol.* 36: 290-300.
Altschul, S. F., M. S. Boguski, et al. (1994). "Issues in searching molecular sequence databases." *Nature Genetics* 6: 119-129.
Aranda, A. and A. Pascual (2001). "Nuclear hormone receptors and gene expression." *Physiol Rev* 81(3): 1269-304.
Ariazi, E. A., G. M. Clark, et al. (2002). "Estrogen-related receptor alpha and estrogen-related receptor gamma associate with unfavorable and favorable biomarkers, respectively, in human breast cancer." *Cancer Res* 62(22): 6510-8.
Bacon, D. J. and J. Moult (1992). "Docking by Least-squares Fitting of Molecular Surface Patterns." *J. Mol. Biol.* 225: 849-858.
Bartlett, P. A., G. T. Shea, et al. (1989). ""CAVEAT: A Program to Facilitate the Structure-Derived Design of Biologically Active Molecules."" In *Molecular Recognition in Chemical and Biological Problems, Special Pub., Royal Chem. Soc.* 78: 82-196.
Berge, S. M., L. D. Bighley, et al. (1977). "Pharmaceutical salts." *J Pharm Sci* 66(1): 1-19.
Bohm, H.-J. (1992). "The Computer Program LUDI: A New Method for the De Novo Design of Enzyme Inhibitors." *J. Computer-Aided Molecular Design* 6: 61-78.
Bonnelye, E., V. Kung, et al. (2002). "Estrogen receptor-related receptor alpha impinges on the estrogen axis in bone: potential function in osteoporosis." *Endocrinology* 143(9): 3658-70.
Bonnelye, E., L. Merdad, et al. (2001). "The orphan nuclear estrogen receptor-related receptor alpha (ERRalpha) is expressed throughout osteoblast differentiation and regulates bone formation in vitro." *J Cell Biol* 153(5): 971-84.
Bonnelye, E., J. M. Vanacker, et al. (1997). "The ERR-1 orphan receptor is a transcriptional activator expressed during bone development." *Mol Endocrinol* 11(7): 905-16.
Brunger, A. T. (1993). *X-Flor Version 3.1: A system for X-ray crystallography and NMR*. New Haven, Conn., Yale Univ. Pr.
Brunger, A. T., P. D. Adams, et al. (1998). "Crystallography & NMR system: A new software suite for macromolecular structure determination." *Acta Crystallogr D Biol Crystallogr* 54(Pt 5): 905-21.
Campbell (1984). *Biological Spectroscopy*. Menlo Park, Calif., The Benjamin/Cummings Publishing Co., Inc.
Cantor, C. R. and P. R. Schimmel (1980). *Biophysical Chemistry, Part II, "Techniques for the Study of Biological Structure and Function"*, W. H. Freeman & Co.
Cohen (editor), N. C. (1996). *Guidebook on Molecular Modeling in Drug Design*, Academic Press.
Cohen, N., J. Blaney, et al. (1990). "Molecular Modeling Software and Methods for Medicinal Chemistry." *J. Med. Chem.* 33: 883-894.
Crowther, J. R. (1995). *ELISA: Theory and Practice (Methods in Molecular Biology)*, Humana Press.
Devlin (editor), J. P. (1998). *In High Throughput Screening: The Discovery of Bioactive Substances*. New York, Marcel Dekker Inc.
Drenth, J. (1999). *Principles of Protein X-ray Crystallography (Springer Advanced Texts in Chemistry)*. Berlin, Springer Verlag.
Emsley, P. and K. Cowtan (2004). "Coot: model-building tools for molecular graphics." *Acta Crystallogr D Biol Crystallogr* 60(Pt 12 Pt 1): 2126-32.
Frisch, M. J., G. W. Trucks, et al. (1992). "Gaussian 92, Revision C." *Gaussian, Inc.*
Fry, D. W., A. J. Bridges, et al. (1998). "Specific, irreversible inactivation of the epidermal growth factor receptor and erbB2, by a new class of tyrosine kinase inhibitor." *Proc Natl Acad Sci USA* 95(20): 12022-7.

Gans, W., A. Amann, et al. (1996). *Fundamental Principals of Molecular Modeling*, Plenum Pub. Corp.

Giguere, V. (1999). "Orphan nuclear receptors: from gene to function." *Endocr Rev* 20(5): 689-725.

Giguere, V. (2002). "To ERR in the estrogen pathway." *Trends Endocrinol Metab* 13(5): 220-5.

Giguere, V., N. Yang, et al. (1988). "Identification of a new class of steroid hormone receptors." *Nature* 331(6151): 91-4.

Goodford, P. J. (1985). "A Computational Procedure for Determining Energetically Favorable Binding Sites on Biologically Important Macromolecules." *J. Med. Chem.* 28: 849-857.

Goodsell, D. S, and A. J. Olsen (1990). "Automated Docking of Substrates to Proteins by Simulated Annealing." *Proteins: Structure, Function, and Genetics* 8: 195-202.

Gould, P. L. (1986). "Salt selection for basic drugs." *International Journal of Pharmaceutics* 33(1-3): 201-217.

Grundy, S. M., H. B. Brewer, Jr., et al. (2004). "Definition of metabolic syndrome: Report of the National Heart, Lung, and Blood Institute/American Heart Association conference on scientific issues related to definition." *Circulation* 109(3): 433-8.

Henikoff, J. G. (1992). "Amino acid substitution matrices from protein blocks." *Proc. Natl. Acad. Sci. USA*(89): 10915-10919.

Hong, H., L. Yang, et al. (1999). "Hormone-independent transcriptional activation and coactivator binding by novel orphan nuclear receptor ERR3." *J Biol Chem* 274(32): 22618-26.

Ishikawa, E. (1999). *Ultrasensitive and rapid enzyme immunoassay, In: Laboratory Techniques in Biochemistry and Molecular Biology*. Amsterdam, Elsevier.

Jones, P. L. and Y. B. Shi (2003). "N-CoR-HDAC corepressor complexes: roles in transcriptional regulation by nuclear hormone receptors." *Curr Top Microbiol Immunol* 274: 237-68.

Jones, T. A., J. Y. Zou, et al. (1991). "Improved methods for building protein models in electron density maps and the location of errors in these models." *Acta Crystallogr A* 47 (Pt 2): 110-9.

Kalgutkar, A. S., B. C. Crews, et al. (1998). "Aspirin-like molecules that covalently inactivate cyclooxygenase-2." *Science* 280(5367): 1268-70.

Kallen, J., R. Lattmann, et al. (2007). "Crystal structure of human estrogen-related receptor alpha in complex with a synthetic inverse agonist reveals its novel molecular mechanism." *J Biol Chem* 282(32): 23231-9.

Kallen, J., J. M. Schlaeppi, et al. (2004). "Evidence for ligand-independent transcriptional activation of the human estrogen-related receptor alpha (ERRalpha): crystal structure of ERRalpha ligand binding domain in complex with peroxisome proliferator-activated receptor coactivator-1alpha." *J Biol Chem* 279(47): 49330-7.

Kamei, Y., H. Ohizumi, et al. (2003). "PPARgamma coactivator 1beta/ERR ligand 1 is an ERR protein ligand, whose expression induces a high-energy expenditure and antagonizes obesity." *Proc Natl Acad Sci USA* 100(21): 12378-83.

Karlin, S, and S. F. Altschul (1990). "Methods for assessing the statistical significance of molecular sequence features by using general scoring schemes." *Proc. Natl. Acad. Sci. USA* 87: 2264-2268.

Kemeny (editor), D. M. and S. J. Challacombe (editor) (1988). *Elisa and Other Solid Phase Immunoassays: Theoretical and Practical Aspects*, New York, John Wiley and Sons.

Kemeny, D. M. (1991). *A Practical Guide to ELISA*, Pergamon Press.

Klostermeier, D. and D. P. Millar (2001). "Time-resolved fluorescence resonance energy transfer: a versatile tool for the analysis of nucleic acids." *Biopolymers* 61(3): 159-79.

Korach, K. S. (1994). "Insights from the study of animals lacking functional estrogen receptor." *Science* 266(5190): 1524-7.

Kraus, R. J., E. A. Ariazi, et al. (2002). "Estrogen-related receptor alpha 1 actively antagonizes estrogen receptor-regulated transcription in MCF-7 mammary cells." *J Biol Chem* 277(27): 24826-34.

Kuntz, I. D., J. M. Blaney, et al. (1982). "A geometric approach to macromolecule-ligand interactions." *J Mol Biol* 161(2): 269-88.

Laudet, V. and H. Gronmeyer (2002). *The nuclear receptor factsbook*. San Diego, Calif. London, Academic.

Lipinski, C., F. Lombardo, et al. (1997). "Experimental and computational approaches to estimate solubility and permeability in drug discovery and development settings" *Advanced Drug Delivery Reviews* 23(1-3): 3-25.

Luo, J., R. Sladek, et al. (2003). "Reduced fat mass in mice lacking orphan nuclear receptor estrogen-related receptor alpha." *Mol Cell Biol* 23(22): 7947-56.

Luo, Y., K. Arita, et al. (2006). "Inhibitors and inactivators of protein arginine deiminase 4: functional and structural characterization." *Biochemistry* 45(39): 11727-36.

Martin, Y. C. (1992). "3D Database Searching in Drug Design." *J. Med. Chem.* 35: 2145-2154.

Mary Ann Liebert (Publishers), I. (1995). *The BIOTECHNOLOGY SOFTWARE DIRECTORY, A Buyer's Guide*. Larchmont, N.Y. Mary Ann Liebert, Inc., Publishers.

Matteucci and J. Caruthers (1981). *J. Am. Chem. Soc.* 103(3): 185-3191.

McKenna, N. J., R. B. Lanz, et al. (1999). "Nuclear receptor coregulators: cellular and molecular biology." *Endocr Rev* 20(3): 321-44.

Meng, E. C., B. K. Shoichet, et al. (1992). "Automated docking with grid-based energy evaluation." *J. Comp. Chem.* 13: 505-524.

Miranker, A. and M. Karplus (1991). "Functionality Maps of Binding Sites: A Multiple Copy Simultaneous Search Method." *Proteins: Structure, Function and Genetics* 11: 29-34.

Navia, M. A. and M. A. Murcko (1992). "The Use of Structural Information in Drug Design." *Current Opinions in Structural Biology* 2: 202-210

Nishibata, Y. and A. Itai (1991). "Automatic creation of drug candidate structures based on receptor structure. Starting point for artificial lead generation." *Tetrahedron* 47: 8985-8990.

Norton, P. A. and J. M. Coffin (1985). "Bacterial beta-galactosidase as a marker of Rous sarcoma virus gene expression and replication." *Mol Cell Biol* 5(2): 281-90.

Olefsky, J. M. (2001). "Nuclear receptor minireview series." *J Biol Chem* 276(40): 36863-4.

Pacifici, R. (1996). "Estrogen, cytokines, and pathogenesis of postmenopausal osteoporosis." *J Bone Miner Res* 11(8): 1043-51.

Pantoliano, M. W., E. C. Petrella, et al. (2001). "High-density miniaturized thermal shift assays as a general strategy for drug discovery." *J Biomol Screen* 6(6): 429-40.

Pojer, F., J. L. Ferrer, et al. (2006). "Structural basis for the design of potent and species-specific inhibitors of 3-hydroxy-3-methylglutaryl CoA synthases." *Proc Natl Acad Sci USA* 103(31): 11491-6.

Rochette-Egly, C., S. Adam, et al. (1997). "Stimulation of RAR alpha activation function AF-1 through binding to the general transcription factor TFIIH and phosphorylation by CDK7." *Cell* 90(1): 97-107.

Rochette-Egly, C., M. P. Gaub, et al. (1992). "Retinoic acid receptor-beta: immunodetection and phosphorylation on tyrosine residues." *Mol Endocrinol* 6(12): 2197-209.

Rossmann, M. G. (1972). *The molecular replacement method; a collection of papers on the use of non-crystallographic symmetry*, Gordon & Breach, New York.

Rotstein, S. H. and M. A. Murcko (1993). "GroupBuild: a fragment-based method for de novo drug design." *J Med Chem* 36(12): 1700-10.

Sambrook, J., E. F. Fritsch, et al. (1989). *Molecular cloning*. 2nd ed. New York: Cold Spring Harbor Laboratory Press.

Schirmer, A., J. Kennedy, et al. (2006). "Targeted covalent inactivation of protein kinases by resorcylic acid lactone polyketides." *Proc Natl Acad Sci USA* 103(11): 4234-9.

Schlecht, M. (1998). *Molecular Modeling on the PC*, John Wiley & Sons.

Segel, I. H. (1975). *Enzyme Kinetics: Behavior and Analysis of Rapid Equilibrium and Steady-State Enzyme Systems*, J. Willey & Sons.

Shiraki, T., N. Kamiya, et al. (2005). "Alpha,beta-unsaturated ketone is a core moiety of natural ligands for covalent binding to peroxisome proliferator-activated receptor gamma" *J Biol Chem* 280(14): 14145-53.

Sladek, R., J. A. Bader, et al. (1997). "The orphan nuclear receptor estrogen-related receptor alpha is a transcriptional regulator of the human medium-chain acyl coenzyme A dehydrogenase gene." *Mol Cell Biol* 17(9): 5400-9.

Smith, W. B. (1996). *Introduction to Theoretical Organic. Chemistry and Molecular Modeling*. New York, VCH Publishers.

Sumi, D. and L. J. Ignarro (2003). "Estrogen-related receptor alpha 1 up-regulates endothelial nitric oxide synthase expression." *Proc Natl Acad Sci USA* 100(24): 14451-6.

Travis, J. (1993). "Proteins and Organic Solvents Make an Eye-Opening Mix." *Science* 262: 1374

Tsirelson, V. G. and R. P. Ozerov (1996). *Electron Density and Bonding in Crystals: Principles, Theory and X-ray Diffraction Experiments in Solid State Physics and Chemistry*, Inst. of Physics Pub.

Turner, R. T., B. L. Riggs, et al. (1994). "Skeletal effects of estrogen." *Endocr Rev* 15(3): 275-300.

Vega, R. B. and D. P. Kelly (1997). "A role for estrogen-related receptor alpha in the control of mitochondrial fatty acid beta-oxidation during brown adipocyte differentiation." *J Biol Chem* 272(50): 31693-9.

Windahl, S. H., O. Vidal, et al. (1999). "Increased cortical bone mineral content but unchanged trabecular bone mineral density in female ERbeta(-/-) mice." *J Clin Invest* 104(7): 895-901.

Wood, E. R., L. M. Shewchuk, et al. (2008). "6-Ethynylthieno[3,2-d]- and 6-ethynylthieno[2,3-d]pyrimidin-4-anilines as tunable covalent modifiers of ErbB kinases." *Proc Natl Acad Sci USA* 105(8): 2773-8.

Woolfson, M. M. (1997). *An Introduction to X-ray Crystallography*. Cambridge, UK, Cambridge Univ. Pr.

Wurtz, J. M., W. Bourguet, et al. (1996). "A canonical structure for the ligand-binding domain of nuclear receptors." *Nat Struct Biol* 3(1): 87-94.

Xu, H. E., T. B. Stanley, et al. (2002). "Structural basis for antagonist-mediated recruitment of nuclear co-repressors by PPARalpha." *Nature* 415(6873): 813-7.

Zhang, Z. and C. T. Teng (2000). "Estrogen receptor-related receptor alpha 1 interacts with coactivator and constitutively activates the estrogen response elements of the human lactoferrin gene." *J Biol Chem* 275(27): 20837-46.

---

The invention claimed is:

1. A co-crystal comprising human ERR-α and a ligand, wherein said ERR-α comprises SEQ ID NO: 2 which forms a thioether bond from Cys325 to the ligand of Compound I, or derivatives thereof, and wherein said crystal forms in space group $P6_522$ with unit cell parameters of about a=b=103 Å, c=110 Å and γ=120°.

2. The crystal of claim 1, wherein said atomic structure is characterized by the atomic coordinates of Table 6.

* * * * *

SEQUENCE LISTING

```
<160> NUMBER OF SEQ ID NOS: 2

<210> SEQ ID NO 1
<211> LENGTH: 519
<212> TYPE: PRT
<213> ORGANISM: Homo Sapiens

<400> SEQUENCE: 1

Met Gly Leu Glu Met Ser Ser Lys Asp Ser Pro Gly Ser Leu Asp Gly
1               5                   10                  15

Arg Ala Trp Glu Asp Ala Gln Lys Pro Gln Ser Ala Trp Cys Gly Gly
            20                  25                  30

Arg Lys Thr Arg Val Tyr Ala Thr Ser Ser Arg Arg Ala Pro Pro Ser
        35                  40                  45

Glu Gly Thr Arg Arg Gly Gly Ala Ala Arg Pro Glu Glu Ala Ala Glu
    50                  55                  60

Glu Gly Pro Pro Ala Ala Pro Gly Ser Leu Arg His Ser Gly Pro Leu
65                  70                  75                  80

Gly Pro His Ala Cys Pro Thr Ala Leu Pro Glu Pro Gln Val Thr Ser
                85                  90                  95

Ala Met Ser Ser Gln Val Val Gly Ile Glu Pro Leu Tyr Ile Lys Ala
                100                 105                 110
```

Glu Pro Ala Ser Pro Asp Ser Pro Lys Gly Ser Ser Glu Thr Glu Thr
115                 120                 125

Glu Pro Pro Val Ala Leu Ala Pro Gly Pro Ala Pro Thr Arg Cys Leu
130                 135                 140

Pro Gly His Lys Glu Glu Asp Gly Glu Gly Ala Gly Pro Gly Glu
145                 150                 155                 160

Gln Gly Gly Gly Lys Leu Val Leu Ser Ser Leu Pro Lys Arg Leu Cys
                165                 170                 175

Leu Val Cys Gly Asp Val Ala Ser Gly Tyr His Tyr Gly Val Ala Ser
                180                 185                 190

Cys Glu Ala Cys Lys Ala Phe Phe Lys Arg Thr Ile Gln Gly Ser Ile
                195                 200                 205

Glu Tyr Ser Cys Pro Ala Ser Asn Glu Cys Glu Ile Thr Lys Arg Arg
210                 215                 220

Arg Lys Ala Cys Gln Ala Cys Arg Phe Thr Lys Cys Leu Arg Val Gly
225                 230                 235                 240

Met Leu Lys Glu Gly Val Arg Leu Asp Arg Val Arg Gly Gly Arg Gln
                245                 250                 255

Lys Tyr Lys Arg Arg Pro Glu Val Asp Pro Leu Pro Phe Pro Gly Pro
                260                 265                 270

Phe Pro Ala Gly Pro Leu Ala Val Ala Gly Gly Pro Arg Lys Thr Ala
                275                 280                 285

Pro Val Asn Ala Leu Val Ser His Leu Leu Val Val Glu Pro Glu Lys
290                 295                 300

Leu Tyr Ala Met Pro Asp Pro Ala Gly Pro Asp Gly His Leu Pro Ala
305                 310                 315                 320

Val Ala Thr Leu Cys Asp Leu Phe Asp Arg Glu Ile Val Val Thr Ile
                325                 330                 335

Ser Trp Ala Lys Ser Ile Pro Gly Phe Ser Ser Leu Ser Leu Ser Asp
                340                 345                 350

Gln Met Ser Val Leu Gln Ser Val Trp Met Glu Val Leu Val Leu Gly
                355                 360                 365

Val Ala Gln Arg Ser Leu Pro Leu Gln Asp Glu Leu Ala Phe Ala Glu
                370                 375                 380

Asp Leu Val Leu Asp Glu Glu Gly Ala Arg Ala Ala Gly Leu Gly Glu
385                 390                 395                 400

Leu Gly Ala Ala Leu Leu Gln Leu Val Arg Arg Leu Gln Ala Leu Arg
                405                 410                 415

Leu Glu Arg Glu Glu Tyr Val Leu Leu Lys Ala Leu Ala Leu Ala Asn
                420                 425                 430

Ser Asp Ser Val His Ile Glu Asp Ala Glu Ala Val Glu Gln Leu Arg
                435                 440                 445

Glu Ala Leu His Glu Ala Leu Leu Glu Tyr Glu Ala Gly Arg Ala Gly
                450                 455                 460

Pro Gly Gly Gly Ala Glu Arg Arg Ala Gly Arg Leu Leu Leu Thr
465                 470                 475                 480

Leu Pro Leu Leu Arg Gln Thr Ala Gly Lys Val Leu Ala His Phe Tyr
                485                 490                 495

Gly Val Lys Leu Glu Gly Lys Val Pro Met His Lys Leu Phe Leu Glu
                500                 505                 510

Met Leu Glu Ala Met Met Asp
                515

<210> SEQ ID NO 2

-continued

```
<211> LENGTH: 248
<212> TYPE: PRT
<213> ORGANISM: Homo Sapiens

<400> SEQUENCE: 2

Met Gly Ser Ser His His His His His His Leu Glu Val Leu Phe Gln
1               5                   10                  15

Gly Pro Val Asn Ala Leu Val Ser His Leu Leu Val Val Glu Pro Glu
                20                  25                  30

Lys Leu Tyr Ala Met Pro Asp Pro Ala Gly Pro Asp Gly His Leu Pro
            35                  40                  45

Ala Val Ala Thr Leu Cys Asp Leu Phe Asp Arg Glu Ile Val Val Thr
        50                  55                  60

Ile Ser Trp Ala Lys Ser Ile Pro Gly Phe Ser Ser Leu Ser Leu Ser
65                  70                  75                  80

Asp Gln Met Ser Val Leu Gln Ser Val Trp Met Glu Val Leu Val Leu
                85                  90                  95

Gly Val Ala Gln Arg Ser Leu Pro Leu Gln Asp Glu Leu Ala Phe Ala
                100                 105                 110

Glu Asp Leu Val Leu Asp Glu Glu Gly Ala Arg Ala Ala Gly Leu Gly
            115                 120                 125

Glu Leu Gly Ala Ala Leu Leu Gln Leu Val Arg Arg Leu Gln Ala Leu
    130                 135                 140

Arg Leu Glu Arg Glu Glu Tyr Val Leu Leu Lys Ala Leu Ala Leu Ala
145                 150                 155                 160

Asn Ser Asp Ser Val His Ile Glu Asp Ala Glu Ala Val Glu Gln Leu
                165                 170                 175

Arg Glu Ala Leu His Glu Ala Leu Leu Glu Tyr Glu Ala Gly Arg Ala
            180                 185                 190

Gly Pro Gly Gly Gly Ala Glu Arg Arg Arg Ala Gly Arg Leu Leu Leu
        195                 200                 205

Thr Leu Pro Leu Leu Arg Gln Thr Ala Gly Lys Val Leu Ala His Phe
    210                 215                 220

Tyr Gly Val Lys Leu Glu Gly Lys Val Pro Met His Lys Leu Phe Leu
225                 230                 235                 240

Glu Met Leu Glu Ala Met Met Asp
                245
```